United States Patent
Kunimoto et al.

(10) Patent No.: US 9,310,677 B2
(45) Date of Patent: Apr. 12, 2016

(54) POLYMERIZABLE COMPOSITION COMPRISING AN OXIME SULFONATE AS THERMAL CURING AGENT

(75) Inventors: Kazuhiko Kunimoto, Kawanishi (JP);
Kaori Sameshima, Tondabayashi (JP);
Yuki Matsuoka, Nishinomiya (JP);
Hisatoshi Kura, Takarazuka (JP)

(73) Assignee: BASF, Ludwigshafen (DE)

( * ) Notice: Subject to any disclaimer, the term of this patent is extended or adjusted under 35 U.S.C. 154(b) by 172 days.

(21) Appl. No.: 13/981,774

(22) PCT Filed: Jan. 27, 2012

(86) PCT No.: PCT/EP2012/051297
§ 371 (c)(1),
(2), (4) Date: Jul. 25, 2013

(87) PCT Pub. No.: WO2012/101245
PCT Pub. Date: Aug. 2, 2012

(65) Prior Publication Data
US 2013/0308219 A1    Nov. 21, 2013

Related U.S. Application Data

(60) Provisional application No. 61/437,024, filed on Jan. 28, 2011.

(30) Foreign Application Priority Data

Jan. 28, 2011  (EP) .................................... 11152582

(51) Int. Cl.
*G03F 7/027* (2006.01)
*G03F 7/00* (2006.01)
(Continued)

(52) U.S. Cl.
CPC ............ *G03F 7/0007* (2013.01); *C07C 309/00* (2013.01); *C07C 309/30* (2013.01); *C07C 327/58* (2013.01); *C07C 327/60* (2013.01); *C07D 213/59* (2013.01); *C07D 265/32* (2013.01); *C07D 277/54* (2013.01); *C07D 279/12* (2013.01); *C07D 291/02* (2013.01); *C07D 307/10* (2013.01); *C07D 309/08* (2013.01); *C07D 327/06* (2013.01); *G02B 5/223* (2013.01); *G03F 7/027* (2013.01); *G03F 7/028* (2013.01); *G03F 7/029* (2013.01);
(Continued)

(58) Field of Classification Search
CPC ....... G03F 7/0007; G03F 7/031; G03F 7/027; G03F 7/028; G03F 7/029; G03F 7/322; G02B 5/201; G02B 5/223
USPC .................................................. 430/7, 281.1
See application file for complete search history.

(56) References Cited

U.S. PATENT DOCUMENTS 5,106,846 A    4/1992  Szabadkai et al.
6,004,724 A    12/1999 Yamato et al.
(Continued)

FOREIGN PATENT DOCUMENTS

EP    0 174 046    3/1986
JP    10 10718     1/1998
(Continued)

OTHER PUBLICATIONS

U.S. Appl. No. 14/001,296, filed Aug. 23, 2013, Kunimoto et al.
(Continued)

*Primary Examiner* — John A McPherson
(74) *Attorney, Agent, or Firm* — Oblon, McClelland, Maier & Neustadt, L.L.P.

(57) ABSTRACT

The present invention relates to a polymerizable composition comprising at least one ethylenically unsaturated, polymerizable compound and at least one oxime sulfonate compound of the formula (I) $QA_aB_bC_c$ where a is 0, 1, 2, 3, 4 or 6, b is 0, 1, 2, 3, 4 or 6, and c is 0, 1, 2, 3, 4 or 6, where the sum of a+b+c is 1, 2, 3, 4 or 6 where (A) is a group (B) is a group (C) is a group where # denotes the point of attachment to Q; X is S or $NR^{14}$ and Q, $R^1$, $R^2$, $R^3$ and $R^{14}$ are as defined in claim 1 and in the description. The present invention also relates to the use of the this composition, to novel oxime sulfonates and the use of the oxime sulfonates as thermal curing promoter.

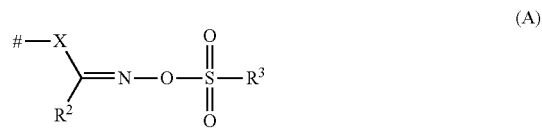

(A)

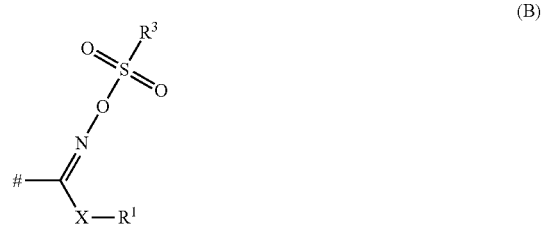

(B)

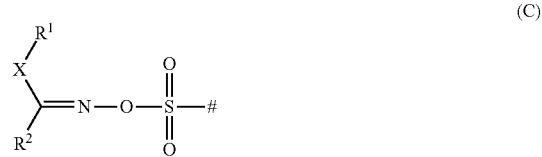

(C)

40 Claims, No Drawings

(51) Int. Cl.

| | | |
|---|---|---|
| G03F 7/032 | (2006.01) | |
| G03F 7/028 | (2006.01) | |
| G02B 5/22 | (2006.01) | |
| C07D 327/06 | (2006.01) | |
| C07C 309/30 | (2006.01) | |
| C07C 327/58 | (2006.01) | |
| C07D 265/32 | (2006.01) | |
| C07D 277/54 | (2006.01) | |
| C07D 291/02 | (2006.01) | |
| C07D 213/59 | (2006.01) | |
| C07C 309/00 | (2006.01) | |
| C07C 327/60 | (2006.01) | |
| C07D 279/12 | (2006.01) | |
| C07D 307/10 | (2006.01) | |
| C07D 309/08 | (2006.01) | |
| G03F 7/029 | (2006.01) | |
| G03F 7/031 | (2006.01) | |
| G03F 7/32 | (2006.01) | |
| G02B 5/20 | (2006.01) | |

(52) U.S. Cl.
CPC .............. *G03F 7/031* (2013.01); *G03F 7/032* (2013.01); *G03F 7/322* (2013.01); *C07C 2101/14* (2013.01); *C07C 2102/42* (2013.01); *G02B 5/201* (2013.01)

(56) References Cited

U.S. PATENT DOCUMENTS

| | | | |
|---|---|---|---|
| 6,261,738 | B1 | 7/2001 | Asakura et al. |
| 6,806,024 | B1 * | 10/2004 | Kura et al. ................. 430/270.1 |
| 2008/0014675 | A1 | 1/2008 | Kameyama et al. |
| 2012/0038996 | A1 | 2/2012 | Kura et al. |

FOREIGN PATENT DOCUMENTS

| | | |
|---|---|---|
| JP | 2003 015288 | 1/2003 |
| JP | 2003 330184 | 11/2003 |
| JP | 2004 026804 | 1/2004 |
| JP | 2009 86357 | 4/2009 |
| WO | 89 05805 | 6/1989 |
| WO | 92 03050 | 3/1992 |
| WO | 99 01429 | 1/1999 |
| WO | 02 25376 | 3/2002 |
| WO | 2004 074242 | 9/2004 |

OTHER PUBLICATIONS

U.S. Appl. No. 13/824,678, filed Mar. 18, 2013, Nishimae et al.
International Search Report Issued Jul. 17, 2012 in PCT/EP12/051297 Filed Jan. 27, 2012.
"Ryan Scientific High Throughput Screening Compound Library", Chemcats, Total 1 Page, (Apr. 11, 2011) XP 002679129.
"Ryan Scientific High Throughput Screening Compound Library", Chemcats, Total 1 Page, (Apr. 11, 2011) XP 002679130.
Hanefeld, W., et al., "Nitrosierungen an Hydrazinderivaten, 10. Mitt. 1):Oxidationen an Thiourethanen, 11. Mitt. 2): Reaktionen von 3-Aminorhodanien unter nitrosierenden Bedigungen", Arch. Phar. (Weinheim), vol. 326, pp. 871-874, (1993) XP 055010509.
Kitamura, M., et al., "Synthesis of Primary Amines and N-Methylamines by the Electrophilic Amination of Grignard Reagents with 2-Imidazolidinone O-Sulfonyl-oxime", Bull. Chem. Soc. Jpn., vol. 76, pp. 1063-1070, (2003) XP 055010572.
Hanefeld, W., et al., "Synthese, Kristallstruktur, Oxidation und Photochemie der Thion-S-oxide cyclischer Dithiourethane und Dithiocarbazate", Liebigs Ann. Chem., pp. 337-344, (1992) (with English abstract) XP 055010577.
Bezdrik, A., et al., "Uber einige Derivate des Thionaphthens", Berichte der Deutschen Chemischen Gesellschaft, vol. 41, No. 1, Total 17 Pages, (Jan. 1, 1908) XP 9153542.
Aitken, R. A., et al., "Product Class 4: 1,4,2-Oxathiazoles and Related Compounds", Science of Synthesis, vol. 13, Total 14 Pages, (Jan. 1, 2004) XP 9153553.
Davies, J.H., et al., "Geometrical Isomerism in the S-Alkyl Thiohydroximate Series: A new Oxime Fragmentation", J. Chem. Soc. (C), pp. 431-435, (1968) XP 009153570.
Baldovini, N., et al., "Amination of Arenes with N,N-Dimethyl-2-imidazolidinone O-Methoxyacetyloxime", Chemistry Letters, vol. 32, No. 6, pp. 548-549, (2003).
Akiba, K., et al., "Reactions of 2-Hydroxyimino-3-methyl-2-3-dihydrobenzothiazole Derivatives with Grignard Reagents and Organolithiums", Bulletin of the Chemical Society of Japan, vol. 52, No. 1, pp. 263-264, (1979).
Chan, F.S.Y., et al., "The Synthesis and Properties of some Novel 5-Amino-1,4,2-dithiazolium Salts and the X-Ray Molecular structure of 5-Morpholino-3-(4-nitropheny0-1,4,2-diathiazolium Fluoroborate", J. Chem. Soc. Perkin Trans. I, Total 9 Pages, (1988).
Chan., F.S.Y., et al., "Novel Synthesis of 1,4,2-Dithiazolium Salts", J. Chem. Soc., Chem. Commun., pp. 1641-1642, (1985).
Perchais, J., et al., "Azomethines a Substituants Electroattracteurs-III Action Des Nucleophiles Sur L'O-PARA-Toulenesulfonylisonitrosomalodinitrile", Tetrahedron, vol. 28, pp. 2267-2283, (1972).
Szabadkai, I., et al., "4-Benzyl-1,4-Thiomorpholine-2,3-Dion-2-Oxime and O-Substituted Derivatives an Interesting new Ring Contraction+", Models in Chemistry, vol. 131, No. 1, Total 7 Pages, (Feb. 1994).

* cited by examiner

POLYMERIZABLE COMPOSITION COMPRISING AN OXIME SULFONATE AS THERMAL CURING AGENT

CROSS REFERENCE TO RELATED APPLICATIONS

The present application is a 35 U.S.C. §371 national stage patent application of International patent application PCT/EP2012/051297, filed on Jan. 27, 2012, published as WO/2012/101245 on Aug. 2, 2012, the text of which is incorporated by reference, and claims the benefit of the filing date of EP application no. 11152582.0, filed on Jan. 28, 2011, and U.S. Provisional application No. 61/437,024, the text of both of which is also incorporated by reference.

BACKGROUND OF THE INVENTION

The present invention relates to a polymerizable composition comprising at least one ethylenically unsaturated, polymerizable compound and at least one oxime sulfonate, to novel oxime sulfonates and to the use of the oxime sulfonates as thermal curing promoter. Furthermore, the present invention relates to the use of said composition.

DESCRIPTION OF THE RELATED ART

There has been an increasing demand for color filters (CF) mainly for liquid crystal displays (LCD). Currently, color filters for liquid crystal display, which comprises black matrix and red, green and blue color pixels on a glass substrate, are manufactured by photolithography using radically photopolymerizable resists. After the photolithographic process, thermal curing is performed at about 230° C. for 30 min to polymerize remaining acrylic double bonds to attain required durability in the production process of CF/LCD and for long-term survival in LCD as permanent coat. An overcoat layer for LCD is used to planarize a surface of the color filter and enhance orientation of liquid crystal and to prevent ion elution from CF to the liquid crystal. As a base material for a colored coating film in a color filter, acrylic resins and/or epoxy resins or polyimide reins are usually employed. The overcoat is usually manufactured by heating, for example, at about 220° C. for 30 min or in combination with photolithoglaphy prior to the post-baking process. Thermal stability, light resistance, adhesiveness, hardness and transparency are required for the overcoat layer.

Spacer for LCD, which controls a cell gap of the liquid crystal layer in LCD panels, is formed with high positional precision by photolithography using a photosensitive composition. A photospacer is manufactured by photolithography using radically polymerizable resist on overcoat or color filter. After photolithography, the photospacer is baked, for example, at 220° C. for 60 min to attain thermal stability, mechanical strength, adhesiveness, cell gap controllability and high deformation restorability.

In providing acceptable color filters, overcoat layers or spacers, a variety of curing compositions comprising a thermal curing promoter require long curing times and/or high curing temperatures. These high curing temperatures raise energy requirements and impose problems in coating substrates such as inexpensive soda-lime glass as substrate which is sensitive to the elevated temperatures. A high curing reactivity of the thermal curing promoter is also desirable from the viewpoint of productivity.

A large number of organic substances belonging to the classes of peroxides or azo compounds are known for the application as thermal curing promoter to attain low curing temperatures. However, compositions comprising them often present difficulties concerning the storage stability and safety during transport due to their comparatively low decomposition temperature. Accordingly, there is a constant need for thermal curing promoters that meet the technical stability requirement. The thermal curing promoter should allow the curing of low temperature curable compositions and the reduction of curing time. The thermal curing promoter should show e.g. a good stability at the pre-baking process to remove the solvent prior to photolithography and enhancement of curing at an elevated temperature in the post-baking process after the photolithography.

W. Hanefeld et al describe in Arch. Pharm. (Weinheim) 326, 871-874 (1993) the preparation of a 5-(4-nitrophenylsulfonyloxyimino)-2-thioxothiazolidin-4-one compound and a 5-(4-nitrophenylsulfonyloximino)-thiazolidin-2,4-dione compound carrying a dimethylamino group in the 3-position of the 2-thioxothiazolidin-4-one ring and thiazolidine-2,4-dione ring, respectively. A use of these compounds as curing promoter is not described.

W. Hanefeld et al describe in Liebigs Ann. Chem. 1992, 337-344 the oxidation of 3-dimethylamino-5-(4-nitrophenylsulfonyloximino)-2-thioxothiazolidine to the corresponding thion-S-oxide.

A. Bezdrik et al describe in Berichte der deutschen chemischen Gesellschaft, vol. 41 (1), 1908, 227-242 the preparation of a sulfonyloxime compound of the formula

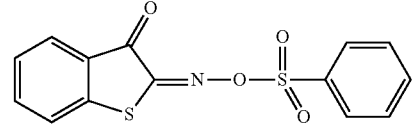 [SMILES: O=C1C(=NOS(=O)(=O)c2ccccc2)Sc2ccccc21]

N. Baldovini, M. Kitamura and K. Narasaka describe in Chemistry Letters 2003, vol 32 (6), 548-549, the amination of arenes with O-sulfonyloxime compounds such as e.g. N-methyl-2-oxazolidinone O-p-tosyloxime and 1,3-dimethyl-2-imidazolidinone O-p-tosyloxime

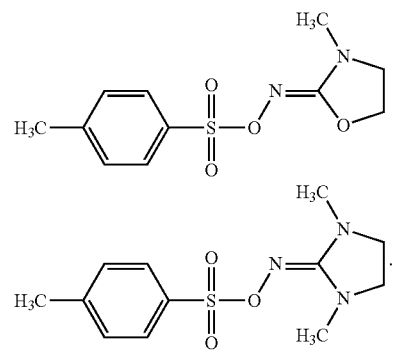

M. Kitamura, S. Chiba and K. Narasaka describe in Bull. Chem. Soc. Jpn, 1063-1070 (2003) the preparation of primary amines by the reaction of 1,3-dimethyl-2-imidazolidinone O-4-methylbenzenesulfonyloxime or 3-methyl-oxazolidin-2-one-O-4-methylbenzenesulfonyloxime with alkyl and aryl Grignard reagents. Described is also the synthesis of the amidoxime of the formula (1) by reacting N-methyl-2-oxazolidinone O-p-tosyloxime with phenylmagnesium bromide

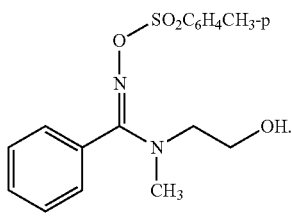
(1)

K. Akiba, H. Shiraishi and N. Inamoto describe in Bulletin of the Chemical Society of Japan, vol. 52, pp. 263-264 the reaction of the tosyloximino compound of the formula

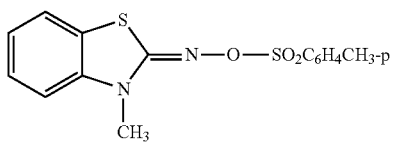

with Grignard reagents.

In Science of Synthesis (2004), 13, 95-107, J. Chem. Soc. Perkin Trans. 1, 1988, 899-906 and J. Chem. Soc., Chem. Commun., 1985, 1641-2, the cyclization of dithiocarbamate of the formula (2)

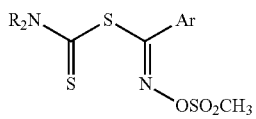
(2)

where Ar is phenyl and $NR_2$ is pyrrolidino, Ar is 4-chlorophenyl and $NR_2$ is morpholino or dimethylamino, Ar is 3-nitrophenyl or 4-nitrophenyl and $NR_2$ is piperidinyl, pyrrolidino, morpholino, dimethylamino or diethylamino, with fluoroboric acid in diethyl ether to dithiazolium salts is described.

J. H. Davies, R. H. Davies and P. Kirby in Journal of the Chemical Society [Section C]: Organic (1968), 431-435 studied S-alkyl thiohydroximates of the formula (3)

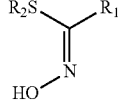
(3)

where $R_1=R_2=CH_3$, $R_1=R_2=C_2H_5$, $R_1$=ethyl or propyl and $R_2$=methyl or $R_1$=allyl and $R_2$=methyl. The syn(alkylthio) isomers of the compounds of the formula 3 give on treatment with toluene-p-sulphonyl chloride in pyridine crystalline toluene-p-sulfonates which were quite stable.

The ambivalent character of O-p-toluenesulfonyloximinocyanoformadies of the formulae

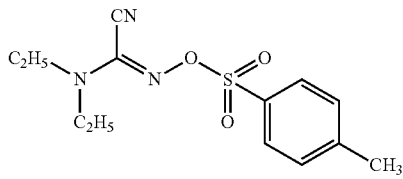

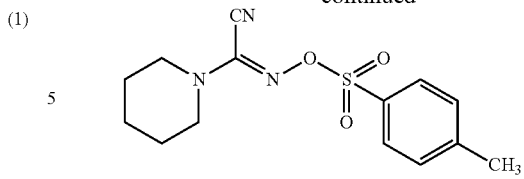

is studied in Tetrahedron, vol. 28, 1972, pp 2267 to 2283.

The compounds 4-phenylmethyl-O-tolylsulfonyl-2,3-thiomorpholinedione-2-oxime, 4-phenylmethyl-O-(fluorophenyl)sulfonyl-2,3-thiomorpholinedione-2-oxime and 4-phenylmethyl-O-phenylsulfonyl-2,3-thiomorpholinedione-2-oxime are known from Models in Chemistry 131 (3-4), pp. 529-534. The use of these compounds as curing promoter is not described.

The compounds 4-phenylmethyl-O-tosyl-2,3-thiomorpholinedione-2-oxime, 4-phenylmethyl-O-phenylsulfonyl-2,3-thiomorpholinedione-2-oxime and 4-phenylmethyl-O-(4-fluorophenylsulfonyl)-2,3-thiomorpholinedione-2-oxime are known from WO 89/05805. These compounds are effective against gastric and duodenal ulcers.

The compound alpha-phenylthio 3-(2-chloro-4-trifluoromethylphenoxy)-6-nitro-benzaldehyde O-methylsulfonyl oxime is known from EP 0174046. The compound can be used in combating undesired plant growth.

JP10010718 discloses a color former, which includes organic peroxides as thermal polymerization initiators and production of a color filter having good solvent resistance by applying post-baking process, preferably at 100~180° C., after photolithography process.

JP 2003330184 discloses a colored photosensitive resin composition capable of forming a color filter having high heat resistance, high hardness and high solvent resistance even after the resin composition is subjected to heat treatment of comparatively low temperature. The resin is composed of a polymerization initiator having an oxadiazole structure or a triazine structure containing a trihalomethyl group.

JP 2003015288 discloses a radiation sensitive composition, including thermal polymerization initiators like organic peroxides, hydroperoxide and azo compounds, capable of forming a color filter having satisfactory adhesion to a plastics substrate even if such low temperature treatment as not to cause deformation or yellowing to the plastics substrate is adopted when the color filter is formed on the plastics substrate and to provide a color filter formed form the composition. The radiation sensitive composition contains (A) a colorant, (B) an alkali-soluble resin, (C) a polyfunctional monomer, (D) a photopolymerization initiator and (E) a thermal polymerization initiator.

In WO 99/01429 (5-alkylsulfonyloxyimino-5H-thiophen-2-ylidene)-acetonitriles and 5-phenylsulfonyloxyimino-5H-thiophen-2-ylidene)-acetonitriles are disclosed. The compounds can be used as latent sulfonic acids.

U.S. Pat. No. 6,261,738, WO 02/25376 and WO 2004/074242 describe oxime sulfonates and their use as latent acids which can be activated by irradiation with actinic electromagnetic radiation and electron beams. These documents do not described oxime sulfonate compounds bearing at the oxime carbon atom a nitrogen-bound or sulfur bound radical.

US 2008/014675 describes the polymerisation of a conjugated diene monomer in the presence of a lanthanide-based catalyst to form a pseudo-living polymer and reacting the pseudo-living polymer with a protected oxime compound to form a functionalized polymer. The protected oxime compound can be an O-sulfonyloxime such as e.g. 1,3-dimethyl-2-imidazolidinone O-benzenesulfonyloxime.

JP 2004026804 teaches the use of S-substituted oxime sulfonates, e.g. 1,2-bis(butylsulfonyloximino)-1,2-bis(methylthio)ethane, 1,2-bis(benzylsulfonyloximino)-1,2-bis(methylthio)ethane, $R_1$: benzyl or n-butyl $R_2$: benzyl, n-propyl or n-butyl as photoacid generator in radiation-sensitive resin composition.

It has now been found, surprisingly, that specific oxime sulfonates can be used as curing promoters for radically polymerizable compositions. Compared with known curing promoters such as peroxides or azo compounds, the oxime sulfonates according to the invention show a higher curing reactivity.

The present invention is based on the object, therefore, of providing a curing promoter having a good curing performance.

SUMMARY OF THE INVENTION

In a first aspect, the invention relates to a polymerizable composition comprising (a) at least one oxime sulfonate compounds of the formula I $$QA_aB_bC_c \quad (I)$$

where
a is 0, 1, 2, 3, 4 or 6;
b is 0, 1, 2, 3, 4 or 6; and
c is 0, 1, 2, 3, 4 or 6;
where the sum of a+b+c is 1, 2, 3, 4 or 6
where
A is a group (A)

B is a group (B)

C is a group (C)

where
denotes the point of attachment to Q;
X is S, $SO_2$ or $NR^{14}$;
Q if a is 1, b is 0 and c is 0,
  is a radical $R^1$;
or
Q if a is 2, b is 0 and c is 0
  is a divalent linker, which is selected from L-$C_1$-$C_{30}$-alkylene-L, L-$C_2$-$C_{30}$-alkenylene-L, L-$C_3$-$C_{16}$-cycloalkylene-L, L-heterocycloalkylene-L, L-$C_6$-$C_{20}$-arylene-L, L-heteroarylene-L, L-$C_1$-$C_{30}$-alkylene-$L^2$-L, L-$C_2$-$C_{30}$-alkenylene-$L^2$-L, L-$C_3$-$C_{16}$-cycloalkylene-$L^1$-$C_3$-$C_{16}$-cycloalkylene-L, L-$C_3$-$C_{16}$-cycloalkylene-$L^1$-heterocycloalkylene-L, L-$C_3$-$C_{16}$-cycloalkylene-$L^1$-$C_6$-$C_{20}$-arylene-L L-$C_3$-$C_{16}$-cycloalkylene-$L^1$-heteroarylene-L, L-$C_6$-$C_{20}$-arylene-$L^1$-$C_6$-$C_{20}$-arylene-L, L-$C_6$-$C_{20}$-arylene-$L^1$-heteroarylene-L, L-heteroarylene-$L^1$-heteroarylene-L, L-$C_3$-$C_{16}$-cycloalkylene-$L^1$-$L^3$-$L^1$-$C_{3016}$-cycloalkylene-L, L-$C_3$-$C_{16}$-cycloalkylene-$L^1$-$L^3$-$L^1$-heterocycloalkylene-L, L-$C_3$-$C_{16}$-cycloalkylene-$L^1$-$L^3$-$L^1$-$C_6$-$C_{20}$-arylene-L L-$C_3$-$C_{16}$-cycloalkylene-$L^1$-$L^3$-$L^1$-heteroarylene-L, L-$C_6$-$C_{20}$-arylene-$L^1$-$L^3$-$L^1$-$C_6$-$C_{20}$-arylene-L, L-$C_6$-$C_{20}$-arylene-$L^1$-$L^3$-$L^1$-heteroarylene-L, L-heteroarylene-$L^1$-$L^3$-$L^1$-heteroarylene-L,
where each alkylene and each alkenylene may be interrupted by one or more identical or different nonadjacent groups $L^4$, and/or may carry one or more identical or different radicals $R^{Qa}$;
where each cycloalkylene and each heterocycloalkylene may be interrupted by one or more CO groups and/or may carry one or more identical or different radicals $R^{Qb}$,
where each arylene and each heteroarylene may carry one or more identical or different radicals $R^{Qc}$,
where
L is independently of one another selected from a single bond, C(S)O, C(S)$NR^{12}$;
$L^1$ is independently of one another a single bond, O, S, $NR^{14}$, CO, OC(O), C(O)O, C(S)O, OC(S), C(O)$NR^{10}$, $NR^{10}$C(O), C(S)$NR^{12}$, $NR^{12}$C(S) or $NR^{10}SO_2$;
$L^2$ is $C_3$-$C_{20}$-cycloalkylene, heterocycloalkylene, $C_6$-$C_{20}$-arylene or heteroarylene, where cycloalkylene and heterocycloalkylene may be interrupted by one or more CO and/or may be substituted by one or more identical or different radicals $R^{L2b}$, where arylene and heteroarylene may be substituted by one or more identical or different radicals $R^{L2c}$, where $R^{L2b}$ is independently of one another selected from $C_1$-$C_{12}$-alkyl, $C_1$-$C_{12}$-haloalkyl, F, Cl, Br, I, CN, $NO_2$, $SR^4$, $OR^5$, $NR^6R^7$, $COR^8$, $COOR^9$, $CONR^{10}R^{11}$ or phenyl;

$R^{L2c}$ has one of the meanings indicated for $R^{L2b}$;

$L^3$ is selected from $C_1$-$C_{30}$-alkylene, $C_2$-$C_{30}$-alkenylene, $C_3$-$C_{20}$-cycloalkylene, heterocycloalkylene, $C_6$-$C_{20}$-arylene and heteroarylene, where alkylene and alkenylene may be interrupted by one or more identical or different O, S, $NR^6$ and CO and/or may carry one or more identical or different radicals $R^{L3a}$, where cycloalkylene and heterocycloalkylene may be interrupted by one or more CO, and/or may be substituted by one or more identical or different radicals $R^{L3b}$, where arylene and hetarylene may be substituted by one or more identical or different radicals $R^{L3c}$, where $R^{L3a}$ is independently of one another selected from F, Cl, Br, I, CN, $SR^4$, $OR^5$, $NR^6R^7$, $COR^8$, $COOR^9$, $CONR^{10}R^{11}$, $C_3$-$C_{10}$-cycloalkyl, heterocyclyl, heteroaryl, phenyl and naphthyl, where the five last-mentioned radicals may be substituted by one or more identical or different radicals $R^{3aa}$, where $R^{3aa}$ has one of the meanings indicated for $R^{L2b}$;

$R^{L3b}$ has one of the meanings indicated for $R^{L2b}$;

$R^{L3c}$ has one of the meanings indicated for $R^{L2c}$;

$L^4$ is independently of one another selected from O, S, $NR^6$, CO, C(O)O, OC(O), C(O)$NR^{10}$, $NR^{10}$C(O), C(S)$NR^{12}$, $NR^{12}$C(S), $NR^{10}SO_2$, $C_3$-$C_{20}$-cycloalkylene, heterocycloalkylene, $C_6$-$C_{20}$-arylene, and heteroarylene, where cycloalkylene and heterocycloalkylene may be interrupted by one or more CO, and/or may be substituted by one or more identical or different radicals $R^{L4b}$, where arylene and heteroarylene may be substituted by one or more identical or different radicals $R^{L4c}$, where $R^{L4b}$ has one of the meanings indicated for $R^{L2b}$; and $R^{L4c}$ has one of the meanings indicated for $R^{L2c}$;

$R^{Qa}$ is selected independently of one another from F, Cl, Br, I, CN, $SR^4$, $OR^5$, $NR^6R^7$, $COR^8$, $COOR^9$, $CONR^{11}R^{11}$, $C_3$-$C_{10}$-cycloalkyl which may be interrupted by one or two CO groups, heterocyclyl which may be interrupted by one or two CO groups, heteroaryl, phenyl and naphthyl, where the five last-mentioned radicals may be substituted by one or more identical or different radicals $R^{Qaa}$, where $R^{Qaa}$ is independently of one another selected from $C_1$-$C_{12}$-alkyl, $C_1$-$C_{12}$-haloalkyl, F, Cl, Br, I, CN, $NO_2$, $SR^4$, $OR^5$, $NR^6R^7$, $COR^8$, $COOR^9$ and $CONR^{10}R^{11}$;

$R^{Qb}$ is selected independently of one another from F, Cl, Br, I, CN, $SR^4$, $OR^5$, $NR^6R^7$, $COR^8$, $COOR^9$, $CONR^{10}R^{11}$, $C_1$-$C_{12}$-alkyl, $C_1$-$C_{12}$-haloalkyl, heteroaryl, phenyl and naphthyl, where the three last-mentioned radicals may be substituted by one or more identical or different radicals $R^{Qba}$, where $R^{Qba}$ has one of the meanings indicated for $R^{Qaa}$;

$R^{Qc}$ is independently of one another selected from $C_1$-$C_{12}$-alkyl, $C_1$-$C_{12}$-haloalkyl, F, Cl, Br, I, CN, $NO_2$, $SR^4$, $OR^5$, $NR^6R^7$, $COR^8$, $COOR^9$, $CONR^{10}R^{11}$, phenyl, $C_3$-$C_{10}$-cycloalkyl and heterocyclyl, where in the two last-mentioned radicals one or two $CH_2$ groups may be replaced by CO;

Q if b is 2, a is 0 and c is 0, is a divalent linker, which is selected from
$L^5$-$C_1$-$C_{30}$-alkylene-$L^5$, $L^5$-$C_2$-$C_{30}$-alkenylene-$L^5$, $L^5$-$C_3$-$C_{16}$-cycloalkylene-$L^5$, $L^5$-heterocycloalkylene-$L^5$,
$L^5$-$C_6$-$C_{20}$-arylene-$L^5$, $L^5$-heteroarylene-$L^5$,
$L^5$-$C_1$-$C_{30}$-alkylene-$L^6$-$L^5$, $L^5$-$C_2$-$C_{30}$-alkenylene-$L^6$-$L^5$,
$L^5$-$C_3$-$C_{16}$-cycloalkylene-$L^7$-$C_3$-$C_{16}$-cycloalkylene-$L^5$,
$L^5$-$C_3$-$C_{16}$-cycloalkylene-$L^7$-heterocycloalkylene-$L^5$,
$L^5$-$C_3$-$C_{16}$-cycloalkylene-$L^7$-$C_6$-$C_{20}$-arylene-$L^5$,
$L^5$-$C_3$-$C_{16}$-cycloalkylene-$L^7$-heteroarylene-$L^5$,
$L^5$-$C_6$-$C_{20}$-arylene-$L^7$-$C_6$-$C_{20}$-arylene-$L^5$,
$L^5$-$C_6$-$C_{20}$-arylene-$L^7$-heteroarylene-$L^5$,
$L^5$-heteroarylene-$L^7$-heteroarylene-$L^5$
$L^5$-$C_3$-$C_{16}$-cycloalkylene-$L^7$-$L^8$-$L^7$-$C_3$-$C_{16}$-cycloalkylene-$L^5$,
$L^5$-$C_3$-$C_{16}$-cycloalkylene-$L^7$-$L^8$-$L^7$-heterocycloalkylene-$L^5$,
$L^5$-$C_3$-$C_{16}$-cycloalkylene-$L^7$-$L^8$-$L^7$-$C_6$-$C_{20}$-arylene-$L^5$,
$L^5$-$C_3$-$C_{16}$-cycloalkylene-$L^7$-$L^8$-$L^7$-heteroarylene-$L^5$,
$L^5$-$C_6$-$C_{20}$-arylene-$L^7$-$L^8$-$L^7$-$C_6$-$C_{20}$-arylene-$L^5$,
$L^5$-$C_6$-$C_{20}$-arylene-$L^7$-$L^8$-$L^7$-heteroarylene-$L^5$,
$L^5$-heteroarylene-$L^7$-$L^8$-$L^7$-heteroarylene-$L^5$, where each alkylene and each alkenylene may be interrupted by one or more identical or different groups $L^9$, and/or may carry one or more identical or different radicals $R^{Qa}$;

where each cycloalkylene and each heterocycloalkylene may be interrupted by one or more CO groups and/or may carry one or more identical or different radicals $R^{Qb}$, where each arylene radicand heteroarylene may carry one or more identical or different radicals $R^{Qc}$, where $L^5$ independently of one another is a single bond, S, O, $NR^6$, CO, C(O)O, OC(O), $NR^{10}$CO or $CONR^{10}$;

$L^6$ has one of the meanings indicated for $L^2$;

$L^7$ has one of the meanings indicated for $L^1$;

$L^8$ has one of the meanings indicated for $L^3$;

$L^9$ has one of the meanings indicated for $L^4$;

or

Q if c is 2, a is 0 and b is 0.

is a divalent linker, which is selected from $C_1$-$C_{30}$-alkylene, $C_2$-$C_{30}$-alkenylene, $C_3$-$C_{16}$-cycloalkylene, heterocycloalkylene, $C_6$-$C_{20}$-arylene, heteroarylene, $C_1$-$C_{30}$-alkylene-$L^{10}$, $C_2$-$C_{30}$-alkenylene-$L^{10}$,
$C_3$-$C_{16}$-cycloalkylene-$L^{11}$-$C_3$-$C_{16}$-cycloalkylene,
$C_3$-$C_{16}$-cycloalkylene-$L^{11}$-heterocycloalkylene,
$C_3$-$C_{16}$-cycloalkylene-$L^{11}$-$C_6$-$C_{20}$-arylene,
$C_3$-$C_{16}$-cycloalkylene-$L^{11}$-heteroarylene,
$C_6$-$C_{20}$-arylene-$L^{11}$-$C_6$-$C_{20}$-arylene,
$C_6$-$C_{20}$-arylene-$L^{11}$-heteroarylene, heteroarylene-$L^{11}$-heteroarylene,
$C_3$-$C_{16}$-cycloalkylene-$L^{11}$-$L^{12}$-$L^{11}$-$C_{3016}$-cycloalkylene,
$C_3$-$C_{16}$-cycloalkylene-$L^{11}$-$L^{12}$-$L^{11}$-$C_6$-$C_{20}$-arylene,
$C_3$-$C_{16}$-cycloalkylene-$L^{11}$-$L^{12}$-$L^{11}$-heterocycloalkylene,
$C_3$-$C_{16}$-cycloalkylene-$L^{11}$-$L^{12}$-$L^{11}$-heteroarylene,
$C_6$-$C_{20}$-arylene-$L^{11}$-$L^{12}$-$L^{11}$-$C_6$-$C_{20}$-arylene,
$C_6$-$C_{20}$-arylene-$L^{11}$-$L^{12}$-$L^{11}$-heteroaylene,
heteroarylene-$L^{11}$-$L^{12}$-$L^{11}$-heteroarylene, where each alkylene and each alkenylene may be interrupted by one or more identical or different groups $L^{13}$, and/or may carry one or more identical or different radicals $R^{Qa}$;

where each cycloalkylene and each heterocycloalkylene may be interrupted by one or more CO groups and/or may carry one or more identical or different radicals $R^{Qb}$,
where each arylene and each heteroarylene may carry one or more identical or different radicals $R^{Qc}$,
where
$L^{10}$ has one of the meanings indicated for $L^2$
$L^{11}$ has one of the meanings indicated for $L^1$;
$L^{12}$ has one the meanings indicated for $L^3$;
$L^{13}$ has one of the meanings indicated for $L^4$;
or
Q if the sum of a+b+c is 2,
is a divalent linker, which is selected from $C_1$-$C_{30}$-alkylene, $C_2$-$C_{30}$-alkenylene, $C_3$-$C_{16}$-cycloalkylene, heterocycloalkylene, $C_6$-$C_{20}$-arylene, heteroarylene, $C_1$-$C_{30}$-alkylene-$L^{10}$, $C_2$-$C_{30}$-alkenylene-$L^{10}$,
$C_3$-$C_{16}$-cycloalkylene-$L^{11}$-$C_3$-$C_{16}$-cycloalkylene,
$C_3$-$C_{16}$-cycloalkylene-$L^{11}$-heterocycloalkylene,
$C_3$-$C_{16}$-cycloalkylene-$L^{11}$-$C_6$-$C_{20}$-arylene,
$C_3$-$C_{16}$-cycloalkylene-$L^{11}$-heteroarylene,
$C_6$-$C_{20}$-arylene-$L^{11}$-$C_6$-$C_{20}$-arylene,
$C_6$-$C_{20}$-arylene-$L^{11}$-heteroarylene, heteroarylene-$L^{11}$-heteroarylene,
$C_3$-$C_{16}$-cycloalkylene-$L^{11}$-$L^{12}$-$L^{11}$-$C_3$-$C_{16}$-cycloalkylene,
$C_3$-$C_{16}$-cycloalkylene-$L^{11}$-$L^{12}$-$L^{11}$-$C_6$-$C_{20}$-arylene,
$C_3$-$C_{16}$-cycloalkylene-$L^{11}$-$L^{12}$-$L^{11}$-heterocycloalkylene,
$C_3$-$C_{16}$-cycloalkylene-$L^{11}$-$L^{12}$-$L^{11}$-heteroarylene,
$C_6$-$C_{20}$-arylene-$L^{11}$-$L^{12}$-$L^{11}$-$C_6$-$C_{20}$-arylene,
$C_6$-$C_{20}$-arylene-$L^{11}$-$L^{12}$-$L^{11}$-heteroaylene, heteroarylene-$L^{11}$-$L^{12}$-$L^{11}$-heteroarylene,
where each alkylene and each alkenylene may be interrupted by one or more identical or different groups $L^{13}$, and/or may carry one or more identical or different radicals $R^{Qa}$;
where each cycloalkylene and each heterocycloalkylene may be interrupted by one or more CO groups and/or may carry one or more identical or different radicals $R^{Qb}$,
where each arylene and each heteroarylene may carry one or more identical or different radicals $R^{Qc}$,
where
$L^{10}$ has one of the meanings indicated for $L^2$
$L^{11}$ has one of the meanings indicated for $L^1$;
$L^{12}$ has one the meanings indicated for $L^3$;
$L^{13}$ has one of the meanings indicated for $L^4$;
or
Q if the sum of a+b+c=3,
is a trivalent linker, which is selected from $C_1$-$C_{30}$-alkanetriyl, $C_2$-$C_{30}$-alkenetriyl, $C_3$-$C_{16}$-cycloalkanetriyl, heterocycloalkanetriyl, $C_6$-$C_{20}$-arenetriyl, heteroarenetriyl, $C_1$-$C_{30}$-alkanetriyl-$L^{14}$-$L^{15}$, $C_2$-$C_{30}$-alkenetriyl-$L^{14}$-$L^{15}$, $C_1$-$C_{30}$-alkylene-$L^{14}$-$L^{16}$, $C_2$-$C_{30}$-alkenetriyl-$L^{14}$-$L^{15}$, $C_2$-$C_{30}$-alkenylene-$L^{14}$-$L^{16}$, $C_3$-$C_{16}$-cycloalkanetriyl-$L^{14}$-$L^{11}$-$C_3$-$C_{16}$-cycloalkylene,
$C_3$-$C_{16}$-cycloalkanetriyl-$L^{14}$-$L^{15}$-$C_6$-$C_{20}$-arylene,
$C_6$-$C_{20}$-arenetriyl-$L^{14}$-$L^{15}$-$C_6$-$C_{20}$-arylene, and
$C_6$-$C_{20}$-arylene-$L^{14}$-$L^{15}$-$C_3$-$C_{16}$-cycloalkanetriyl
where each alkanetriyl, each alkylene, each alkenetriyl and each alkenylene may be interrupted by one or more identical or different groups $L^{17}$ and/or may carry one or more identical or different radicals $R^{Qa}$;
where each cycloalkanetriyl, each cycloalkylene, each heterocycloalkanetriyl and each heterocycloalkylene may be interrupted by one or more CO groups and/or may carry one or more identical or different radicals $R^{Qb}$, where each arenetriyl, each arylene, each heteroarenetriyl and each heteroarylene may carry one or more identical or different radicals $R^{Qc}$, where
$L^{14}$ has one of the meanings indicated for $L^1$;
$L^{15}$ has one of the meanings indicated for $L^2$;
$L^{16}$ is $C_6$-$C_{20}$-arenetriyl, heteroarenetriyl, $C_3$-$C_{20}$-cycloalkanetriyl and heterocycloalkanetriyl, where cycloalkanetriyl and heterocycloalkanetriyl may be interrupted by one or more CO, and/or may be substituted by one or more identical or different radicals $R^{L16b}$,
where arenetriyl and heteroarenetriyl may be substituted by one or more identical or different radicals $R^{L16c}$,
where
$R^{L16b}$ has one of the meanings indicated for $R^{L2b}$;
$R^{L16c}$ has one of the meanings indicated for $R^{L2c}$;
$L^{17}$ has one of the meanings indicated for $L^4$;
Q if the sum of a+b+c=4,
is a tetravalent linker, which is selected from $C_1$-$C_{30}$-alkanetetrayl which may be interrupted by one or more identical or different groups $L^{18}$ and/or may carry one or more identical or different radicals $R^{Qa}$;
where
$L^{18}$ has one of the meanings given for $L^{17}$;
Q if the sum of a+b+c=6
is a hexavalent linker which is selected from $C_2$-$C_{30}$-alkanehexayl which may be interrupted by one or more identical or different groups $L^{19}$ and/or may carry one or more identical or different radicals $R^{Qa}$;
where
$L^{19}$ has one of the meanings given for $L^{17}$;
$R^1$ is $C_1$-$C_{20}$-alkyl, $C_2$-$C_{20}$-alkenyl, $C_2$-$C_{20}$-alkynyl, $C_3$-$C_{20}$-cycloalkyl, heterocyclyl, $C_6$-$C_{20}$-aryl, heteroaryl, $C_1$-$C_{20}$-alkanoyl, $C_3$-$C_{20}$-cycloalkanoyl, $C_2$-$C_{20}$-alkenoyl, $C_6$-$C_{20}$-aroyl, $CSNR^{12}R^{13}$, $C(O)OR^9$ or $CSOR^9$,
where $C_1$-$C_{20}$-alkyl, $C_2$-$C_{20}$-alkenyl and $C_2$-$C_{20}$-alkynyl may be interrupted by one or more identical or different groups selected —O—, —S—, —N($R^6$)— and CO, and/or may carry one or more identical or different radicals $R^{1a}$,
where $C_3$-$C_{20}$-cycloalkyl and heterocyclyl may be interrupted by one or more CO groups, and/or may carry one or more identical or different radicals $R^{1b}$,
where $C_6$-$C_{20}$-aryl and heteroaryl may carry one or more identical or different radicals $R^{1c}$,
where $C_1$-$C_{20}$-alkanoyl and $C_2$-$C_{20}$-alkenoyl may carry one or more identical or different radicals $R^{1a}$,
where $C_3$-$C_{20}$-cycloalkanoyl may carry one or more identical or different radicals $R^{1b}$
where $C_6$-$C_{20}$-aroyl may carry one or more identical or different radicals $R^{1d}$
where
$R^{1a}$ is selected independently of one another from F, Cl, Br, I, CN, $SR^4$, $OR^5$, $NR^6R^7$, $COR^8$, $COOR^9$, $CONR^{10}R^{11}$, $C_3$-$C_{20}$-cycloalkyl which may be interrupted by one or more CO groups, heterocyclyl which may be interrupted by one or more CO groups, heteroaryl and $C_6$-$C_{10}$-aryl where the four last-mentioned radicals may carry one or more identical or different radicals $R^{1aa}$,
where
$R^{1aa}$ is selected independently of one another from $C_1$-$C_{12}$-alkyl, $C_1$-$C_{12}$-alkyl which may be interrupted by one or more groups selected from CO, O, S, C(O)O, OC(O), C(O)S and SC(O), $C_1$-$C_{12}$-haloalkyl, $C_1$-$C_{12}$-hydroxyalkyl, $C_2$-$C_{12}$-alkenyl, F, Cl, Br, I, $NO_2$, $SR^4$, $OR^5$, $NR^6R^7$, $COR^8$, $COOR^9$ and $CONR^{10}R^{11}$;

$R^{1b}$ is selected independently of one another from F, Cl, Br, I, CN, $SR^4$, $OR^5$, $NR^6R^7$, $COR^8$, $COOR^9$, $CONR^{10}R^{11}$, $C_1$-$C_{12}$-alkyl, $C_1$-$C_{12}$-hydroxyalkyl, $C_1$-$C_{12}$-haloalkyl, $C_2$-$C_{12}$-alkenyl, heteroaryl and $C_6$-$C_{10}$-aryl where the two last-mentioned radicals may carry one or more identical or different radicals $R^{1ba}$, where
$R^{1ba}$ has one of the meanings indicated for $R^{1aa}$;
$R^{1c}$ is selected independently of one another from $C_1$-$C_{12}$-alkyl, $C_1$-$C_{12}$-haloalkyl, $C_1$-$C_{12}$-hydroxyalkyl, $C_2$-$C_{12}$-alkenyl, F, Cl, Br, I, CN, $NO_2$, $SR^4$, $OR^5$, $NR^6R^7$, $COR^8$, $COOR^9$, $CONR^{10}R^{11}$, phenyl, heteroaryl, heterocyclyl and $C_3$-$C_{10}$-cycloalkyl where the two last-mentioned radicals may be interrupted by one or two C=O groups and where phenyl, heteroaryl, heterocyclyl and $C_3$-$C_{10}$-cycloalkyl may carry one or more identical or different radicals $R^{1ca}$, where
$R^{1ca}$ has one of the meanings indicated for $R^{1aa}$;
$R^{1d}$ is selected independently of one another from $C_1$-$C_{12}$-alkyl, $C_1$-$C_{12}$-haloalkyl, $C_1$-$C_{12}$-hydroxyalkyl, $C_2$-$C_{12}$-alkenyl, F, Cl, Br, I, CN, $SR^4$, $OR^5$, $NR^6R^7$, $COR^8$, $COOR^9$, $CONR^{10}R^{11}$, $C_3$-$C_{20}$-cycloalkyl which may be interrupted by one or more CO groups, heterocyclyl which may be interrupted by one or more CO groups, $C_6$-$C_{10}$-aryl and heteroaryl where the four last-mentioned radicals may carry one or more radicals $R^{1da}$, where $R^{1da}$ has one of the meanings indicated for $R^{1aa}$;

or if b is 2, 3, 4, or 6 and/or c is 2, 3, 4 or 6, two radicals $R^1$ together can be a divalent bridging group having 1 to 20 atoms between the flanking bonds, or if b is 2, 3, 4 or 6, at least one group-X—$R^1$ may be bound to a carbon atom or nitrogen atom of Q via a divalent bridging group having 1 to 10 atoms between the flanking bonds, $R^2$ is hydrogen, $SR^4$, $OR^5$, $NR^1R^{14}$, $COR^8$, $SO_2R^4$, $COOR^9$, $CONR^{10}R^{11}$, $SO_2NR^{10}R^{11}$, $PO(OR^9)_2$, CN, $C_1$-$C_{16}$-alkyl, $C_2$-$C_{20}$-alkenyl, $C_2$-$C_{20}$-alkynyl, $C_3$-$C_{20}$-cycloalkyl, heterocyclyl, $C_6$-$C_{20}$-aryl, heteroaryl, $C_1$-$C_{20}$-alkanoyl, $C_2$-$C_{20}$-alkenoyl, $C_3$-$C_{20}$-cycloalkanoyl, $C_6$-$C_{20}$-aroyl or a group E,
where $C_1$-$C_{16}$-alkyl, $C_2$-$C_{20}$-alkenyl and $C_2$-$C_{20}$-alkynyl may be interrupted by one or more identical or different groups selected from —O—, —S—, —N($R^6$)— and CO, and/or may carry one or more identical or different radicals $R^{2a}$,
where $C_3$-$C_{20}$-cycloalkyl and heterocyclyl may be interrupted by one or more CO groups, and/or may carry one or more identical or different radicals $R^{2b}$,
where $C_6$-$C_{20}$-aryl and heteroaryl may carry one or more identical or different radicals $R^{2c}$,
where $C_1$-$C_{20}$-alkanoyl and $C_2$-$C_{20}$-alkenoyl may carry one or more identical or different radicals $R^{2a}$,
where $C_3$-$C_{20}$-cycloalkanoyl may carry one or more identical or different radicals $R^{2b}$
where $C_6$-$C_{20}$-aroyl may carry one or more identical or different radicals $R^{2d}$, where
$R^{2a}$ is selected independently of one another from F, Cl, Br, I, CN, $SR^4$, $OR^5$, $NR^6R^7$, $COR^8$, $COOR^9$, $CONR^{10}R^{11}$, $C_3$-$C_{20}$-cycloalkyl which may be interrupted by one or more CO groups, heterocyclyl which may be interrupted by one or more CO groups, heteroaryl and $C_6$-$C_{10}$-aryl where the four last-mentioned radicals may carry one or more identical or different radicals $R^{2aa}$,
where
$R^{2aa}$ is selected independently of one another from $C_1$-$C_{12}$-alkyl, $C_1$-$C_{12}$-alkyl which may be interrupted by one or more groups selected from CO, O, S, C(O)O, OC(O), C(O)S and SC(O), $C_1$-$C_{12}$-haloalkyl, $C_1$-$C_{12}$-hydroxyalkyl, $C_2$-$C_{12}$-alkenyl, phenyl, F, Cl, Br, I, CN, $NO_2$, $SR^4$, $OR^5$, $NR^6R^7$, $COR^8$, $COOR^9$ and $CONR^{10}R^{11}$;

$R^{2b}$ has one of the meanings indicated for $R^{1b}$;
$R^{2c}$ has one of the meanings indicated for $R^{1c}$;
$R^{2d}$ has one of the meanings indicated for $R^{1d}$;
E is selected from

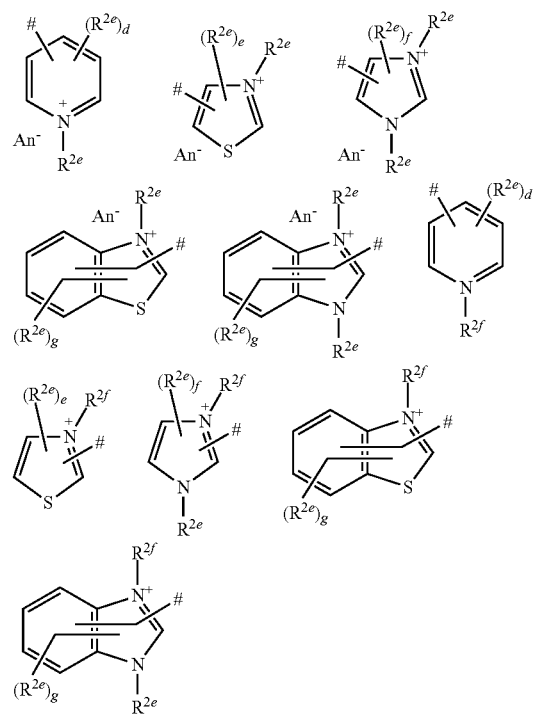

where
is the point of attachment to the remainder of the molecule;
d is 0, 1, 2, 3 or 4;
e is 0, 1, or 2;
f is 0, 1, or 2;
g is 0, 1, 2, 3 or 4;
$R^{2e}$ has one of the meanings indicated for $R^{2c}$;
$R^{2f}$ is $C_1$-$C_{20}$-alkylene-$COO^-$, $C_2$-$C_{20}$-alkenylene-$COO^-$, $C_2$-$C_{20}$-alkynylene-$COO^-$, $C_3$-$C_{20}$-cycloalkylene-$COO^-$, heterocycloalkylene-$COO^-$, $C_6$-$C_{20}$-arylene-$COO^-$, heteroarylene-$COO^-$, $C_1$-$C_{20}$-alkylene-$S(O_2)O^-$, $C_2$-$C_{20}$-alkenylene-$S(O_2)O^-$, $C_2$-$C_{20}$-alkynylene-$S(O_2)O^-$, $C_3$-$C_{20}$-cycloalkylene-$S(O_2)O^-$, heterocycloalkylene-$S(O_2)O^-$, $C_6$-$C_{20}$-arylene-$S(O_2)O^-$, heteroarylene-$S(O_2)O^-$, $C_1$-$C_{20}$-alkylene-$OS(O_2)O^-$, $C_2$-$C_{20}$-alkenylene-$OS(O_2)O^-$, $C_2$-$C_{20}$-alkynylene-$OS(O_2)O^-$, $C_3$-$C_{20}$-cycloalkylene-$OS(O_2)O^-$, heterocycloalkylene-$OS(O_2)O^-$, $C_6$-$C_{20}$-arylene-$OS(O_2)O^-$ or heteroarylene-$OS(O_2)O^-$
where each alkylene, each alkenyle and each alkynyle may be interrupted by one or more identical or different groups selected from —O—, —S—, —N($R^6$)— and CO, and/or may carry one or more identical or different radicals $R^{2a}$, where each cycloalkylene and each heterocycloalkylene may be interrupted by one or two groups CO and/or may carry one or more identical or different radicals $R^{2b}$, where each arylene and each heteroarylene may carry one or more radicals $R^{2c}$, $An^-$ is $Cl^-$, $Br^-$, $I^-$, $SCN^-$, $BF_4^-$, $PF_6^-$, $ClO_4^-$, $SbF_6^-$, $AsF_6^-$, $C_1$-$C_{20}$-alkyl-$COO^-$, $C_1$-$C_{20}$-alkyl-$S(O)_2O^-$, $C_1$-$C_{20}$-alkyl-$OS(O)_2O^-$, $C_6$-$C_{20}$-aryl-$COO^-$, $C_6$-$C_{20}$-aryl-$S(O)_2O^-$ or $C_6$-$C_{20}$-aryl-$OS(O)_2O^-$, where the aryl moiety of the three last-mentioned radicals may be substituted by 1, 2, 3 or 4 identical or different $C_1$-$C_{20}$-alkyl;

or

—$R^2$ together with —X—$R^1$ may be X—($C_1$-$C_{20}$-alkylene)-Y, X—($C_2$-$C_{20}$-alkenylene)-Y, X—($C_3$-$C_{20}$-cycloalkylene)-Y, X-(heterocycloalkylene)-Y, X-(o-phenylene)-Y, X-(o-xylylene)-Y, X-(o-phenylene-$C_1$-$C_{12}$-alkylene)-Y, X—($C_1$-$C_{12}$-alkylene-o-phenylene)-Y, X—(O—$C_1$-$C_{20}$-alkylene)-Y, X—(S—$C_1$-$C_{20}$-alkylene)-Y or X—(N($R^6$)—$C_1$-$C_{20}$-alkylene)-Y, Y being attached to the oxime carbon atom carrying X, where each alkylene and alkenylene may comprise one or more identical or different groups selected from O, S, $NR^6$ and CO and/or may be substituted by one or more radicals $R^{2g}$, where cycloalkylene and heterocycloalkylene may be interrupted by one or more groups CO and/or may be optionally substituted by one or more identical or different radicals $R^{2h}$, where each phenylene and the phenylene moiety of o-xylylene may be substituted by one or more identical or different radicals $R^{2h}$, where Y is O, S, $NR^{14}$, CO, SC(O), OC(O), C(O)O, $NR^{10}$C(O), C(O)$NR^{10}$, $NR^{10}SO_2$ or a single bond;

$R^{2g}$ is independently of one another selected from F, Cl, Br, I, $SR^4$, $OR^5$, $NR^6R^7$, $COR^8$, $COOR^9$, $CONR^{10}R^{11}$, heteroaryl and $C_6$-$C_{10}$-aryl where the two last-mentioned radicals may carry one or more radicals $R^{2ga}$, where $R^{2ga}$ is phenoxy or has one of the meanings indicated for $R^{1aa}$;

$R^{2h}$ is independently of one another selected from F, Cl, Br, I, $SR^4$, $OR^5$, $NR^6R^7$, $COR^8$, $COOR^9$, $CONR^{10}R^{11}$, $C_1$-$C_{12}$-alkyl, $C_1$-$C_{12}$-haloalkyl, heteroaryl and $C_6$-$C_{10}$-aryl where the two last-mentioned radicals may carry one or more radicals $R^{2ha}$, where $R^{2ha}$ has one of the meanings indicated for $R^{1aa}$;

or if X is S, —$R^2$ together with —S—$R^1$ may be S—C(S)—$NR^{12}$—C(O) or S—C(=$NOR^{15}$)—C(O)—$NR^{12}$—C(O), where $R^{15}$ is hydrogen or phenylsulfonyl where the phenyl moiety may be substituted by $C_1$-$C_4$-alkyl or $C_1$-$C_4$-alkoxy, or if a is 2, 3, 4 or 6 and/or c is 2, 3, 4 or 6, two radicals $R^2$ together may be a divalent bridging group having 1 to 20 atoms between the flanking bonds;

$R^3$ is $C_1$-$C_{20}$-alkyl, $C_2$-$C_{20}$-alkenyl, $C_2$-$C_{20}$-alkynyl, $C_3$-$C_{20}$-cycloalkyl, heterocyclyl, $C_6$-$C_{20}$-aryl or heteroaryl, where $C_1$-$C_{20}$-alkyl, $C_2$-$C_{20}$-alkenyl and $C_2$-$C_{20}$-alkynyl may be interrupted by one or more identical or different groups selected from —O—, —S—, —N($R^6$)— and CO, and/or may carry one or more identical or different radicals $R^{3a}$, where $C_3$-$C_{20}$-cycloalkyl and heterocyclyl may be interrupted by one or more CO groups, and/or may carry one or more identical or different radicals $R^{3b}$, where $C_6$-$C_{20}$-aryl and heteroaryl may carry one or more identical or radicals $R^{3c}$, where $R^{3a}$ has one of the meanings indicated for $R^{2a}$;

$R^{3b}$ has one of the meanings indicated for $R^{1b}$;

$R^{3c}$ has one of the meanings indicated for $R^{1c}$;

or

—X—$R^1$ and $R^3$ may together form a divalent radical selected from X—($C_1$-$C_{20}$-alkylene)-Z, X—($C_2$-$C_{20}$-alkenylene)-Z, X—($C_3$-$C_{20}$-cycloalkylene)-Z, X-(heterocycloalkylene)-Z, X-(o-phenylene)-Z, X-(o-xylylene)-Z, X—($C_1$-$C_{12}$-alkylene-heteroarylene-$C_1$-$C_{12}$-alkylene)-Z; X-(o-phenylene-$C_1$-$C_{12}$-alkylene)-Z, X—($C_1$-$C_{12}$-alkylene-o-phenylene)-Z and S—C(S)—$NR^{12}$—C(O), where Z is attached to the sulfur atom of the sulfonate group, where each alkylene and each alkenylene may be interrupted by one or more identical or different groups selected from O, S, $NR^6$ and CO and/or may be substituted by one or more radicals $R^{3g}$, where each cycloalkylene and each heterocycloalkylene may be interrupted by one or more groups CO and/or may be optionally substituted by one or more identical or different radicals $R^{3h}$, where each phenylene and the phenylene moiety of o-xylylene may be substituted by one or more identical or different radicals $R^{3h}$, where $R^{3g}$ has one of the meanings indicated for $R^{2g}$;

$R^{3h}$ has one of the meanings indicated for $R^{2h}$; and

Z is O, S, $NR^{14}$, CO, OC(O), SC(O), C(O)O, $NR^{10}$C(O), C(O)$NR^{10}$, $NR^{10}(SO_2)$ or a single bond;

$R^4$ is selected independently of one another from hydrogen, $C_1$-$C_{20}$-alkyl, $C_2$-$C_{12}$-alkenyl, $C_3$-$C_{10}$-cycloalkyl, heterocyclyl, where the two last-mentioned radicals may be interrupted by one or more C=O groups, $C_1$-$C_{20}$-alkyl which is interrupted by one or more identical or different groups selected from —O—, —S—, —N($C_1$-$C_8$-alkyl)- and CO, and/or may carry one or more identical or different radicals $R^{4a}$, $C_2$-$C_{12}$-alkenyl which is interrupted by one or more identical or different groups selected from —O—, —S—, and —N($C_1$-$C_8$-alkyl)-, —($CH_2CH_2O)_m$H, with m being 1-20, —($CH_2CH_2O)_n$(CO)—($C_1$-$C_8$-alkyl), with n being 1-20, $C_2$-$C_8$-alkanoyl, $C_3$-$C_6$-alkenoyl, where the two-last mentioned radicals may be substituted by one or more identical or different radicals selected from F, Cl, Br, I, OH or $C_1$-$C_6$-alkoxy, benzoyl which may be substituted by one or more identical or different radicals selected from F, Cl, Br, I, $C_1$-$C_6$-alkyl, OH or $C_1$-$C_6$-alkoxy, phenyl and naphthyl, where the two last-mentioned radicals may be substituted by one or more identical or different radicals $R^{4c}$, phenyl which forms a 5- or 6-membered ring with the phenyl ring to which the $SR^4$ is attached via a single bond, $C_1$-$C_4$-alkylene, O, S, $NR^6$ or CO, or naphthyl which forms a 5- or 6-membered ring with the phenyl ring to which the $SR^4$ is attached via a single bond, $C_1$-$C_4$-alkylene, O, S, $NR^6$ or CO, where $R^{4a}$ is selected independently of one another from F, Cl, Br, I, $C_3$-$C_{10}$-cycloalkyl, heterocyclyl, phenyl, OH, SH, CN, $C_3$-$C_6$-alkenoxy, $OCH_2CH_2CN$, $OCH_2CH_2(CO)O$($C_1$-$C_8$-alkyl), O(CO)—($C_1$-$C_8$-alkyl), O(CO)-phenyl, (CO)OH and (CO)O($C_1$-$C_8$-alkyl);

$R^{4c}$ is selected independently of one another from F, Cl, Br, I, $C_1$-$C_{12}$-alkyl, $C_1$-$C_{12}$-haloalkyl, $C_1$-$C_{12}$-alkoxy, phenyl-$C_1$-$C_3$-alkoxy, phenoxy, $C_1$-$C_{12}$-alkylsulfanyl, phenylsulfanyl, —(CO)O($C_1$-$C_8$-alkyl), (CO)N($C_1$-$C_8$-alkyl)$_2$ and phenyl;

$R^5$ is selected independently of one another from hydrogen, $C_1$-$C_{20}$-alkyl, $C_2$-$C_{12}$-alkenyl, $C_3$-$C_{10}$-cycloalkyl, heterocyclyl, where the two last-mentioned radicals may be interrupted by one or two C=O groups, $C_1$-$C_{20}$-alkyl which is interrupted by one or more identical or different groups selected from —O—, —S—, —N($C_1$-$C_8$-alkyl)- and CO, and/or may carry one or more identical or different radicals $R^{5a}$, $C_2$-$C_{12}$-alkenyl which is interrupted by one or more identical or different groups selected from —O—, —S—, and —N($C_1$-$C_8$-alkyl)-, —(CH$_2$CH$_2$O)$_m$H, with m being 1-20, —(CH$_2$CH$_2$O)$_n$(CO)—($C_1$-$C_8$-alkyl), with n being 1-20, $C_2$-$C_8$-alkanoyl, $C_3$-$C_6$-alkenoyl, where the two-last mentioned radicals may be substituted by one or more identical or different radicals selected from F, Cl, Br, I, OH or $C_1$-$C_6$-alkoxy, $C_2$-$C_8$-alkanoyl, which is interrupted by one or more identical or different groups selected from —O— and —S— and may be substituted by one or more identical or different radicals selected from hydroxyaminylene (=N—OH), F, Cl, Br, I, OH and $C_1$-$C_6$-alkoxy, benzoyl which may be substituted by one or more identical or different radicals selected from F, Cl, Br, I, $C_1$-$C_6$-alkyl, OH or $C_1$-$C_6$-alkoxy, phenyl and naphthyl, where the two last-mentioned radicals may be substituted by one or more identical or different radicals $R^{5c}$, phenyl which forms a 5- or 6-membered ring with the phenyl ring to which the $OR^5$ is attached via a single bond, $C_1$-$C_4$-alkylene, O, S, $NR^6$ or CO, or naphthyl which forms a 5- or 6-membered ring with the phenyl ring to which the $OR^5$ is attached via a single bond, $C_1$-$C_4$-alkylene, O, S, $NR^6$ or CO, where $R^{5a}$ has one of the meanings indicated for $R^{4a}$;

$R^{5c}$ has one of the meanings indicated for $R^{4c}$;

$R^6$, $R^{10}$ and $R^{12}$ are selected independently of one another from hydrogen, $OR^5$, $C_1$-$C_{20}$-alkyl, $C_2$-$C_{12}$-alkenyl, $C_3$-$C_{10}$-cycloalkyl, heterocyclyl, where the two last-mentioned radicals may be interrupted by one or two C=O groups, $C_1$-$C_{20}$-alkyl which is interrupted by one or more identical or different groups selected from —O—, —S—, —N($C_1$-$C_8$-alkyl)- and CO, and/or may carry one or more identical or different radicals $R^{6a}$, $C_2$-$C_{12}$-alkenyl which is interrupted by one or more identical or different groups selected from —O—, —S—, and —N($C_1$-$C_8$-alkyl)-, —(CH$_2$CH$_2$O)$_o$OH, with o being 1-20, —(CH$_2$CH$_2$O)$_p$(CO)—($C_1$-$C_8$-alkyl), with p being 1-20, $C_2$-$C_8$-alkanoyl, $C_3$-$C_6$-alkenoyl, where the two-last mentioned radicals may be substituted by one or more identical or different radicals selected from F, Cl, Br, I, OH or $C_1$-$C_6$-alkoxy, benzoyl which may be substituted by one or more identical or different radicals selected from F, Cl, Br, I, $C_1$-$C_6$-alkyl, —OH or $C_1$-$C_6$-alkoxy, phenyl and naphthyl, where the two last-mentioned radicals may be substituted by one or more identical or different radicals $R^{6c}$, where $R^{6a}$ has one of the meanings indicated for $R^{4a}$;

$R^{6c}$ has one of the meanings indicated for $R^{4c}$;

or two radicals $R^6$ together may be a divalent bridging group having 1 to 20 atoms between the flanking bonds;

or two radicals $R^{10}$ together may be a divalent bridging group having 1 to 20 atoms between the flanking bonds;

or two radicals $R^{12}$ together may be a divalent bridging group having 1 to 20 atoms between the flanking bonds;

$R^7$, $R^{11}$ and $R^{13}$ are independently of one another selected from $OR^5$, $C_1$-$C_{20}$-alkyl, $C_2$-$C_{12}$-alkenyl, $C_3$-$C_{10}$-cycloalkyl, heterocyclyl, where in the two last-mentioned radicals one or two CH$_2$ groups may be replaced by a C=O group, $C_1$-$C_{20}$-alkyl which is interrupted by one or more identical or different groups selected from —O—, —S—, —N($C_1$-$C_8$-alkyl)- and CO, and/or may carry one or more identical or different radicals $R^{7a}$, $C_2$-$C_{12}$-alkenyl which is interrupted by one or more identical or different groups selected from —O—, —S—, and —N($C_1$-$C_8$-alkyl)-, —(CH$_2$CH$_2$O)$_q$H, with q being 1-20, —(CH$_2$CH$_2$O)$_r$(CO)—($C_1$-$C_8$-alkyl), with r being 1-20, $C_2$-$C_8$-alkanoyl, $C_3$-$C_6$-alkenoyl, where the two-last mentioned radicals may be substituted by one or more identical or different radicals selected from F, Cl, Br, I, OH or $C_1$-$C_6$-alkoxy, benzoyl which may be substituted by one or more identical or different radicals selected from F, Cl, Br, I, $C_1$-$C_6$-alkyl, OH or $C_1$-$C_6$-alkoxy, phenyl and naphthyl, where the two last-mentioned radicals may be substituted by one or more identical or different radicals $R^{7c}$, where $R^{7a}$ has one of the meanings indicated for $R^{4a}$;

$R^{7c}$ has one of the meanings indicated for $R^{4c}$;

or $R^6$ and $R^7$ together with the nitrogen atom to which they are attached form a saturated 5-, 6- or 7-membered nitrogen heterocycle which may have a further heteroatom or heteroatomic group selected from the group consisting of CO, O, S and N($C_1$-$C_8$-alkyl) as ring member and which may carry 1, 2, 3 or 4 $C_1$-$C_4$-alkyl;

or $R^{10}$ and $R^{11}$ together with the nitrogen atom to which they are attached form a saturated 5-, 6- or 7-membered nitrogen heterocycle which may have a further heteroatom or heteroatomic group selected from the group consisting of CO, O, S and N($C_1$-$C_8$-alkyl) as ring member and which may carry 1, 2, 3 or 4 $C_1$-$C_4$-alkyl;

or $R^{12}$ and $R^{13}$ together with the nitrogen atom to which they are attached form a saturated 5-, 6- or 7-membered nitrogen heterocycle which may have a further heteroatom or heteroatomic group selected from the group consisting of CO, O, S and N($C_1$-$C_8$-alkyl) as ring member and which may carry 1, 2, 3 or 4 $C_1$-$C_4$-alkyl;

$R^8$ is independently of one another selected from hydrogen, $C_1$-$C_{20}$-alkyl, $C_2$-$C_{12}$-alkenyl, $C_3$-$C_{10}$-cycloalkyl, heterocyclyl, where the two last-mentioned radicals may be interrupted by one or more C=O groups, $C_1$-$C_{20}$-alkyl which is interrupted by one or more identical or different groups selected from —O—, —S—, —N($C_1$-$C_8$-alkyl)- and CO, and/or may carry one or more identical or different radicals $R^{8a}$, $C_2$-$C_{12}$-alkenyl which is interrupted by one or more identical or different groups selected from —O—, —S—, and —N($C_1$-$C_8$-alkyl)-, —($CH_2CH_2O$)$_s$H, with s being 1-20, —($CH_2CH_2O$)$_t$(CO)—($C_1$-$C_8$-alkyl), with t being 1-20, $C_6$-$C_{20}$-aryl and heteroaryl, where the two last-mentioned radicals may be substituted by one or more identical or different radicals $R^{8c}$, where $R^{8a}$ has one of the meanings indicated for $R^{4a}$;

$R^{8c}$ has one of the meanings indicated for $R^{4c}$;

$R^9$ is independently of one another selected from hydrogen, $C_1$-$C_{20}$-alkyl, $C_2$-$C_{12}$-alkenyl, $C_3$-$C_{10}$-cycloalkyl, heterocyclyl, where the two last-mentioned radicals may be interrupted by one or more C=O groups, $C_1$-$C_{20}$-alkyl which is interrupted by one or more identical or different groups selected from —O—, —S—, —N($C_1$-$C_8$-alkyl)- and CO, and/or may carry one or more identical or different radicals $R^{9a}$, $C_2$-$C_{12}$-alkenyl which is interrupted by one or more identical or different groups selected from —O—, —S—, and —N($C_1$-$C_8$-alkyl)-, —($CH_2CH_2O$)$_u$H, with u being 1-20, —($CH_2CH_2O$)$_v$(CO)—($C_1$-$C_8$-alkyl), with v being 1-20, phenyl and naphthyl, where the two last-mentioned radicals may be substituted by one or more identical or different radicals $R^{9c}$, where $R^{9a}$ has one of the meanings indicated for $R^{4a}$;

$R^{9c}$ has one of the meanings indicated for $R^{4c}$;

$R^{14}$ is $C_1$-$C_{20}$-alkyl, $C_2$-$C_{20}$-alkenyl, $C_2$-$C_{20}$-alkynyl, $C_3$-$C_{20}$-cycloalkyl, heterocyclyl, $C_6$-$C_{20}$-aryl, heteroaryl, $C_1$-$C_{20}$-alkanoyl, $C_2$-$C_{20}$-alkenoyl, $C_3$-$C_{20}$-cycloalkanoyl, $C_6$-$C_{20}$-aroyl, CSNR$^{12}$R$^{13}$ or CSOR$^9$, where $C_1$-$C_{20}$-alkyl, $C_2$-$C_{20}$-alkenyl and $C_2$-$C_{20}$-alkynyl may be interrupted by one or more identical or different groups selected —O—, —S—, —N(R$^6$)— and CO and/or may carry one or more identical or different radicals $R^{14a}$, where $C_3$-$C_{20}$-cycloalkyl and heterocyclyl may be interrupted by one or more CO groups and/or may carry one or more identical or different radicals $R^{14b}$, where $C_6$-$C_{20}$-aryl, heteroaryl may carry one or more identical or radicals $R^{14c}$, where $C_1$-$C_{20}$-alkanoyl, $C_2$-$C_{20}$-alkenoyl may carry one or more identical or different radicals $R^{14a}$, where $C_3$-$C_{20}$-cycloalkanoyl may carry one or more identical or different radicals $R^{14b}$, where $C_6$-$C_{20}$-aroyl may carry one or more identical or different radicals $R^{14d}$, where $R^{14a}$ has one of the meanings indicated for $R^{2a}$, $R^{14b}$ has one of the meanings indicated for $R^{1b}$, $R^{14c}$ has one of the meanings indicated for $R^{1c}$;

$R^{14d}$ has one of the meanings indicated for $R^{1d}$;

or $R^1$ together with $R^{14}$ may be a divalent bridging group having 1 to 20 atoms between the flanking bonds;

or two radicals $R^{14}$ together may be a divalent bridging group having 1 to 20 atoms between the flanking bonds, and (b) at least one ethylenically unsaturated, polymerizable compound.

The compounds of the formula I are novel except for:

compounds of the formula I in which if a is 1, b=c=0, X—R$^1$ is phenylsulfanyl and R$^2$ is 5-(2-chloro-4-trifluoromethyl-phenoxy)-2-nitro-phenyl, R$^3$ is methyl;

compounds of the formula I in which if a is 1, b=c=0, X—R$^1$ and R$^2$ together are N(CH$_3$)-ethylene-N(CH$_3$), R$^3$ is phenyl or p-tolyl;

compounds of the formula I in which if a is 1, b=c=0, X—R$^1$ and R$^2$ together are CON(benzyl)-ethylene-S, R$^3$ is phenyl, tolyl or fluorophenyl;

compounds of the formula I in which if a is 1, b=c=0, X—R$^1$ is 3,4,5-trihydroxymethyl-6-hydroxymethyl-tetrahydropyran-2-ylsulfanyl and R$^2$ is benzyl, R$^3$ is 4-methylphenyl;

compounds of the formula I in which if a is 1, b=c=0, X—R$^1$ and R$^2$ together are N(CH$_3$)-ethylene-O, R$^3$ is p-tolyl;

compounds of the formula I in which if a is 1, b=c=0, X—R$^1$ and R$^2$ together are N(CH$_3$)-o-phenylene-S, R$^3$ is p-tolyl;

compounds of the formula I in which if a is 1, b=c=0, X—R$^1$ and R$^2$ together are N(CH$_3$)-propylene, R$^3$ is p-tolyl;

compounds of the formula I in which if a is 1, b=c=0, X—R$^1$ is SCH$_3$ and R$^2$ is propyl or allyl, R$^3$ is p-tolyl;

compounds of the formula I in which if a is 1, b=c=0, X—R$^1$ is SCH$_3$ or SC$_2$H$_5$ and R$^2$ is methyl or ethyl, R$^3$ is p-tolyl;

compounds of the formula I in which if a is 1, b=c=0, X—R$^1$ is N(CH$_3$)CH$_2$CH$_2$OH and R$^2$ is phenyl, R$^3$ is p-tolyl;

compounds of the formula I in which if a is 1, b=c=0, X—R$^1$ is piperidino or N(C$_2$H$_5$)$_2$ and R$^2$ is CN, R$^3$ is p-tolyl;

compounds of the formula I in which if a is 1, b=c=0, X—R$^1$ is N(CH$_3$)$_2$ and R$^2$ is 2,6-dichlorophenyl, R$^3$ is methyl;

compounds of the formula I in which if a is 1, b=c=0, X—R$^1$ is SC(S)NR$^{12}$R$^{13}$, where NR$^{12}$R$^{13}$ is N(CH$_3$)$_2$, N(C$_2$H$_5$)$_2$, morpholino, piperidino or pyrrolidino and R$^2$ is phenyl, 3-nitrophenyl, 4-nitrophenyl or 4-chlorophenyl, R$^3$ is methyl, and compounds of the formula I in which if a is 1, b=c=0, X—R$^1$ and R$^2$ together are S-(1,2-phenylene)-CO and R$^3$ is phenyl.

Accordingly, ia further aspect of the invention relates to novel compounds of the general formula (I) as defined above and in the following A further aspect of the invention relates to the use of a composition as defined above for the production of color filters for display applications, spacers for LCD, overcoat layer for color filter and LCD, sealant for LCD, optical films for a variety of display applications, anisotropy conducting adhesive for LCD, insulation layer for LCD, to generate structures or layers in the manufacturing processes of plasma-display panels, electroluminescence displays and LCD, to manufacture solder mask, dielectric layers in a sequential build-up layer of a printed circuit board.

A further aspect of the invention relates to a coated substrate which is coated on at least one surface with a composition as defined above.

A further aspect of the invention relates to a color filter prepared by providing red, green and blue picture elements and a black matrix, all comprising a photosensitive resin and a pigment on a transparent substrate and providing a transparent electrode either on the surface of the substrate or on the surface of the color filter layer, wherein said photosensitive resin comprises a polyfunctional acrylate monomer, an organic polymer binder, a photopolymerization initiator and an oxime sulfonate compound of the formula I as defined above as thermal curing promoter.

DESCRIPTION OF THE INVENTION

The compounds of the general formula I are characterized in that at least one heteroatom selected from S and N is attached to the oxime carbon atom. The compounds of the general formula I have at least one of the following advantageous properties:
- enabling of reduction of curing time;
- enabling of reduction of curing temperature;
- thermal stability,
- high compatibility with the composition to be polymerized,
- high cross-linking density
- high curing speed
- low shrinkage
- storage stability and
- long pot-life.

The expression "halogen" denotes in each case fluorine, bromine, chlorine or iodine, preferably fluorine, chlorine or bromine, in particular fluorine or chlorine.

For the purpose of the present invention the term halogen denotes fluorine, chlorine, bromine or iodine, particularly fluorine or chlorine.

The term "alkyl" as used herein refers to saturated straight-chain or branched hydro-carbon radicals having usually 1 to 4, to 6, to 8, to 12, to 16 or to 30 carbon atoms. Alkyl is preferably $C_1$-$C_{12}$-alkyl and more preferably $C_1$-$C_8$-alkyl. Examples of alkyl groups are especially methyl, ethyl, n-propyl, isopropyl, n-butyl, isobutyl, sec-butyl, tert-butyl, n-pentyl, neo-pentyl, n-hexyl, n-heptyl, n-octyl, n-nonyl, n-decyl, n-undecyl, n-dodecyl, n-tridecyl, n-tetradecyl, n-hexadecyl, n-octadecyl and n-eicosyl.

Alkyl interrupted by CO, and/or heteroatoms such as —O—, —S— and —N($R^6$)— is for example interrupted once or more times, e.g. 1, 2, 3, 4, 5, 6, 7, 8 or 9, or once or twice. If alkyl is interrupted, for example once, twice, three or four times by CO, and/or heteroatoms such as —O—, —S— and —N($R^6$)—, at least one internal methylene group of alkyl is replaced by C(O), —O—, —S— or —N($R^6$)—, i.e. —O—, —S—, —N($R^6$)— and CO are not located at the termini of the alkyl group. $R^6$ is as defined above. If a plurality of O, S or $NR^6$ occurs, they are usually non-adjacent, i.e. they are separated from one another by at least one methylene group. If a plurality of those interrupting heteroatoms selected from O, S or $NR^6$ occurs in alkyl, those heteroatoms are usually identical. Examples for alkyl interrupted by one or more O-atoms are —$CH_2$—O—$CH_3$, —$CH_2CH_2$—O—$CH_2CH_3$, —[$CH_2CH_2$O]$_y$—$CH_3$, with y=1-9, —($CH_2CH_2$O)$_y$ $CH_2CH_3$ with y=1-9, —$CH_2$—CH($CH_3$)—O—$CH_2$—$CH_2CH_3$, —$CH_2$—$CH_2$CH($CH_3$)—O—$CH_2$—$CH_2CH_3$, —$CH_2$—$CH_2$CH($CH_3$)—O—$CH_2CH_3$, —$CH_2$—$CH_2$CH($CH_3$)—O—$CH_3$, and —$CH_2$—CH($CH_3$)—O—$CH_2CH_3$. A skilled person will readily understand that alkyl interrupted by 1 oxygen atom may also be referred to as alkoxy-alkyl or alkyl interrupted by 2 oxygen atoms may also be referred to as alkoxy-alkoxy-alkyl. Likewise, alkyl interrupted by 1 sulfur atom may also be referred to as alkyl-S-alkyl(alkylsulfanyl-alkyl) or, alkyl interrupted by 2 sulfur atoms may also be referred to as alkyl-S-alkyl-S-alkyl(alkylsulfanyl-alkylsulfa-nyl-alkyl).

Substituted alkyl groups may, depending on the length of the alkyl chain, have one or more (e.g. 1, 2, 3, 4, 5, 6, 7, 8 or more than 9) identical or different substituents.

An example for alkyl substituted by cycloalkyl, where cycloalkyl is interrupted by one CO group and carries one or more alkyl groups is camphoryl, especially camphor-10-yl

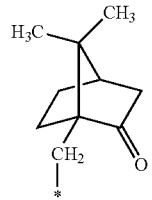

where * is the point of attachment to the remainder of the molecule.

The term "haloalkyl" as used herein, which is also expressed as "alkyl which may be substituted by halogen", refers to straight-chain or branched hydrocarbon radicals (as mentioned above), where some or all of the hydrogen atoms in these groups are replaced by halogen atoms as mentioned above, in particular fluorine, chlorine and bromine. Examples for haloalkyl are $C_1$-$C_{20}$-fluoroalkyl, especially $C_1$-$C_6$-fluoroalkyl, $C_1$-$C_{20}$ chloroalkyl, especially $C_1$-$C_6$-chloroalkyl and $C_1$-$C_{20}$-bromoalkyl, especially $C_1$-$C_6$-bromoalkyl such as chloromethyl, trichloromethyl, fluoromethyl, difluoromethyl, trifluoromethyl, 2,2,2,-trifluoroethyl and 2-bromopropyl.

The term "alkoxy" as used herein refers to a saturated straight-chain or branched, alkyl radical having usually 1 to 4, to 6, to 8, to 12, to 16 or to 20 carbon atoms which is attached via an oxygen atom to the remainder of the molecule. Examples are methoxy, ethoxy, propoxy, isopropoxy, n-butyloxy, sec-butyloxy, iso-butyloxy, tert-butyloxy, pentyloxy, hexyloxy, heptyloxy, 2,4,4-trimethylpentyloxy, 2-ethylhexyloxy, octyloxy, nonyloxy, decyloxy, dodecyloxy, hexadecyloxy, octadecyloxy or icosyloxy, in particular methoxy, ethoxy, propoxy, isopropoxy, n-butyloxy, sec-butyloxy, iso-butyloxy, tert-butyloxy, especially methoxy.

The term "phenylalkoxy" as used herein refers to phenyl, which is bound via an alkoxy group having preferably 1 to 4 carbon atoms, in particular 1 or 2 carbon atoms, to the remainder of the molecule, examples including phenoxymethyl, 1-phenoxyethyl, 2-phenoxyethyl, and the like.

The term "alkylsulfanyl" as used herein refers to a saturated straight-chain or branched, alkyl radical having usually 1 to 4, to 6, to 8, to 12, to 16 or to 20 carbon atoms as defined above which is attached via a sulfur atom to the remainder of the molecule. Examples are methylsulfanyl, ethylsulfanyl, propylsulfanyl, isopropylsulfanyl, n-butylsulfanyl, sec-butylsulfanyl, isobutylsulfanyl and tert-butylsulfanyl.

The term "$C_1$-$C_{20}$-alkanoyl" as used herein refers to formyl and a saturated straight-chain or branched alkyl radical having 1 to 19 carbon atoms attached through the carbon atom of the carbonyl group at any position in the alkyl group, for example acetyl, propanoyl, 2-methyl-propanoyl, butanoyl, pentanoyl, hexanoyl.

The term "$C_2$-$C_8$-alkanoyl" ($C_1$-$C_7$-alkyl-C(=O)— or alkylcarbonyl) as used herein refers to a saturated straight-chain or branched alkyl radical having 1 to 7 carbon atoms attached through the carbon atom of the carbonyl group at any position in the alkyl group, for example acetyl, propanoyl, 2-methyl-propanoyl, butanoyl, pentanoyl, hexanoyl.

The term "$C_1$-$C_6$-alkoxycarbonyl" ($C_1$-$C_6$-alkyl-O—C(O)—) as used herein refers to a saturated straight-chain or branched alkoxy radical having 1 to 6 carbon atoms as defined above attached through the carbon atom of the carbonyl group to the remainder of the molecule. Examples are methoxycarbonyl, ethoxycarbonyl, propoxycarbonyl, butoxycarbonyl, isobutoxycarbonyl or pentoxycarbonyl.

The term "alkenyl" as used herein refers to mono- or polyunsaturated, straight-chain or branched hydrocarbon radicals having usually 2 to 30, preferably 2 to 20, more preferably 2 to 10 carbon atoms, having one or more, e.g. 1, 2, 3 or more than two double bonds, e.g., $C_2$-$C_6$-alkenyl having one double bond such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, or alkadienyl having usually 4 to 10 carbon atoms and two double bonds in any position, for example 1,3-butadienyl, 1,3-pentadienyl, hexa-1,4-dien-1-yl, hexa-1,4-dien-3-yl, hexa-1,4-dien-6-yl, hepta-1,4-dien-7-yl, hepta-1,5-dien-1-yl and the like.

Alkenyl interrupted by CO, and/or heteroatoms such as —O—, —S— or —N($R^6$)— is for example interrupted once or more times, e.g. 1, 2, 3, 4, 5, 6, 7, 8 or 9, or once or twice. If alkenyl is interrupted by CO, and/or heteroatoms such as —O—, —S— and —N($R^6$)—, at least one internal methylene group of alkenyl is replaced by C(O), —O—, —S— or —N($R^6$)—, i.e. —O—, —S—, —N($R^6$)— and CO are not located at the termini of the alkenyl group. $R^6$ is as defined above. If a plurality of O, S or $NR^6$ occurs, they are usually non-adjacent, i.e. they are separated from one another by at least one methylene group). If a plurality of those interrupting heteroatoms selected from O, S or $NR^6$ occurs in alkenyl, those heteroatoms are usually identical.

Substituted alkenyl groups may, depending on the length of the alkenyl chain, have one or more (e.g. 1, 2, 3, 4, 5, 6, 7, 8 or more than 8) identical or different substituents.

The term "haloalkenyl" as used herein, which is also expressed as "alkenyl which may be substituted by halogen", refers to unsaturated straight-chain or branched hydrocarbon radicals having one or more double bonds (as mentioned above), where some or all of the hydrogen atoms in these groups are replaced by halogen atoms as mentioned above, in particular fluorine, chlorine and bromine. Examples for haloalkenyl are $C_2$-$C_{20}$-fluoroalkenyl, $C_2$-$C_{20}$ chloroalkenyl and $C_2$-$C_{20}$-bromoalkenyl.

The term "$C_3$-$C_6$-alkenoxy" as used herein refers to a mono- or diunsaturated straight-chain or branched alkenyl radical having 3 to 6 carbon atoms as defined above linked via an oxygen atom to the remainder of the molecule. Examples are vinyloxy, 1-propenyloxy, 2-propenyloxy, 1-methylethenyloxy, 1-butenyloxy, 2-butenyloxy, 3-butenyloxy, 1-methyl-1-propenyloxy, 2-methyl-1-propenyloxy, 1-methyl-2-propenyloxy, 2-methyl-2-propenyloxy, 1-pentenyloxy, 2-pentenyloxy, 3-pentenyloxy, 4-pentenyloxy, 1-methyl-1-butenyloxy, 2-methyl-1-butenyloxy, 3-methyl-1-butenyloxy, 1-methyl-2-butenyloxy, 2-methyl-2-butenyloxy, 3-methyl-2-butenyloxy, 1-methyl-3-butenyloxy, 2-methyl-3-butenyloxy, 3-methyl-3-butenyl, 1,1-dimethyl-2-propenyloxy, 1,2-dimethyl-1-propenyloxy, 1,2-dimethyl-2-propenyloxy, 1-ethyl-1-propenyloxy, 1-ethyl-2-propenyloxy, 1-hexenyloxy, 2-hexenyloxy, 3-hexenyloxy, 4-hexenyloxy and 5-hexenyloxy.

The term "$C_3$-$C_6$-alkenoyl($C_2$-$C_5$-alkenyl-C(O)—)" as used herein refers to a mono- or diunsaturated straight-chain or branched alkenyl radical having 2 to 5 carbon atoms as defined above attached through the carbon atom of the carbonyl group at any position in the alkenyl group, for example propenoyl, 2-methyl-propenoyl, butenoyl, pentenoyl, 1,3-pentadienoyl, 5-hexenoyl.

The term "alkynyl" as used herein refers to unsaturated straight-chain or branched hydrocarbon radicals having usually 2 to 30, preferably 2 to 20, more preferably 2 to 10 carbon atoms and one or more, e.g. two, three or four triple bonds, e.g. ethynyl, propargyl (2-propyn-1-yl), 1-propyn-1-yl, 1-methylprop-2-yn-1-yl), 2-butyn-1-yl, 3-butyn-1-yl, 1-pentyn-1-yl, 3-pentyn-1-yl, 4-pentyn-1-yl, 1-methylbut-2-yn-1-yl, 1-ethylprop-2-yn-1-yl and the like.

Alkynyl interrupted by CO, and/or heteroatoms such as —O—, —S— and —N($R^6$)— is for example interrupted once or more times, e.g. 1, 2, 3, 4, 5, 6, 7, 8 or 9, or once or twice. If alkynyl is interrupted by CO and/or heteroatoms such as —O—, —S— and —N($R^6$)—, at least one internal methylene group of alkynyl is replaced by C(O)—O—, —S— and —N($R^6$)—, i.e. —O—, —S—, —N($R^6$)— and CO are not located at the termini of the alkynyl group. $R^6$ is as defined above. If a plurality of O, S or $NR^6$ occurs, they are usually non-adjacent, i.e. they are separated from one another by at least one methylene group. If a plurality of those interrupting heteroatoms selected from O, S or $NR^6$ occurs in alkynyl, those heteroatoms are usually identical.

Substituted alkynyl groups may, depending on the length of the alkynyl chain, have one or more (e.g. 1, 2, 3, 4, 5 or more than 5) identical or different substituents.

The term "haloalkynyl" as used herein, which is also expressed as "alkynyl which may be substituted by halogen", refers to unsaturated straight-chain or branched hydrocarbon radicals having one or more triple bonds (as mentioned above), where some or all of the hydrogen atoms in these groups are replaced by halogen atoms as mentioned above, in particular fluorine, chlorine and bromine. Examples for haloalkynyl are $C_2$-$C_{20}$-fluoroalkynyl, $C_2$-$C_{20}$ chloroalkynyl and $C_2$-$C_{20}$-bromoalkynyl.

The term "$C_3$-$C_6$-alkynyloxy" as used herein refers to a mono- or diunsaturated straight-chain or branched alkynyl radical having 3 to 6 carbon atoms as defined above which is attached via an oxygen atom to the remainder of the molecule, for example 2-propynyloxy, 2-butynyloxy, 3-butynyloxy, 1-methyl-2-propynyloxy, 2-pentynyloxy, 3-pentynyloxy, 4-pentynyloxy, 1-methyl-2-butynyloxy, 1-methyl-3-butynyloxy, 2-methyl-3-butynyloxy, 1-ethyl-2-propynyloxy, 2-hexynyloxy, 3-hexynyloxy, 4-hexynyloxy, 5-hexynyloxy, 1-methyl-2-pentynyloxy and 1-methyl-3-pentynyloxy.

The term "cycloalkyl" as used herein refers to a mono- or polycyclic, e.g. bi- or tricyclic aliphatic radical having usually from 3 to 30, preferably 3 to 20, more preferably 3 to 16, or 3 to 12 carbon atoms or in particular 3 to 8 carbon atoms. Examples of monocyclic rings are cyclopropyl, cyclobutyl, cyclopentyl, cyclohexyl, cycloheptyl or cyclooctyl, especially cyclopentyl and cyclohexyl. Examples of polycyclic rings are perhydroanthracyl, perhydronaphthyl, perhydrofluorenyl, perhydrochrysenyl, perhydropicenyl, adamantyl, bicyclo[1.1.1]pentyl, bicyclo[2.2.1]heptyl, bicyclo[4.2.2]decyl, bicyclo[2.2.2]octyl, bicyclo[3.3.0]octyl bicyclo[3.3.2]decyl, bicyclo[4.4.0]decyl, bicyclo[4.3.2]undecyl, bicyclo[4.3.3]dodecyl, bicyclo[3.3.3]undecyl, bicyclo[4.3.1]decyl, bicyclo[4.2.1]nonyl, bicyclo[3.3.1]nonyl, bicyclo[3.2.1]octyl and the like. Cycloalkyl may be interrupted by one or more CO groups, usually one or two groups. An example for cycloalkyl interrupted by 1 CO group is 3-oxobicyclo[2.2.1]heptyl. When cycloalkyl is substituted by one or more identical or different radicals, it is for example mono-, di-, tri-, tetra- or pentasubstituted, e.g. by $C_1$-$C_4$-alkyl. When cycloalkyl is substituted by one or more substituents, it is, for example, mono-, di-, tri-, tetra- or pentasubstituted or more than pentasubstituted.

The term "heterocyclyl" (also referred to as heterocycloalkyl) as used herein includes in general 3-, 4-, 5-, 6-, 7- or 8-membered, in particular 5-, 6-, 7- or 8-membered monocyclic heterocyclic non-aromatic radicals and 8 to 10 membered bicyclic heterocyclic non-aromatic radicals, the mono- and bicyclic non-aromatic radicals may be saturated or unsaturated. The mono- and bicyclic heterocyclic non-aromatic radicals usually comprise 1, 2, 3 or 4 heteroatoms, in particular 1 or 2 heteroatoms selected from N, O and S as ring members, where S-atoms as ring members may be present as S, SO or $SO_2$. Heterocycloalkyl may be interrupted by one or more CO groups, usually one or two groups. When heterocyclyl is substituted by one or more identical or different radicals, it is for example mono-, di-, tri-, tetra- or pentasubstituted. Examples of saturated or unsaturated 3-, 4-, 5-, 6-, 7- or 8-membered heterocyclic radicals comprise saturated or unsaturated, non-aromatic heterocyclic rings, such as oxiranyl, oxetanyl, thietanyl, thietanyl-S-oxid (S-oxothietanyl), thietanyl-S-dioxid (S-dioxothiethanyl), pyrrolidinyl, pyrazolinyl, imidazolinyl, pyrrolinyl, pyrazolinyl, imidazolinyl, tetrahydrofuranyl, dihydrofuranyl, 1,3-dioxolanyl, dioxolenyl, thiolanyl, S-oxothiolanyl, S-dioxothiolanyl, dihydrothienyl, S-oxodihydrothienyl, S-dioxodihydrothienyl, oxazolidinyl, isoxazolidinyl, oxazolinyl, isoxazolinyl, thiazolinyl, isothiazolinyl, thiazolidinyl, isothiazolidinyl, oxathiolanyl, piperidinyl, piperazinyl, pyranyl, dihydropyranyl, tetrahydropyranyl, 1,3- and 1,4-dioxanyl, thiopyranyl, S-oxothiopyranyl, S-dioxothiopyranyl, dihydrothiopyranyl, S-oxodihydrothiopyranyl, S-dioxodihydrothiopyranyl, tetrahydrothiopyranyl, S-oxotetrahydrothiopyranyl, S-dioxotetrahydrothiopyranyl, morpholinyl, thiomorpholinyl, S-oxothiomorpholinyl, S-dioxothiomorpholinyl, thiazinyl and the like. Examples for heterocyclic ring also comprising 1 or 2 carbonyl groups as ring members comprise pyrrolidin-2-onyl, pyrrolidin-2,5-dionyl, imidazolidin-2-onyl, oxazolidin-2-onyl, thiazolidin-2-onyl and the like.

If heterocyclyl is substituted by one or more substituents, it is, for example, mono-, di-, tri-, tetra- or pentasubstituted or more than pentasubstituted.

The term "$C_3$-$C_{20}$-cycloalkanoyl" ($C_3$-$C_{20}$-cycloalkyl-C(=O)) as used herein refers to a mono- or polycyclic, e.g. bi- or tricyclic aliphatic radical having from 3 to 20 carbon atoms attached through the carbon atom of the carbonyl group at any position in the cycloalkyl group, for example cyclobutylcarbonyl, cyclopentylcarbonyl, cyclohexylcarbonyl.

The term "aryl" as used herein refers to a monovalent aromatic group having 6 to 20 ring carbon atoms. The term aryl includes a monocyclic radical, such as phenyl, or polycyclic, e.g. bi-, tri- or tetracyclic radicals, for example naphthyl, phenanthrenyl or anthracenyl. Preferred examples for aryl are phenyl and naphthyl. Substituted phenyl is substituted once, twice, three times, four times or five times. Polycylic radicals aryl are usually substituted by 1, 2, 3, 4, 5, 6, 7 or 8 substituents, preferably 1, 2, 3 or 4.

The term "$C_6$-$C_{20}$-aroyl" ($C_6$-$C_{20}$aryl-C(=O)) as used herein refers to a monovalent aromatic group having 6 to 20 ring carbon atoms as defined above attached through the carbon atom of the carbonyl group at any position in the aryl group, for example benzoyl and naphthoyl.

The term "heteroaryl" (also referred to as "hetaryl") includes in general 5- or 6-membered unsaturated monocyclic heterocyclic radicals and 8 to 10 membered unsaturated bicyclic heterocyclic radicals which are aromatic, i.e. they comply with Hückel's rule (4n+2 rule). Hetaryl usually comprise besides carbon atom(s) as ring member(s) 1, 2, 3 or 4 heteroatoms selected from N, O and S as ring members. Examples of 5- or 6-membered heteroaromatic radicals include: 2-furyl, 3-furyl, 2-thienyl, 3-thienyl, 1-pyrrolyl, 2-pyrrolyl, 3-pyrrolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 3-isoxazolyl, 4-isoxazolyl or 5-isoxazolyl, 3-isothiazolyl, 4-isothiazolyl or 5-isothiazolyl, 1-imidazolyl, 2-imidazolyl, 4-imidazolyl, 2- or 5-[1,3,4]oxadiazolyl, 4- or 5-(1,2,3-oxadiazol)yl, 3- or 5-(1,2,4-oxadiazol)yl, 2- or 5-(1,3,4-thiadiazol)yl, 2- or 5-(1,3,4-thiadiazol)yl, 4- or 5-(1,2,3-thiadiazol)yl, 3- or 5-(1,2,4-thiadiazol)yl, 1H-, 2H- or 3H-1,2,3-triazol-4-yl, 1,3,4-triazol-2-yl, 2H-triazol-3-yl, 1H-, 2H-, or 4H-1,2,4-triazolyl, 1H- or 2H-tetrazolyl 2-pyridinyl, 3-pyridinyl, 4-pyridinyl, 3-pyridazinyl, 4-pyridazinyl, 2-pyrimidinyl, 4-pyrimidinyl, 5-pyrimidinyl and 2-pyrazinyl. When heteroaryl is substituted by one or more identical or different radicals, it is for example mono-, di-, tri-, tetra- or pentasubstituted.

The term "heteroaryl" also includes bicyclic 8- to 10-membered heteroaromatic radicals comprising as ring members 1, 2 or 3 heteroatoms selected from N, O and S, wherein a 5- or 6-membered heteroaromatic ring is fused to a phenyl ring or to a 5- or 6-membered heteroaromatic radical. Examples of a 5- or 6-membered heteroaromatic ring fused to a phenyl ring or to a 5- or 6-membered heteroaromatic radical include benzofuranyl, benzothienyl, indolyl, indazolyl, benzimidazolyl, benzoxathiazolyl, benzoxadiazolyl, benzothiadiazolyl, benzoxazinyl, chinolinyl, isochinolinyl, purinyl, 1,8-naphthyridyl, pteridyl, pyrido[3,2-d]pyrimidyl or pyridoimidazolyl and the like. These fused hetaryl radicals may be bonded to the remainder of the molecule via any ring atom of 5- or 6-membered heteroaromatic ring or via a carbon atom of the fused phenyl moiety.

If heteroaryl is substituted by one or more substituents, it is, for example, mono-, di-, tri-, tetra- or pentasubstituted or more than pentasubstituted.

The term "$C_1$-$C_{30}$-alkylene" (or alkanediyl) as used herein in each case denotes an alkyl radical having 1 to 30 carbon atoms as defined above, wherein one hydrogen atom at any position of the alkyl radical is replaced by one further binding site, thus forming a bivalent radical. Accordingly, $C_1$-$C_{20}$-alkylene is a divalent branched or unbranched saturated aliphatic chain having 1 to 20 carbon atoms, for example —$CH_2$—, —$CH_2CH_2$—, —$CH(CH_3)$—, —$CH_2CH_2CH_2$—, —$CH(CH_3)CH_2$—, —$CH_2CH_2CH_2CH_2$—, —$CH_2CH(CH_3)CH_2$—, —$CH(CH_3)CH(CH_3)$—, —$CH_2CH_2CH_2CH_2CH_2$—, —$CH_2(CH_2)_2CH(CH_3)$—, —$CH_2C(CH_3)_2CH_2$—, and the like.

The term "each alkylene may be interrupted by one or more identical or different groups selected from —O—, —S—, —N($R^6$)— and CO" denotes an alkylene chain having usually 1 to 20 carbon atoms as defined above where at least one internal methylene group of the alkylene chain is replaced by O—, —S—, —N($R^6$)— or CO. The alkylene moiety may comprise, e.g. 1, 2, 3, 4, 5, or more than 5 identical or different groups selected from O, S, $NR^6$ and CO. $R^6$ is as defined above. If a plurality of CO, O, S or $NR^6$ occurs, they are usually non-adjacent, i.e. they are separated from one another by at least one methylene group. If a plurality of those interrupting heteroatoms selected from O, S or $NR^6$ occurs in alkylene, those heteroatoms are usually identical.

If the radical alkylene is substituted by one or more substituents, it is, for example, mono-, di-, tri-, tetra- or pentasubstituted or more than pentasubstituted.

The term "alkenylene" (or alkenediyl) as used herein in each case denotes a straight-chain or branched alkenyl radical having usually 2 to 30, preferably 2 to 20 carbon atoms as defined above, wherein one hydrogen atom at any position of the carbon backbone is replaced by one further binding site, thus forming a bivalent moiety. Accordingly, $C_2$-$C_{20}$-alkenylene is a divalent straight-chain or branched aliphatic chain having 2 to 20 carbon atoms, for example vinylene, propenylene, but-1-enylene, but-2-enylene, penta-1,3-dienylene, and the like.

The term "each alkenylene may be interrupted by one or more identical or different groups selected from —O—, —S—, —N($R^6$)— and CO" denotes an alkenylene chain having usually 2 to 30, preferably 2 to 20 carbon atoms as defined above where at least one internal methylene group of the alkenylene chain is replaced by O—, —S—, —N($R^6$)— or CO. The alkenylene moiety may comprise, e.g. 1, 2, 3, 4, 5, or more than 5 identical or different groups selected from O, S, $NR^6$ and CO. $R^6$ is as defined above. If a plurality of O, S or $NR^6$ occurs, they are usually non-adjacent, i.e. they are separated from one another by at least one methylene group. If a plurality of those interrupting heteroatoms selected from O, S or $NR^6$ occurs in alkenylene, those heteroatoms are usually identical.

If the radical alkenylene is substituted by one or more substituents, it is, for example, mono-, di-, tri-, tetra- or pentasubstituted or more than pentasubstituted.

The term "$C_2$-$C_{30}$-alkynylene" (or alkynediyl) as used herein in each case denotes a straight-chain or branched alkynyl radical having 2 to 30 carbon atoms as defined above, wherein one hydrogen atom at any position of the carbon backbone is replaced by one further binding site, thus forming a bivalent moiety. Accordingly, $C_2$-$C_{20}$-alkynylene is a divalent straight-chain or branched aliphatic chain having 2 to 20 carbon atoms.

The term "each alkynylene may be interrupted by one or more identical or different groups selected from —O—, —S—, —N($R^6$)— and CO" denotes an alkynylene chain having usually 2 to 30, preferably 2 to 20 carbon atoms as defined above where at least one internal methylene group of the alkynylene chain is replaced by O—, —S—, —N($R^6$)— or CO.

The alkynylene moiety may comprise, e.g. 1, 2, 3, 4, 5, or more than 5 identical or different groups selected from O, S, $NR^6$ and CO. $R^6$ is as defined above. If a plurality of O, S or $NR^6$ occurs, they are usually non-adjacent, i.e. they are separated from one another by at least one methylene group. If a plurality of those interrupting heteroatoms selected from O, S or $NR^6$ occurs in alkynylene, those heteroatoms are usually identical.

If the radical alkynylene is substituted by one or more substituents, it is, for example, mono-, di-, tri-, tetra-, penta-, hexa-, hepta- or octasubstituted or more than octasubstituted.

The term "$C_1$-$C_{30}$-alkanetriyl" as used herein in each case denotes an alkanediyl radical having 1 to 30 carbon atoms as defined above, wherein one hydrogen atom at any position of the alkanediyl is replaced by one further binding site, thus forming a trivalent radical. Accordingly, $C_1$-$C_{20}$-alkanetriyl is a trivalent branched or unbranched saturated aliphatic chain having 1 to 20 carbon atoms. If alkanetriyl is substituted by one or more substituents, it is, for example, mono-, di-, tri-, tetra- or pentasubstituted or more than pentasubstituted.

The term "$C_1$-$C_{30}$-alkanetriyl which may be interrupted by one or more identical or different groups $L^{17}$ denotes an alkanetriyl chain having 1 to 30, preferably 1 to 20 carbon atoms as defined above where at least one internal methylene group of the alkynylene chain is replaced by a group $L^{17}$. The alkanetriyl chain moiety may comprise, e.g. 1, 2, 3, 4, 5, or more than 5 identical or different groups $L^{17}$. If a plurality of O or S as interrupting groups $L^{17}$ occurs, they are usually non-adjacent, i.e. they are separated from one another by at least one methylene group.

The term "$C_2$-$C_{30}$-alkenetriyl" as used herein in each case denotes an alkenediyl radical having 2 to 30 carbon atoms as defined above, wherein one hydrogen atom at any position of the alkenediyl is replaced by one further binding site, thus forming a trivalent radical. Accordingly, $C_2$-$C_{20}$-alkenetriyl is a trivalent branched or unbranched unsaturated aliphatic chain having 2 to 20 carbon atoms. If alkenetriyl is substituted by one or more substituents, it is, for example, mono-, di-, tri-, tetra- or pentasubstituted or more than pentasubstituted.

The term "$C_1$-$C_{30}$-alkanetetrayl" as used herein in each case denotes an alkanetriyl radical having 1 to 30 carbon atoms as defined above, wherein one hydrogen atom at any position of the alkanetriyl is replaced by one further binding site, thus forming a tetravalent radical. Accordingly, $C_1$-$C_{30}$-alkanetetrayl is a tetravalent branched or unbranched saturated aliphatic chain having 1 to 30 carbon atoms. If alkanetetrayl is substituted by one or more substituents, it is, for example, mono-, di-, tri-, tetra- or pentasubstituted or more than pentasubstituted.

The term "$C_2$-$C_{30}$-alkanehexayl" as used herein in each case denotes an alkanetetrayl radical having 2 to 30 carbon atoms, wherein 2 hydrogen atoms at any position of the alkanetetrayl are replaced by two further binding site, thus forming a hexavalent radical. Accordingly, $C_2$-$C_{30}$-alkanehexayl is a hexavalent branched or unbranched saturated aliphatic chain having 2 to 30 carbon atom. If alkanehexayl is substituted by one or more substituents, it is, for example, mono-, di-, tri-, tetra- or pentasubstituted or more than pentasubstituted.

The term "$C_3$-$C_{16}$-cycloalkanediyl" (also referred to as cycloalkylene) refers to cycloalkyl radical having 3 to 16 carbon atoms as defined above, wherein one hydrogen atom at any position of cycloalkyl is replaced by one further binding site, thus forming a divalent radical. In case of polycyclic cycloalkanediyl, the bonding sites are either situated in the same ring or in different rings. Examples of monocyclic rings are cyclopropylene, cyclobutylene, cyclopentylene, cyclohexylene or cycloheptylen, especially cyclohexylene. Examples of polycyclic rings are perhydroanthracylene, perhydronaphthylene, perhydrofluorenylene, perhydrochrysenylene, perhydropicenylene, adamantylene, bicyclo[1.1.1]pentylen, bicycle[2.2.1]heptylene, bicyclo[4.2.2]decylene, bicycle-[2.2.2]octylene, bicyclo[3.3.2]decylene, bicyclo[4.3.2]undecylene, bicyclo[4.3.3]dodecylene, bicyclo[3.3.3]undecylene, bicyclo[4.3.1]decylene, bicyclo[4.2.1]nonylene, bicyclo[3.3.1]nonylene, bicyclo[3.2.1]octylene and the like. If cycloalkanediyl is substituted by one or more substituents, it is, for example, mono-, di-, tri-, tetra- or pentasubstituted or more than pentasubstituted, e.g. by $C_1$-$C_4$-alkyl.

The term "$C_3$-$C_{16}$-cycloalkanetriyl" refers to cycloalkenyl radical having 3 to 16 carbon atoms as defined above, wherein one hydrogen atom at any position of the cycloalkanediyl is replaced by one further binding site, thus forming a trivalent radical. In case of polycyclic cycloalkanetriyl, the bonding sites are either situated in the same ring or in different rings. If cycloalkanetriyl is substituted by one or more substituents, it is, for example, mono-, di-, tri-, tetra- or pentasubstituted or more than pentasubstituted The term "$C_6$-$C_{20}$-arylene" (also referred to as arenediyl) as used herein refers to an aryl group as defined above, wherein one hydrogen atom at any position of the aryl group is replaced by one further binding site, thus forming a bivalent radical. In case of polycyclic arylene, the bonding sites are either situated in the same ring or in different rings. Examples of arylene are phenylen, naphthylene, anthracenediyl or phenanthrenediyl. If arylene is substituted by one or more substituents, it is, for example, mono-, di-, tri-, tetra- or pentasubstituted or more than pentasubstituted.

The term "phenylene" refers to 1,2-phenylene (o-phenylene or 1,2-benzenediyl), 1,3-phenylene (m-phenylene, 1,3-benzenediyl) and 1,4-phenylene (p-phenylene or 1,4-benzenediyl). The term "naphthylene" refers to 1,2-naphthylene, 1,3-naphthylene, 1,4-naphthylene, 1,5-naphthylene, 1,8-naphthylene, 2,3-naphthylene and 2,7-naphthylene.

The term "xylylene" refers to 1,2-xylylene (1,2-methylenephenylenemethylene, 1,2-CH$_2$—C$_6$H$_4$—CH$_2$), 1,3-xylylene (1,3-methylenephenylenemethylene, 1,3-CH$_2$—C$_6$H$_4$—CH$_2$) and 1,4-xylylene (1,4-methylenephenylenemethylene, 1,4-CH$_2$—C$_6$H$_4$—CH$_2$).

The term "arenetriyl" as used herein refers to an arylene group as defined above, wherein one hydrogen atom at any position of the arylene group is replaced by one further binding site, thus forming a trivalent radical. In case of polycyclic arenetriyl, the bonding sites are either situated in the same ring or in different rings. Examples of arenetriyl are 1,2,4-benzenetriyl, 1,3,5-benzenetriyl, 1,3,5-naphthalenetriyl, 1,4,5-naphthalenediyl, anthracenetriyl or phenanthrenetriyl. If arenetriyl is substituted by one or more substituents, it is, for example, mono-, di-, tri-, tetra- or pentasubstituted or more than pentasubstituted.

The term "heteroarenediyl" refers to a heteroaryl radical as defined above, where one hydrogen atom at any position of the heteroaryl group is replaced by a further binding site, thus forming a divalent radical. In case of polycyclic heteroarenediyl, the bonding sites are either situated in the same ring or in different rings. Heteroarenediyl can be C-attached or N-attached where such is possible. For example, a pyrrolediyl, imidiazolediyl or pyrazolediyl can be N-attached or C-attached. Examples for heteroarenediyl are pyridinediyl, pyrimidinediyl, pyridazinediyl, 1,2,3-triazinediyl, 1,2,4-triazinediyl, 1,2,3,4-tetrazinediyl, furandiyl, thiophenediyl, pyrrolediyl, thiazolediyl, thiadiazolediyl, pyrazolediyl, imidazolediyl, triazolediyl, oxazolediyl, isoxazolediyl, isothiazolediyl, oxadiazolediyl and the like. If heteroarenediyl is substituted by one or more substituents, it is, for example, mono-, di-, tri-, tetra- or pentasubstituted or more than pentasubstituted.

The term "heteroarenetriyl" as used herein refers to a heteroarenediyl as defined above, wherein one hydrogen atom at any position of the heteroarenediyl is replaced by one further binding site, thus forming a trivalent radical. In case of polycyclic heteroarenetriyl, the bonding sites are either situated in the same ring or in different rings. If heteroarenetriyl is substituted by one or more substituents, it is, for example, mono-, di-, tri-, tetra- or pentasubstituted or more than pentasubstituted.

The term "C$_n$-C$_m$-alkoxy-C$_0$-C$_p$-alkyl" as used herein refers to an alkoxy group, as defined above, having n to m carbon atoms, which is bound to the remainder of the molecule via an alkylene group, as defined above, having o to p carbon atoms. Examples thereof are CH$_2$—OCH$_3$, CH$_2$—OC$_2$H$_5$, n-propoxymethyl, CH$_2$—OCH(CH$_3$)$_2$, n-butoxymethyl.

The term "C$_k$—C$_l$-alkoxy-C$_n$-C$_m$-alkoxy-C$_0$-C$_p$-alkyl" as used herein refers to an alkoxy group, as defined above, having k to l carbon atoms, which is bound to the remainder of the molecule via a C$_n$-C$_m$-alkoxy-C$_0$-C$_p$-alkyl group, as defined above.

The term "hydroxy-C$_n$-C$_m$-alkoxy-carbonyl" as used herein refers to an alkoxy group carrying usually one hydroxy group and having n to m carbon atoms, which is bound to the remainder of the molecule via a carbonyl group.

The term "C$_n$—C$_n$-alkoxycarbonyl-C$_o$-C$_p$-alkyl" as used herein refers to an alkoxy radical having n to m carbon atoms which is attached through the carbon atom of the carbonyl group to an alkylene group, as defined above, having o to p carbon atoms. Examples are C$_1$-C$_4$-alkoxycarbonyl-C$_1$-C$_4$-alkyl such as methoxycarbonylmethyl, ethoxycarbonylmethyl, 2-methoxycarbonylethyl, 2-ethoxycarbonylethyl, 3-methoxycarbonylpropyl, 3-ethoxycarbonylpropyl, 4-methoxycarbonylbutyl or 4-ethoxycarbonylbutyl.

The term "arylalkyl" (also referred to as aryl-alkylene) as used herein refers to an aryl radical as defined above which is linked via an alkylene group, in particular via a methylene, 1,1-ethylene or 1,2-ethylene group, e.g. benzyl, 1-phenylethyl or 2-phenylethyl.

The term "C$_n$-C$_m$-cycloalkyl-C$_0$-C$_p$-alkyl" (also referred to as cycloalkyl-alkylene) as used herein refers to a cycloalkyl group, as defined above, having n to m carbon atoms, which is bound to the remainder of the molecule via an alkylene group, as defined above, having o to p carbon atoms. Examples are cyclopropylmethyl, cyclopropylethyl, cyclopropylpropyl, cyclobutylmethyl, cyclobutylethyl, cyclobutylpropyl, cyclopentylmethyl, cycloppentylethyl, cyclopentylpropyl, cyclohexylmethyl, cyclohexylethyl, cyclohexylpropyl, and the like.

The term "heterocycloalkyl-C$_o$-C$_p$-alkyl" (also referred to as heterocycloalkyl-alkylene) as used herein refers to a heterocycloalkyl group, as defined above, which is bound to the remainder of the molecule via an alkylene group, as defined above, having o to p carbon atoms. Examples are hetarylmethyl, 1-hetarylethyl or 2-hetarylethyl.

If the substituents R$^4$ and R$^5$ are attached to a phenyl or naphthyl ring, they may also be phenyl or naphthyl which forms a 5- or 6-membered ring with the phenyl ring to which the SR$^4$ or OR$^5$ is attached via a direct bond, C$_1$-C$_4$-alkylene, O, S, NR$^6$ or CO. For example, the following structural units are obtained

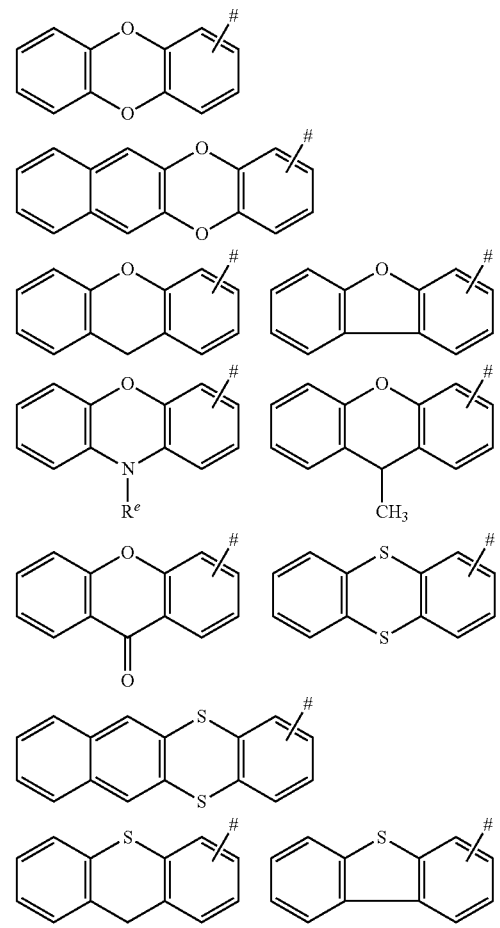

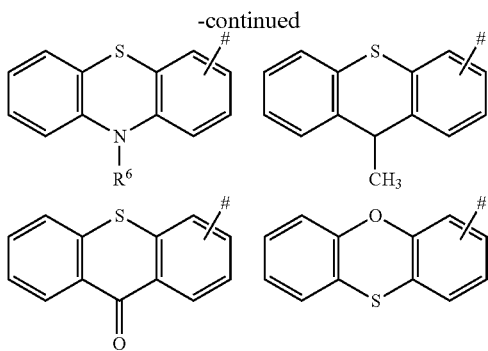

where # denotes the point of attachment and $R^6$ is as defined above.

$R^6$ and $R^7$, $R^{10}$ and $R^{11}$ and/or $R^{12}$ and $R^{13}$ together with the N atom to which they are attached, may form a 5-, 6-, or 7-membered ring which optionally has a further heteroatom or heteroatomic group selected from CO, O, S or N($C_1$-$C_8$-alkyl) as ring members and which may carry 1, 2, 3 or 4 $C_1$-$C_4$-alkyl. Examples are morpholine, pyrrole, pyrrolidine, imidazolidine, piperidine or piperazine, preferably morpholine, piperidine or piperazine.

In compounds of the formula I, the term "b is 2 or b is 3 and —X—$R^1$ is bound to a carbon atom or nitrogen atom of Q via a divalent bridging group having 1 to 10 atoms between the flanking bonds", examples form the divalent bridging group are X—($C_1$-$C_6$-alkylene)-Y', X—($C_3$-$C_6$-cycloalkylene)-Y', X-(heterocycloalkylene)-Y', X—($C_2$-$C_6$-alkenylene)-Y', X-(o-phenylene)-Y', X-(o-xylylene)-Y', X-(o-phenylene-$C_1$-$C_4$-alkylene)-Y', X—($C_1$-$C_4$-alkylene-o-phenylene)-Y' or S—C(S)—N($R^{12}$)—CO. Each alkylene and alkenylene may be interrupted by one or more, e.g. 1 or 2, O, S, $NR^{12}$ or CO and/or may be substituted by one or more, e.g. 1, 2, 3, 4 or more than 4, F, Cl, Br, I, $SR^4$, $OR^5$, $NR^6R^7$, $COR^8$, $COOR^9$, $CONR^{10}R^{11}$, $C_6$-$C_{10}$-aryl, heteroaryl or $C_6$-$C_{10}$-aryl which is substituted by one or more $C_1$-$C_{12}$-alkyl, $C_1$-$C_4$-haloalkyl, F, Cl, Br, I, CN, $NO_2$, $SR^4$, $OR^5$, $NR^6R^7$, $COR^8$, $COOR^9$ or $CONR^{10}R^{11}$; cycloalkylene and heterocycloalkylene may be interrupted by one or more, e.g. 1 or 2 CO and/or may be substituted by one or more e.g. 1, 2, 3, 4 or more than 4, $C_1$-$C_{12}$-alkyl, $C_1$-$C_{12}$-haloalkyl, F, Cl, Br, I, $SR^4$, $OR^5$, $NR^6R^7$, $COR^8$, $COOR^9$, $CONR^{10}R^{11}$, $C_6$-$C_{10}$-aryl, heteroaryl or $C_6$-$C_{10}$-aryl which is substituted by one or more $C_1$-$C_{12}$-alkyl, $C_1$-$C_4$-haloalkyl, F, Cl, Br, I, CN, $NO_2$, $SR^4$, $OR^5$, $NR^6R^7$, $COR^8$, $COOR^9$ or $CONR^{10}R^{11}$, and each phenylene may be substituted by one or more e.g. 1, 2, 3, or 4, $C_1$-$C_{12}$-alkyl, $C_1$-$C_{12}$-haloalkyl, F, Cl, Br, I, $SR^4$, $OR^5$, $NR^6R^7$, $COR^8$, $COOR^9$, $CONR^{10}R^{11}$, $C_6$-$C_{10}$-aryl, heteroaryl or $C_6$-$C_{10}$-aryl which is substituted by one or more $C_1$-$C_{12}$-alkyl, $C_1$-$C_4$-haloalkyl, F, Cl, Br, I, CN, $NO_2$, $SR^4$, $OR^5$, $NR^6R^7$, $COR^8$, $COOR^9$ or $CONR^{10}R^{11}$, where Y' is O, S, $NR^{14}$, CO, OC(O), C(O)O, $NR^{10}$C(O), $CONR^{10}$, $NR^{10}SO_2$ or a single bond and $R^4$, $R^5$, $R^6$, $R^7$, $R^8$, $R^9$, $R^{10}$, $R^{11}$ and $R^{12}$ are as defined above. In particular X-ethylene, X-propylene and X-butylene bridges are formed.

In compounds of the formula I, where the sum of a+b+c is 2, 3, 4 or 6 and two radicals $R^{14}$ together or two radicals $R^6$ together or two radicals $R^{10}$ together and/or two radicals $R^{12}$ together may be a divalent bridging group having 1 to 20 atoms between the flanking bonds, the divalent bridging group is preferably selected from phenylene and $C_1$-$C_6$-alkylene, where the last-mentioned radical may be interrupted by one or more, e.g. 1, 2 or 3, identical or different groups selected from O, S, N($C_1$-$C_8$-alkyl) and CO.

The term "and/or" or "or/and" are meant to express that not only one of the defined alternatives (substituents) may be present, but also several of the defined alternatives (substituents) together, namely mixtures of different alternatives (substituents).

The term "at least" is meant to define one or more than one, for example one, two, three, preferably one to two.

The term "one or more identical or different radicals" is meant to define one, two, three, four, five, six, seven, eight or more than eight identical or different radicals.

The remarks made below as to preferred embodiments of the variables (substituents) and indices of the compounds of formula I are valid on their own as well as preferably in combination with each other.

The remarks made below concerning preferred embodiments of the variables (substituents) and indices further are valid concerning the compounds of formula I as well as concerning the uses and methods according to the invention and the compositions according to the present invention.

With a view to the activity of the compounds of the formula I according to the invention as thermal curing promoter, the substituents Q, X, $R^1$, $R^2$ and $R^3$ and the indices a, b and c independently of one another and preferably in combination have the meanings given below.

A preferred embodiment of the invention relates to compositions, compounds methods and uses, wherein a in formula I is 0, 1, 2, 3, 4 or 6, in particular 0, 1, 2 or 3. According to a further particular aspect of this embodiment, a is 4.

A further preferred embodiment of the invention relates to compositions, compounds methods and uses, wherein b in formula I is preferably 0 or 2.

A further preferred embodiment of the invention relates to compositions, compounds methods and uses, wherein c in formula I is preferably 0 or 2. According to a further particular aspect of this embodiment c is 1.

A further preferred embodiment of the invention relates to compositions, compounds methods and uses, wherein X in formula I is S or $NR^{14}$. According to a particular aspect of this embodiment, X is S.

According to a further particular aspect of this embodiment X is a radical $NR^{14}$. $R^{14}$ is preferably selected from $C_1$-$C_{12}$-alkyl, which may be interrupted by one or more, e.g. 1, 2 or 3, identical or different O, S, $NR^6$ or CO and/or may be substituted by one or more, e.g. 1 or 2, identical or different radicals $R^{14a}$ selected from $C_3$-$C_8$-cycloalkyl, CN, $COR^8$, $COOR^9$, $CONR^{10}R^{11}$, phenyl, phenyl which is substituted by one, two, three, four or five radicals selected from $C_1$-$C_8$-alkyl, $C_1$-$C_4$-haloalkyl, F, Cl, Br, I, CN, $NO_2$, $SR^4$, $OR^5$, $NR^6R^7$, $COR^8$, $COOR^9$ and $CONR^{10}R^{11}$, and $C_3$-$C_8$-cycloalkyl which is interrupted by one or two CO groups and/or may be substituted by one, two, three, four or five radicals selected from $C_1$-$C_8$-alkyl, $C_1$-$C_4$-haloalkyl, F, Cl, Br, I, CN, $NO_2$, $SR^4$, $OR^5$, $NR^6R^7$, $COR^8$, $COOR^9$ and $CONR^{10}R^{11}$; $C_2$-$C_{12}$-alkenyl, which may be interrupted by one or more, e.g. 1, 2 or 3, identical of different O, S, $NR^6$ or CO and/or may be substituted by one or more, e.g. 1 or 2, identical or different radicals $R^{14a}$ selected from $C_3$-$C_8$-cycloalkyl, CN, $COR^8$, $COOR^9$, $CONR^{10}R^{11}$, phenyl, phenyl which is substituted by one, two, three, four or five identical or different radicals selected from $C_1$-$C_8$-alkyl, $C_1$-$C_4$-haloalkyl, F, Cl, Br, I, CN, $NO_2$, $SR^4$, $OR^5$, $NR^6R^7$, $COR^8$, $COOR^9$ and $CONR^{10}R^{11}$, and $C_3$-$C_8$-cycloalkyl which is interrupted by one or two CO groups and/or may be substituted by one, two, three, four or five radicals selected from $C_1$-$C_8$-alkyl, $C_1$-$C_4$-haloalkyl, F, Cl, Br, I, CN, $NO_2$, $SR^4$, $OR^5$, $NR^6R^7$, $COR^8$, $COOR^9$ and $CONR^{10}R^{11}$;

$C_3$-$C_{12}$-cycloalkyl, which may be interrupted by one or more CO and/or may be substituted by one or more identical or different radicals $R^{14b}$ selected from $C_1$-$C_8$-alkyl, CN, $COR^8$, $COOR^9$, $CONR^{10}R^{11}$; or phenyl which may be substituted by one or more, e.g. 1, 2, 3, 4 or 5, identical or different radicals $R^{14c}$ selected from $C_1$-$C_8$-alkyl, $C_1$-$C_4$-haloalkyl, F, Cl, Br, I, CN, $NO_2$, $SR^4$, $OR^5$, $NR^6R^7$, $COR^8$, $COOR^9$, $CONR^{10}R^{11}$ and phenyl;

where $R^4$, $R^5$, $R^6$, $R^7$, $R^8$, $R^9$, $R^{10}$, $R^{11}$ are as defined above and preferably have one of the preferred meanings.

More preferably, $R^{14}$ is $C_1$-$C_{12}$-alkyl, $C_1$-$C_6$-alkoxy-$C_1$-$C_{12}$-alkyl, $C_3$-$C_8$-cycloalkyl-$C_1$-$C_{12}$-alkyl, $C_3$-$C_8$-cycloalkyl or phenyl-$C_1$-$C_{12}$-alkyl, where the phenyl moiety of the last-mentioned radical is unsubstituted or substituted by one, two, three, four or five radicals selected from $C_1$-$C_8$-alkyl, $C_1$-$C_4$-haloalkyl, F, Cl, Br, I, CN, $NO_2$, $SR^4$, $OR^5$, $NR^6R^7$, $COR^8$, $COOR^9$ and $CONR^{10}R^{11}$. Likewise, more preferably, $R^{14}$ is $C_2$-$C_6$-alkenyl. Likewise, more preferably $R^{14}$ is phenyl, which is unsubstituted or substituted by one, two, three, four or five identical or different radicals selected from $C_1$-$C_8$-alkyl, $C_1$-$C_4$-haloalkyl, F, Cl, Br, I, CN, $NO_2$, $SR^4$, $OR^5$, $NR^6R^7$, $COR^8$, $COOR^9$, $CONR^{10}R^{11}$ and phenyl. Even more preferably, $R^{14}$ is $C_1$-$C_6$-alkyl, especially methyl, ethyl, n-propyl, iso-propyl or n-butyl; benzyl; phenethyl; $C_2$-$C_6$-alkenyl especially allyl; $C_1$-$C_4$-alkoxy-$C_1$-$C_4$-alkyl especially 2-methoxyethyl, 2-methoxypropyl, 2-ethoxyethyl or 2-ethoxypropyl; or $C_3$-$C_8$-cycloalkyl-$C_1$-$C_4$-alkyl, especially cyclopentylmethyl, cyclohexylmethyl, 2-cyclohexylethyl or 2-cyclopentylethyl.

Suitable examples for $R^{14}$ are methyl, ethyl, propyl, butyl, benzyl, phenethyl, allyl, 2-methoxyethyl, 3-methoxypropyl, cyclopentyl, cyclohexyl, cyclohexylmethyl or phenyl.

A further preferred embodiment of the invention relates to compositions, compounds methods and uses, where in formula I two radicals $R^{14}$ together are a divalent bridging group having 1 to 20, preferably 1 to 10, atoms between the flanking bonds. The divalent bridging group is preferably selected from $C_1$-$C_{10}$-alkylene, $C_3$-$C_{12}$-cycloalkylene, heterocycloalkylene, $C_2$-$C_{10}$-alkenylene, phenylene or naphthylene, where each alkylene and alkenylene may be interrupted by one or more, e.g. 1 or 2, O, S, N(H), N($C_1$-$C_8$-alkyl) or CO and where cycloalkylene and heterocycloalkylene may be interrupted by one or more, e.g. 1 or 2 CO.

A further preferred embodiment of the invention relates to compositions, compounds methods and uses, wherein $R^1$ in formula I is $CSNR^{12}R^{13}$; $C(O)R^9$; $CSOR^9$; $C_3$-$C_{12}$-alkyl; $C_2$-$C_{12}$-alkenyl; $C_3$-$C_{12}$-cycloalkyl; $C_1$-$C_{12}$-alkyl, which is interrupted by one or more, e.g. 1, 2 or 3, identical or different groups selected from O, S, $NR^6$ or CO and/or which is substituted by one, two or three identical or different radicals $R^{1a}$; $C_2$-$C_{12}$-alkenyl, which is interrupted by one or more, e.g. 1, 2 or 3, identical or different groups selected from O, S, $NR^6$ or CO and/or which is substituted by one, two or three identical or different radicals $R^{1a}$;

$C_3$-$C_{12}$-cycloalkyl, which may be interrupted by 1 or 2 CO group and/or which may be substituted by one, two or three radicals $R^{1b}$;

heterocyclyl, which may be interrupted by 1 or 2 CO group and/or which may be substituted by one, two or three radicals $R^{1b}$;

phenyl, naphthyl, or hetaryl, where the 3 last-mentioned radicals may be substituted by one or more identical or different radicals $R^{1c}$ and where heteroaryl comprises besides carbon atoms one, two or three heteroatoms selected from O, S and N as ring members; and $C_6$-$C_{10}$-aroyl, which may be substituted by one or more identical or different radicals $R^{1d}$;

where $R^{1a}$, $R^{1b}$, $R^{1c}$, $R^{1d}$, $R^6$, $R^9$, $R^{12}$, $R^{13}$ are as defined above and preferably have one of the preferred meanings.

In a specific aspect, $R^{1a}$ is selected independently of one another from F, Cl, Br, I, CN, $SR^4$, $OR^5$, $NR^6R^7$, $COR^8$, $COOR^9$, $CONR^{10}R^{11}$, $C_3$-$C_{20}$-cycloalkyl which may be interrupted by one or more CO groups, heterocyclyl which may be interrupted by one or more CO groups, heteroaryl and $C_6$-$C_{10}$-aryl where the four last-mentioned radicals may carry one or more identical or different radicals $R^{1aa}$, where $R^{1aa}$ is selected independently of one another from $C_1$-$C_{12}$-alkyl, $C_1$-$C_{12}$-haloalkyl, $C_1$-$C_{12}$-hydroxyalkyl, $C_2$-$C_{12}$-alkenyl, F, Cl, Br, I, $NO_2$, $SR^4$, $OR^5$, $NR^6R^7$, $COR^8$, $COOR^9$ and $CONR^{01}R^{11}$;

$R^{1a}$ is preferably $SR^4$, $COOR^9$, $C_3$-$C_8$-cycloalkyl, phenyl or 5- or 6-membered heteroaryl comprising besides carbon atoms 1 or 2 heteroatoms selected from N, O and S as ring members, where phenyl and heteroaryl may be unsubstituted or substituted by one, two, three, four or five identical or different radicals $R^{1aa}$. $R^{1aa}$, $R^4$ and $R^9$ are as defined above. In this embodiment, $R^4$ is preferably phenyl-$C_1$-$C_4$-alkyl where the phenyl moiety may carry one or more identical or different radicals $R^{1aa}$. An example for phenyl-$C_1$-$C_4$-alkyl is benzyl or phenethyl. In this embodiment, $R^9$ is preferably $C_1$-$C_8$-alkyl which may be interrupted by 1 or 2 oxygen atoms and/or may carry a radical $R^{9a}$. $R^{9a}$ is preferably phenyl. Examples are methyl, ethyl, propy, butyl, 3-methoxybutyl or benzyl. More preferably $R^{1a}$ is $C_1$-$C_4$-alkoxycarbonyl, such as methoxycarbonyl or ethoxycarbonyl; $C_1$-$C_4$-alkoxy-$C_1$-$C_6$-alkoxycarbonyl such as 3-methoxybutoxycarbonyl; phenyl-$C_1$-$C_4$-alkylsulfanyl such as benzylsulfanyl or phenethylsulfanyl; 5- or 6-membered heteroaryl comprising besides carbon atoms 1 or 2 heteroatoms selected from O, S and N such as thiophen-2-yl, thiophen-3-yl, furan-2-yl or furan-3-yl, or $C_3$-$C_8$-cycloalkyl such as cyclopentyl, cyclohexyl or cycloheptyl. Likewise, $R^{1a}$ is 5- or 6-membered saturated heterocyclyl comprising besides carbon atoms one or two identical or different heteroatoms selected from O and S such as tetrahydrofuranyl, tetrahydrothienyl, tetrahydropyranyl or tetrahydrothiopyranyl. Likewise, $R^{1a}$ is 4-cyanophenyl.

$R^{1b}$ is preferably $C_1$-$C_6$-alkyl or $C_2$-$C_6$-alkenyl.

$R^{1c}$ is preferably $C_1$-$C_6$-alkyl, $C_2$-$C_6$-alkenyl or nitro. Especially, $R^{1c}$ is methyl, ethyl, propyl, allyl or nitro.

$R^{1d}$ is preferably $C_1$-$C_6$-alkyl, $C_2$-$C_6$-alkenyl or nitro. Especially $R^{1d}$ is $C_2$-$C_4$-alkenyl, in particular vinyl or allyl.

If $R^1$ is $C_1$-$C_{12}$-alkyl which is interrupted by one or more, e.g. 1, 2 or 3 identical or different groups selected from O, S, $NR^6$ or CO and/or which is substituted by one, two or three identical or different radicals $R^{1a}$, it is preferably $C_1$-$C_6$-alkoxy-$C_2$-$C_6$-alkyl; $C_1$-$C_6$-alkoxycarbonyl-$C_1$-$C_6$-alkyl; $C_1$-$C_4$-alkoxy-$C_1$-$C_4$-alkoxycarbonyl-$C_1$-$C_3$-alkyl, especially $C_1$-$C_4$-alkoxy-$C_1$-$C_4$-alkoxycarbonyl-$C_1$-$C_3$-alkyl; $C_3$-$C_8$-cycloalkyl-$C_1$-$C_6$-alkyl; phenyl-$C_1$-$C_6$-alkyl; phenyl-$C_1$-$C_4$-alkyl-S—$C_1$-$C_4$-alkoxy-$C_1$-$C_6$-alkyl or heteroaryl-$C_1$-$C_6$-alkyl, where the aromatic ring in the three last-mentioned radicals may be substituted by one, two or three radicals independently of one another selected from $C_1$-$C_4$-alkyl, $C_2$-$C_4$-alkenyl and nitro.

If $R^1$ is heteroaryl, $R^1$ is preferably 5- or 6-membered heteroaryl comprising besides carbon atoms 1 or 2 heteroatoms selected from N, O and S as ring members or 8-, 9- or 10-membered heteroaryl comprising as ring members 1, 2 or 3 heteroatoms selected from N, O and S. Suitable examples are pyridyl, thiazolyl, benzothiazolyl or benzoxazolyl. Further suitable examples are benzothiazolyl or benzofuranyl.

If $R^1$ is $C(O)OR^9$, $R^9$ is preferably $C_1$-$C_{20}$-alkyl or $C_1$-$C_{20}$-alkyl in which the alkyl moiety is interrupted by one or more, e.g. 1, 2, 3, 4 or 5, non-adjacent oxygen atoms. In this embodiment, $R^9$ is preferably $(CH_2CH_2O)_x(C_1-C_4\text{-alkyl})$ with x being 1, 2, 3, 4 or 5, in particular $(CH_2CH_2O)_x(C_1-C_4\text{-alkyl})$ with x being 1, 2 or 3.

If $R^1$ is heterocyclyl, $R^1$ is preferably 5- or 6-membered saturated or partially unsaturated heterocyclyl comprising besides carbon atoms one or two identical or different heteroatoms selected from N, NH and $N(C_1-C_8\text{-alkyl})$, such as morpholinyl, thiomorpholinyl, tetrahydrofuranyl, tetrahydrothienyl, 4,5-dihydrothienyl, tetrahydropyranyl or tetrahydrothiopyranyl.

If $R^1$ is $C_6-C_{10}$-aroyl, which may be substituted by one or more identical or different radicals $R^{1d}$, it is preferably benzoyl or benzoyl substituted by $C_1-C_6$-alkyl or $C_2-C_6$-alkenyl, especially $C_1-C_4$-alkyl or $C_2-C_4$-alkenyl.

According to a particular aspect of this embodiment, $R^1$ in formula I is $C_3-C_{12}$-alkyl such as propyl or butyl; $C_1-C_4$-alkoxycarbonyl-$C_1-C_2$-alkyl such as methoxycarbonylmethyl, ethoxycarbonylmethyl or propoxycarbonylmethyl; $C_1-C_4$-alkoxy-$C_1-C_4$-alkoxycarbonyl-$C_1-C_2$-alkyl such as ethoxyethoxycarbonylmethyl, ethoxyethoxycarbonylethyl, propoxypropoxycarbonylethyl, propoxypropoxycarbonylmethyl or 3-methoxybutoxycarbonylmethyl; $C_2-C_4$-alkenyl such as vinyl or allyl; benzyl; benzyl in which the phenyl moiety is substituted by one, two or three radicals selected independently of one another from $C_1-C_4$-alkyl, $C_2-C_4$-alkenyl and nitro; phenethyl; benzylsulfanyl-$C_1-C_4$-alkyl-O—$C_1-C_4$-alkyl, in particular benzylsulfanyl-$C_1-C_2$-alkyl-O—$C_1-C_2$-alkyl; phenethylsulfanyl-$C_1-C_4$-alkyl-O—$C_1-C_4$-alkyl, in particular phenethylsulfanyl-$C_1-C_2$-alkyl-O—$C_1-C_2$-alkyl; $C_3-C_8$-cycloalkyl; $C_3-C_8$-cycloalkyl which is substituted by one, two or three radicals selected independently of one another from $C_1-C_4$-alkyl and $C_2-C_4$-alkenyl; —COO$(CH_2CH_2O)_v(C_1-C_4\text{-alkyl})$ with v being 1, 2, 3, 4 or 5 such as ethoxyethoxycarbonyl or (2-butoxyethoxy)-ethoxycarbonyl; benzoyl; benzoyl which is substituted by one, two or three radicals selected independently of one another from $C_1-C_4$-alkyl and $C_2-C_4$-alkenyl; phenyl; or phenyl which is substituted by one, two or three radicals selected from $C_1-C_4$-alkyl, $C_2-C_4$-alkenyl and nitro. According to a further aspect, $R^1$ is $C_3-C_{12}$-alkyl which is interrupted by one, two or three S heteroatoms and is substituted by SH, such as mercapto-$C_3-C_{12}$-alkyl or mercapto-$C_3-C_6$-alkyl-S—$C_1-C_2$-alkyl. In a further embodiment, $R^1$ is $C_1-C_{12}$-alkyl, which is substituted by $SR^4$, where $R^4$ is $C_2-C_8$-alkanoyl. In this embodiment, $R^4$ is preferably $C_2-C_4$-alkanoyl. In a further embodiment, $R^1$ is $C_1-C_{12}$-alkyl, which is substituted by $OR^5$. In this embodiment, $R^5$ is preferably $C_2-C_8$-alkanoyl, which may be substituted by one or more identical or different radicals selected from F, Cl, Br, I, OH or $C_1-C_6$-alkoxy or $R^5$ is $C_2-C_8$-alkanoyl, which is interrupted by one or more identical or different groups selected from —O— and —S— and may be substituted by one or more identical or different radicals selected from hydroxyaminylene (=N—OH), F, Cl, Br, I, OH and $C_1-C_6$-alkoxy. In particular, $R^5$ is $C_1-C_7$-chloroalkylcarbonyl or —C(=O)—CH$_2$—S—$(C_1-C_2\text{-alkyl})$-S—C(=NOH)—$C_1-C_2$-alkyl. In a further embodiment, $R^1$ is $C_1-C_{12}$-alkyl which is substituted by $C_1-C_4$-alkoxycarbonyl. In a further embodiment $R^1$ is benzyl which is substituted by $C_1-C_4$-alkanoyl-S—$C_1-C_2$-alkyl. In a further embodiment, $R^1$ is benzyl which is substituted by $C_1-C_4$-alkylthio, or benzyl which is substituted by chlorine. In a further embodiment $R^1$ is phenyl which is substituted by $NR^6R^7$. $R^6$ is preferably $C_2-C_4$-alkanoyl and $R^7$ is H. In a further embodiment, $R^1$ is 5- or 6-membered saturated heterocyclyl comprising besides carbon atoms one or two identical or different heteroatoms selected from N, NH and $N(C_1-C_8\text{-alkyl})$.

Suitable examples for $R^1$ are phenyl, 4-methylphenyl, 4-ethylphenyl, 4-propylphenyl, 4-nitrophenyl, 4-vinylphenyl, 4-allylphenyl, benzoyl, 4-vinylbenzoyl, (2-butoxyethoxy)-ethoxycarbonyl, methyl, ethyl, propyl, butyl, methoxycarbonylmethyl, methoxycarbonylethyl, ethoxycarbonylmethyl, ethoxycarbonylethyl, 3-methoxybutoxycarbonylmethyl, benzyl, phenethyl, benzylsulfanylethoxyethyl, benzylsulfanylpropoxypropyl, phenethylsulfanylethoxyethyl phenethylsulfanylpropoxypropyl, cyclohexyl, cyclohexylmethyl, 4-vinylcyclohexyl or allyl. Further suitable examples for $R^1$ are 6-mercaptohexyl, 2-(2-mercaptoethylsulfanyl)-ethyl, 2-(2-chloro-acetoxy)-ethyl, 4-morpholinyl, tetrahydropyran-3-yl, tetrahydrofuran-2-ylmethyl, 4,5-dihydrothien-2-yl, 4-acetylsulfanylmethylbenzyl, 4-methylsulfanylbenzyl, 4-chlorobenzyl, 4-acetylaminobenzyl, 6-acetylsulfanylhexyl, 4-cyanobenzyl, $CH_3C(=NOH)$—S—$C_2H_4$—S—$CH_2$—C(=O)—O—$C_2H_4$, methoxycarbonylmethyl, 2-benzothiazolyl, 4-hydroxyphenyl.

A further preferred embodiment of the invention relates to compositions, compounds methods and uses, wherein in formula I $R^1$ and $R^{14}$ together with the nitrogen atom to which they are attached form a 5-, 6- or 7-membered saturated or unsaturated heterocycle which may comprise a further heteroatom or heteroatomic group selected from O, S, NH, $N(C_1-C_8\text{-alkyl})$ and CO and which may carry 1, 2, 3 or 4 substituents independently of one another selected from halogen, cyano, $C_1-C_4$-alkyl, nitro, $C_1-C_4$-haloalkyl, $C_1-C_4$-alkoxy and $C_1-C_4$-haloalkoxy. Amongst those compounds, more preference is given to those, where $R^1$ and $R^{14}$ together with the nitrogen atom to which they are attached form a 5-, 6- or 7-membered saturated heterocycle which may comprise a further heteroatom or heteroatomic group selected from O, S, NH, $N(C_1-C_8\text{-alkyl})$. Examples are piperidin-1-yl, morpholin-4-yl, thiomorpholin-4-yl or piperazin-1-yl or 4-$(C_1-C_4\text{-alkyl})$piperazin-1-yl.

A further preferred embodiment of the invention relates to compositions, compounds methods and uses, where in formula I $R^1$ and $R^{14}$ together are a divalent bridging group selected from $C_2-C_8$-alkylene which may be interrupted by one or more, e.g. 1, 2 or 3, identical or different groups selected from O, S, $N(C_1-C_8\text{-alkyl})$ and CO.

A further preferred embodiment of the invention relates to compositions, compounds methods and uses, wherein in compounds of the formula I comprising at least two radicals $R^1$, two radicals $R^1$ together may be a divalent bridging group having 1 to 20 atoms between the flanking bonds. In this embodiment, b is 2, 3, 4 or 6 and/or c is 2, 3, 4 or 6, provided that the sum of a+b+c=2, 3, 4 or 6. The bridging group is preferably selected from $C_1-C_{10}$-alkylene, $C_2-C_{10}$-alkenylene, phenylene, phenylene-$C_1-C_4$-alkylene, $C_1-C_4$-alkylene-phenylen-$C_1-C_4$-alkylene, heteroarylene, heteroarylene-$C_1-C_4$-alkylene and $C_1-C_4$-alkylene-heteroarylene-$C_1-C_2$-alkylene or. Each alkylene and alkenylene may be interrupted by one or more, e.g. 1, 2 or 3, identical or different groups selected from O, S, $NR^6$ and CO and/or may be substituted by one or more, e.g. 1, 2, 3 or more than 3 radicals selected from F, Cl, Br, I, CN, $SR^4$, $OR^5$, $NR^6R^7$, $COR^8$, $COOR^9$, $CONR^{10}R^{11}$, $C_3-C_{20}$-cycloalkyl, heterocyclyl, heteroaryl and $C_6-C_{10}$-aryl where the 4 last-mentioned radicals may carry one or more, e.g. 1, 2, 3 or more than 3, identical or different radicals $C_1-C_{12}$-alkyl, $C_1-C_{12}$-haloalkyl, F, Cl, Br, I, CN, $NO_2$, $SR^4$, $OR^5$, $NR^6R^7$, $COR^8$, $COOR^9$ and $CONR^{10}R^{11}$, and each phenylene and heteroarylene may be substituted by one or more, e.g. 1, or 2 identical or different radicals $C_1-C_{12}$-alkyl, $C_1-C_{12}$-haloalkyl, F, Cl, Br, I, CN, $NO_2$, $SR^4$, $OR^5$, $NR^6R^7$, $COR^8$, COOR$^9$ and CONR$^{10}$R$^{11}$. According to a particular preferred aspect, the bridging group is selected from —C(=O)—O—C$_1$-C$_{10}$-alkylene-O—C(=O)—.

A further preferred embodiment of the invention relates to compositions, compounds methods and uses, wherein R$^2$ in formula I is COR$^8$; COOR$^9$; CONR$^{10}$R$^{11}$;

C$_1$-C$_{12}$-alkyl, C$_2$-C$_{12}$-alkenyl, where the 2 last-mentioned radicals may be substituted by one or more, e.g. 1, 2, or 3 identical or different radicals R$^{2a}$;

C$_3$-C$_{12}$-cycloalkyl, which may be substituted by one or more, e.g. 1, 2 or 3, identical or different radicals R$^{2b}$;

C$_6$-C$_{10}$-aryl, which may be substituted by one or more, e.g. 1, 2, 3, 4 or 5, identical or different radicals R$^{2c}$;

5- or 6-membered heteroaryl comprising besides carbon atoms one or two heteroatoms selected from N, O and S and which may be substituted by one or more, e.g. 1, 2, 3, 4 or 5, identical or different radicals R$^{2c}$; or pyridinium of the formula

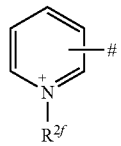

where # is the point of attachment to the remainder of the molecule and R$^{2f}$ is C$_1$-C$_{12}$-alkylene-COO$^-$, C$_1$-C$_{12}$-alkylene-S(O)$_2$O$^-$ or C$_1$-C$_{12}$-alkylene-OS(O)$_2$O$^-$;

where R$^{2a}$, R$^{2b}$, R$^{2c}$, R$^8$, R$^9$, R$^{10}$ and R$^{11}$ are as defined and preferably have one of the preferred meanings.

R$^{2a}$ has preferably one of the preferred meanings indicated for R$^{1a}$.

R$^{2b}$ has preferably one of the preferred meanings indicated for R$^{1a}$.

R$^{2c}$ is preferably C$_1$-C$_6$-alkyl, C$_2$-C$_4$-alkenyl, C$_1$-C$_6$-alkoxy, C$_1$-C$_6$-alkoxycarbonyl or nitro.

According to a particular preferred aspect of this embodiment, R$^2$ is C$_1$-C$_6$-alkyl; C$_5$-C$_8$-cycloalkyl; C$_1$-C$_4$-alkoxycarbonyl; CO(N—(C$_1$-C$_8$-alkyl)$_2$); —C(O)O(CH$_2$CH$_2$O)$_x$(C$_1$-C$_4$-alkyl) with x being 1, 2, 3, 4, 5 or 6; —C(O)O—C$_1$-C$_4$-alkyl-phenyl; pyridyl; phenyl; phenyl which is substituted by one or two radicals selected from nitro, C$_1$-C$_4$-alkoxy, C$_1$-C$_4$-alkyl, C$_2$-C$_4$-alkenyl, and C$_1$-C$_4$-alcoxycarbonyl; benzyl; benzyl where the phenyl moiety is substituted by one or more, e.g. one or two, identical or different radicals selected from nitro, C$_2$-C$_4$-alkenyl, C$_1$-C$_4$-alkoxy, C$_1$-C$_4$-alkyl and C$_1$-C$_4$-alcoxycarbonyl; or pyridinium substituted by C$_1$-C$_{12}$-alkylene-S(O)$_2$O—. According to a further aspect, R$^2$ is morpholinoamide or C$_1$-C$_4$-haloalkoxycarbonyl, in particular C$_1$-C$_4$-fluoroalkoxycarbonyl.

Suitable examples for R$^2$ are methyl, ethyl, propyl or butyl, cyclopentyl, cyclohexyl, n-propoxycarbonyl, ethoxycarbonyl, methoxycarbonyl, dimethylaminocarbonyl, diethylaminocarbonyl, —C(O)O(CH$_2$CH$_2$O)CH$_2$CH$_3$, —C(O)O(CH$_2$CH$_2$O)$_2$CH$_2$CH$_3$, —C(O)O(CH$_2$CH$_2$O)$_3$CH$_2$CH$_3$, —C(O)O(CH$_2$CH$_2$O)$_4$CH$_2$CH$_3$, benzyloxycarbonyl, pyridin-2-yl, pyridin-3-yl, pyridin-4-yl; 4-nitrophenyl, 4-methoxycarbonylphenyl, 4-ethoxycarbonylphenyl, 4-propoxycarbonylphenyl or

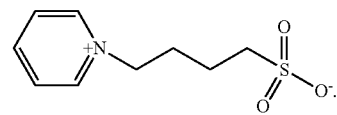

Further suitable examples for R$^2$ are morpholinoamide and 2,2,2-trifluoroethoxycarbonyl.

A further preferred embodiment of the invention relates to compositions, compounds methods and uses, wherein in formula I —X—R$^1$ together with R$^2$ are X—(O—C$_1$-C$_{20}$-alkylene)-Y, X—(S—C$_1$-C$_{20}$-alkylene)-Y or X—(N(R$^6$)—C$_1$-C$_{20}$-alkylene)-Y. According to a preferred aspect of this embodiment, Y is a direct bond and R$^6$ is as defined above, preferably C$_1$-C$_8$-alkyl. Suitable examples for this embodiment are compounds where —X—R$^1$ together with R$^2$ are —N(C$_1$-C$_8$-alkyl)-(O—C$_2$-C$_8$-alkylene)-, —S—(S—C$_2$-C$_8$-alkylene)- or —N(C$_1$-C$_8$-alkyl)-(N(C$_1$-C$_8$-alkyl)-C$_2$-C$_8$-alkylene)-. According to a further preferred aspect of this embodiment, —X—R$^1$ together with R$^2$ are selected from:

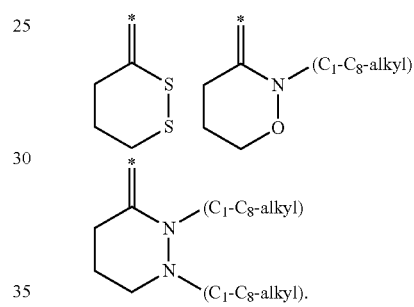

where * denotes the point of attachment to the oxime nitrogen atom.

According to a further preferred aspect of this embodiment, —X—R$^1$ together with R$^2$ are —X—(C$_1$-C$_8$-alkylene)-O—C(O)—; —X—(C$_3$-C$_6$-cycloalkylene)-O—C(O)—; —X-(o-phenylene)-O—C(O)—; X—(C$_1$-C$_8$-alkylene)-NR$^{10}$—C(O)—; or —X—(C$_3$-C$_6$-cycloalkylene)-NR$^{10}$—C(O)—; where each alkylene moiety may be substituted by one or more identical or different radicals R$^{2g}$, cycloalkylene may be substituted by one or more identical or different radicals R$^{2h}$, and o-phenylene may be substituted by one or more identical or different radicals R$^{2h}$, where R$^{10}$, R$^{2g}$, R$^{2h}$ and X have one of the meanings given above. In this embodiment, X—R$^1$ together with R$^2$ and the oxime carbon atom, to which X and R$^2$ are bound, preferably form a 5- or 6-membered heterocycle. X is preferably S, —N(benzyl) or N(C$_1$-C$_8$-alkyl), in particular S, —N(benzyl) or N(C$_1$-C$_4$-alkyl). Suitable examples are —S—CH(CH$_3$)CH(CH$_3$)—O—C(=O)—, —S—CH$_2$CH$_2$—O—C(=O)— and —N(benzyl)-CH$_2$CH$_2$—O—C(=O)—.

According to a further particular preferred aspect of this embodiment, —X—R$^1$ together with R$^2$ are X—(C$_1$-C$_8$-alkylene)-S—C(O)—, in particular —S—(C$_1$-C$_8$-alkylene)-S—C(O)—.

X—R$^1$ and R$^2$ together with the oxime carbon atom to which they are attached are preferably one of the following rings, with particular preference given to R-1, R-3, R-5, and R-13

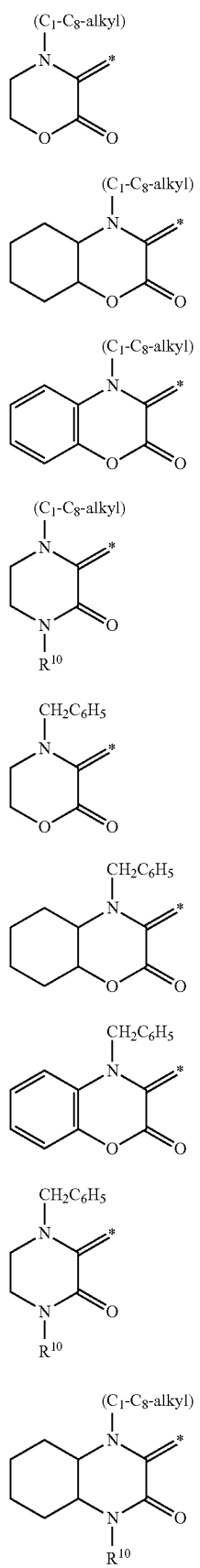
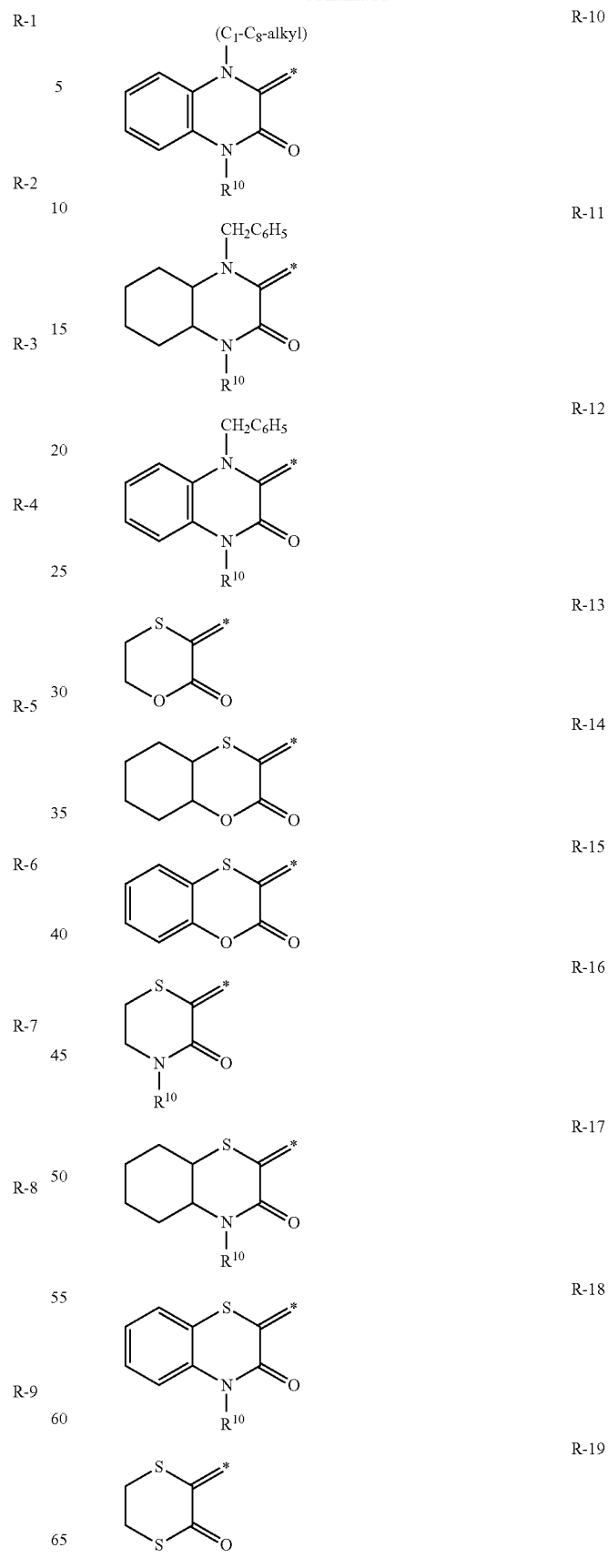

where

* is the point of attachment to the oxime nitrogen atom; and $R^{10}$ is as defined above, preferably H or $C_1$-$C_8$-alkyl.

Another preferred embodiment of the invention relates to compositions, compounds methods and uses, where in formula I —X—$R^1$ together with $R^2$ are —S—C(S)—$NR^{12}$—C(O)—, where $R^{12}$ is as defined above. According to a particular preferred aspect of this embodiment, X—$R^1$ and $R^2$ together with the carbon atom of the oxime group ring to which they are attached form the following ring R-20

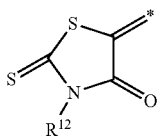

R-20 where

* is the point of attachment to the oxime nitrogen atom; and $R^{12}$ is as defined above, preferably H, $C_1$-$C_8$-alkyl or $C_2$-$C_6$-alkenyl, in particular allyl.

Another preferred embodiment of the invention relates to compositions, compounds methods and uses, where in formula I —X—$R^1$ together with $R^2$ are S—C(=$NOR^{15}$)—C(O)—$NR^{12}$—C(O), where $R^{12}$ is as defined above and $R^{15}$ is hydrogen or phenylsulfonyl where the phenyl moiety may be substituted by $C_1$-$C_4$-alkyl or $C_1$-$C_4$-alkoxy. According to a particular preferred aspect of this embodiment, X—$R^1$ and $R^2$ together with the carbon atom of the oxime group ring to which they are attached form the following ring R-21

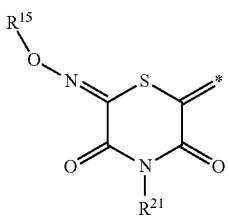

R-21 where

* is the point of attachment to the oxime nitrogen atom; and $R^{12}$ is as defined above, preferably H, $C_1$-$C_8$-alkyl or $C_2$-$C_6$-alkenyl.

In compounds of the formula I comprising at least two radicals $R^2$, two radicals $R^2$ together may be a divalent bridging group having 1 to 20 atoms between the flanking bonds. In this embodiment, a is 2, 3, 4 or 6 and/or c is 2, 3, 4 or 6, provided that the sum of a+b+c=2, 3, 4 or 6. The bridging group is preferably selected from $C_1$-$C_{10}$-alkylene, $C_2$-$C_{10}$-alkenylene, phenylene, phenylene-$C_1$-$C_4$-alkylene, $C_1$-$C_4$-alkylene-phenylen-$C_1$-$C_4$-alkylene, heteroarylene, heteroarylene-$C_1$-$C_4$-alkylene and $C_1$-$C_4$-alkylene-heteroarylene-$C_1$-$C_2$-alkylene or. Each alkylene and alkenylene may be interrupted by one or more, e.g. 1, 2 or 3, identical or different groups selected from O, S, $NR^6$ and CO and/or may be substituted by one or more, e.g. 1, 2, 3 or more than 3 radicals selected from F, Cl, Br, I, CN, $SR^4$, $OR^5$, $NR^6R^7$, $COR^8$, $COOR^9$, $CONR^{10}R^{11}$, $C_3$-$C_{20}$-cycloalkyl, heterocyclyl, heteroaryl and $C_6$-$C_{10}$-aryl where the 4 last-mentioned radicals may carry one or more, e.g. 1, 2, 3 or more than 3, identical or different radicals $C_1$-$C_{12}$-alkyl, $C_1$-$C_{12}$-haloalkyl, F, Cl, Br, I, CN, $NO_2$, $SR^4$, $OR^5$, $NR^6R^7$, $COR^8$, $COOR^9$ and $CONR^{10}R^{11}$, and each phenylene and heteroarylene may be substituted by one or more, e.g. 1, or 2 identical or different radicals $C_1$-$C_{12}$-alkyl, $C_1$-$C_{12}$-haloalkyl, F, Cl, Br, I, CN, $NO_2$, $SR^4$, $OR^5$, $NR^6R^7$, $COR^8$, $COOR^9$ and $CONR^{10}R^{11}$, where $R^4$, $R^5$, $R^6$, $R^7$, $R^8$, $R^9$, $R^{10}$, $R^{11}$ and $R^{12}$ are as defined above. Suitable examples are ethylene, propylene and butylene bridges. According to a particular preferred aspect of this embodiment, a is 2, 3, 4 or 6 and/or c is 2, 3, 4 or 6, provided that the sum of a+b+c=2, 3, 4 or 6. The bridging group is preferably selected from —C(=O)—O—$C_1$-$C_{10}$-alkylene-O—C(=O)—.

A specific embodiment of the invention relates to compositions, compounds, uses and methods, wherein $R^3$ in formula I is $C_1$-$C_{20}$-alkyl, $C_2$-$C_{20}$-alkenyl and $C_2$-$C_{20}$-alkynyl may be interrupted by one or more identical or different groups selected from —O—, —S—, —N($R^6$)— and CO, and/or may carry one or more identical or different radicals $R^{3a}$, where $R^{3a}$ is selected independently of one another from F, Cl, Br, I, CN, $SR^4$, $OR^5$, $NR^6R^7$, $COR^8$, $COOR^9$, $CONR^{10}R^{11}$, $C_3$-$C_{20}$-cycloalkyl which may be interrupted by one or more CO groups, heterocyclyl which may be interrupted by one or more CO groups, heteroaryl and $C_6$-$C_{10}$-aryl where the four last-mentioned radicals may carry one or more identical or different radicals $R^{3aa}$. $R^{3aa}$ is selected independently of one another from $C_1$-$C_{12}$-alkyl, $C_1$-$C_{12}$-haloalkyl, $C_1$-$C_{12}$-hydroxyalkyl, $C_2$-$C_{12}$-alkenyl, F, Cl, Br, I, CN, $NO_2$, $SR^4$, $OR^5$, $NR^6R^7$, $COR^8$, $COOR^9$ and $CONR^{11}R^{11}$.

According to a preferred aspect of this embodiment, $R^3$ is selected from $C_2$-$C_{12}$-alkyl; $C_2$-$C_{12}$-alkenyl; phenyl-$C_1$-$C_4$-alkyl; $C_1$-$C_6$-haloalkyl, in particular $C_1$-$C_4$-haloalkyl, especially $C_1$-$C_4$-fluoroalkyl; $C_3$-$C_{12}$-cycloalkyl-$C_1$-$C_{12}$-alkyl; $C_3$-$C_{12}$-cycloalkyl; heterocyclyl; $C_6$-$C_{10}$-aryl; $C_3$-$C_{12}$-cycloalkyl which is interrupted by one or two CO and/or may be substituted by one or more, e.g. 1, 2, 3, 4, 5 or 6 $C_1$-$C_{12}$-alkyl; heterocyclyl which is interrupted by one or two CO and/or may be substituted by one or more, e.g. 1, 2, 3, 4, 5 or 6 $C_1$-$C_{12}$-alkyl; $C_3$-$C_{12}$-cycloalkyl-$C_1$-$C_{12}$-alkyl where the cycloalkyl moiety is interrupted by one or two CO and/or may be substituted by one or more, e.g. 1, 2, 3, 4, 5 or 6 $C_1$-$C_{12}$-alkyl; and $C_6$-$C_{10}$-aryl which may be substituted by one or more, e.g. 1, 2, 3, 4 or 5, $C_1$-$C_{12}$-alkyl, $C_1$-$C_4$-haloalkyl, $C_2$-$C_4$-alkenyl, F, Cl, Br, I, CN, $NO_2$, $SR^4$, $OR^5$, $NR^6R^7$, $COR^8$, $COOR^9$, $CONR^{10}R^{11}$ or phenyl. According to a more preferred aspect of this embodiment, $R^3$ is $C_2$-$C_{12}$-alkyl which is substituted by $C_1$-$C_4$-alkoxycarbonyl. In a further embodiment $R^3$ is naphthyl-$C_1$-$C_4$-alkyl. According to a further preferred aspect of this embodiment, $R^3$ is heteroaryl, in particular 5- or 6-membered heteroaryl comprising besides carbon ring members 1 or 2 heteroatoms selected from O, S and N. According to a further preferred aspect of this embodiment $R^3$ is phenyl-$C_1$-$C_4$-alkyl, where the phenyl moiety is substituted by one or more radicals selected from F, Cl, Br, I, $C_1$-$C_4$-alkylsulfanyl, $C_1$-$C_4$-alkoxycarbonylsulfanyl-$C_1$-$C_4$-alkyl, $C_1$-$C_4$-alkoxycarbonyl, $C_1$-$C_4$-haloalkyl, phenyl, phenoxy and cyano.

According to a particular preferred aspect of this embodiment, $R^3$ is $C_2$-$C_6$-alkyl, in particular ethyl, propyl or butyl; $C_3$-$C_{12}$-cycloalkyl in particular cyclopentyl or cyclohexyl; $C_3$-$C_{12}$-cycloalkyl-$C_1$-$C_6$-alkyl where the cycloalkyl moiety is interrupted by one or two carbonyl groups and carries 1, 2, 3 or 4 $C_1$-$C_4$-alkyl, in particular camphoryl, especially camphor-10-yl; $C_2$-$C_6$-alkenyl such as vinyl or allyl; phenyl; naphthyl; phenyl which carries one, two, three, four or five substituents selected independently of one another from nitro, fluorine, $C_1$-$C_4$-alkyl, $C_1$-$C_4$-fluoroalkyl, $C_1$-$C_4$-alkoxycarbonyl and $C_2$-$C_4$-alkenyl; benzyl; phenethyl; or phenyl-$C_1$-$C_2$-alkyl where the aromatic ring of the last-mentioned radical carries one, two, three, four or five substituents selected from nitro, fluorine, $C_1$-$C_4$-alkyl, $C_1$-$C_4$-alkoxy, $C_1$-$C_4$-fluoroalkyl, $C_1$-$C_4$-alkoxy, $C_1$-$C_4$-alkoxycarbonyl and $C_2$-$C_4$-alkenyl. According to a particular preferred aspect $R^3$ is 5- or 6-membered saturated heterocyclyl comprising besides carbon atoms 1 or 2 heteroatoms or heteroatomic groups selected from O, S, SO, $SO_2$, NH and $N(C_1$-$C_8$-alkyl). According to a particular preferred aspect $R^3$ is thienyl. In a further embodiment $R^3$ is phenyl-$C_1$-$C_2$-alkyl. According to a particular preferred aspect $R^3$ is phenyl-$C_1$-$C_2$-alkyl, where the phenyl moiety is substituted by one or more radicals selected from Cl, $C_1$-$C_4$-alkoxycarbonylsulfanyl-$C_1$-$C_4$-alkyl, $C_1$-$C_4$-alkoxycarbonyl, phenoxy, phenyl and cyano.

According to an even more particular aspect of this embodiment, $R^3$ is $C_2$-$C_4$-alkyl; $C_1$-$C_4$-fluoroalkyl; camphor-10-yl; $C_2$-$C_4$-alkenyl; benzyl; benzyl which is substituted by one or two substituents selected from $C_1$-$C_4$-alkyl, $C_2$-$C_4$-alkenyl and nitro; naphthyl; phenyl; or phenyl which is substituted by one, two, three, four or five substituents selected from nitro, fluorine, $C_1$-$C_4$-alkyl, $C_1$-$C_4$-alkoxy, $C_1$-$C_4$-alkoxycarbonyl and $C_2$-$C_4$-alkenyl. According to a particular preferred aspect $R^3$ is phenyl which carries one, two, three, four or five substituents selected independently of one another from chlorine, cyano, NHC(O)—$C_1$-$C_4$-alkyl, nitro, $C_1$-$C_4$-alkyl, $C_1$-$C_4$-alkylthio, $C_1$-$C_4$-alkoxy, $C_1$-$C_4$-fluoroalkyl, $C_1$-$C_4$-alkoxycarbonyl and $C_2$-$C_4$-alkenyl. According to a particular preferred aspect, $R^3$ is thienyl or 5- or 6-membered saturated heterocyclyl comprising besides carbon atoms 1 or 2 heteroatoms or heteroatomic groups selected from O and S.

Suitable examples for $R^3$ are methyl, ethyl, propyl, vinyl, allyl, trifluoromethyl, camphor-10-yl, 2-naphthyl, 1-naphthyl, phenyl, pentafluorophenyl, 4-methylphenyl, 4-ethylphenyl, 4-methoxyphenyl, 4-ethoxyphenyl, 4-nitrophenyl, 4-vinylphenyl, 4-trifluoromethylphenyl, 3-nitrophenyl, 3-methylphenyl, 3-ethylphenyl, 3-vinylphenyl, 3,5-diethoxycarbonylphenyl, benzyl, 4-methylbenzyl, 4-ethylbenzyl, 4-nitrobenzyl, 4-vinylbenzyl, 3-nitrobenzyl, 3-methylbenzyl, 3-ethylbenzyl or 3-vinylbenzyl. Further examples are 4-methylsulfanylphenyl, 4-acetylaminophenyl, 4-methoxyphenyl, 4-acetylsulfanylmethylbenzyl, 4-cyanobenzyl, 4-chlorobenzyl, 4-methoxycarbonylbenzyl, 4-chlorobenzyl, 1-naphthylmethyl, 2-naphthylmethyl, 4-phenoxybenzyl, 4-vinylbenzyl, 3,4-dimethylsulfanylbenzyl, 3,5-ditrifluoromethylbenzyl, 4-tert-butylbenzyl, 4-phenylbenzyl, 2-thienyl, 3-thienyl, tetrahydropyran-3-yl and tetrahydrofuran-2-ylmethyl.

Another preferred embodiment of the invention relates to compositions, compounds methods and uses, where in formula I —X—$R^1$ together with $R^3$ are a divalent radical selected from X—($C_1$-$C_{10}$-alkylene)-Z,   X—($C_2$-$C_{10}$-alkenylene)-Z, X—($C_3$-$C_{20}$-cycloalkylene)-Z,  X-(heterocycloalkylene)-Z, X-(o-phenylene)-Z, where X is as defined above and Z is attached to the sulfur atom of the sulfonate group and has one of the meanings given above, preferably a single bond. According to this embodiment, the following structural units are obtained

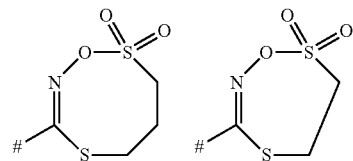

Another preferred embodiment of the invention relates to compositions, compounds methods and uses, where in formula I a is 1 and b and c are both 0. In this embodiment Q is $R^1$ and has preferably one the meanings mentioned as being preferred for $R^1$.

Another preferred embodiment of the invention relates to compositions, compounds methods and uses, where in formula I a is 2, and b and c are both 0. In this embodiment Q is a divalent radical. In a specific embodiment, Q is Q is L-$C_1$-$C_{30}$-alkylene-L, L-$C_3$-$C_{16}$-cycloalkylene-L, L-heterocycloalkylene-L, L-$C_6$-$C_{20}$-arylene-L, L-$C_1$-$C_{30}$-alkylene-$L^2$-L, L-$C_3$-$C_{16}$-cycloalkylene-$L^1$-$C_3$-$C_{16}$-cycloalkylene-L or L-$C_6$-$C_{20}$-arylene-$L^1$-$C_6$-$C_{20}$-arylene-L, where each alkylene may be interrupted by one or more identical or different non-adjacent O or S, where each cycloalkylene and each heterocycloalkylene may be interrupted by one or more CO, and where L is a single bond, C(S)O or C(S)$NR^{12}$; $L^1$ is a single bond, O or S; and $L^2$ is $C_3$-$C_{20}$-cycloalkylene, heterocycloalkylene or $C_6$-$C_{20}$-arylene.

According to a particular preferred aspect of this embodiment, Q is L-$C_1$-$C_{30}$-alkylene-L, L-$C_3$-$C_{16}$-cycloalkylene-L, L-heterocycloalkylene-L, L-$C_6$-$C_{20}$-arylene-L, L-$C_1$-$C_{30}$-alkylene-$L^2$-L, L-$C_3$-$C_{16}$-cycloalkylene-$L^1$-$C_3$-$C_{16}$-cycloalkylene-L or L-$C_6$-$C_{20}$-arylene-$L^1$-$C_6$-$C_{20}$-arylene-L, where each alkylene may be interrupted by one or more identical or different non-adjacent phenylene, OC(O), C(O)O, O or S, where each cycloalkylene and each heterocycloalkylene may be interrupted by one or more CO, and where L is a single bond, C(S)O or C(S)$NR^{12}$, more preferably a single bond, where $R^{12}$ is as defined above and has preferably one of the preferred meanings; $L^1$ is a single bond, O or S; and $L^2$ is $C_3$-$C_{20}$-cycloalkylene, heterocycloalkylene or $C_6$-$C_{20}$-arylene, more preferably, phenylen or naphthylen. In this embodiment, more preference is given to those compounds, where Q is $C_1$-$C_{30}$-alkylene; $C_1$-$C_{30}$-alkylene which is interrupted once, twice, three times, four times, five times or six times by non-adjacent O; $C_1$-$C_{30}$-alkylene which is interrupted once, twice, three times, four times, five times or six times by non-adjacent S; phenylen; naphthylen; phenylen-O-phenylen; phenylen-S-phenylen; napthylen-O-naphthylen; or napthylen-S-naphthylen. In particular, Q is phenylen-S-phenylen; $C_1$-$C_{10}$-alkylene; or $C_1$-$C_{20}$-alkylene which is interrupted by one, two, three or four more non-adjacent atoms selected from O and S. In this embodiment, examples of Q are linear $C_1$-$C_{10}$-alkylene, branched $C_1$-$C_{10}$-alkylene, —$CH_2$—$CH_2$—O—$CH_2$—$CH_2$—, —$CH_2$—$CH_2$—S—$CH_2$—$CH_2$—, —$CH_2$—$CH_2$—O—$CH_2$—$CH_2$—O—$CH_2$—$CH_2$—, —$CH_2$—$CH_2$—S—$CH_2$—$CH_2$—S—$CH_2$—$CH_2$—,

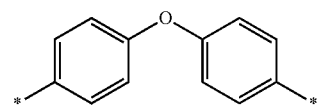

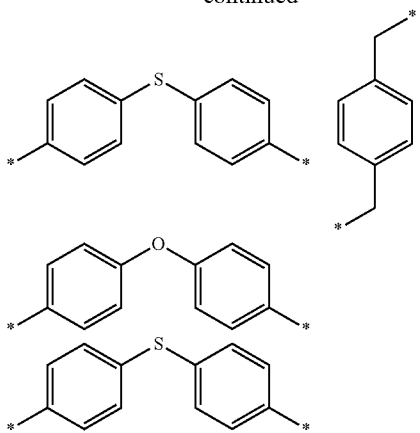

where * denotes the point of attachment to X. In a further aspect of this embodiment, Q is $C_1$-$C_{10}$-alkylene which is interrupted by 1, 2, 3 or 4 groups selected from O, S, C(O)O and OC(O); examples are —$CH_2$—C(O)—O—$CH_2$—$CH_2$—$CH_2$—$CH_2$—O—C(O)—$CH_2$—, 1,4-phenylene, $CH_2$C(O)—O—$CH_2$—$CH_2$—O—C(O)—$CH_2$.

Another preferred embodiment of the invention relates to compositions, compounds methods and uses, where in formula I b is 2, and a and c are both 0. In this embodiment Q is a divalent radical. According to a preferred aspect of this embodiment, Q is $L^5$-$C_1$-$C_{30}$-alkylene-$L^5$, $L^5$-$C_3$-$C_{16}$-cycloalkylene-$L^5$, $L^5$-heterocycloalkylene-$L^5$, $L^5$-$C_6$-$C_{20}$-arylene-$L^5$, $L^5$-$C_3$-$C_{16}$-cycloalkylene-$L^7$-$C_3$-$C_{16}$-cycloalkylene-$L^5$ or $L^5$-$C_6$-$C_{20}$-arylene-$L^7$-$C_6$-$C_{20}$-arylene-$L^5$, where alkylene may be interrupted by one or more identical or different non-adjacent O or S, where each cycloalkylene and each heterocycloalkylene may be interrupted by one or more CO, where $L^5$ is a single bond, S, O, $NR^6$, CO, C(O)O, OCO, $NR^{10}$C(O) or $CONR^{10}$, $L^7$ is a single bond, O or S and $R^6$ and $R^{10}$ are as defined above and have preferably one of the preferred meanings. More preferably, $L^5$ is a single bond, S, O, C(O), OC(O) or C(O)O. In this embodiment, more preference is given to those compounds, where Q is $C_1$-$C_{30}$-alkylene; —C(O)O—$C_1$-$C_{30}$-alkylene-O—C(O)—; $C_1$-$C_{30}$-alkylene which is interrupted once, twice, three times, four times, five times or six times by non-adjacent O; $C_1$-$C_{30}$-alkylene which is interrupted once, twice, three times, four times, five times or six times by non-adjacent S; —C(O)O—$C_1$-$C_{30}$-alkylene-O—C(O)— in which alkylene is interrupted once, twice, three times, four times, five times or six times by non-adjacent O; phenylen; naphthylen; phenylen-O-phenylen; phenylen-S-phenylen; naphthylen-O-naphthylen; or naphthylen-S-naphthylen. Even more preferably Q is $C_1$-$C_{10}$-alkylene which may be interrupted by one, two, three or four more non-adjacent atoms selected from O and S. In this embodiment, examples of Q are linear or branched $C_1$-$C_{10}$-alkylene, —$CH_2$—$CH_2$—O—$CH_2$—$CH_2$—, —$CH_2$—$CH_2$—S—$CH_2$—$CH_2$—, —$CH_2$—$CH_2$—O—$CH_2$—$CH_2$—O—$CH_2$—$CH_2$—, —$CH_2$—$CH_2$—S—$CH_2$—$CH_2$—S—$CH_2$—$CH_2$— or —C(O)O—$C_2$-$C_4$-alkylene-O—C(O)—. In a further preferred aspect of this embodiment, Q is —C(O)O—$C_1$-$C_{30}$-alkylene-O—C(O)—.

Another preferred embodiment of the invention relates to compositions, compounds methods and uses, where in formula I b is 2 or 3 and —X—$R^1$ together with a carbon atom or nitrogen atom of Q form a 5-, 6- or 7-membered ring via X—($C_1$-$C_6$-alkylene)-N($R^{10}$)CO, X—($C_3$-$C_6$-cycloalkylene)-N($R^{10}$)CO, X-(o-phenylene)-N($R^{10}$)CO, or S—C(S)—N($R^{12}$)—CO, where $R^{10}$ and $R^{12}$ are as defined above and preferably have one of the preferred meanings.

Another preferred embodiment of the invention relates to compositions, compounds methods and uses, where in formula I c is 2, a and b are both 0. In this embodiment Q is a divalent radical. According to a preferred aspect of this embodiment, Q is selected from $C_1$-$C_{30}$-alkylene, $C_3$-$C_{16}$-cycloalkylene, heterocycloalkylene, $C_6$-$C_{20}$-arylene, $C_3$-$C_{16}$-cycloalkylene-$L^{11}$-$C_3$-$C_{16}$-cycloalkylene, $C_6$-$C_{20}$-arylene-$L^{11}$-$C_6$-$C_{20}$-arylene, where alkylene may be interrupted by one or more identical or different non-adjacent O or S, where each cycloalkylene and each heterocycloalkylene may be interrupted by one or more CO, and where $L^{11}$ is a single bond, O or S. In this embodiment, more preference is given to those compounds, where Q is $C_1$-$C_{30}$-alkylene; $C_1$-$C_{30}$-alkylene which is interrupted once, twice, three times, four times, five times or six times by non-adjacent O; $C_1$-$C_{30}$-alkylene which is interrupted once, twice, three times, four times, five times or six times by non-adjacent S; phenylen; naphthylen; phenylen-O-phenylen; phenylen-S-phenylen; napthylen-O-naphthylen; or napthylen-S-naphthylen. Even more preferably, Q is phenylen or naphthylene. In this embodiment, examples of Q are 1,3-phenylen, 1,4-phenylen, 1,8-naphthylen and 2,7-naphthylen.

Another preferred embodiment of the invention relates to compounds, methods and uses, where in formula I the sum of a+b+c is 2. In this embodiment Q is a divalent radical. According to a preferred aspect of this embodiment, Q is selected from $C_1$-$C_{30}$-alkylene, $C_3$-$C_{16}$-cycloalkylene, heterocycloalkylene, $C_6$-$C_{20}$-arylene, $C_3$-$C_{16}$-cycloalkylene-$L^{11}$-$C_3$-$C_{16}$-cycloalkylene, $C_6$-$C_{20}$-arylene-$L^{11}$-$C_6$-$C_{20}$-arylene, where alkylene may be interrupted by one or more identical or different non-adjacent O or S, where each cycloalkylene and each heterocycloalkylene may be interrupted by one or more CO, and where $L^{11}$ is a single bond, O or S. More preference is given to those compounds, where Q is $C_1$-$C_{30}$-alkylene; $C_1$-$C_{30}$-alkylene which is interrupted once, twice, three times, four times, five times or six times by non-adjacent O; $C_1$-$C_{30}$-alkylene which is interrupted once, twice, three times, four times, five times or six times by non-adjacent S; phenylen; naphthylen; phenylen-O-phenylen; phenylen-S-phenylen; napthylen-O-naphthylen; or napthylen-S-naphthylen. Even more preferably, Q is $CH_2$-phenylene-$CH_2$, phenylen2 or naphthylene. In this embodiment, examples of Q are $CH_2$-(1,4-phenylene)-$CH_2$—, 1,3-phenylen, 1,4-phenylen, 1,8-naphthylen and 2,7-naphthylen.

Another preferred embodiment of the invention relates to compositions, compounds methods and uses, where in formula I the sum of a+b+c is 3. Q is a trivalent linker. According to a preferred aspect of this embodiment, Q is selected from $C_1$-$C_{30}$-alkanetriyl, $C_3$-$C_{16}$-cycloalkanetriyl, $C_6$-$C_{20}$-arenetriyl, $C_1$-$C_{30}$-alkanetriyl-$L^{14}$-$L^{15}$, $C_1$-$C_{30}$-alkylene-$L^{14}$-$L^{16}$, $C_6$-$C_{20}$-arenetriyl-$L^{14}$-$L^{15}$-$C_6$-$C_{20}$-arylene, and $C_6$-$C_{20}$-arylene-$L^{14}$-$L^{15}$-$C_3$-$C_{16}$-cycloalkanetriyl
where each alkanetriyl and each alkylene may be interrupted by one or more, e.g. 1, 2, 3, 4, 5, 6 or more than 6 identical or different non-adjacent groups O, S, $NR^6$, CO, C(O)O, OC(O), $NR^{10}$C(O) or C(O)$NR^{10}$ and/or may carry one or more identical or different radicals $R^{Qa}$, where $R^{Qa}$ and $R^6$ as defined above;
where each cycloalkanetriyl may be interrupted by one or more CO groups, where $L^{14}$ is a single bond, O or S, $L^{15}$ is $C_3$-$C_{20}$-cycloalkylene, heterocycloalkylene or $C_6$-$C_{20}$-arylene and where $L^{16}$ is arenetriyl. In this embodiment, more preference is given to those compounds of the formula I, in which Q is $C_1$-$C_{30}$-alkanetriyl or $C_1$-$C_{30}$-alkanetriyl which is interrupted by one, two, three, four, five, or six non-adjacent groups independently of one another selected from O, S, $NR^6$, $NR^{10}C(O)$, $CONR^{10}$, CO, OC(O) and C(O)O, where $R^6$ and $R^{10}$ are as defined above and preferably have one of the preferred meanings. In this embodiment, examples of Q are Suitable examples are $C_1$-$C_{30}$-alkanetetrayl which may be interrupted by one or more, preferably 1, 2, 3, 4, 5, 6, 7, 8 or more than 8 groups $L^{18}$. $L^{18}$ is preferably O, S, $NR^6$, CO, C(O)O, OC(O), C(O)$NR^{10}$ or $NR^{10}$C(O). In this embodiment, examples of Q are

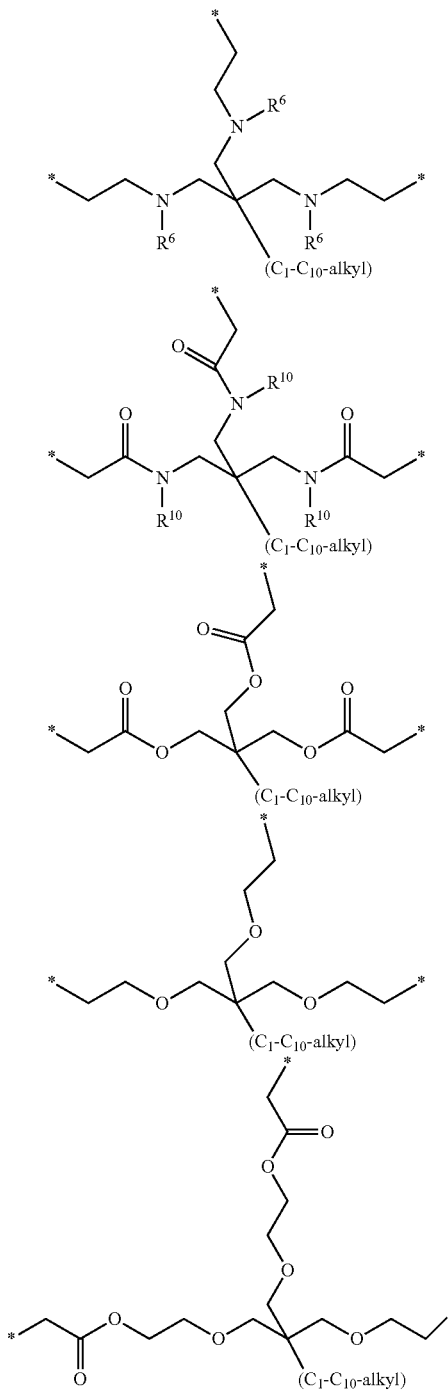

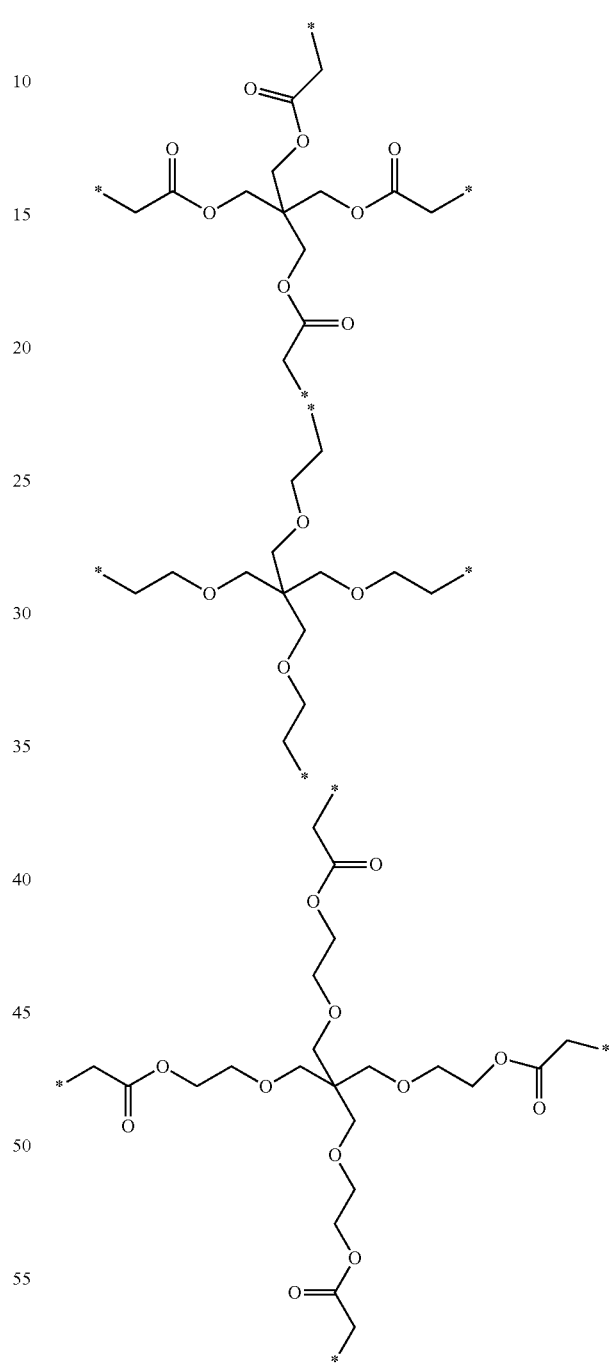

where

* denotes the point of attachment to X,
$R^6$ is as defined above, preferably H or $C_1$-$C_{10}$-alkyl;
$R^{10}$ is as defined above, preferably H or $C_1$-$C_{10}$-alkyl.

Another preferred embodiment of the invention relates to compositions, compounds methods and uses, where in formula I the sum of a+b+c is 4. Q is a tetravaalent linker.

Another preferred embodiment of the invention relates to compositions, compounds methods and uses, where in formula I the sum of a+b+c is 6. Q is a hexavalent linker. Suitable examples are $C_2$-$C_{30}$-alkanehexayl which may be interrupted by one or more, preferably 1, 2, 3, 4, 5, 6, 7, 8, 9, 10, 11, 12 or more than 12 groups $L^{19}$. $L^{19}$ is preferably O, S, $NR^6$, CO, C(O)O, OC(O), C(O)$NR^{10}$ or $NR^{10}$C(O).

Apart from that, the variables $R^4$, $R^5$, $R^6$, $R^7$, $R^8$, $R^9$, $R^{10}$, $R^{11}$, $R^{12}$ and $R^{13}$, independently of each other, preferably have one of the following meanings:

$R^4$ is hydrogen, $C_1$-$C_{12}$-alkyl; $C_1$-$C_4$-haloalkyl; phenyl-$C_1$-$C_4$-alkyl; $C_2$-$C_{12}$-alkenyl; $C_3$-$C_{10}$-cycloalkyl; heterocyclyl; $C_1$-$C_{12}$-alkyl which is interrupted by one or more, e.g. 1, 2, 3 or 4, O, S, N($C_1$-$C_8$alkyl) or CO; $C_1$-$C_{12}$-haloalkyl which is interrupted by one or more, e.g. 1, 2 or 3, O, S, N($C_1$-$C_8$alkyl) or CO; phenyl-$C_1$-$C_4$-alkyl where the alkyl moiety is interrupted by 1 or 2 O, S, N($C_1$-$C_8$alkyl) or CO; $C_2$-$C_{12}$-alkenyl which is interrupted by one or more, e.g. 1, 2 or 3, O, S, N($C_1$-$C_8$alkyl) or CO; $C_3$-$C_{10}$-cycloalkyl which is interrupted by 1 or 2 CO; heterocyclyl which is interrupted by 1 or 2 CO; phenyl; naphthyl; phenyl which is substituted by one or more, e.g. 1, 2, 3, 4 or 5 radicals selected independently of one another from F, Cl, Br, I, $C_1$-$C_{12}$-alkyl, $C_1$-$C_{12}$-alkoxy, phenyl-$C_1$-$C_3$-alkoxy, phenoxy, $C_1$-$C_{12}$-alkylsulfanyl, phenylsulfanyl, —(CO)O($C_1$-$C_8$-alkyl), (CO)N($C_1$-$C_8$-alkyl)$_2$ and phenyl; naphthyl which is substituted by one or more, e.g. 1, 2, 3, 4 or 5 radicals selected independently of one another from F, Cl, Br, I, $C_1$-$C_{12}$-alkyl, $C_1$-$C_{12}$-alkoxy, phenyl-$C_1$-$C_3$-alkyloxy, phenoxy, $C_1$-$C_{12}$-alkylsulfanyl, phenylsulfanyl, —(CO)O($C_1$-$C_8$alkyl), (CO)N($C_1$-$C_8$alkyl)$_2$ and phenyl; phenyl or naphthyl which forms 5- or 6-membered rings with the phenyl ring to which the $SR^4$ is attached via a single bond, $C_1$-$C_4$-alkylene, O, S, $NR^6$ or CO;

$R^5$ is hydrogen, $C_1$-$C_{12}$-alkyl; $C_1$-$C_4$-haloalkyl; phenyl-$C_1$-$C_4$-alkyl; $C_2$-$C_{12}$-alkenyl; $C_3$-$C_{10}$-cycloalkyl; heterocyclyl; $C_1$-$C_{12}$-alkyl which is interrupted by one or more, e.g. 1, 2, 3 or 4, O, S, N($C_1$-$C_8$alkyl) or CO; $C_1$-$C_{12}$-haloalkyl which is interrupted by one or more, e.g. 1, 2 or 3, O, S, N($C_1$-$C_8$alkyl) or CO; phenyl-$C_1$-$C_4$-alkyl where the alkyl moiety is interrupted by 1 or 2 O, S, N($C_1$-$C_8$alkyl) or CO; $C_2$-$C_{12}$-alkenyl which is interrupted by one or more, e.g. 1, 2 or 3, O, S, N($C_1$-$C_8$alkyl) or CO; $C_3$-$C_{10}$-cycloalkyl which is interrupted by 1 or 2 CO; heterocyclyl which is interrupted by 1 or 2 CO; phenyl; naphthyl; phenyl which is substituted by one or more, e.g. 1, 2, 3, 4 or 5 radicals selected independently of one another from F, Cl, Br, I, $C_1$-$C_{12}$-alkyl, $C_1$-$C_{12}$-alkoxy, phenyl-$C_1$-$C_3$-alkoxy, phenoxy, $C_1$-$C_{12}$-alkylsulfanyl, phenylsulfanyl, —(CO)O($C_1$-$C_8$-alkyl), (CO)N($C_1$-$C_8$-alkyl)$_2$ and phenyl; naphthyl which is substituted by one or more, e.g. 1, 2, 3, 4 or 5 radicals selected independently of one another from F, Cl, Br, I, $C_1$-$C_{12}$-alkyl, $C_1$-$C_{12}$-alkoxy, phenyl-$C_1$-$C_3$-alkyloxy, phenoxy, $C_1$-$C_{12}$-alkylsulfanyl, phenylsulfanyl, —(CO)O($C_1$-$C_8$alkyl), (CO)N($C_1$-$C_8$alkyl)$_2$ and phenyl; phenyl or naphthyl which forms 5- or 6-membered rings with the phenyl ring to which the $SR^4$ is attached via a single bond, $C_1$-$C_4$-alkylene, O, S, $NR^6$ or CO $R^6$, $R^{10}$, and $R^{12}$, each independently of one another are hydrogen; $OR^5$; $C_1$-$C_{12}$-alkyl; $C_1$-$C_4$haloalkyl; $C_2$-$C_{12}$-alkenyl; $C_3$-$C_{10}$-cycloalkyl; $C_1$-$C_{12}$-alkyl which is interrupted by one, two or three O, S, N($C_1$-$C_8$alkyl) or CO; $C_2$-$C_{12}$-alkenyl which is interrupted by one, two or three O, S, N($C_1$-$C_8$alkyl) or CO; $C_3$-$C_{10}$-cycloalkyl which is interrupted by one, two or three O, S, N($C_1$-$C_8$alkyl) or CO; $C_2$-$C_8$-alkanoyl; $C_2$-$C_8$-alkanoyl which is substituted by one, two, or three —OH or $C_1$-$C_6$alkoxy; $C_2$-$C_4$-haloalkanoyl; $C_2$-$C_4$-haloalkanoyl which is substituted by one —OH or $C_1$-$C_6$alkoxy; benzoyl; benzoyl which is substituted by one, two, three, four or five $C_1$-$C_6$-alkyl, F, Cl, Br, I, —OH or $C_1$-$C_6$alkoxy; phenyl; phenyl which is substituted by one, two, three, four or five F, Cl, Br, I, $C_1$-$C_{12}$-alkyl, $C_1$-$C_4$-haloalkyl, $C_1$-$C_{12}$-alkoxy, phenyl-$C_1$-$C_3$-alkoxy, phenoxy, $C_1$-$C_{12}$-alkylsulfanyl, phenylsulfanyl, —(CO)O($C_1$-$C_8$alkyl), (CO)N($C_1$-$C_8$alkyl)$_2$ or phenyl; naphthyl; or naphthyl which is substituted by one, two, three, four or five F, Cl, Br, I, $C_1$-$C_{12}$-alkyl, $C_1$-$C_4$-haloalkyl, $C_1$-$C_{12}$-alkoxy, phenyl-$C_1$-$C_3$-alkoxy, phenoxy, $C_1$-$C_{12}$-alkylsulfanyl, phenylsulfanyl, —(CO)O($C_1$-$C_8$alkyl), (CO)N($C_1$-$C_8$alkyl)$_2$ or phenyl;

$R^7$, $R^{11}$ and $R^{13}$ each independently of one another are $OR^5$; $C_1$-$C_{12}$-alkyl; $C_1$-$C_4$haloalkyl; $C_2$-$C_{12}$-alkenyl; $C_3$-$C_{10}$-cycloalkyl; $C_1$-$C_{12}$-alkyl which is interrupted by one, two or three O, S, N($C_1$-$C_8$alkyl) or CO; $C_2$-$C_{12}$-alkenyl which is interrupted by one, two or three O, S, N($C_1$-$C_8$alkyl) or CO; $C_3$-$C_{10}$-cycloalkyl which is interrupted by one, two or three O, S, N($C_1$-$C_8$alkyl) or CO; $C_2$-$C_8$-alkanoyl; $C_2$-$C_8$-alkanoyl which is substituted by one, two, or three —OH or $C_1$-$C_6$alkoxy; $C_2$-$C_4$-haloalkanoyl; $C_2$-$C_4$-haloalkanoyl which is substituted by one —OH or $C_1$-$C_6$alkoxy; benzoyl; benzoyl which is substituted by one, two, three, four or five $C_1$-$C_6$-alkyl, F, Cl, Br, I, —OH or $C_1$-$C_6$alkoxy; phenyl; phenyl which is substituted by one, two, three, four or five F, Cl, Br, I, $C_1$-$C_{12}$-alkyl, $C_1$-$C_4$-haloalkyl, $C_1$-$C_{12}$-alkoxy, phenyl-$C_1$-$C_3$-alkoxy, phenoxy, $C_1$-$C_{12}$-alkylsulfanyl, phenylsulfanyl, —(CO)O($C_1$-$C_8$alkyl), (CO)N($C_1$-$C_8$alkyl)$_2$ or phenyl; naphthyl; or naphthyl which is substituted by one, two, three, four or five F, Cl, Br, I, $C_1$-$C_{12}$-alkyl, $C_1$-$C_4$-haloalkyl, $C_1$-$C_{12}$-alkoxy, phenyl-$C_1$-$C_3$-alkoxy, phenoxy, $C_1$-$C_{12}$-alkylsulfanyl, phenylsulfanyl, —(CO)O($C_1$-$C_8$alkyl), (CO)N($C_1$-$C_8$alkyl)$_2$ or phenyl;

or $R^6$ and $R^7$, $R^{10}$ and $R^{11}$ and/or $R^{12}$ and $R^{13}$ together with the nitrogen atom to which they are bound form a 5- or 6-membered, saturated heterocycle, which may carry a further heteroatom being selected from O, S and N($C_1$-$C_8$-alkyl) as a ring member atom and wherein one methylene group of the heterocycle may be replaced by a CO group;

$R^8$ is $C_1$-$C_{12}$-alkyl; $C_1$-$C_{12}$-alkyl which is interrupted by one or more, e.g. two, three or four O, S, N($C_1$-$C_8$alkyl) or CO; $C_1$-$C_4$-haloalkyl; $C_1$-$C_4$-haloalkyl which is interrupted by one or more, e.g. two, three or four O, S, N($C_1$-$C_8$alkyl) or CO; phenyl-$C_1$-$C_4$-alkyl; phenyl-$C_1$-$C_4$-alkyl in which the alkyl moiety is interrupted by one or two O, S, N($C_1$-$C_8$alkyl) or CO; $C_2$-$C_{12}$-alkenyl; $C_2$-$C_{12}$-alkenyl which is interrupted by one or more, e.g. two, three or four O, S, N($C_1$-$C_8$alkyl) or CO; $C_3$-$C_{10}$-cycloalkyl; $C_3$-$C_{10}$-cycloalkyl which is interrupted by one CO; heterocycly; heterocyclyl which is interrupted by one CO; phenyl; phenyl which is substituted by one, two, three, four or five or more F, Cl, Br, I, $C_1$-$C_{12}$-alkyl, $C_1$-$C_4$-haloalkyl, $C_1$-$C_{12}$-alkoxy, phenyl-$C_1$-$C_3$-alkoxy, phenoxy, $C_1$-$C_{12}$-alkylsulfanyl, phenylsulfanyl, —(CO)O($C_1$-$C_8$alkyl), (CO)N($C_1$-$C_8$-alkyl)$_2$; naphthyl; or naphthyl which is substituted by one or more, e.g. 1, 2, 3, 4 or more F, Cl, Br, I, $C_1$-$C_{12}$-alkyl, $C_1$-$C_4$-haloalkyl, $C_1$-$C_{12}$-alkoxy, phenyl-$C_1$-$C_3$-alkoxy, phenoxy, $C_1$-$C_{12}$-alkylsulfanyl, phenylsulfanyl, —(CO)O ($C_1$-$C_8$-alkyl), (CO)N($C_1$-$C_8$-alkyl)$_2$ or phenyl;

$R^9$ is hydrogen; $C_1$-$C_{12}$-alkyl; $C_1$-$C_{12}$-alkyl which is interrupted by one or more, e.g. two, three or four O, S, N($C_1$-$C_8$alkyl) or CO; $C_1$-$C_4$-haloalkyl; $C_1$-$C_4$-haloalkyl which is interrupted by one or more, e.g. two, three or four O, S, N($C_1$-$C_8$alkyl) or CO; phenyl-$C_1$-$C_4$-alkyl; phenyl-$C_1$-$C_4$-alkyl in which the alkyl moiety is interrupted by one or two O, S, N($C_1$-$C_8$alkyl) or CO; $C_2$-$C_{12}$-alkenyl; $C_2$-$C_{12}$-alkenyl which is interrupted by one or more, e.g. two, three or four O, S, N($C_1$-$C_8$alkyl) or CO; $C_3$-$C_{10}$-cycloalkyl; $C_3$-$C_{10}$-cycloalkyl which is interrupted by one CO; heterocycly; heterocyclyl which is interrupted by one CO; phenyl; phenyl which is substituted by one, two, three, four or five or more F, Cl, Br, I, $C_1$-$C_{12}$-alkyl, $C_1$-$C_4$-haloalkyl, $C_1$-$C_{12}$-alkoxy, phenyl-$C_1$-$C_3$-alkoxy, phenoxy, $C_1$-$C_{12}$-alkylsulfanyl, phenylsulfanyl, —(CO)O($C_1$-$C_8$alkyl), (CO)N($C_1$-$C_8$-alkyl)$_2$; naphthyl; or naphthyl which is substituted by one or more, e.g. 1, 2, 3, 4 or more F, Cl, Br, I, $C_1$-$C_{12}$-alkyl, $C_1$-$C_4$-haloalkyl, $C_1$-$C_{12}$-alkoxy, phenyl-$C_1$-$C_3$-alkoxy, phenoxy, $C_1$-$C_{12}$-alkylsulfanyl, phenylsulfanyl, —(CO)O($C_1$-$C_8$-alkyl), (CO)N($C_1$-$C_8$-alkyl)$_2$ or phenyl.

Another more preferred embodiment of the invention relates to compositions, compounds methods and uses, where in formula I a is 0, 1, 2 or 3;

b is 0, 2 or 3, preferably 0 or 2;

c is 0, 2 or 3, preferably 0 or 2; in a further embodiment c is 1,

X is S or $NR^{14}$;

$R^{14}$ is selected from

- $C_1$-$C_{12}$-alkyl, which may be interrupted by one or more, e.g. 1, 2 or 3, identical or different O, S, $NR^6$ or CO and/or may be substituted by one or more, e.g. 1 or 2 identical or different radicals $R^{14a}$ selected from $C_3$-$C_8$-cycloalkyl, CN, $COR^8$, $COOR^9$, $CONR^{10}R^{11}$, phenyl, phenyl which is substituted by one, two, three, four or five radicals selected from $C_1$-$C_8$-alkyl, $C_1$-$C_4$-haloalkyl, F, Cl, Br, I, CN, $NO_2$, $SR^4$, $OR^5$, $NR^6R^7$, $COR^8$, $COOR^9$ and $CONR^{10}R^{11}$, and $C_3$-$C_8$-cycloalkyl which is interrupted by one or two CO groups and/or may be substituted by one, two, three, four or five radicals selected from $C_1$-$C_8$-alkyl, $C_1$-$C_4$-haloalkyl, F, Cl, Br, I, CN, $NO_2$, $SR^4$, $OR^5$, $NR^6R^7$, $COR^8$, $COOR^9$ and $CONR^{10}R^{11}$;
- $C_2$-$C_{12}$-alkenyl, which may be interrupted by one or more, e.g. 1, 2 or 3, identical of different O, S, $NR^6$ or CO and/or may be substituted by one or more, e.g. 1 or 2 identical or different radicals $R^{14a}$ selected from $C_3$-$C_8$-cycloalkyl, CN, $COR^8$, $COOR^9$, $CONR^{10}R^{11}$, phenyl, phenyl which is substituted by one, two, three, four or five radicals selected from $C_1$-$C_8$-alkyl, $C_1$-$C_4$-haloalkyl, F, Cl, Br, I, CN, $NO_2$, $SR^4$, $OR^5$, $NR^6R^7$, $COR^8$, $COOR^9$ and $CONR^{10}R^{11}$, and $C_3$-$C_8$-cycloalkyl which is interrupted by one or two CO groups and/or may be substituted by one, two, three, four or five radicals selected from $C_1$-$C_8$-alkyl, $C_1$-$C_4$-haloalkyl, F, Cl, Br, I, CN, $NO_2$, $SR^4$, $OR^5$, $NR^6R^7$, $COR^8$, $COOR^9$ and $CONR^{10}R^{11}$;
- $C_3$-$C_{12}$-cycloalkyl, which may be interrupted by one or more, e.g. 1 or 2, CO and/or may be substituted by one or more identical or different radicals $R^{14b}$ selected from $C_1$-$C_8$-alkyl, CN, $COR^8$, $COOR^9$, $CONR^{10}R^{11}$; or
- phenyl, where the phenyl ring of the last-mentioned radical may be substituted by one or more radicals $R^{14c}$ selected from $C_1$-$C_8$-alkyl, $C_1$-$C_4$-haloalkyl, F, Cl, Br, I, CN, $NO_2$, $SR^4$, $OR^5$, $NR^6R^7$, $COR^8$, $COOR^9$, $CONR^{10}R^{11}$ or phenyl;

or

- two radicals $R^{14}$ together are a divalent bridging group having 1 to 10 atoms between the flanking bonds, the divalent bridging group is selected from $C_1$-$C_{10}$-alkylene, $C_3$-$C_{12}$-cycloalkylene, heterocycloalkylene, $C_2$-$C_{10}$-alkenylene, phenylene or naphthylene, where each alkylene and alkenylene may be interrupted by one or more, e.g. 1 or 2, O, S, NH, N($C_1$-$C_8$-alkyl) or CO and where cycloalkylene and heterocycloalkylene may be interrupted by one or more, e.g. 1 or 2 CO;

$R^1$ $CSNR^{12}R^{13}$; $C(O)OR^9$; $CSOR^9$; $C_3$-$C_{12}$-alkyl; $C_2$-$C_{12}$-alkenyl; $C_3$-$C_{12}$-cycloalkyl; $C_1$-$C_{12}$-alkyl, which is interrupted by one or more, e.g. 1, 2, or 3, identical or different groups selected from O, S, $NR^6$ or CO and/or which is substituted by one, two or three identical or different radicals $R^{1a}$;

- $C_2$-$C_{12}$-alkenyl, which is interrupted by one or more, e.g. 1, 2, or 3, identical or different groups selected from O, S, $NR^6$ or CO and/or which is substituted by one, two or three identical or different radicals $R^{1a}$;
- $C_3$-$C_{12}$-cycloalkyl, which may be interrupted by 1 or 2 CO group and/or which may be substituted by one, two or three radicals $R^{1b}$;
- heterocyclyl, which may be interrupted by 1 or 2 CO group and/or which may be substituted by one, two or three radicals $R^{1b}$;
- phenyl, naphthyl, or hetaryl, where the 3 last-mentioned radicals may be substituted by one or more identical or different radicals $R^{1c}$ and where heteroaryl comprises besides carbon atoms one, two or three heteroatoms selected from O, S and N as ring members; and
- $C_6$-$C_{10}$-aroyl which may be substituted by one or more, e.g. 1, 2 or 3, identical or different radicals $R^{1d}$;

or $R^1$ and $R^{14}$ together with the nitrogen atom to which they are attached form a 5-, 6- or 7-membered saturated or unsaturated heterocycle which may comprise a further heteroatom or heteroatomic group selected from O, S, NH, N($C_1$-$C_8$-alkyl) and CO and which may carry 1, 2, 3 or 4 substituents independently of one another selected from halogen, cyano, $C_1$-$C_4$-alkyl, nitro, $C_1$-$C_4$-haloalkyl, $C_1$-$C_4$-alkoxy and $C_1$-$C_4$-haloalkoxy;

or $R^1$ and $R^{14}$ together are a divalent bridging group selected from $C_2$-$C_8$-alkylene which may be interrupted by one or more, e.g. 1, 2 or 3, identical or different groups selected from O, S, N($C_1$-$C_8$-alkyl) and CO $R^2$ is $COR^8$; $COOR^9$; $C(O)NR^{10}R^{11}$;

- $C_1$-$C_{12}$-alkyl, $C_2$-$C_{12}$-alkenyl, where the 2 last-mentioned radicals may be substituted by one or more, e.g. 1, 2 or 3, identical or different radicals $R^{2a}$;
- $C_3$-$C_{12}$-cycloalkyl, which may be substituted by one or more, e.g. 1, 2 or 3, identical or different radicals $R^{2b}$;
- $C_6$-$C_{10}$-aryl, which may be substituted by one or more, e.g. 1, 2, 3, 4, or 5, identical or radicals $R^{2c}$;
- 5- or 6-membered heteroaryl comprising besides carbon atoms one or two heteroatoms selected from N, O and S and which may be substituted by one or more, e.g. 1, 2, 3, 4, or 5, identical or different radicals $R^{2c}$; or
- pyridinium of the formula

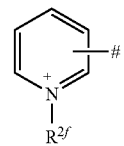

where # is the point of attachment to the remainder of the molecule and $R^{2f}$ is $C_1$-$C_{12}$-alkylene-$COO^-$, $C_1$-$C_{12}$-alkylene-$S(O)_2O^-$ or $C_1$-$C_{12}$-alkylene-$OS(O)_2O^-$;

or

X—$R^1$ together with $R^2$ are —X—($C_1$-$C_8$-alkylene)-O—C(O)—; —X—($C_1$-$C_8$-alkylene)-S—C(O)—; X—($C_3$-$C_6$-cycloalkylene)-O—C(O)—; —X—(o-phenylene)-O—C(O)—; X—($C_1$-$C_8$-alkylene)-$NR^{10}$—C(O)—; —X—($C_3$-$C_6$-cycloalkylene)-$NR^{10}$—C(O)—; —N($C_1$-$C_8$-alkyl)-

(O—$C_2$-$C_8$-alkylene)-; —S—(S—$C_2$-$C_8$-alkylene)- or —N($C_1$-$C_8$-alkyl)-(N($C_1$-$C_8$-alkyl)-$C_2$-$C_8$-alkylene)-,
  where each alkylene moiety may be substituted by one or more, e.g. 1, 2 or 3, identical or different radicals $R^{2g}$, each cycloalkylene may be substituted by one or more, e.g. 1, 2 or 3, identical of different radicals $R^{2h}$, and o-phenylene may be substituted by one or more identical or different radicals $R^{2h}$,
or
  —X—$R^1$ together with $R^2$ are —S—C(S)—$NR^{12}$—C(O)—;
$R^3$ is $C_2$-$C_{12}$-alkyl; $C_2$-$C_{12}$-alkenyl; phenyl-$C_1$-$C_4$-alkyl; $C_1$-$C_4$-haloalkyl; $C_3$-$C_{12}$-cycloalkyl-$C_1$-$C_{12}$-alkyl; $C_3$-$C_{12}$-cycloalkyl; heterocyclyl; $C_6$-$C_{10}$-aryl; $C_3$-$C_{12}$-cycloalkyl which is interrupted by one or two CO and/or may be substituted by one or more, e.g. 1, 2, 3, 4, 5 or 6 $C_1$-$C_{12}$-alkyl; heterocyclyl which is interrupted by one or two CO and/or may be substituted by one or more, e.g. 1, 2, 3, 4, 5 or 6 $C_1$-$C_{12}$-alkyl; $C_3$-$C_{12}$-cycloalkyl-$C_1$-$C_{12}$-alkyl where cycloalkyl is interrupted by one or two CO and/or may be substituted by one or more, e.g. 1, 2, 3, 4, 5 or 6 $C_1$-$C_{12}$-alkyl; and $C_6$-$C_{10}$-aryl which may be substituted by one or more, e.g. 1, 2, 3, 4, or 5, $C_1$-$C_{12}$-alkyl, $C_1$-$C_4$-haloalkyl, $C_1$-$C_4$-alkoxy, $C_2$-$C_4$-alkenyl, F, Cl, Br, I, CN, $NO_2$, $SR^4$, $OR^5$, $NR^6R^7$, $COR^8$, $COOR^9$, $CONR^{10}R^{11}$ or phenyl
or
  —X—$R^1$ together with $R^3$ are a divalent radical selected from X—($C_1$-$C_{10}$-alkylene)-, X—($C_2$-$C_{10}$-alkenylene)-, X—($C_3$-$C_{20}$-cycloalkylene)-, X-(heterocycloalkylene)-, X-(o-phenylene)-;
Q if a is 2, and b and c are both 0
  is L-$C_1$-$C_{30}$-alkylene-L, L-$C_3$-$C_{16}$-cycloalkylene-L, L-heterocycloalkylene-L, L-$C_6$-$C_{20}$-arylene-L, L-$C_1$-$C_{30}$-alkylene-$L^2$-L, L-$C_3$-$C_{16}$-cycloalkylene-$L^1$-$C_3$-$C_{16}$-cycloalkylene-L or L-$C_6$-$C_{20}$-arylene-$L^1$-$C_6$-$C_{20}$-arylene-L, where each alkylene may be interrupted by one or more identical or different non-adjacent O or S, where each cycloalkylene and each heterocycloalkylene may be interrupted by one or more CO, and where
  L is a single bond, C(S)O or C(S)$NR^{12}$,
  $L^1$ is a single bond, O or S; and
  $L^2$ is $C_3$-$C_{20}$-cycloalkylene, heterocycloalkylene or $C_6$-$C_{20}$-arylene;
Q if b is 2, and a and c are both 0
  is $L^5$-$C_1$-$C_{30}$-alkylene-$L^5$, $L^5$-$C_3$-$C_{16}$-cycloalkylene-$L^5$, $L^5$-heterocycloalkylene-$L^5$, $L^5$-$C_6$-$C_{20}$-arylene-$L^5$, $L^5$-$C_3$-$C_{16}$-cycloalkylene-$L^7$-$C_3$-$C_{16}$-cycloalkylene-$L^5$ or $L^5$-$C_6$-$C_{20}$-arylene-$L^7$-$C_6$-$C_{20}$-arylene-$L^5$, where alkylene may be interrupted by one or more identical or different non-adjacent O or S, where each cycloalkylene and each heterocycloalkylene may be interrupted by one or more CO, where $L^5$ is a single bond S, O, $NR^6$, CO, COO, OCO, $NR^{10}$C(O) or $CONR^{10}$, $L^7$ is a single bond, O or S;
Q if c is 2, and a and b are both 0
  is $C_1$-$C_{30}$-alkylene, $C_3$-$C_{16}$-cycloalkylene, heterocycloalkylene, $C_6$-$C_{20}$-arylene, $C_3$-$C_{16}$-cycloalkylene-$L^{11}$-$C_3$-$C_{16}$-cycloalkylene, $C_6$-$C_{20}$-arylene-$L^{11}$-$C_6$-$C_{20}$-arylene, where alkylene may be interrupted by one or more identical or different non-adjacent O or S, where each cycloalkylene and each heterocycloalkylene may be interrupted by one or more CO, and where $L^{11}$ is a single bond, O or S;
Q if the sum of a+b+c is 3
  is $C_1$-$C_{30}$-alkanetriyl, $C_3$-$C_{16}$-cycloalkanetriyl, $C_6$-$C_{20}$-arenetriyl, $C_1$-$C_{30}$-alkanetriyl-$L^{14}$-$L^{15}$, $C_1$-$C_{30}$-alkylene-$L^{14}$-$L^{16}$, $C_6$-$C_{20}$-arenetriyl-$L^{14}$-$L^{15}$-$C_6$-$C_{20}$-arylene, and $C_6$-$C_{20}$-arylene-$L^{14}$-$L^{15}$-$C_3$-$C_6$-cycloalkanetriyl
  where each alkanetriyl and each alkylene may be interrupted by one or more identical or different non-adjacent groups O, S, CO, C(O), $NR^6$, $NR^{10}$C(O), $CONR^{10}$, C(O)O or OC(O) and/or may carry one or more identical or different radicals $R^{Qa}$,
  where each cycloalkanetriyl may be interrupted by one or more CO groups, where $L^{14}$ is a single bond, O or S, $L^{15}$ is $C_3$-$C_{20}$-cycloalkylene, heterocycloalkylene or $C_6$-$C_{20}$-arylene and where $L^{16}$ is arenetriyl,
where $R^{1a}$, $R^{1b}$, $R^{1c}$, $R^{1d}$, $R^{2a}$, $R^{2b}$, $R^{2c}$, $R^{2g}$, $R^{2h}$, $R^{Qa}$, $R^4$, $R^5$, $R^6$, $R^7$, $R^8$, $R^9$, $R^{10}$, $R^{11}$, $R^{12}$ and $R^{13}$ are as defined above and have preferably one of the preferred meanings and where the sum of a+b+c is 1, 2 or 3.

Another more preferred embodiment of the invention relates to compositions, compounds methods and uses, where in formula I the sum of a+b+c is 2. Q is a divalent linker, which is selected from $C_1$-$C_{30}$-alkylene, $C_3$-$C_{16}$-cycloalkylene, heterocycloalkylene, $C_6$-$C_{20}$-arylene, $C_3$-$C_{16}$-cycloalkylene-$L^{11}$-$C_3$-$C_6$-cycloalkylene, $C_6$-$C_{20}$-arylene-$L^{11}$-$C_6$-$C_{20}$-arylene, where alkylene may be interrupted by one or more identical or different non-adjacent phenylene, C(O)O, OC(O); O or S, where each cycloalkylene and each heterocycloalkylene may be interrupted by one or more CO, and where $L^{11}$ is a single bond, O or S.

Another more preferred embodiment of the invention relates to compositions, compounds methods and uses where in formula I X is S, and $R^1$ and $R^2$ in combination have the following meanings:

$R^1$ is $C_6$-$C_{10}$-aryl which may be substituted by one, two or three radicals selected from nitro and $C_1$-$C_4$-alkyl; and $R^2$ is $COOR^9$, where $R^9$ is $C_1$-$C_{12}$-alkyl which may be interrupted by one, two or three oxygen and/or may be substituted by phenyl or $R^1$ is $C_1$-$C_{12}$-alkyl; $C_1$-$C_{12}$-alkyl which is substituted by $C_1$-$C_4$-alkoxycarbonyl or phenyl-$C_1$-$C_4$-alkyl-S—$C_1$-$C_4$-alkoxy; $C_3$-$C_8$-cycloalkyl; or $C_2$-$C_4$-alkenyl; and $R^2$ is $COOR^9$, where $R^9$ is $C_1$-$C_{12}$-alkyl which may be interrupted by one, two or three oxygen and/or may be substituted by phenyl;

or $R^1$ is $C_3$-$C_{12}$-alkyl which is interrupted by one, two, three or more than three groups selected independently of each other from O and S; and $R^2$ is $COOR^9$, where $R^9$ is $C_1$-$C_{12}$-alkyl which may be interrupted by one, two or three oxygen and/or may be substituted by phenyl;

or $R^1$ is benzyl, where the aromatic ring is substituted by $C_1$-$C_4$-alkanoyl-S—$C_1$-$C_2$-alkyl or chlorine; and $R^2$ is $COOR^9$, where $R^9$ is $C_1$-$C_{12}$-alkyl which may be interrupted by one, two or three oxygen and/or may be substituted by phenyl or $R^1$ $C_1$-$C_{12}$-alkyl which is substituted by $C_1$-$C_4$-alkoxy-$C_1$-$C_4$-alkoxycarbonyl or $C_1$-$C_4$-alkoxycarbonyl; $C_3$-$C_8$-cycloalkyl; $C_6$-$C_{10}$-aryl which may be substituted by one, two or three radicals selected from nitro, $C_2$-$C_4$-alkenyl and $C_1$-$C_4$-alkyl; and $R^2$ is $C_1$-$C_6$-alkyl;
or
$R^1$ is benzyl or phenethyl, where the aromatic ring of two last-mentioned radicals may be substituted by one, two or three radicals selected from nitro, $C_2$-$C_4$-alkenyl and $C_1$-$C_4$-alkyl; and
$R^2$ is $C_1$-$C_6$-alkyl;
or
$R^1$ is $C_1$-$C_{12}$-alkyl which is substituted by SH or $C_1$-$C_3$alkylcarbonylsulfanyl; and
$R^2$ is $C_1$-$C_6$-alkyl;
or
$R^1$ is $C_6$-$C_{10}$-aryl, which may be substituted by substituted by one, two or three radicals selected from nitro and $C_1$-$C_4$-alkyl; and
$R^2$ is 5- or 6-membered heteroaryl, especially pyridyl such as 2-pyridiyl or 4-pyridyl.

Another more preferred embodiment of the invention relates to compositions, compounds methods and uses, where in formula I X—$R^1$ and $R^2$ together with the oxime carbon atom to which they are attached are a ring R-1, R-3, R-5, R-13 or R-19

R-1

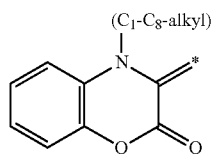
R-3

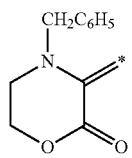
R-5

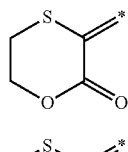
R-13

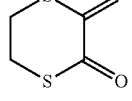
R-19 where * denotes the point of attachment to the oxime nitrogen atom.

According to a further particular aspect of this embodiment —X—$R^1$ together with $R^2$ are —S—($C_1$-$C_8$-alkylene)-S—C(O)—.

According to a further particular aspect of this embodiment —X—$R^1$ together with $R^2$ are —S—C(S)—$NR^{12}$—C(O)—, where $R^{12}$ is as defined above. In this embodiment, X—$R^1$ and $R^2$ together with the oxime carbon atom to which they are the following ring R-20

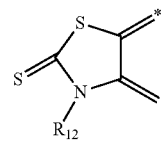
R-20 where
* is the point of attachment to the oxime nitrogen atom; and $R^{12}$ is as defined above, preferably H, $C_1$-$C_8$-alkyl or $C_2$-$C_6$-alkenyl, in particular allyl.

According to a further particular aspect of this embodiment —X—$R^1$ together with $R^2$ are S—C(=$NOR^{15}$)—C(O)—$NR^{12}$—C(O), where $R^{12}$ is as defined above and $R^{15}$ is hydrogen or phenylsulfonyl where the phenyl moiety may be substituted by $C_1$-$C_4$-alkyl or $C_1$-$C_4$-alkoxy. According to this aspect of the embodiment, X—$R^1$ and $R^2$ together with the carbon atom of the oxime group ring to which they are attached form the ring R-21

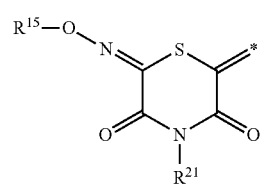
R-21 where
* is the point of attachment to the oxime nitrogen atom; and $R^{12}$ is as defined above, preferably H, $C_1$-$C_8$-alkyl or $C_2$-$C_6$-alkenyl Another more preferred embodiment of the invention relates to compositions, compounds methods and uses, where in formula I $R^3$ is preferably selected from $C_2$-$C_{12}$-alkyl, $C_2$-$C_{12}$-alkenyl, phenyl-$C_1$-$C_4$-alkyl, $C_1$-$C_4$-haloalkyl, $C_3$-$C_{12}$-cycloalkyl, $C_3$-$C_{12}$-cycloalkyl-$C_1$-$C_{12}$-alkyl, heterocyclyl and $C_6$-$C_{10}$-aryl, where
each cycloalkyl and heterocyclyl may be interrupted by one or two CO and/or may be substituted by one or more $C_1$-$C_{12}$-alkyl and
where aryl may be substituted by one or more identical or different radicals selected from $C_1$-$C_{12}$-alkyl, $C_1$-$C_4$-haloalkyl, $C_2$-$C_{12}$-alkenyl, F, Cl, Br, I, CN, $NO_2$, $SR^4$, $OR^5$, $NR^6R^7$, $COR^8$, $COOR^9$, $CONR^{11}R^{11}$ or phenyl,
where $R^4$, $R^5$, $R^6$, $R^7$, $R^8$, $R^9$, $R^{10}$ and $R^{11}$ are as defined above.

Another more preferred embodiment of the invention relates to compositions, compounds methods and uses, where in formula I a is 2, b and c are both 0. According to a particular aspect of this embodiment, X is S, $R^2$ is $C_1$-$C_{12}$-alkyl and Q is $C_1$-$C_{30}$-alkylene which may be interrupted by one, two, three or four non-adjacent heteroatoms selected from O and S.

According to a further particular aspect of this embodiment, X is S, $R^2$ is $COOR^9$ and Q is $C_6$-$C_{20}$-arylen-S—$C_6$-$C_{20}$-arylen. $R^9$ is as defined above and preferably has one of the preferred meanings.

Another more preferred embodiment of the invention relates to compositions, compounds methods and uses, where in formula I a is 3, b and c are both 0, more preference is likewise given to those compounds, in which X is S, $R^2$ is $COOR^9$ and Q is $C_1$-$C_{20}$-alkanetriyl which may be interrupted by 3, 4, 5, 6, 7, 8, or 9 identical or different groups selected from O, S, $NR^6$, CO, C(O)O. $R^9$ is as defined above and preferably has one of the preferred meanings.

Another more preferred embodiment of the invention relates to compositions, compounds methods and uses, where in formula I b is 2, a and c are both 0, more preference is likewise given to those compounds, in which X is S, $R^1$ is $C_1$-$C_{12}$-alkyl which is substituted by $COOR^9$ and Q is $C_1$-$C_{30}$-alkylene which may be interrupted once, twice, three times, four times, five times or six times by non-adjacent O or S. $R^9$ is as defined above and preferably has one of the preferred meanings.

Another more preferred embodiment of the invention relates to compositions, compounds methods and uses, where in formula I c is 2, a and b are both 0, more preference is likewise given to those compounds, in which X is S, $R^2$ is $COOR^9$ and Q is $C_6$-$C_{20}$-arylen.

Compounds of the formula I, where a is 1, b is 0, c is 0 and Q is a radical $R^1$ are also referred to as compounds IA.1

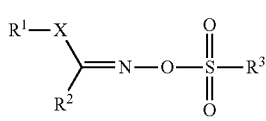
(IA.1)

where $R^1$, $R^2$, $R^3$ and X are as defined above and preferably have one of the meanings being preferred.

Compounds of the formula I, where a is 2, 3 or 4 are referred to as compounds IA

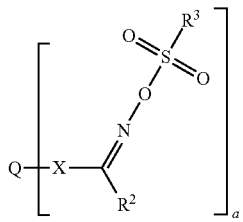
(IA)

where Q, $R^1$, $R^2$, $R^3$ and X are as defined above and preferably have one of the meanings being preferred.

Compounds of the formula IA, where a is 2, b and c are both 0 are also referred to as compounds IA.2. Compounds of the formula IA, where a is 3, b and c are both 0 are also referred to as compounds IA.3. Compounds of the formula IA, where a is 4, b and c are both 0 are also referred to as compounds IA.4.

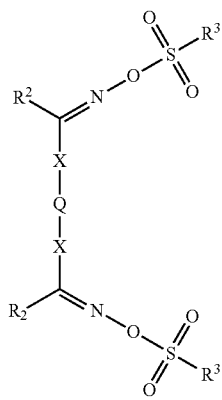
(IA.2)

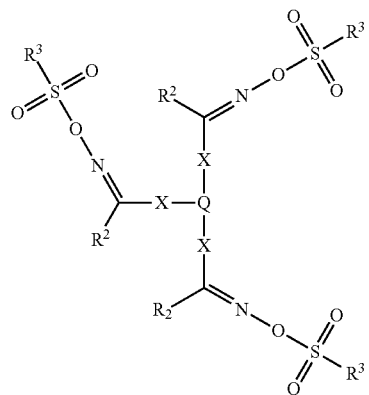
(IA.3)

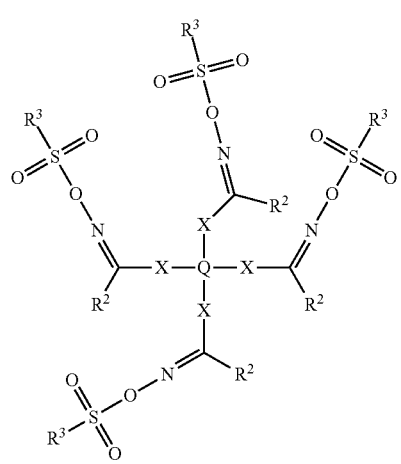
(IA.4)

where Q, $R^1$, $R^2$, $R^3$ and X are as defined above and preferably have one of the meanings being preferred.

Compounds of the formula I, where b is 2 or 3 are also referred to as compounds IB

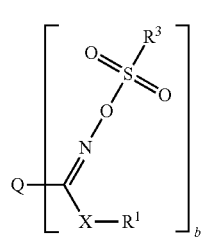
(IB)

where Q, $R^1$, $R^2$, $R^3$ and X are as defined above and preferably have one of the meanings being preferred.

Compounds of the formula IB, where b is 2, a and c are both 0 are also referred to as compounds IB.2. Compounds of the formula IB, where b is 3, a and c are both 0 are also referred to as compounds IB.3

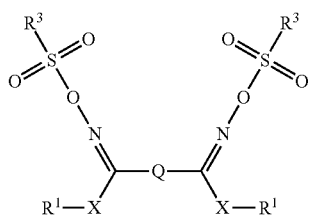

(IB.2)

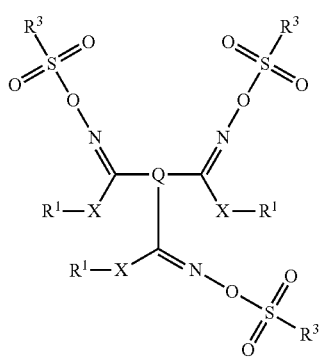

(IB.3)

where Q, $R^1$, $R^2$, $R^3$ and X are as defined above and preferably have one of the meanings being preferred.

Compounds of the formula I, where c is 2 or 3 are also referred to as compounds IC

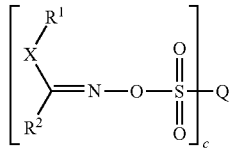

(IC)

where Q, $R^1$, $R^2$, $R^3$ and X are as defined above and preferably have one of the meanings being preferred.

Compounds of the formula IC, where c is 2, a and b are both 0 are also referred to as compounds IC.2. Compounds of the formula IC, where C is 3, a and b are both 0 are also referred to as compounds IC.3.

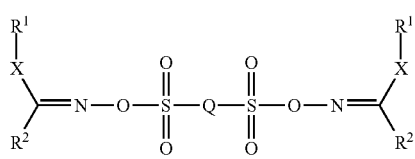

(IC.2)

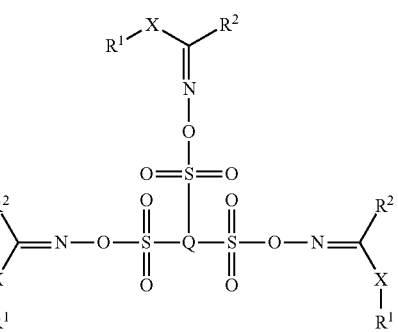

(IC.3)

where Q, $R^1$, $R^2$, $R^3$ and X are as defined above and preferably have one of the meanings being preferred A skilled person will readily understand that the preferences given for Q, X, $R^1$, $R^2$, $R^3$, a, b and c in connection with compounds of formula (I) also apply for formulae IA, IA.1, IA.2, IA.3, IA.4, IB, IB.2, IB.3, IC, IC.2 and IC.3 as defined hereinafter.

Another more preferred embodiment of the invention relates to compositions, compounds methods and uses, where in formula I IA.1, $R^3$ is $C_2$-$C_4$-alkyl, $C_2$-$C_6$-alkenyl, phenyl or benzyl where each of the two last mentioned radicals may be unsubstituted or may carry one, two, three, four or five radicals independently of one another selected fluorine, nitro, $C_1$-$C_4$-alkyl, $C_1$-$C_4$-alkoxy, $C_1$-$C_4$-fluoroalkyl, $C_1$-$C_4$-alkoxycarbonyl and $C_2$-$C_6$-alkenyl; and —X—$R^1$ together with $R^2$ are —X—($C_1$-$C_8$-alkylene)-O—C(O)— or —X-(o-phenylene)-O—C(O)— and X is N($C_1$-$C_8$-alkyl), N(benzyl), N($C_1$-$C_4$-alkoxy-$C_1$-$C_4$-alkyl) or S. In a further specific embodiment $R^3$ is 5- or 6-membered saturated heterocyclyl comprising besides carbon atoms 1 or 2 heteroatoms or heteroatomic groups selected from O, S, SO and $SO_2$, thienyl, Another more preferred embodiment of the invention relates to compositions, compounds methods and uses, where in formula IA.1, X is S, N(benzyl) or N($C_1$-$C_6$-alkyl);

$R^1$ $C_3$-$C_6$-alkyl; $C_1$-$C_4$-alkoxycarbonyl-$C_1$-$C_2$-alkyl; $C_1$-$C_4$-alkoxy-$C_1$-$C_4$-alkoxycarbonyl-$C_1$-$C_2$-alkyl; $C_2$-$C_4$-alkenyl; benzylsulfanyl-$C_1$-$C_4$-alkyl-O—$C_1$-$C_4$-alkyl; phenethylsulfanyl-$C_1$-$C_4$-alkyl-O—$C_1$-$C_4$-alkyl; —COO($CH_2CH_2O$)$_x$($C_1$-$C_4$-alkyl) with x being 1, 2, 3, 4 or 5; benzoyl; benzoyl which is substituted by one, two or three radicals selected independently of one another from $C_1$-$C_4$-alkyl and $C_2$-$C_4$-alkenyl; phenyl; phenyl which is substituted by one, two or three radicals selected from nitro and $C_1$-$C_4$-alkyl; benzyl; or benzyl where the phenyl moiety of benzyl is substituted by one, two or three radicals selected from nitro and $C_1$-$C_4$-alkyl; or $R^1$ is $C_1$-$C_4$-haloalkoxycarbonyl-$C_1$-$C_2$-alkyl, $C_3$-$C_8$-cycloalkyl; benzyl in which the phenyl moiety is substituted by chlorine; benzyl which is substituted by $C_1$-$C_4$-alkanoyl-S—$C_1$-$C_2$-alkyl; mercapto-$C_3$-$C_6$-alkyl; mercapto-$C_3$-$C_6$-alkyl-S—$C_1$-$C_2$-alkyl; $C_1$-$C_{12}$-alkyl which is substituted by —O—C(=O)—$CH_2$—S—($C_1$-$C_2$-alkyl)-S—C(=NOH)—$C_1$-$C_2$-alkyl; 5-, 6-, 9- or 10 membered heteroaryl comprising besides carbon atoms 1 or 2 heteroatoms selected from O, S and N; 5- or 6-membered saturated or partially unsaturated heterocyclyl comprising besides carbon atoms 1 or 2 heteroatoms selected from O, S and N;

$R^2$ is $C_1$-$C_6$-alkyl; $C_3$-$C_8$-cycloalkyl; $C_1$-$C_4$-alkoxycarbonyl; —C(O)O—$C_1$-$C_4$-alkyl-phenyl; —COO($CH_2CH_2O$)$_v$($C_1$-$C_4$-alkyl) with v being 1, 2, 3 or 4;

phenyl;
phenyl which is substituted by 1, 2 or 3 radicals selected from nitro, $C_1$-$C_4$-alkyl and $C_1$-$C_4$-akoxycarbonyl;
pyridyl; or

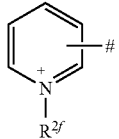

with $R^{2f}$ being $C_1$-$C_{12}$-alkylene-COO$^-$, $C_1$-$C_{12}$-alkylene-$S(O)_2O^-$ or $C_1$-$C_{12}$alkylene-$OS(O)_2O^-$; or $R^2$ is $C_1$-$C_4$-haloalkoxycarbonyl or morpholinoamide, and;
$R^3$ is $C_1$-$C_4$-alkyl; $C_1$-$C_4$-haloalkyl; $C_3$-$C_{12}$-cycloalkyl-$C_1$-$C_6$-alkyl, where the cycloalkyl moiety may be interrupted by one or two CO groups and which may carry 1, 2, 3 or 4 $C_1$-$C_4$-alkyl groups; $C_2$-$C_4$-alkenyl; $C_3$-$C_{12}$-cycloalkyl which may be interrupted by one or two CO groups and which may carry 1, 2, 3 or 4 $C_1$-$C_4$-alkyl groups; $C_2$-$C_4$-alkenyl; phenyl-$C_1$-$C_4$-alkyl where the aromatic ring in the last-mentioned radical may be substituted by one, two, three, four or five radicals independently of one another selected from fluorine, $C_1$-$C_4$-alkyl, $C_1$-$C_4$-haloalkyl, $C_2$-$C_4$-alkenyl, $C_1$-$C_4$-alkoxy, $C_1$-$C_4$-alkoxycarbonyl and nitro, especially benzyl or benzyl, where the aromatic ring is substituted by 1, 2, 3, 4 or 5 radicals selected from fluorine, $C_1$-$C_2$-fluoroalkyl, vinyl, allyl, nitro, methoxy, methoxycarbonyl, ethoxycarbonyl; naphthyl where the aromatic ring in the last-mentioned radical may be substituted by one, two, three, four or five radicals independently of one another selected from fluorine, $C_1$-$C_4$-alkyl, $C_1$-$C_4$-haloalkyl, $C_2$-$C_4$-alkenyl, $C_1$-$C_4$-alkoxy, $C_1$-$C_4$-alkoxycarbonyl and nitro, preferably $C_1$-$C_4$-alkyl; camphoryl; phenyl; or phenyl which is substituted by 1, 2, 3, 4 or 5 radicals selected from fluorine, $C_1$-$C_2$-fluoroalkyl, vinyl, allyl, nitro, methoxy, methoxycarbonyl, ethoxycarbonyl, or $R^3$ is 5- or 6-membered saturated heterocyclyl comprising besides carbon atoms 1 or 2 heteroatoms or heteroatomic groups selected from O, S, SO and $SO_2$, thienyl.

Another more preferred embodiment of the invention relates to compositions, compounds methods and uses, where in formula IA.1
$R^3$ is $C_1$-$C_4$-alkyl; naphthyl; phenyl; phenyl which is substituted by one or two $C_1$-$C_4$-alkyl, $C_1$-$C_4$-alkoxy or nitro; or phenyl-$C_1$-$C_2$-alkyl in which the phenyl ring may be substituted; and
—X—$R^1$ together with $R^2$ are —S—($C_1$-$C_8$-alkylene)-O—C(O)—; —S-(o-phenylene)-O—C(O)—; —N($C_1$-$C_8$-alkyl)-($C_1$-$C_8$-alkylene)-O—C(O)—; N (benzyl)($C_1$-$C_8$-alkylene)-O—C(O)—; —N($C_1$-$C_8$-alkyl)-(o-phenylene)-O—C(O)— or S—($C_1$-$C_8$-alkylene)-S—C(O).

Another more preferred embodiment of the invention relates to compositions, compounds methods and uses, where in formula IA.
$R^3$ is $C_1$-$C_4$-alkyl; $C_3$-$C_{12}$-cycloalkyl-$C_1$-$C_{12}$-alkyl; naphthyl; phenyl; phenyl which is substituted by one or two $C_1$-$C_4$-alkyl, $C_1$-$C_4$-alkoxy or nitro; or phenyl-$C_1$-$C_2$-alkyl in which the phenyl ring may be substituted; and
—X—$R^1$ together with $R^2$ are S—C(S)—$NR^{12}$—C(O) or S—C(=$NOR^{15}$)—C(O)—$NR^{12}$—C(O), where $R^{12}$ and $R^{15}$ are as defined above.

Another even more preferred embodiment of the invention relates to compositions, compounds methods and uses, where in formula IA.1, —X—$R^1$ together with $R^2$ are —N($C_1$-$C_8$-alkyl)-($C_1$-$C_8$-alkylene)-O—C(O)—, N(benzyl)($C_1$-$C_8$-alkylene)-O—C(O)— or —N($C_1$-$C_8$-alkyl)-(o-phenylene)-O—C(O)—; and
$R^3$ is $C_1$-$C_4$-alkyl; $C_2$-$C_4$-alkenyl; benzyl; naphthyl, phenyl; or phenyl which is substituted by one, two, three, four or five radicals selected from fluorine, $C_1$-$C_4$-alkyl, vinyl, $C_1$-$C_4$-alkoxy or nitro.

Another even more preferred embodiment of the invention relates to compositions, compounds methods and uses, where in formula IA.1
X is S;
$R^1$ is phenyl or phenyl which is substituted by one, two or three radicals selected from $C_1$-$C_4$-alkyl and nitro; and
$R^2$ is $C_1$-$C_4$-alkoxycarbonyl, —C(O)O—$C_1$-$C_4$-alkyl-phenyl or —COO($CH_2CH_2O)_x$($C_1$-$C_4$-alkyl) with x being 1, 2, 3 or 4; and
$R^3$ is $C_1$-$C_4$-alkyl; $C_2$-$C_4$-alkenyl; benzyl; phenyl; or phenyl which is substituted by one, two, three, four or five radicals selected from fluorine, $C_1$-$C_4$-alkyl, $C_1$-$C_4$-alkoxy, vinyl or nitro.

Another even more preferred embodiment of the invention relates to compositions, compounds methods and uses, where in formula IA.1
X is S;
$R^1$ is $C_3$-$C_6$-alkyl; $C_2$-$C_4$-alkenyl; or $C_1$-$C_4$-alkoxycarbonyl-$C_1$-$C_2$-alkyl;
$R^2$ is $C_1$-$C_4$-alkoxycarbonyl, —C(O)O—$C_1$-$C_4$-alkyl-phenyl or —COO($CH_2CH_2O)_x$($C_1$-$C_4$-alkyl) with x being 1, 2, 3 or 4; and
$R^3$ is $C_1$-$C_4$-alkyl; $C_2$-$C_4$-alkenyl; benzyl; napthyhl, phenyl; or phenyl which is substituted by one, two, three, four or five radicals selected from fluorine, $C_1$-$C_4$-alkyl, $C_1$-$C_4$-alkoxy, vinyl or nitro.

Another even more preferred embodiment of the invention relates to compositions, compounds methods and uses, where in formula IA.1
X is S;
$R^1$ is phenyl or phenyl which is substituted by one, two or three radicals selected from $C_1$-$C_4$-alkyl and nitro;
$R^2$ is methyl, ethyl or $C_3$-$C_6$-alkyl and
$R^3$ is $C_1$-$C_4$-alkyl; $C_2$-$C_4$-alkenyl; benzyl; naphthyl, phenyl; or phenyl which is substituted by one, two, three, four or five radicals selected from fluorine, $C_1$-$C_4$-alkyl, $C_1$-$C_4$-alkoxy, vinyl or nitro.

Another even more preferred embodiment of the invention relates to compositions, compounds methods and uses, where in formula IA.1
X is S;
$R^1$ is phenyl or phenyl which is substituted by one, two or three radicals selected from $C_1$-$C_4$-alkyl and nitro;
$R^2$ is pyridyl; phenyl or phenyl which is substituted by one, two or three radicals selected from $C_1$-$C_4$-alkyl and nitro; and
$R^3$ is $C_1$-$C_4$-alkyl; $C_2$-$C_4$-alkenyl; benzyl; phenyl; or phenyl which is substituted by one, two, three, four or five radicals selected from fluorine, $C_1$-$C_4$-alkyl, $C_1$-$C_4$-alkoxy, vinyl or nitro.

Another even more preferred embodiment of the invention relates to compositions, compounds methods and uses, where in formula IA.1
X is S;
$R^1$ is phenyl-$C_1$-$C_4$-alkylene, where the phenyl moiety may be substituted by one, two or three radicals selected from nitro and $C_1$-$C_4$-alkyl
$R^2$ is $C_1$-$C_6$-alkyl, and $R^3$ is $C_1$-$C_4$-alkyl; $C_2$-$C_4$-alkenyl; benzyl; naphthyl; phenyl; or phenyl which is substituted by one, two, three, four or five radicals selected from fluorine, $C_1$-$C_4$-alkyl, $C_1$-$C_4$-alkoxy, vinyl or nitro.

Another even more preferred embodiment of the invention relates to compositions, compounds methods and uses, where in formula IA.2

X is S; $N(C_1$-$C_6$-alkyl), $N(C_1$-$C_4$-alkoxy-$C_1$-$C_4$-alkyl), N(benzyl), N(phenethyl), $N(C_2$-$C_6$-alkenyl) or $N(C_3$-$C_8$-cycloalkyl-$C_1$-$C_4$-alkyl);

each $R^2$ is independently selected from the group consisting of $C_1$-$C_4$-alkyl; —C(O)O—$C_1$-$C_4$-alkyl-phenyl or $C_1$-$C_4$-alkoxycarbonyl; in addition, $R^2$ may be selected from morpholinoamide;

each $R^3$ is independently selected from the group consisting of $C_1$-$C_4$-alkyl; $C_2$-$C_4$-alkenyl; benzyl; napthyl, phenyl; phenyl which is substituted by one, two, three, four or five radicals selected from fluorine $C_1$-$C_4$-alkyl, $C_1$-$C_4$-alkoxy, vinyl or nitro; in addition, $R^3$ may be selected from 5- or 6-membered saturated heterocyclyl comprising besides carbon atoms 1 or 2 heteroatoms or heteroatomic groups selected from O, S, SO and $SO_2$; and thienyl;

Q is phenylen-S-phenylen; $C_1$-$C_{10}$-alkylene; $C_1$-$C_{10}$-alkylene which is interrupted by one, two, three or four non-adjacent heteroatoms selected from phenylene, C(O)O, OC(O), O and S or Q is phenylene.

According to a particular preferred aspect of this embodiment, each $R^2$ has the same meaning. According to a further particular preferred aspect of this embodiment, each $R^2$ has different meanings. According to a further preferred aspect of this embodiment, each $R^3$ has the same meaning. According to a further preferred aspect of this embodiment, each $R^3$ has different meanings. According to a further preferred aspect of this embodiment, each $R^2$ has a different meaning and each $R^3$ has a different meaning.

Another even more preferred embodiment of the invention relates to compositions, compounds methods and uses, where in formula IA.3, X is S;
each $R^2$ is independently selected from the group consisting of $C_1$-$C_4$-alkyl, —C(O)O—$C_1$-$C_4$-alkyl-phenyl or $C_1$-$C_4$-alkoxycarbonyl; in addition, $R^2$ may be selected from morpholinoamide;
each $R^3$ is independently selected from the group consisting of $C_1$-$C_4$-alkyl; $C_2$-$C_4$-alkenyl; benzyl; napthyl; phenyl; or phenyl which is substituted by one, two, three, four or five radicals selected from fluorine, $C_1$-$C_4$-alkyl, $C_1$-$C_4$-alkoxy, vinyl or nitro; in addition $R^3$ may be selected from 5- or 6-membered saturated heterocyclyl comprising besides carbon atoms 1 or 2 heteroatoms or heteroatomic groups selected from O, S, SO and $SO_2$, thienyl,
Q is $C_1$-$C_{20}$-alkanetriyl; $C_1$-$C_{20}$-alkanetriyl, which is interrupted by 3, 4, 5, 6, 7, 8, or 9 identical or different groups selected from O, S, $NR^6$, CO, C(O)O, where $R^6$ is as defined above.

Another even more preferred embodiment of the invention relates to compositions, compounds methods and uses, where in formula IA.4

X is S;
each $R^2$ is independently selected from the group consisting of $C_1$-$C_4$-alkyl or $C_1$-$C_4$-alkoxycarbonyl;
each $R^3$ is independently selected from the group consisting of $C_1$-$C_4$-alkyl, $C_2$-$C_6$-alkenyl, 5- or 6-membered saturated heterocyclyl comprising besides carbon atoms 1 or 2 heteroatoms or heteroatomic groups selected from O, S, SO and $SO_2$, thienyl, phenyl or benzyl where each of the two last mentioned radicals may be unsubstituted or may carry one, two, three, four or five radicals independently of one another selected fluorine, nitro, $C_1$-$C_4$-alkyl, $C_1$-$C_4$-alkoxy, $C_1$-$C_4$-fluoroalkyl, $C_1$-$C_4$-alkoxycarbonyl and $C_2$-$C_6$-alkenyl;

Q is $C_1$-$C_{20}$-alkanetetrayl, which may be interrupted by 3, 4, 5, 6, 7, 8, or 9 identical or different groups selected from O, S, $NR^6$, CO and C(O)O.

Another even more preferred embodiment of the invention relates to compositions, compounds methods and uses, where in formula IB.2 b is 2;
X is S;
each $R^1$ is selected from the group consisting of $C_1$-$C_6$-alkyl; $C_2$-$C_4$-alkenyl; benzyl; $C_1$-$C_4$-alkoxycarbonyl-$C_1$-$C_4$-alkyl; phenyl; phenyl which is substituted by one or two identical or different $C_1$-$C_4$-alkyl or $C_2$-$C_4$-alkenyl; in addition $R^1$ may be selected from mercapto-$C_3$-$C_6$-alkyl, mercapto-$C_3$-$C_6$-alkyl-S—$C_1$-$C_2$-alkyl, and
Q is $C_1$-$C_{10}$-alkylene which may be interrupted by one, two, three or four more non-adjacent atoms selected from O and S.

Another even more preferred embodiment of the invention relates to compositions, compounds methods and uses, where in formula IC.2

X is S;
each $R^1$ is selected from $C_1$-$C_6$-alkyl, $C_1$-$C_4$-alkoxy-$C_1$-$C_4$-alkoxycarbonyl-$C_1$-$C_2$-alkyl, $C_1$-$C_4$-alkoxycarbonyl-$C_1$-$C_2$-alkyl, $C_2$-$C_4$-alkenyl, $C_3$-$C_8$-cycloalkyl, $C_3$-$C_8$-cycloalkyl-$C_1$-$C_2$-alkyl, phenyl-$C_1$-$C_4$-alkylsulfanyl-$C_1$-$C_4$-alkyl-O—$C_1$-$C_4$-alkyl, phenethylsulfanyl-$C_1$-$C_4$-alkyl-O—$C_1$-$C_2$-alkyl, phenyl, phenethyl or benzyl where each phenyl moiety in the five last mentioned radicals may be substituted by one, two or three radicals selected from nitro, $C_2$-$C_4$-alkenyl and $C_1$-$C_4$-alkyl; in addition $R^1$ may be selected from $C_3$-$C_8$-alkenyl, mercapto-$C_3$-$C_6$-alkyl and mercapto-$C_3$-$C_6$-alkyl-S—$C_1$-$C_2$-alkyl,
each $R^2$ is selected from $C_1$-$C_6$-alkyl, $C_1$-$C_4$-alkoxycarbonyl or $C_1$-$C_4$-alkoxy-$C_1$-$C_4$-alkoxy-$C_1$-$C_4$-alkoxycarbonyl; in addition $R^2$ may be selected from morpholino-amide and
Q is phenylen or naphthylen.

Compounds of the formula I, where the sum of a+b+c is 2 and a is 1 and c is 1 and b is 0 are also referred to as compounds ID.

Another even more preferred embodiment of the invention relates to compositions, compounds methods and uses, where in formula ID

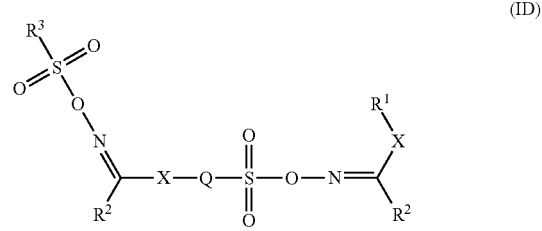

(ID)

where
Q is a divalent linker selected from is phenylene, phenylen-S-phenylene, or $C_1$-$C_{10}$-alkylene which may be interrupted by one, two, three or four non-adjacent groups selected from phenylene, O and S;
each X is S;
$R^1$ is $C_3$-$C_6$-alkyl, mercapto-$C_3$-$C_6$-alkyl, mercapto-$C_3$-$C_6$-alkyl-S—$C_1$-$C_2$-alkyl, $C_2$-$C_4$-alkenyl, $C_3$-$C_8$-cycloalkyl-$C_1$-$C_4$-alkyl, $C_1$-$C_4$-alkoxy-$C_1$-$C_4$-alkoxycarbonyl-$C_1$-$C_2$-alkyl, $C_1$-$C_4$-alkoxycarbonyl-$C_1$-$C_2$-alkyl, benzylsulfanyl-$C_1$-$C_4$-alkyl-O—$C_1$-$C_4$-alkyl, phenethylsulfanyl-$C_1$-$C_4$-alkyl-O—$C_1$-$C_4$-alkyl, phenyl or benzyl where phenyl and the phenyl moiety of benzyl may be substituted by one, two or three radicals selected from nitro and $C_1$-$C_4$-alkyl, benzyl which is substituted by $C_1$-$C_4$-alkanoyl-S—$C_1$-$C_2$-alkyl;

each $R^2$ is independently of each other selected from independently selected from the group consisting of $C_1$-$C_6$-alkyl, $C_1$-$C_4$-alkoxycarbonyl, morpholinoamide or $C_1$-$C_4$-alkoxy-$C_1$-$C_4$-alkoxy-$C_1$-$C_4$-alkoxycarbonyl; and $R^3$ is $C_1$-$C_4$-alkyl, $C_2$-$C_6$-alkenyl, 5- or 6-membered saturated heterocyclyl comprising besides carbon atoms 1 or 2 heteroatoms or heteroatomic groups selected from O, S, SO and $SO_2$, thienyl, phenyl or benzyl where each of the two last mentioned radicals may be unsubstituted or may carry one, two, three, four or five radicals independently of one another selected fluorine, nitro, $C_1$-$C_4$-alkyl, $C_1$-$C_4$-alkoxy, $C_1$-$C_4$-fluoroalkyl, $C_1$-$C_4$-alkoxycarbonyl and $C_2$-$C_6$-alkenyl.

Oxime sulfonates of the formula I can generally be prepared by methods described in the literature or in the experimental part. For example, oxime sulfonates of the formula I can generally be prepared by reacting suitable free oximes with the sulfonic acid halides. Accordingly, oxime sulfonates of the formulae IA, IA.1, IB and IC can be prepared by reacting suitable free oximes of the formula IIA, IIA,1, IIB or IIC with the sulfonic acid halides as shown in Scheme 1.

Scheme 1:

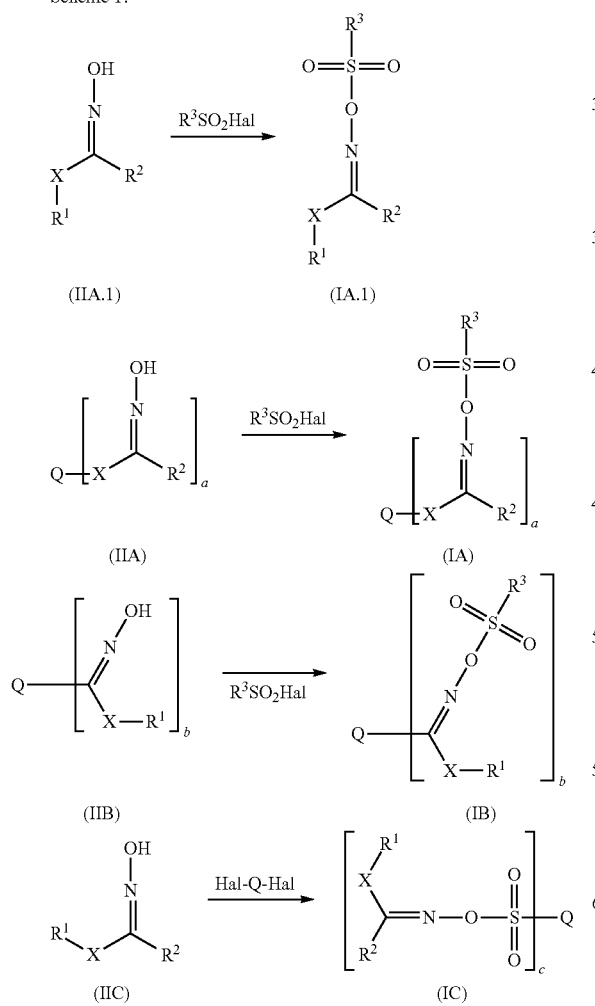

In Scheme 1, $R^1$, $R^2$, $R^3$ and Q are as defined above, a is 2 or 3 b is 2 or 3 and c is 2 or 3, Hal is halogen, preferably chlorine. A skilled person will readily understand that the oxime IIC is identical with the oxime IIA. Furthermore, a skilled person will readily understand that 2 equivalents of compound IIC are required as starting material if c is 2 in the compound IC. 3 equivalents of compound IIC are required as starting material if c is 3 in the compound IC.

These reactions usually are carried out in pyridine as solvent and base or in an inert solvent such as for example toluene, tetrahydrofuran (THF) or dimethylformamide (DMF) in the presence of a base for example a tertiary amine, such as triethylamine and diisopropylethylamine, or a secondary amine, such as diisopylamine or by reaction of the salt of an oxime with the desired acid chloride. These methods are disclosed, for example, in EP48615. The sodium salts of oximes can be obtained, for example, by reacting the oxime in question with a sodium alkoxide in dimethylformamide. Such reactions are well known to those skilled in the art, and are generally carried out at temperatures in the range of −30 to +50° C., preferably −10 to 20° C.

The oxime sulfonates of the formulae IA and IA.1 can be also prepared by reacting a suitable sulfonyloxyimidoyl chloride of the formula IIIA with a substance carrying one or more SH or NH groups, sulfinic acids or those salts as shown in Scheme 2.

Scheme 2:

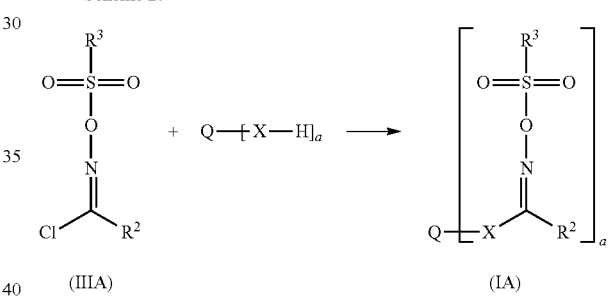

In Scheme 2, $R^2$, $R^3$, X and Q are as defined above, a is 1, 2, 3 or 4.

The compound of the formula (IIA) can be obtained as described in Scheme 3.

Scheme 3:

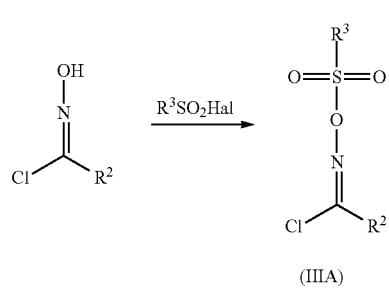

In Scheme 3, $R^2$ and $R^3$ are as defined above and Hal is halogen, preferably chlorine.

Compounds of the formula IA.2, where $R^2$ have the same or different meaning and/or $R^3$ have the same or can be prepared as outlined in Scheme 4:

Scheme 4:
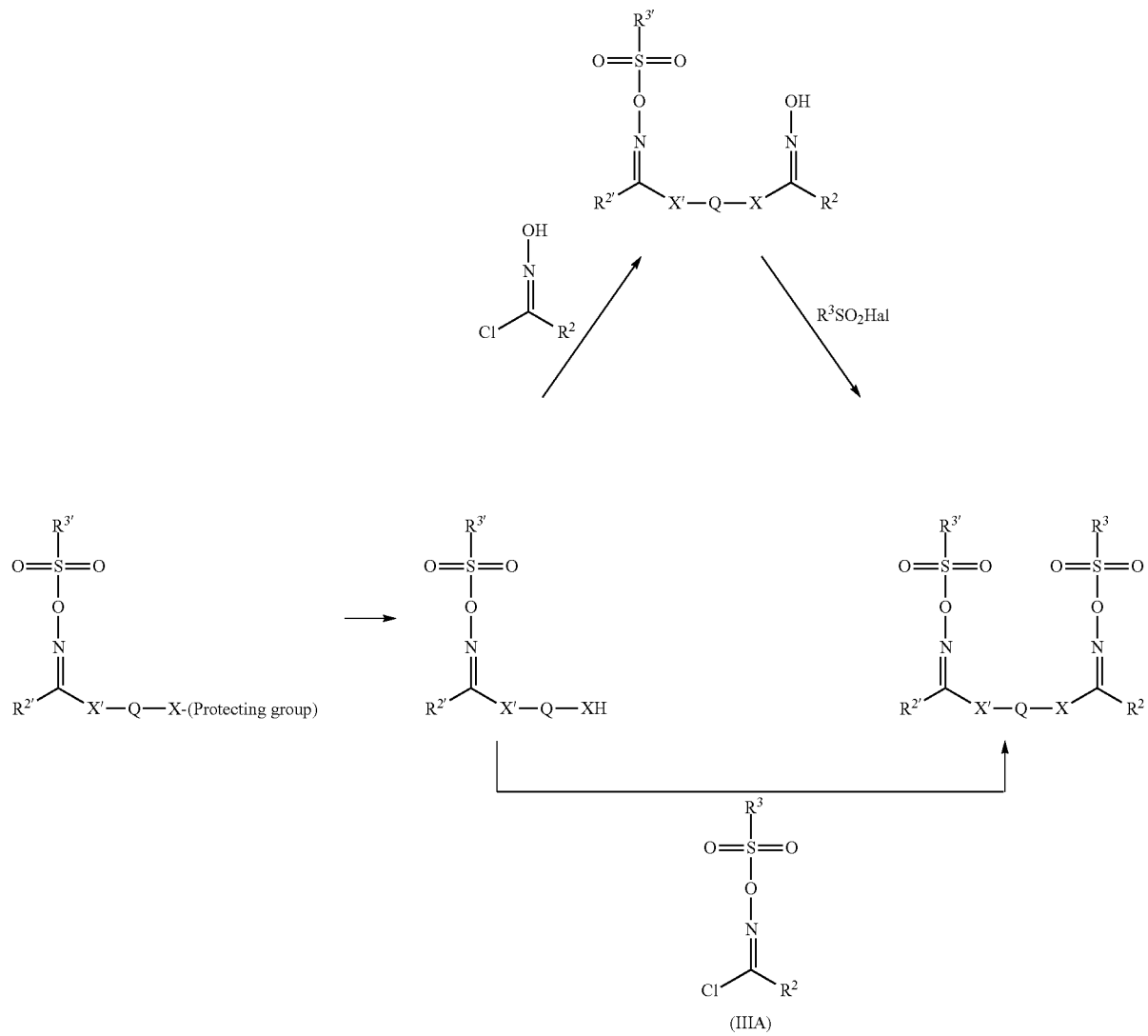
In Scheme 4, X, $R^2$, Q and $R^3$ are as defined above, $R^{2\prime}$ is as defined $R^2$, $R^{3\prime}$ is as defined $R^3$, X' is as defined X, Hal is halogen, preferably chlorine.
Compounds of the formula IC.2, where $R^2$ have the same or different meaning and/or $R^1$ have the same or can be prepared as outlined in Scheme 5:
Scheme 5:
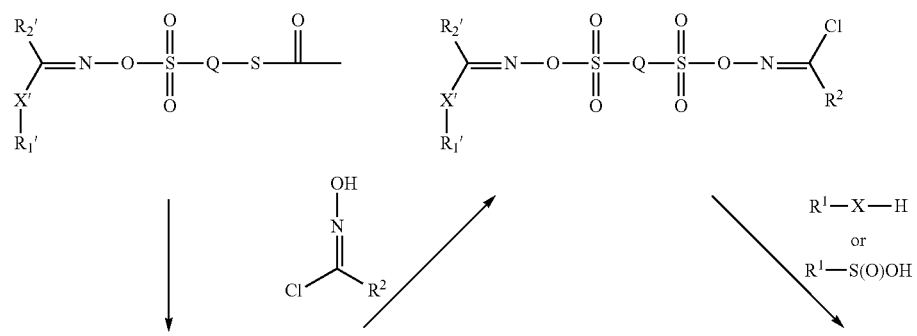

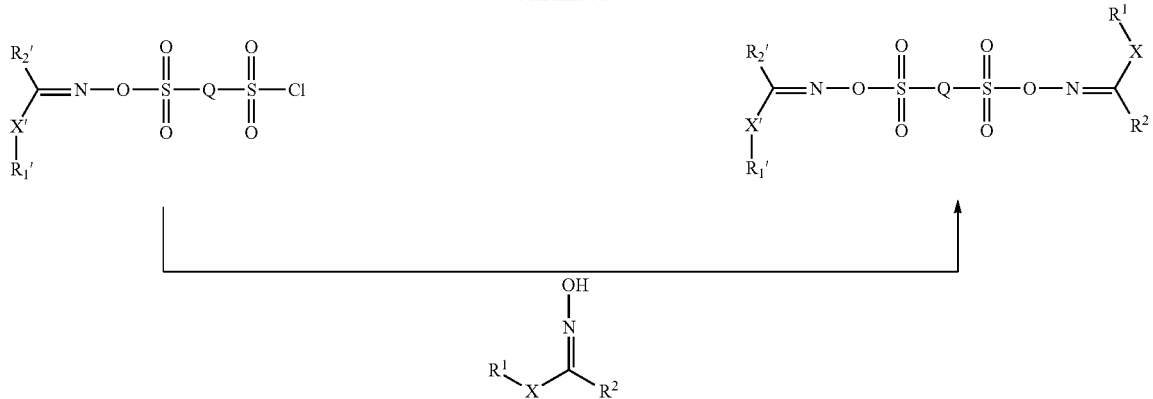

In Scheme 5, X, R¹, Q and R² are as defined above, R¹' is as defined R¹, R²' is as defined R².

Compounds of the formula ID, can be prepared as outlined in Scheme 6.

of the reaction mixture. It is well known that the rate of the reaction is pH-dependent, and the base can be added at the beginning or continuously during the reaction. Basic solvents such as pyridine can also be used as base and/or solvent or Scheme 6:

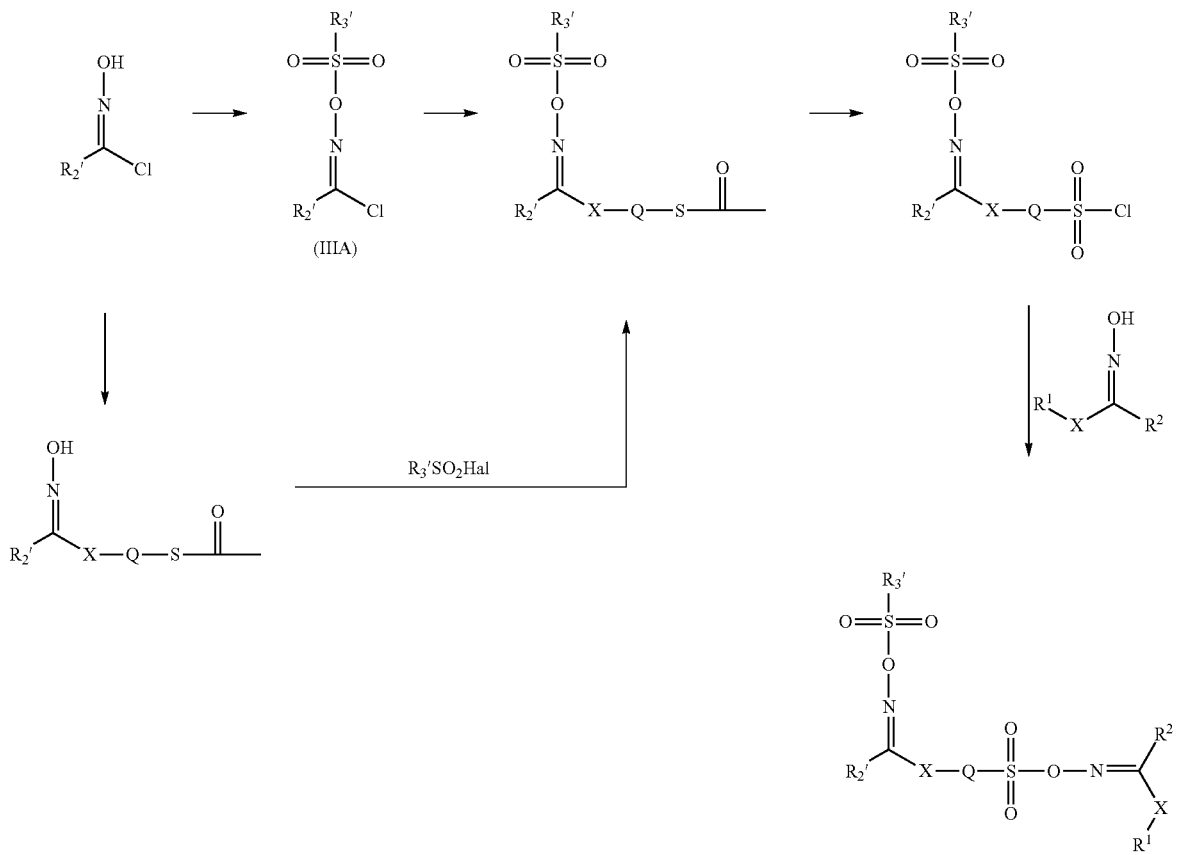

In Scheme 6, X, Q, R¹, and R² are as defined above, R²' is as defined R², R³' is as defined R³.

The oximes required as the starting materials can be obtained by a variety of methods described in literatures, for example, the reaction of ketones with hydroxylamine or its salt in polar solvents like ethanol or aqueous ethanol. In that case, a base such as sodium acetate is added to control the pH cosolvent. The reaction temperature is generally the refluxing temperature of the mixture, usually about 60-120° C.

Another convenient synthesis of oximes is the reaction of a suitable oximidoyl halide, such as oximidoyl chloride or oximidoyl bromide with a thiol as described, for example, in *Synlett*, 937 (2001) or EP64091 and with a primary or secondary amine as described, for example, in *J. Chem. Soc.*,

*Perkin Trans.* 1, 1999, 1789, *J. Heterocyclic Chem.*, 43, 579 (2006). or *Tetrahedron Letters*, 47(51), 9029 (2006). These reactions are usually carried out in an inert solvent like toluene, dioxane, tetrahydrofuran (THF), diethyl ether, dichloromethane, dimethylformamide (DMF), methanol or aqueous methanol in the presence of a base, for example, a tertiary amine, such as triethylamine, or metal hydroxide, such as NaOH, LiOH and KOH.

The oximidoyl halides can be obtained by reacting the corresponding aldoximes with halogenation reagents, for example, N-chlorosccinimide (NCS) as described, for example, in J. Chem. Soc., Perkin Trans. 1, 2627 (1991) or J. Org. Chem., 45, 3916 (1980), N-bromosccinimide (NBS), chlorine as described, for example, in EP64091 or, bromine or tert-butyl hypochlorite. These reactions are usually carried out in an inert solvent such as toluene, tetrahydrofuran (THF), dimethylformamide (DMF), chloroform, dichloromethane, or in a polar solvent such as methanol or aqueous methanol.

Another synthesis of oximidoyl chloride is the oximination of glycine ethyl ester hydrochloride with sodium nitrite in aq. HCl solution as described, for example, in J. Org. Chem., 48(3), 366 (1983).

Organic Syntheses, Coll. Vol. 3, p. 191 (1955) discloses preparation of chloroisonitrosoacetophenone from phenacyl chloride using n-butyl nitrite in the presence of HCl.

The described syntheses can result in the formation of isomeric forms of the compounds of formulae I, IA.1, IA, IB, IC or ID. The double bond of the oximino group can exist in both the syn (cis, Z) and the anti (trans, E) form or as mixtures of the two geometrical isomers. In the present invention, both the individual geometrical isomers and any mixtures of two geometrical isomers can be used. The invention accordingly also relates to mixtures of isomeric forms of the compounds of formulae I, IA.1, IA, IB and IC.

The compounds of formulae I, IA.1, IA, IB and IC can be used as thermal curing promoters to enhance the polymerization, especially in the post-baking process when manufacturing liquid crystal display components such as color filters, photospacer, overcoat and interlayer dielectric.

The compounds of formulae I, IA.1, IA, IB, IC and ID can be used in principle to polymerize all types of ethylenically unsaturated compounds.

Suitable ethylenically unsaturated compounds (b) are monomers or oligomers that can be polymerized in a manner known per se using the methods of free-radical polymerization.

The term "(meth)acrylate" in the context of the present application is meant to refer to the acrylate as well as to the corresponding methacrylate.

Preferably, compound (b) is selected from esters of $\alpha,\beta$-ethylenically unsaturated monocarboxylic and dicarboxylic acids with $C_1$-$C_{20}$ alkanols, vinylaromatics, esters of vinyl alcohol with $C_1$-$C_{30}$ monocarboxylic acids, ethylenically unsaturated nitriles, vinyl halides, vinylidene halides, monoethylenically unsaturated carboxylic and sulfonic acids, esters of $\alpha,\beta$-ethylenically unsaturated monocarboxylic and dicarboxylic acids with $C_2$-$C_{30}$ alkanediols, amides of $\alpha,\beta$-ethylenically unsaturated monocarboxylic and dicarboxylic acids with $C_2$-$C_{30}$ amino alcohols which contain a primary or secondary amino group, primary amides of $\alpha,\beta$-ethylenically unsaturated monocarboxylic acids and their N-alkyl and N,N-dialkyl derivatives, N-vinyllactams, open-chain N-vinylamide compounds, esters of allyl alcohol with $C_1$-$C_{30}$ monocarboxylic acids, esters of $\alpha,\beta$-ethylenically unsaturated monocarboxylic and dicarboxylic acids with amino alcohols, amides of $\alpha,\beta$-ethylenically unsaturated monocarboxylic and dicarboxylic acids with diamines which contain at least one primary or secondary amino group, N,N-diallylamines, N,N-diallyl-N-alkylamines, vinyl- and allyl-substituted nitrogen heterocycles, vinyl ethers, $C_2$-$C_8$-monoolefins, nonaromatic hydrocarbons having at least two conjugated double bonds, polyether(meth)acrylates, heterocyclyl-($C_2$-$C_4$-alkyl)(meth)acrylates, silyl group-containing (meth)acrylates, and mixtures thereof.

Suitable ethylenically unsaturated carboxylic acids and sulfonic acids or their derivatives are acrylic acid, methacrylic acid, ethacrylic acid, $\alpha$-chloroacrylic acid, crotonic acid, maleic acid, maleic anhydride, itaconic acid, citraconic acid, mesaconic acid, glutaconic acid, aconitic acid, fumaric acid, the monoesters of monoethylenically unsaturated dicarboxylic acids having 4 to 10, preferably 4 to 6, C atoms, e.g., monomethyl maleate, vinylsulfonic acid, allylsulfonic acid, sulfoethyl acrylate, sulfoethyl methacrylate, sulfopropyl acrylate, sulfopropyl methacrylate, 2-hydroxy-3-acryloyloxypropylsulfonic acid, 2-hydroxy-3-methacryloyloxypropylsulfonic acid, styrenesulfonic acid, and 2-acrylamido-2-methylpropanesulfonic acid.

Suitable derivatives of ethylenically unsaturated carboxylic acids and sulfonic acids are their salts. Suitable salts of acrylic acid or methacrylic acid are, for example, ($C_1$-$C_4$-alkyl)$_4$ammonium or ($C_1$-$C_4$-alkyl)$_3$NH salts, e.g. the tetramethylammonium, tetraethylammonium, trimethylammonium or triethylammonium salts, the trimethyl-2-hydroxyethylammonium or triethyl-2-hydroxyethylammonium salts, the dimethyl-2-hydroxyethylammonium or diethyl-2-hydroxyethylammonium salts.

Suitable esters of $\alpha,\beta$-ethylenically unsaturated monocarboxylic and dicarboxylic acids with $C_1$-$C_{20}$ alkanols are methyl (meth)acrylate, methyl ethacrylate, ethyl (meth)acrylate, ethyl ethacrylate, n-propyl(meth)acrylate, isopropyl (meth)acrylate, n-butyl (meth)acrylate, sec-butyl (meth)acrylate, tert-butyl (meth)acrylate, tert-butyl ethacrylate, n-hexyl (meth)acrylate, n-heptyl(meth)acrylate, n-octyl(meth)acrylate, 1,1,3,3-tetramethylbutyl(meth)acrylate, ethylhexyl (meth)acrylate, n-nonyl(meth)acrylate, n-decyl(meth)acrylate, n-undecyl(meth)acrylate, tridecyl(meth)acrylate, myristyl(meth)acrylate, pentadecyl(meth)acrylate, palmityl (meth)acrylate, heptadecyl(meth)acrylate, nonadecyl(meth)acrylate, arachidyl(meth)acrylate, behenyl(meth)acrylate, lignoceryl(meth)acrylate, cerotinyl(meth)acrylate, melissinyl(meth)acrylate, palmitoleyl(meth)acrylate, oleyl(meth)acrylate, linolyl(meth)acrylate, linolenyl(meth)acrylate, stearyl(meth)acrylate, lauryl(meth)acrylate, and mixtures thereof.

Preferred vinylaromatics are styrene, 2-methylstyrene, 4-methylstyrene, 2-(n-butyl)styrene, 4-(n-butyl)styrene, 4-(n-decyl)styrene, and, with particular preference, styrene.

Suitable esters of vinyl alcohol with $C_1$-$C_{30}$ monocarboxylic acids are, for example, vinyl formate, vinyl acetate, vinyl propionate, vinyl butyrate, vinyl laurate, vinyl stearate, vinyl propionate, versatic acid vinyl esters, and mixtures thereof.

Suitable ethylenically unsaturated nitriles are acrylonitrile, methacrylonitrile, and mixtures thereof.

Suitable vinyl halides and vinylidene halides are vinyl chloride, vinylidene chloride, vinyl fluoride, vinylidene fluoride, and mixtures thereof.

Suitable esters of $\alpha,\beta$-ethylenically unsaturated monocarboxylic and dicarboxylic acids with $C_2$-$C_{30}$ alkanediols are, for example, 2-hydroxyethyl acrylate, 2-hydroxyethyl methacrylate, 2-hydroxyethyl ethacrylate, 2-hydroxypropyl acrylate, 2-hydroxypropyl methacrylate, 3-hydroxypropyl acrylate, 3-hydroxypropyl methacrylate, 3-hydroxybutyl acrylate, 3-hydroxybutyl methacrylate, 4-hydroxybutyl acrylate, 4-hydroxybutyl methacrylate, 6-hydroxyhexyl acrylate, 6-hydroxyhexyl methacrylate, 3-hydroxy-2-ethylhexyl acrylate, 3-hydroxy-2-ethylhexyl methacrylate, etc.

Suitable primary amides of α,β-ethylenically unsaturated monocarboxylic acids and their N alkyl and N,N-dialkyl derivatives are acrylamide, methacrylamide, N-methyl(meth)acrylamide, N-ethyl(meth)acrylamide, N-propyl(meth)acrylamide, N-(n-butyl)(meth)acrylamide, N-(tert-butyl)(meth)acrylamide, N-(n-octyl)(meth)acrylamide, N-(1,1,3,3-tetramethylbutyl)(meth)acrylamide, N-ethylhexyl(meth)acrylamide, N-(n-nonyl)(meth)acrylamide, N-(n-decyl)(meth)acrylamide, N-(n-undecyl)(meth)acrylamide, N,N-dimethyl(meth)acrylamide, N,N-diethyl(meth)acrylamide, morpholinyl(meth)acrylamide, etc.

Suitable N-vinyllactams and their derivatives are, for example, N-vinylpyrrolidone, N-vinylpiperidone, N-vinylcaprolactam, etc.

Suitable open-chain N-vinylamide compounds are, for example, N-vinylformamide, N-vinyl-N-methylformamide, N-vinylacetamide, N-vinylpropionamide, N-vinylbutyramide, etc.

Suitable esters of α,β-ethylenically unsaturated monocarboxylic and dicarboxylic acids with amino alcohols are N,N-dimethylaminomethyl(meth)acrylate, N,N-dimethylaminoethyl(meth)acrylate, N,N-diethylaminoethylacrylate, N,N-dimethylaminopropyl(meth)acrylate, N,N-diethylaminopropyl(meth)acrylate and N,N-dimethylaminocyclohexyl(meth)acrylate.

Suitable amides of α,β-ethylenically unsaturated monocarboxylic and dicarboxylic acids with diamines which contain at least one primary or secondary amino group are N-[2-(dimethylamino)ethyl]acrylamide, N-[2-(dimethylamino)ethyl]methacrylamide, N-[3-(dimethylamino)propyl]acrylamide, N-[3-(dimethylamino)propyl]methacrylamide, N-[4-(dimethylamino)butyl]acrylamide, N-[4-(dimethylamino)-butyl]methacrylamide, N-[2-(diethylamino)ethyl]acrylamide, N-[4-(dimethylamino)cyclohexyl]acrylamide, N-[4-(dimethylamino)cyclohexyl]methacrylamide, etc.

Suitable monomers (b) are, furthermore, N,N-diallylamines and N,N-diallyl-N-alkylamines and their acid addition salts and quaternization products. Alkyl here is preferably $C_1$-$C_{24}$ alkyl. Preference is given to N,N-diallyl-N-methylamine and to N,N-diallyl-N,N-dimethylammonium compounds, such as the chlorides and bromides, for example.

Further suitable monomers (b) are vinyl- and allyl-substituted nitrogen heterocycles, such as N-vinylimidazole, N-vinyl-2-methylimidazole, and vinyl- and allyl-substituted heteroaromatic compounds, such as 2- and 4-vinylpyridine, 2- and 4-allylpyridine, and the salts thereof.

Suitable $C_2$-$C_8$ monoolefins and nonaromatic hydrocarbons having at least two conjugated double bonds are, for example, ethylene, propylene, isobutylene, isoprene, butadiene, etc.

Examples of silyl group-containing (meth)acrylates are silyloxy-$C_2$-$C_4$-(meth)alkyl acrylates, e.g. 2-trimethylsilyloxyethyl acrylate or methacrylate (TMS-HEA, TMS-HEMA). Examples of $(C_1$-$C_4$-alkyl$)_3$-silyl-$C_2$-$C_4$ alkyl (meth)acrylates are 2-trimethylsilylethyl acrylate or methacrylate and 3-trimethylsilyl-n-propyl acrylate or methacrylate.

In particular, compound (b) is selected from acrylic acid, methacrylic acid, maleic anhydride, acrylic acid derivatives, styrene, vinyl acetate, vinyl halides and vinylidene halides, acrolein, vinylpyrrolidone, vinylimidazole, alkenes, conjugated dienes and mixtures thereof.

Examples of heterocycyl-($C_2$-$C_4$-alkyl)(meth)acrylates are 2-(N-morpholinyl, 2-pyridyl, 1-imidazolyl, 2-oxo-1-pyrrolidinyl, 4-methylpiperidin-1-yl or 2-oxoimidazolidin-1-yl) ethyl acrylate or methacrylate.

Suitable polyether(meth)acrylates (b) are compounds of the general formula (A)

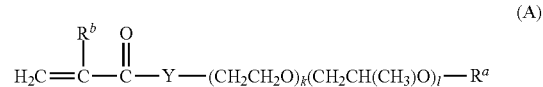

in which
the sequence of the alkylene oxide units is arbitrary,
k and l independently of one another are an integer from 0 to 100, the sum of k and l being at least 3,
$R^a$ is hydrogen, $C_1$-$C_{30}$ alkyl, $C_5$-$C_8$ cycloalkyl or $C_6$-$C_{14}$ aryl,
$R^b$ is hydrogen or $C_1$-$C_8$ alkyl,
Y is O or $NR^c$, where $R^c$ is hydrogen, $C_1$-$C_{30}$ alkyl or $C_5$-$C_8$ cycloalkyl.

Preferably k is an integer from 3 to 50, more particularly 4 to 25. Preferably l is an integer from 3 to 50, more particularly 4 to 25.

Preferably $R^a$ in the formula (AA) is hydrogen, methyl, ethyl, n-propyl, isopropyl, n-butyl, sec-butyl, n-pentyl, n-hexyl, octyl, 2-ethylhexyl, decyl, lauryl, palmityl or stearyl. Preferably $R^b$ is hydrogen, methyl, ethyl, n-propyl, isopropyl, n-butyl, sec-butyl, tert-butyl, n-pentyl or n-hexyl, more particularly hydrogen, methyl or ethyl. With particular preference $R^b$ is hydrogen or methyl.

Preferably Y in the formula (A) is O.

The polymerizable composition according to the invention preferably comprises the component (b) in an amount of from 0.01 to 50% by weight, more preferably 0.1 to 40% by weight, in particular 0.5 to 30% by weight, based on the total weight of the composition.

The composition according to the invention preferably comprises at least one photoinitiator (c) as further component.

The composition according to the invention preferably comprises at least one binder polymer (d) as further component.

The composition according to the invention preferably comprises at least one further component (e) selected from
(e1) pigments,
(e2) dyes,
(e3) fillers,
(e4) dispersants,
(e5) sensitizers,
(e6) thermosetting compounds, being different from compounds of the formula (I) and binder polymers (d),
mixtures thereof.

The composition according to the invention preferably comprises at least one additive (f) selected from solvents, reinforcing materials, flow control assistants, UV stabilizers, heat stabilizers, weatherability improvers, rheology modifiers, flame retardants, antioxidants, discoloration inhibitors, biocides, antistatic agents, plasticizers, lubricants, slip additives, wetting agents, film-forming assistants, adhesion promoters, corrosion inhibitors, antifreeze agents, defoamers, mold release agents, etc., and mixtures thereof.

Suitable photoinitiators (c) are described in the following with regard to a polymerizable composition comprising an alkaline developable resin (d). This disclosure is incorporated here for all polymerizable compositions of the invention.

Photoinitiators (c) are preferably used in an amount of from 0.001% to 15% by weight, more preferably from 0.01 to 10% by weight, based on the total weight of the polymerizable composition according to the invention.

Suitable binder polymers (d) are e.g. physically drying polymer compositions, self-crosslinking polymer compositions, UV-curable polymer compositions, thermosetting polymer compositions, polymer compositions crosslinkable by addition of a crosslinker (2-component dispersions), or dual-cure systems. Suitable thermosetting polymer compositions are described in the following as component (e6).

In a preferred embodiment the binder polymer component (d) comprises at least one alkaline developable resin. Suitable alkaline developable resins (d) are described in detail in the following.

Binder polymers (d) are preferably used in an amount of from 0.5% to 98% by weight, more preferably from 1 to 95% by weight, in particular from 2 to 90% by weight, based on the total weight of the polymerizable composition according to the invention.

Suitable colorants, i.e. pigments (e1) and dyes (e2) are described in the following with regard to a polymerizable composition comprising an alkaline developable resin (d). This disclosure is incorporated here for all polymerizable compositions of the invention.

Suitable fillers (e3) are organic and inorganic fillers, examples being aluminosilicates, such as feldspars, silicates, such as kaolin, talc, mica, magnesite, alkaline earth metal carbonates, such as calcium carbonate, in the form of calcite or chalk, for example, magnesium carbonate, dolomite, alkaline earth metal sulfates, such as calcium sulfate, silicon dioxide, etc. Suitable organic fillers are, for example, textile fibers, cellulose fibers, polyethylene fibers or wood flour. In coating materials, of course, finely divided fillers are preferred. The fillers may be used as individual components. In practice, mixtures of fillers have also proven particularly appropriate, examples being calcium carbonate/kaolin, calcium carbonate/talc. For further details refer to Römpp-Lexikon, Lacke und Druckfarben, Georg Thieme Verlag, 1998, pages 250 ff., "fillers".

Fillers (e3) are preferably used in an amount of from 0% to 95% by weight, more preferably from 0.5 to 90% by weight, in particular from 1 to 80% by weight, and especially 4% to 75% by weight, based on the total weight of the polymerizable composition according to the invention.

The term dispersant (=component e4) as used herein is understood in a broad sense. Dispersant are dispersing agents (including polymeric dispersants), surfactants, texture improving agents, and the like. Suitable dispersants (e4) are described in the following with regard to a polymerizable composition comprising an alkaline developable resin (d). This disclosure is incorporated here for all polymerizable compositions of the invention.

Where the polymerizable compositions of the invention comprise at least one dispersant (e4), it is preferably used in an amount of 0.01% to 50% by weight, preferably 0.1% to 30% by weight, based on the total weight of the polymerizable composition.

Suitable (photo)sensitizers (e5) are described in the following with regard to a polymerizable composition comprising an alkaline developable resin (d). This disclosure is incorporated here for all polymerizable compositions of the invention.

Sensitizers (e5) are preferably used in an amount of from 0.001% to 15% by weight, more preferably from 0.01 to 10% by weight, based on the total weight of the polymerizable composition according to the invention.

Suitable thermosetting compounds (e6) have at least one group selected from an epoxy group, oxetane group and vinyl ether group.

Suitable compounds (e6) are:

compounds comprising an oxygen- or sulphur-containing saturated heterocycle, ethylenically unsaturated compounds which are polymerisable by a cationic mechanism, prepolymers of phenol-formaldehyde resins, acrylic resins, alkyd resins or polyester resins containing heat curable functional groups, mixtures of heat curable compounds and compounds polymerisable by a different mechanism, e.g. free radicals or UV irradiation, mixtures thereof.

Compounds (e6) which comprise an oxygen- or sulphur-containing saturated heterocycle preferably comprise at least one heterocycle having 3, 4, 5 or 6 ring members.

Preferred compounds (e6) which comprise an oxygen- or sulphur-containing saturated heterocycle are selected from compounds containing at least one epoxy group, oxetanes, oxolanes, cyclic acetals, cyclic lactones, thiiranes, thietanes and mixtures thereof.

Suitable compounds (e6) containing one epoxy group are ethylene oxide, propylene oxide, styrene oxide, phenyl glycidyl ether, butyl glycidyl ether, etc.

In a preferred embodiment of the invention, compound (e6) is selected from epoxy resins. The term "epoxy resin" as utilized in the description of the curable compositions of the present invention, is understood in a broad sense and includes any monomeric, dimeric, oligomeric or polymeric epoxy material containing a plurality (2, 3, 4, 5, 6 or more than 6) of epoxy groups. The term "epoxy resins" also encompasses prepolymers which comprise two or more epoxide groups, wherein some of the epoxide groups (oxiran rings) may also have been opened to a hydroxyl group. The term also identifies part-cured epoxy resins, i.e., epoxy resins which have been crosslinked by means of suitable hardeners. If component (a) is a part cured epoxy resin, it still contains heat curable epoxy groups that are still capable of undergoing cationic polymerization. The term "epoxy resins" also encompasses modified epoxy resins, such as esterified or etherified epoxy resins, obtainable for example by reaction with carboxylic acids or alcohols. Again, modified epoxy resins that are employed in a composition according to the invention still contain heat curable epoxy groups that are still capable of undergoing cationic polymerization. A complete definition of the term "epoxy resins" is found for example in Ullmann's Encyclopedia of Industrial Chemistry, 5th edition, on CD-ROM, 1997, Wiley-VCH, in the "Epoxy Resins" section.

The majority of commercial epoxy resins are prepared by coupling epichlorohydrin onto compounds which possess at least two reactive hydrogen atoms, such as polyphenols, monoamines and diamines, aminophenols, heterocyclic imides and amides, aliphatic diols or polyols or dimeric fatty acids. Epoxy resins derived from epichlorohydrin are referred to as glycidyl-based resins.

The majority of epoxy resins available commercially at the present time derive from the diglycidyl ether of bisphenol A (DGEBA resins) and possess the general formula

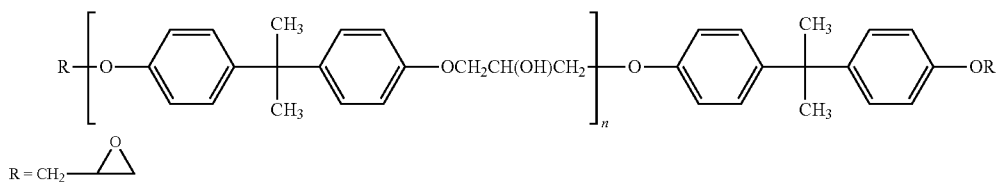

in which n stands for 0 to approximately 40.

Other important epoxy resins are phenol-based and cresol-based epoxy novolaks, examples being epoxy resins which derive from the diglycidyl ether of bisphenol F. Novolaks are prepared by the acid-catalyzed condensation of formaldehyde and phenol or cresol. The epoxidation of the novolaks leads to epoxy novolaks.

Other classes of glycidyl-based epoxy resins derive from glycidyl ethers of aliphatic diols, such as butane-1,4-diol, hexane-1,6-diol, pentaerythritol or hydrogenated bisphenol A; aromatic glycidylamines, an example being the triglycidyl adduct of p-aminophenol or the tetraglycidylamine of methylenedianilide; heterocyclic glycidylimides and amides, e.g., triglycidyl isocyanurate; and glycidyl esters, such as the diglycidyl ester of dimeric linoleic acid, for example.

The epoxy resins (e6) may also derive from other epoxides (non-glycidyl ether epoxy resins). Examples are the diepoxides of cycloaliphatic dienes, such as 3,4-epoxycyclohexylmethyl 3,4-epoxycyclohexanecarboxylate and 4-epoxyethyl-1,2-epoxycyclohexane.

Suitable oxetanes (e6) are trimethylene oxide, 3,3-dimethyloxetane, 3,3-di(chloromethyl)oxetane, etc.

Suitable oxolanes (e6) are tetrahydrofuran, 2,3-dimethyltetrahydrofuran, etc.

Suitable cyclic acetals (e6) are trioxan, 1,3-dioxolane, 1,3,6-trioxacyclooctane, etc.

Suitable cyclic lactones (e6) are β-propiolactone, β-caprolactone, the alkyl derivatives of β-propiolactone and ε-caprolactone, etc.

Suitable thiiranes (e6) are ethylene sulfide, 1,2-propylene sulphide, thioepichlorohydrin, etc.

Suitable thietanes (e6) are 1,3-propylene sulphide, 3,3-dimethylthietane, etc.

The thermosetting compounds (e6) can be cured by thermal curing promoters. Suitable thermal curing promotors can be selected by the skilled artisan by the nature of the reactive functional groups in the binder. Suitable thermal curing promotors catalysts are e.g. sulfonium and phosphonium salts of organic or inorganic acids, imidazole and imidazole derivatives, quaternary ammonium compounds, and amines. The thermal curing promotors, where desired, are preferably used in an amount of from 0.001% by weight to about 10% by weight, based on the total weight of the polymerizable composition according to the invention.

It has been found that the afore-mentioned compounds of the formula (I) are in particular advantageous as thermal curing promoters for radically polymerizable compositions. In a special embodiment, they are used as resists to manufacture color filters for a variety of display applications and for image sensors such as charge coupled device (CCD) and complementary metal-oxide semiconductor (CMOS). The polymerizable compositions according to the invention can further be used for manufacturing spacers, which control a cell gap of the liquid crystal part in liquid crystal display panels. The polymerizable compositions according to the invention are also suitable as overcoat layer for color filters and LCDs, sealants for LCDs, insulation layers for LCDs, resists or photosensitive compositions to generate structures or layers in the manufacturing processes of plasma-display panels, electroluminescence displays and LCDs, solder resists, and as a photoresist material used for forming dielectric layers in a sequential build-up layer of a printed circuit board. The use of compounds of the formula (I) results in a sufficiently high C=C conversion surprisingly at lower temperature and/or in shorter time in the thermal curing (post baking) process which takes place after the photo curing process both in comparison to corresponding compositions lacking these compounds (I) and in comparison to corresponding compositions comprising other thermal curing promoters (TCPs) known from the prior art.

According to a special embodiment, the polymerizable composition according to the invention comprises at least one binder polymer (d), wherein component (d) is selected from alkaline developable resins. Alkaline developable resins comprise functional groups that provide the resin with good alkaline solubility. They are suitable for all types of applications comprising a development step, wherein the uncured resin is dissolved in an alkaline developer solution.

Thus, the invention relates to a polymerizable composition comprising:
(a) at least one oxime sulfonate compound of the formula I as defined above,
(b) at least one acrylate monomer,
(c) at least one photoinitiator, and
(d) at least one alkaline developable resin.

Acrylate Monomer (b)

The polymerizable composition according to the invention preferably comprises the component (b) in an amount of from about 2 to 80% by weight, more preferably from about 5 to 70% by weight, based on the whole solid contents of the polymerizable composition (i.e. the amount of all components without the solvent(s)).

The acrylate monomer (b) is preferably selected from compounds that contain one or more (e.g. 1, 2, 3 or 4) acryloyl and/or methacryloyl moieties.

The term "acrylate monomer" encompasses also acrylate oligomers that contain one or more (e.g. 1, 2, 3 or 4) acryloyl and/or methacryloyl moieties.

Examples of compounds (b) containing a double bond are (meth)acrylic acid, alkyl(meth)acrylates, hydroxyalkyl (meth)acrylates or aminoalkyl(meth)acrylates. Preferred compounds (b) are for example methyl(meth)acrylate, ethyl (meth)acrylate, n-butyl(meth)acrylate, isobutyl(meth)acrylate, tert-butyl(meth)acrylate, n-propyl(meth)acrylate, isopropyl(meth)acrylate, n-hexyl(meth)acrylate, cyclohexyl (meth)acrylate, 2-ethylhexyl(meth)acrylate, isobornyl(meth) acrylate, benzyl(meth)acrylate, 2-hydroxyethyl(meth) acrylate, 2-hydroxypropyl(meth)acrylate, methoxyethyl (meth)acrylate, ethoxyethyl(meth)acrylate, glycerol(meth) acrylate, phenoxyethyl(meth)acrylate, methoxydiethylene glycol(meth)acrylate, ethoxydiethylene glycol(meth)acrylate, polyethylene glycol(meth)acrylate, polypropylene glycol(meth)acrylate, glycidyl(meth)acrylate, N,N-dimethylaminoethyl(meth)acrylate, N,N-diethylaminoethyl(meth)acrylate, and mixtures thereof.

Other examples of compounds (b) are (meth)acrylonitrile, (meth)acrylamide, N-substituted (meth)acrylamides, vinyl esters, vinyl ethers, styrene, alkylstyrenes, hydroxystyrenes, halostyrenes, N-vinylpyrrolidone, N-vinylcaprolactam, N-vinylacetamide, N-vinylformamide, vinyl chloride, vinylidene chloride, and mixtures thereof.

Suitable N-substituted (meth)acrylamides are e.g. N,N-dimethyl(meth)acrylamide, N,N-diethyl(meth)acrylamide, N,N-dibutyl(meth)acrylamide, N-methyl(meth)acrylamide, N-ethyl(meth)acrylamide, N-butyl(meth)acrylamide, N-(meth)acryloylmorpholine, and mixtures thereof.

Suitable vinyl esters are as vinyl acetate, vinyl propionate and mixtures thereof.

A suitable vinyl ether is isobutyl vinyl ether.

Examples of polyunsaturated compounds (b) of relatively high molecular mass (oligomers) are polyesters, polyurethanes, polyethers and polyamides, which contain ethylenically unsaturated carboxylate groups. Particularly suitable examples are esters of an ethylenically unsaturated carboxylic acid with a polyol and/or polyepoxide.

Examples of unsaturated carboxylic acids are acrylic acid, methacrylic acid, crotonic acid, itaconic acid, cinnamic acid, and unsaturated fatty acids, such as linolenic acid or oleic acid. Acrylic acid and methacrylic acid are preferred.

Suitable polyols are aromatic, in particular, aliphatic and cycloaliphatic polyols. Examples of aromatic polyols are hydroquinone, 4,4'-dihydroxydiphenyl, 2,2-bis(4-hydroxyphenyl)methane, 2,2-bis(4-hydroxyphenyl)propane, 2,2-bis(4-hydroxyphenyl)hexafluoropropane, 9,9-bis(4hydroxyphenyl)fluorene, novolacs and resols. Examples of aliphatic and cycloaliphatic polyols are alkylenediols having preferably 2 to 12 C atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, triethanolamine, trimethylolethane, trimethylolpropane, pentaerythritol, pentaerythritol monooxalate, dipentaerythritol, ethers of pentaerythritol with ethylene glycol or propylene glycol, ethers of dipentaerythritol with ethylene glycol or propylene glycol, sorbitol, 2,2-bis[4-(2-hydroxyethoxy)phenyl]methane, 2,2-bis[4-(2-hydroxyethoxy)phenyl]propane and 9,9-bis[4-(2-hydroxyethoxy)phenyl]fluorene.

Further suitable polyols are polymers and copolymers containing hydroxyl groups in the polymer chain or in side groups, examples being homopolymers or copolymers comprising vinyl alcohol or comprising hydroxyalkyl(meth)acrylates.

Further suitable polyols are esters and urethanes having hydroxyl end groups.

The polyols may be partially or completely esterified with one unsaturated carboxylic acid or with different unsaturated carboxylic acids. In partial esters the free hydroxyl groups may be modified, for example etherified or esterified with other carboxylic acids.

Examples of esters based on polyols are trimethylolpropane tri(meth)acrylate, trimethylolpropane tri(acryloyloxypropyl)ether, trimethylolethane tri(meth)acrylate, ethylene glycol di(meth)acrylate, diethylene glycol di(meth)acrylate, triethylene glycol di(meth)acrylate, tetraethylene glycol di(meth)acrylate, tetramethylene glycol di(meth)acrylate, neopentyl glycol di(meth)acrylate, pentaerythritol di(meth)acrylate, pentaerythritol tri(meth)acrylate, pentaerythritol tetra(meth)acrylate, pentaerythritol tri(meth)acrylate monooxalate, dipentaerythritol di(meth)acrylate, dipentaerythritol tri(meth)acrylate, dipentaerythritol tetra(meth)acrylate, dipentaerythritol penta(meth)acrylate, dipentaerythritol hexa(meth)acrylate, dipentaerythritol penta(meth)acrylate mono(2-hydroxyethyl)ether, tripentaerythritol octa(meth)acrylate, 1,3-butanediol di(meth)acrylate, 1,4-butanediol diitaconate, hexanediol di(meth)acrylate, 1,4-cyclohexanediol di(meth)acrylate, sorbitol tri(meth)acrylate, sorbitol tetra(meth)acrylate, sorbitol penta(meth)acrylate, sorbitol hexa(meth)acrylate, oligoester (meth)acrylates, glycerol di(meth)acrylate and tri(meth)acrylate, di(meth)acrylates of polyethylene glycol with a molecular weight of from 200 to 1500, pentaerythritol diitaconate, dipentaerythritol trisitaconate, dipentaerythritol pentaitaconate, dipentaerythritol hexaitaconate, ethylene glycol diitaconate, propylene glycol diitaconate, 1,3-butanediol diitaconate, 1,4-butanediol diitaconate, tetramethylene glycol diitaconate, sorbitol tetraitaconate, ethylene glycol dicrotonate, tetramethylene glycol dicrotonate, pentaerythritol dicrotonate, ethylene glycol dimaleate, triethylene glycol dimaleate, pentaerythritol dimaleate, sorbitol tetramaleate, or mixtures thereof.

Other examples are pentaerythritol and dipentaerythritol derivatives shown in the following formula (XII) and (XIII):

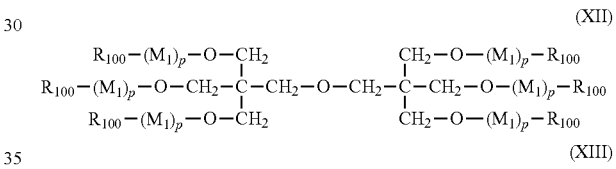

(XII)

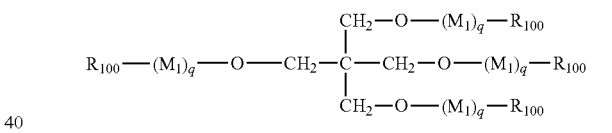

(XIII)

wherein
$M_1$ is —($CH_2CH_2O$)— or —[$CH_2CH(CH_3)O$]—,
$R_{100}$ is —$COCH=CH_2$ or —$COC(CH_3)=CH_2$,
each p is independently 0 to 6,
the sum of all variables p is 3 to 24,
each q is independently 0 to 6, and
the sum of all variables q is 2 to 16.

Examples of polyepoxides are those based on the above-mentioned polyols and epichlorohydrin. Typical examples are bis(4-glycidyloxyphenyl)methane, 2,2-bis(4-glycidyloxyphenyl)propane, 2,2-bis(4-glycidyloxyphenyl)hexafluoropropane, 9,9-bis(4-glycidyloxyphenyl)fluorene, bis[4-(2-glycidyloxyethoxy)phenyl]methane, 2,2-bis[4-(2-glycidyloxyethoxy)phenyl]propane, 2,2-bis[4-(2-glycidyloxyethoxy)phenyl]hexafluoropropane, 9,9-bis[4-(2-glycidyloxyethoxy)phenyl]fluorene, bis[4-(2-glycidyloxypropoxy)phenyl]methane, 2,2-bis[4-(2-glycidyloxypropoxy)phenyl]propane, 2,2-bis[4-(2-glycidyloxypropoxy)phenyl]hexafluoropropane, 9,9-bis[4-(2-glycidyloxypropoxy)phenyl]fluorene, glycerol diglycidyl ether and glycidyl ethers of phenol and cresol novolacs.

Typical examples based on polyepoxides are 2,2-bis[4-{(2-hydroxy-3-acryloxy)propoxy}phenyl]propane, 2,2-bis[4-{(2-hydroxy-3-acryloxy)propoxyethoxy}phenyl]propane, 9,9-bis[4-{(2-hydroxy-3-acryloxy)propoxy}phenyl]fluorene, 9,9-bis[4-{(2-hydroxy-3-acryloxy)

propoxyethoxy}phenyl]fluorine, glycerol 1,3-diglycerolate diacrylate and reaction products of epoxy resins based on novolacs with (meth)acrylic acid.

Preferred multifunctional (meth)acrylate monomers or oligomers include pentaerythritol tetraacrylate, dipentaerythritol pentaacrylate, dipentaerythritol hexaacrylate, di-trimethylolpropane tetraacrylate, pentaerythritol triacrylate, tris (2-hydroxy ethyl)iso-cyanurate triacrylate.

A particularly preferred acrylate monomers (b) is dipentaerythritol-hexaacrylate (DPHA). A further particularly preferred acrylate monomers (b) is dipentaerythritol-pentaacrylate (DPPA).

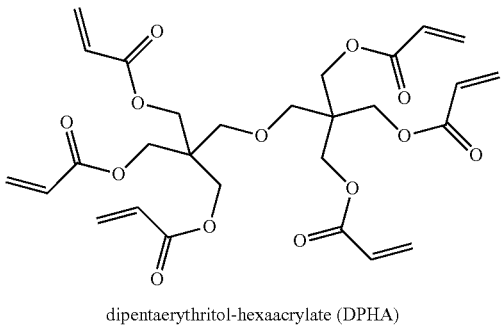

dipentaerythritol-hexaacrylate (DPHA)

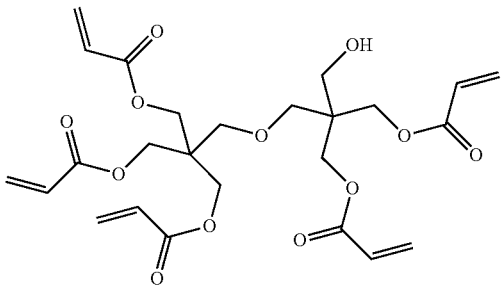

dipentaerythritol-pentaacrylate (DPPA)

Examples of commercially available compounds (b) having two acryloyl or methacryloyl moietyies are Aronix®M-210, Aronix®M-240, Aronix®M-6200 (TOAGOSEI Co., LDT., KAYARAD HDDA, KAYARAD HX-220, KAYARAD HX-620, KAYARAD R-526, KAYARAD UX-2201, KAYARAD MU-2100 (NIPPON KAYAKU Co., LTD.), VISCOAT-260, VISCOAT-355HP (OSAKA ORGANIC CHEMICAL INDUSTRY LTD.).

Examples of commercially available compounds (b) having three or more acryloyl or methacryloyl moietyies are Aronix®M-309, Aronix®M-400, Aronix®M-1310, Aronix®M-1960, Aronix®M-7100, Aronix®M-8530, Aronix®TO-1450 (TOAGOSEI Co., LDT.), KAYARAD TMPTA, KAYARAD DPHA, KAYARAD DPCA-20, KAYARAD MAX-3510 (NIPPON KAYAKU Co., LTD.), VISCOAT-295, VISCOAT-300, VISCOAT-GPT, VISCOAT-3PA, VISCOAT-400 (OSAKA ORGANIC CHEMICAL INDUSTRY LTD.).

Examples of commercially available urethane acrylate monomers (b) having two or more acryloyl or methacryloyl moietyies are NEW FRONTIER R-1150 (DAI-ICHI KOGYO SEIYAKU CO., LTD.) KAYARAD DPHA-40H, KAYARAD UX-5000 (NIPPON KAYAKU Co., LTD.), UN-9000H (Negami Chemical Industrial Co., Ltd.).
Photoinitiator (c)

The choice of a suitable photoinitiator (c) is usually not critical. The photoinitiator (c) is for example selected from benzophenones, bisimidazoles, aromatic α-hydroxyketones, benzylketals, aromatic α-aminoketones, phenylglyoxalic acid esters, mono-acylphosphinoxides, bis-acylphosphinoxides, tris-acylphosphinoxides, oximesters derived from aromatic ketones and/or oxime esters of the carbazol type.

Examples of photoinitiators (c) are
camphorquinone (1,7,7-trimethyl-bicyclo[2.2.1]heptane-2,3-dione);
benzophenone and benzophenone derivatives, such as 2,4,6-trimethylbenzophenone, 2-methylbenzophenone, 3-methylbenzophenone, 4-methylbenzophenone, 2-methoxycarbonylbenzophenone, 4,4'-bis(chloromethyl)benzophenone, 4-chlorobenzophenone, 4-phenylbenzophenone, 3,3'-dimethyl-4-methoxybenzophenone, [4-(4-methylphenylthio)phenyl]-phenylmethanone, methyl-2-benzoylbenzoate, 3-methyl-4'-phenylbenzophenone, 2,4,6-trimethyl-4'-phenylbenzophenone, 4,4'-bis(dimethylamino)benzophenone, 4,4'-bis(diethylamino)benzophenone; thioxanthones and thioxanthone derivatives, e.g. polymeric thioxanthones like OMNI-POL TX (diester of 2-carboxymethoxy thioxanthone and polytetramethyleneglycol 250);
ketal compounds, as for example benzildimethylketal (IRGACURE® 651);
acetophenone and acetophenone derivatives, for example α-hydroxycycloalkyl phenyl ketones or α-hydroxyalkyl phenyl ketones, such as for example 2-hydroxy-2-methyl-1-phenyl-propanone (DAROCURE® 1173), 1-hydroxy-cyclohexyl-phenyl-ketone (IRGACURE®184), 1-(4-dodecylbenzoyl)-1-hydroxy-1-methyl-ethane, 1-(4-isopropylbenzoyl)-1-hydroxy-1-methyl-ethane, 1-[4-(2-hydroxyethoxy)-phenyl]-2-hydroxy-2-methyl-1-propan-1-one (IRGACURE®2959); 2-hydroxy-1-{4-[4-(2-hydroxy-2-methyl-propionyl)-benzyl]-phenyl}-2-methyl-propan-1-one (IRGACURE®127); 2-hydroxy-1-{4-[4-(2-hydroxy-2-methyl-propionyl)-phenoxy]-phenyl}-2-methyl-propan-1-one; dialkoxyacetophenones, α-hydroxyacetophenones or α-aminoacetophenones, e.g. (4-methylthiobenzoyl)-1-methyl-1-morpholinoethane (IRGACURE® 907), (4-morpholinobenzoyl)-1-benzyl-1-dimethylaminopropane (IRGACURE® 369), (4-morpholinobenzoyl)-1-(4-methylbenzyl)-1-dimethylaminopropane (IRGACURE® 379), (4-(2-hydroxyethyl)aminobenzoyl)-1-benzyl-1-dimethylaminopropane), (3,4-dimethoxybenzoyl)-1-benzyl-1-dimethylaminopropane;
4-aroyl-1,3-dioxolanes, benzoin alkyl ethers and benzil ketals, e.g. dimethyl benzil ketal, phenylglyoxalic esters and derivatives thereof, e.g. methyl α-oxo benzene-acetate, oxophenyl-acetic acid 2-(2-hydroxy-ethoxy)-ethyl ester, dimeric phenylglyoxalic esters, e.g. oxo-phenyl-acetic acid 1-methyl-2-[2-(2-oxo-2-phenyl-acetoxy)-propoxy]-ethyl ester (IRGACURE® 754);
ketosulfones, e.g. ESACURE KIP 1001 M;
oximeesters, e.g. 1,2-octanedione 1-[4-(phenylthio)phenyl]-2-(O-benzoyloxime) (IRGACURE® OXE01), ethanone 1-[9-ethyl-6-(2-methylbenzoyl)-9H-carbazol-3-yl]-1-(O-acetyloxime) (IRGACURE® OXE02), ethanone 1-[9-ethyl-6-(2-methyl-4-(2,2-dimethyl-1,3-dioxolanyl)methoxybenzoyl)-9H-carbazol-3-yl]-1-(O-acetyloxime), N-Acetoxy-N-{3-[9-ethyl-6-(naphthalene-1-carbonyl)-9H-carbazol-3-yl]-1-methyl-3-acetoxyimino-propyl}-acetamide, 9H-thioxanthene-2-carboxaldehyde 9-oxo-2-(O-acetyloxime), the oxime esters described in WO 07/062,963, WO 07/071,797, WO 07/071,497, WO 05/080337, JP2010-049238, WO2008078678, JP2010-15025 and JP2010-49238 peresters, e.g. benzophenone tetracarboxylic peresters as described for example in EP 126541;

monoacylphosphine oxides, e.g. (2,4,6-trimethylbenzoyl) diphenylphosphine oxide (DAROCURE® TPO), ethyl (2,4,6 trimethylbenzoyl phenyl)phosphinic acid ester;

bisacylphosphine oxides, e.g. bis(2,6-dimethoxy-benzoyl)-(2,4,4-trimethylpentyl)phosphine oxide, bis(2,4,6-trimethyl-benzoyl)-phenylphosphine oxide (IRGACURE® 819), bis(2,4,6-trimethylbenzoyl)-2,4-dipentoxyphenylphosphine oxide;

trisacylphosphine oxides;

halomethyltriazines, e.g. 2-[2-(4-methoxy-phenyl)-vinyl]-4,6-bis-trichloromethyl-[1,3,5]triazine, 2-(4-methoxy-phenyl)-4,6-bis-trichloromethyl-[1,3,5]triazine, 2-(3,4-dimethoxy-phenyl)-4,6-bis-trichloromethyl-[1,3,5]triazine, 2-methyl-4,6-bis-trichloromethyl-[1,3,5]triazine;

hexaarylbisimidazole/coinitiators systems, e.g. ortho-chloro-hexaphenyl-bisimidazole combined with 2-mercaptobenz-thiazole, ferrocenium compounds, or titanocenes, e.g. bis (cyclopentadienyl)-bis(2,6-difluoro-3-pyrryl-phenyl) titanium (IRGACURE®784). Further, borate compounds can be used as coinitiators.

As additional photoinitiators oligomeric compounds such as for example oligomeric alpha hydroxyl ketones e.g. 2-hydroxy-1-{1-[4-(2-hydroxy-2-methyl-propionyl)-phenyl]-1,3,3-trimethyl-indan-S-yl}-2-methyl-propan-1-one, ESA-CURE KIP provided by Fratelli Lamberti, or oligomeric alpha amino ketones may be employed as well.

Specific examples of photoinitiators (c) are:
IRGACURE®369 (2-Benzyl-2-(dimethylamino)-1-[4-(4-morpholinyl)phenyl]-1-butanone)

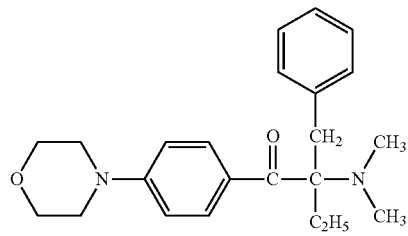 [SMILES: CCC(Cc1ccccc1)(C(=O)c1ccc(N2CCOCC2)cc1)N(C)C]

IRGACURE®379 (2-(4-Methylbenzyl)-2-(dimethylamino)-1-[4-(4-morpholinyl)phenyl]-1-butanone

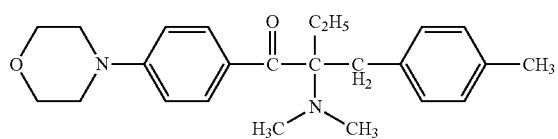 [SMILES: CCC(Cc1ccc(C)cc1)(C(=O)c1ccc(N2CCOCC2)cc1)N(C)C]

oxime ester: 1,2-octanedione, 1-[4-(phenylthio)phenyl]-2-(O-benzoyloxime)

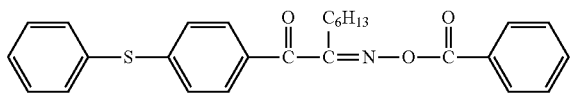

ethanone: 1-[9-ethyl-6-(2-methylbenzoyl)-9H-carbazol-3-yl]-1-(O-acetyloxime)

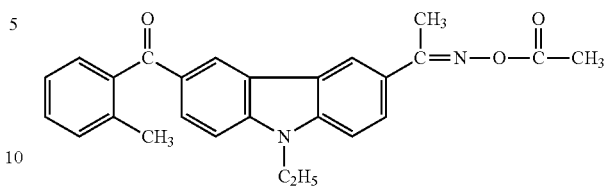

Alkaline Developable Resin (d)

The polymerizable composition according to the invention preferably comprises the component (d) in an amount of from 2 to 98% by weight, more preferably from 5 to 90% by weight, in particular from 10 to 80% by weight, based on the whole solid contents of the polymerizable composition (i.e. the amount of all components without the solvent(s)).

Preferably, the alkaline developable resin has free carboxylic groups. The acid number is preferably from 50 to 600 mg KOH/g, more preferably 100 to 300 mg KOH/g. The acid numbers stated here are the acid number according to DIN EN 12634.

Examples of alkali developable resins are acrylic polymers having carboxylic acid function as a pendant group, such as copolymers obtained by copolymerizing an ethylenic unsaturated carboxylic acid such as (meth)acrylic acid, 2-carboxyethyl(meth)acrylic acid, 2-carboxypropyl(meth)acrylic acid, itaconic acid, citraconic acid, mesaconic acid, fumaric acid, crotonic acid, maleic acid, maleic anhydride, fumaric anhydride, citraconic acid, mesaconic acid, itaconic acid, half-ester of maleic acid, cinnamic acid, mono[2-(meth)acryloyloxyethyl]succinate, mono[2-(meth)acryloyloxyethyl]adipate, mono[2-(meth)acryloyloxyethyl]phthalate, mono[2-(meth)acryloyloxyethyl]hexahydrophthalate, mono[2-(meth)acryloyloxyethyl]maleate, mono[2-(meth)acryloyloxypropyl]succinate, mono[2-(meth)acryloyloxypropyl]adipate, mono[2-(meth)acryloyloxypropyl]phthalate, mono[2-(meth)acryloyloxypropyl]hexahydrophthalate, mono[2-(meth)acryloyloxypropyl]maleate, mono[2-(meth)acryloyloxybutyl]succinate, mono[2-(meth)acryloyloxybutyl]adipate, mono[2-(meth)acryloyloxybutyl]phthalate, mono[2-(meth)acryloyloxybutyl]hexahydrophthalate, mono[2-(meth)acryloyloxybutyl]maleate, 3-(alkylcarbamoyl)acrylic acid, α-chloroacrylic acid, maleic acid, monoesterified maleic acid, citraconic acid and ω-carboxypolycaprolactone mono(meth)acrylate, with one or more monomers selected from esters of (meth)acrylic acid, such as methyl (meth)acrylate, ethyl (meth)acrylate, propyl(meth)acrylate, butyl (meth)acrylate, benzyl (meth) acrylate, 2-ethylhexyl(meth)acrylate, hydroxyethyl(meth) acrylate, hydroxypropyl(meth)acrylate, tetrahydrofurfuryl (meth)acrylate, hydroxybutyl(meth)acrylate, glycerol mono (meth)acrylate, dihydroxypropyl(meth)acrylate, allyl(meth) acrylate, cyclohexyl(meth)acrylate, phenyl(meth)acrylate, methoxyphenyl(meth)acrylate, methoxyethyl(meth)acrylate, phenoxyethyl(meth)acrylate, methoxydiethyleneglycol (meth)acrylate, methoxytriethyleneglycol(meth)acrylate, methoxypropyl(meth)acrylate, methoxydipropyleneglycol (meth)acrylate, (3-trimetoxysilyl)propyl(meth)acrylate, (meth)acrylic acid trimethyl silyl ester, (meth)acrylate, isobornyl(meth)acrylate, dicyclopentadienyl(meth)acrylate, 2-hydroxy-3-phenoxypropyl(meth)acrylate, tricyclo[5.2.1.0$^{2,6}$]decan-8-yl(meth)acrylate, aminoethyl(meth) acrylate, N,N-dimethylaminoethyl(meth)acrylate, aminopropyl(meth)acrylate, N,N-dimethylaminopropyl(meth) acrylate, glycidyl(meth)acrylate, 2-methylglycidyl(meth)

acrylate, 3,4-epoxybutyl(meth)acrylate, 6,7-epoxyheptyl (meth)acrylate; vinyl aromatic compounds, such as styrene, α-methylstyrene, vinyltoluene, p-chlorostyrene, polychlorostyrene, fluorostyrene, bromostyrene, ethoxymethyl styrene, methoxystyrene, 4-methoxy-3-methylstyrene, dimethoxystyrene, vinylbenzyl methyl ether, vinylbenzyl glycidyl ether, indene, 1-methylindene, 1-ethenyl-4-silylbenzen, 1-ethenyl-4-trimethylsilyl-benzene, t-buthyl dimethylsilyl p-vinyl phenyl ether; amide type unsaturated compounds, such as (meth)acrylamide, diacetone acrylamide, N-methylolacrylamide, N-butoxymethacrylamide, N,N-dimethyl (meth)acrylamide, N, N-diethyl(meth)acrylamide, N,N-dibutyl(meth)acrylamide, N,N-diethylhexyl(meth)acrylamide, N,N-dicyclohexyl(meth)acrylamide, N,N-diphenyl(meth)acrylamide, N-methyl-N-phenyl(meth)acrylamide, N-hydroxyethyl-N-methyl(meth)acrylamide, N-methyl (meth)acrylamide, N-ethyl (meth)acrylamide, N-propyl(meth)acrylamide, N-butyl (meth)acrylamide, N-hydroxyethyl(meth)acrylamide, N-heptyl(meth)acrylamide, N-octyl(meth)acrylamide, N-ethylhexyl(meth)acrylamide, N-hydroxyethyl(meth)acrylamidecyclohexyl, N-benzyl (meth)acrylamide, N-phenyl(meth)acrylamide, N-tolyl (meth)acrylamide, N-hydroxyphenyl(meth)acrylamide, N-naphthyl(meth)acrylamide, N-phenylsulfonyl(meth)acrylamide, N-methylphenylsulfonyl(meth)acrylamide and N-(meth)acryloylmorpholine; acetal ester or ketal ester compounds, such as norbornene, 2,3-di-trimethylsilanyloxycarbonyl-S-norbornene, 3-di-trietylsilanyloxycarbonyl-S-norbornene, 2,3-di-t-butyldimethylsilanyloxycarbonyl-5-norbornene, 2,3-di-trimethylgermyloxycarbonyl-S-norbornene, 2,3-di-triethylgelmyloxycarbonyl-S-norbornene, 2,3-di-t-butyldimethylgermyloxycarbonyl-5-norbornene, 2,3-di-t-butyloxycarbonyl-S-norbornene, 2,3-di-benzyloxycarbonryl-5-norbornene, 2,3-di-tetrahydrofurane-2-yloxycarbonyl-S-norbornene, 2,3-di-cyclopentyloxycarbonyl-S-norbornene, 2,3-di-cyclohexyloxycarbonyl-S-norbornene, 2,3-di-cycloheptyloxycarbonyl-S-norbornene, 2,3-di-1-methoxyethoxycarbonyl-5-norbornene, 2,3-di-1-t-buthoxyethoxycarbonyl-S-norbornene, 2,3-di-1-benzyloxyethoxycarbonyl-S-norbornene, 2,3-di-(cyclohexyl)(ethoxy)methoxycarbonyl-norbornene, 2,3-di-1-methyl-1-methoxyethoxycarbonyl-S-norbornene, 2,3-di-1-methyl-1-i-buthoxyethoxycarbonyl-S-norbornene, 2,3-di-(benzyl)(ethoxy)methoxycarbonyl-5-norbornene;
1-alkylcycloalkylester compounds, such as 1-methylcyclopropane(meth)acrylate, 1-methylcyclobutane(meth)acrylate, 1-methylcyclopentyl(meth)acylate, 1-methylcyclohexyl (meth)acrylate, 1-methylcycloheptane(meth)acrylate, 1-methylcyclooctane(meth)acrylate, 1-methylcyclononane(meth) acrylate, 1-ethylcyclodecane(meth)acrylate, 1-ethylcyclopuropane(meth)acrylate, 1-ethylcyclobutane (meth)acrylate, 1-ethylcyclopentyl(meth)acrylate, 1-ethylcyclohexyl(meth)acrylate, 1-ethylcycloheptane(meth)acrylate, 1-ethylcyclooctane(meth)acrylate, 1-ethylcyclononane (meth)acrylate, 1-ethylcyclodecane(meth)acrylate, 1-(iso) puropylcyclopuropane(meth)acrylate, 1-(iso) puropylcyclopuropane(meth)acrylate, 1-(iso) puropylcyclopentyl(meth)acrylate, 1-(iso) puropylcyclohexyl(meth)acrylate, 1-(iso) puropylcycloheptane(meth)acrylate, 1-(iso) puropylcyclooctane(meth)acrylate, 1-(iso) puropylcyclononane(meth)acrylate 1-(iso) puropylcyclodecane(meth)acrylate, 1-(iso) butylcyclopuropane(meth)acrylate, 1-(iso)butylcyclobutane (meth)acrylate, 1-(iso)butylcyclopentyl(meth)acrylate, 1-(iso)butylcyclohexyl(meth)acrylate, 1-(iso)butylcyclohexyl(meth)acrylate, 1-(iso)butylcyclooctane(meth)acrylate, 1-(iso)-butylcyclononane(meth)acrylate, 1-(iso)butylcyclodecanyl(meth)acrylate, 1-(iso)pentylcyclopuropanyl(meth) acrylate, 1-(iso)pentylcyclopentyl(meth)acrylate, 1-(iso) pentylcyclopentyl(meth)acrylate, 1-(iso)pentylcyclohexyl (meth)acrylate, 1-(iso)pentylcycloheptanyl(meth)acrylate, 1-(iso)pentylcyclooctane(meth)acrylate, 1-(iso)pentylcyclononyl(meth)acrylate, 1-(iso)pentylcyclodecanyl(meth) acrylate, 1-(iso)octylcyclopuropanyl(meth)acrylate, 1-(iso) octylcyclobutabtyl(meth)acrylate, 1-(iso)octylcyclooctyl (meth)acrylate, 1-(iso)octylcycloheptanyl(meth)acrylate, 1-(iso)octylcycloheptanyl(meth)acrylate, 1-(iso)octylcyclooctanyl(meth)acrylate, 1-(iso)octylcyclononanyl(meth) acrylate, 1-(iso)octylcyclodecanyl(meth)acrylate; methacryl acids, such as 3-(methacryloyloxymethyl)oxetane, 3-(methacryloyloxymethyl)-3-ethyloxetane, 3-(methacryloyloxymethyl)-2-methyloxetane, 3-(methacryloyloxymethyl)-2-methyloxetane, 3-(methacryloyloxymethyl)-2-trifrollomethyloxetane, 3-(methacryloyloxynethyl)-2-pentafrolloethyloxetane, 3-(methacryloyloxymethyl)-2-phenyloxetane, 3-(methacryloyloxymethyl)-2,2-difrollooxetane, 3-(methacryloyloxymethyl)-2,2,4,-trifrollooxetane, 3-(methacryloyloxymethyl)-2,2,4,4-tetrafrollooxetane, 3-(methacryloyloxyethyl)oxetane, 3-(methacryloyloxyethyl)-3-ethyloxetane, 2-ethyl-3-(methacryloyloxyethyl)oxetane, 3-(methacryloyloxyethyl)-2-trifrollomethyloxetane, 3-(methacryloyloxyethyl)-2-pentafrolloethyloxetane, 3-(methacryloyloxyethyl)-2-phenyloxetane, 2,2-difrollo-3-(methacryloyloxyethyl)oxetane, 3-(methacryloyloxyethyl)-2,2,4-trifrollooxetane, 3-(methacryloyloxyethyl)-2,2,4,4,-tetrafrollooxetane; polycyclic compounds or anhydride, such as 5-carboxybicyclo[2.2.1]hept-2-ene, 5,6-dicarbocybicyclo[2.2.1]hept-2-ene, 5-carboxy-5-methylbicyclo[2.2.1]hept-2-ene, 5-carboxy-6-ethylbicyclo[2.2.1] hept-2-ene, 5-carboxy-6-methylbicyclo[2.2.1]hept-2-ene, 5-carboxy-6-ethylbicyclo[2.2.1]hept-2-ene, 5,6-dicarboxybicyclo[2.2.1]hept-2-eneanhydride; vinyl or allyl esters, such as vinyl acetate, vinyl propionate, vinyl butylate, vinyl pivalate, vinyl benzoate, vinyl trimethylacetate, vinyl diethylacetate, vinyl barate, vinyl caproate, vinyl chloroacetate, vinyl dichloroacetate, vinyl methoxyacetate, vinyl butoxyacetate, vinyl phenylacetate, vinyl acetate, vinyl acetoacetate, vinyl lactate, vinyl phenylbutylate, vinyl cyclohexylcarboxylate, vinyl salicylate, vinyl chlorobenzoate, vinyl tetrachlorobenzoate, vinyl naphthoate, vinyl triethoxysilane, allyl acetate, allyl propionate, allyl butylate, allyl pivalate, allyl benzoate, allyl caproate, allyl stearate, allyl acetoacetate, allyl lactate; vinyl or allyl ethers, such as vinyl methyl ether, vinyl ethyl ether, vinyl hexyl ether, vinyl octyl ether, vinyl ethylhexyl ether, vinyl methoxyethyl ether, vinyl ethoxyethyl ether, vinyl chloroethyl ether, vinyl hydroxyethyl ether, vinyl ethylbutyl ether, vinyl hydroxyethoxyethyl ether, vinyl dimethylaminoethyl ether, vinyl diethylaminoethyl ether, vinyl butylaminoethyl ether, (ethenyloxy)methyl silane, vinyl benzyl ether, vinyl tetrahydrofurfuryl ether, vinyl phenyl ether, vinyl tolyl ether, vinyl chlorophenyl ether, vinyl chloroethyl ether, vinyl dichlorophenyl ether, vinyl naphthyl ether, vinyl anthryl ether, allyl glycidyl ether; crotonates, such as butyl crotonate, hexyl crotonate, glycerine monocrotonate; itaconates, such as dimethyl itaconate, diethyl itaconate, dibutyl itaconate; and maleates or fumarates, such as dimethyl mareate, dibutyl fumarate; polyolefin type compounds, such as butadiene, isoprene, chloroprene and the like; methacrylonitrile, methyl isopropenyl ketone, vinyl acetate, vinyl propionate, vinyl pivalate, maleimide, N-phenylmaleimide, N-methylmaleimide, N-methoxyphenylmaleimide, N-cyclohexylmaleimide, N-alkylmaleimide, maleic anhydride, polystyrene macromonomer, polymethyl(meth)acrylate macromonomer, polybutyl(meth)acrylate macromonomer. Examples of copolymers are copolymers of acrylates and methacrylates with acrylic acid or methacrylic acid and with styrene or substituted styrene, phenolic resins, for example novolak, (poly)hydroxystyrene, and copolymers of hydroxystyrene with alkyl acrylates, acrylic acid and/or methacrylic acid. Preferable examples of copolymers are copolymers of methyl (meth)acrylate/(meth)acrylic acid, copolymers of benzyl (meth)acrylate/(meth)acrylic acid, copolymers of methyl (meth)acrylate/ethyl (meth)acrylate/(meth)acrylic acid, copolymers of benzyl (meth)acrylate/(meth)acrylic acid/styrene, copolymers of benzyl (meth)acrylate/(meth)acrylic acid/hydroxyethyl(meth)acrylate, copolymers of benzyl (meth)acrylate/(meth)acrylic acid/glycidyl(meth)acrylate, copolymers of benzyl (meth)acrylate/(meth)acrylic acid/3-(methacryloyloxymethyl)oxetane, copolymers of methyl (meth)acrylate/butyl (meth)acrylate/(meth)acrylic acid/styrene, copolymers of methyl (meth)acrylate/benzyl (meth)acrylate/(meth)acrylic acid/hydroxyphenyl(meth)acrylate, copolymers of methyl (meth)acrylate/(meth)acrylic acid/polymethyl(meth)acrylate macromonomer, copolymers of benzyl (meth)acrylate/(meth)acrylic acid/polymethyl(meth)acrylate macromonomer, copolymers of tetrahydrofurfuryl (meth)acrylate/styrene/(meth)acrylic acid, copolymers of methyl (meth)acrylate/(meth)acrylic acid/polystyrene macromonomer, copolymers of benzyl (meth)acrylate/(meth)acrylic acid/polystyrene macromonomer, copolymers of benzyl (meth)acrylate/(meth)acrylic acid/2-hydroxyethyl(meth)acrylate/polystyrene macromonomer, copolymers of benzyl (meth)acrylate/(meth)acrylic acid/2-hydroxypropyl(meth)acrylate/polystyrene macromonomer, copolymers of benzyl (meth)acrylate/(meth)acrylic acid/2-hydroxy-3-phenoxypropyl(meth)acrylate/polymethyl(meth)acrylate macromonomer, copolymers of methyl (meth)acrylate/(meth)acrylic acid/2-hydroxyethyl(meth)acrylate/polystyrene macromonomer, copolymers of benzyl (metha)crylate/(meth)acrylic acid/2-hydroxyethyl(meth)acrylate/polymethyl(meth)acrylate macromonomer, copolymers of N-phenylmaleimide/benzyl (meth)acrylate/(meth)acrylic acid and styrene, copolymers of benzyl (meth)acrylate/(meth)acrylic acid/N-phenylmaleimide/mono-[2-(meth)acryloyloxyethyl]succinate/styrene, copolymers of allyl(meth)acrylate/(meth)acrylic acid/N-phenylmaleimide/mono-[2-(meth)acryloyloxyethyl]succinate/styrene, copolymers of benzyl (meth)acrylate/(meth)acrylic acid/N-phenylmaleimide/glycerol mono(meth)acrylate/styrene, copolymers of benzyl (meth)acrylate/co-carboxypolycaprolactone mono(meth)acrylate/(meth)acrylic acid/N-phenylmaleimide/glycerol mono(meth)acrylate/styrene, and copolymers of benzyl (meth)acrylate/(meth)acrylic acid/N-cyclohexylmaleimide/styrene. Example of commercial product is Ripoxy SPC-2000 provided by Showa Highpolymer.

As mentioned before, the alkaline developable resin (d) has preferably free carboxylic groups, which provide the compounds with good alkaline solubility. However, it is also possible to employ functional groups that are different from carboxylic groups, in order to obtain a resin with good alkaline solubility. Examples for such groups are phenolic groups, sulfonic acid groups, anhydride groups, and combinations thereof.

Typical examples of the aforementioned acid anhydride are dibasic acid anhydrides such as for example maleic anhydride, succinic anhydride, itaconic anhydride, phthalic anhydride, tetrahydrophthalic anhydride, hexahydrophthalic anhydride, methylhexahydrophthalic anhydride, endo-methylenetetrahydrophthalic anhydride, methyl-endomethylene-tetrahydrophthalic anhydride, chlorendic anhydride, and methyltetrahydrophthalic anhydride. Suitable are also aromatic polycarboxylic anhydrides, for example trimellitic anhydride, pyromelic anhydride and benzophenone tetracarboxylic dianhydride. Suitable are also polycarboxylic anhydride derivatives such as 5-(2,5-dioxotetrahydrofuryl)-3-methyl-3-cyclohexene-1,2-dicarboxylic anhydride.

Further examples of alkaline developable resins (d) are polymers or oligomers having at least two ethylenically unsaturated groups and at least one carboxyl function within the molecule structure, such as a resin obtained by the reaction of a saturated or unsaturated polybasic acid anhydride with a product of the reaction of an epoxy compound and an unsaturated monocarboxylic acid (for example, EB9696 from UCB Chemicals; KAYARAD TCR1025 from Nippon Kayaku Co. LTD.; NK OLIGO EA-6340, EA-7440 from Shin-Nakamura Chemical Co., Ltd.). Other examples of such binders are described in JP2002-206014A, JP2004-69754A, JP2004-302245A, JP2005-77451A, JP2005-316449A, JP2005-338328A and JP3754065B2.

Further examples of alkaline developable resins (d) are the above-mentioned polymers or oligomers having at least one ethylenically unsaturated groups Further examples of alkaline developable resins (d) are reaction products obtained by adding an epoxy group containing unsaturated compound to a part of the carboxyl groups of a carboxylic acid group containing polymer (for ex., ACA200, ACA200M, ACA210P, ACA230AA, ACA250, ACA300, ACA320 from Daicel Chemical Industries, Ltd. and Ripoxy SPC-1000 provided by Showa Highpolymer). As the carboxylic acid containing polymer, the abovementioned binder polymers which are resulting from the reaction of an unsaturated carboxylic acid compound with one or more polymerizable compounds, for example, copolymers of (meth)acrylic acid, benzyl (meth)acrylate, styrene and 2-hydroxyethyl(meth)acrylate, copolymers of (meth)acrylic acid, styrene and α-methystyrene, copolymers of (meth)acrylic acid, N-phenylmaleimide, styrene and benzyl (meth)acrylate, copolymers of (meth)acrylic acid and styrene, copolymers of (meth)acrylic acid and benzyl (meth)acrylate, copolymers of tetrahydrofurfuryl(meth)acrylate, styrene and (meth)acrylic acid and the like.

Examples of the unsaturated compounds having an epoxy group are given below in the formula (V-1)-(V-15);

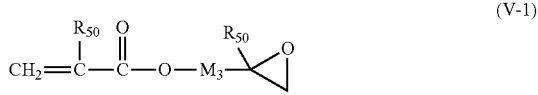

(V-1)

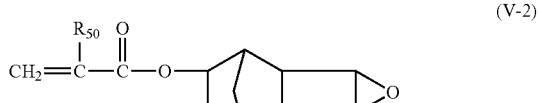

(V-2)

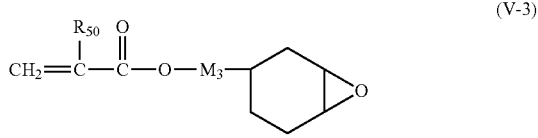

(V-3)

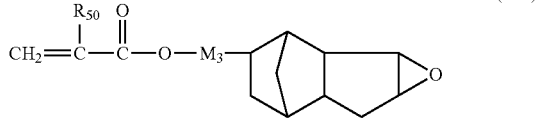

(V-4)

-continued (V-5)
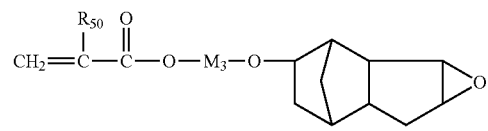

(V-6)
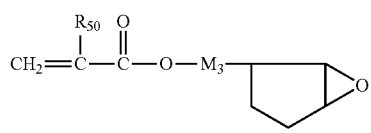

(V-7)
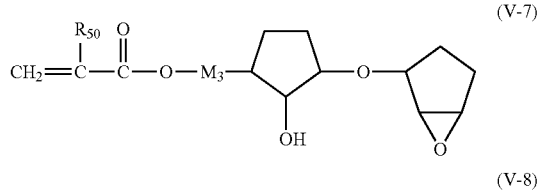

(V-8)
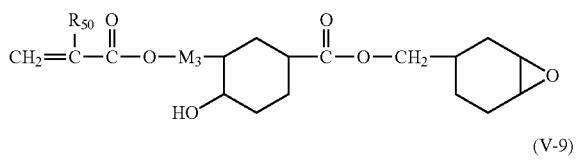

(V-9)
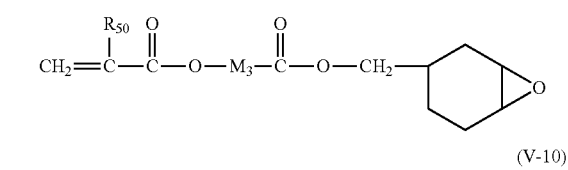

(V-10)
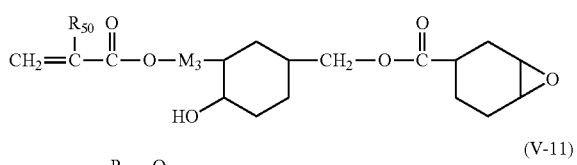

(V-11)
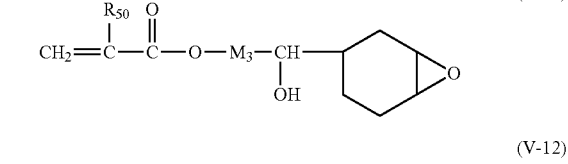

(V-12)
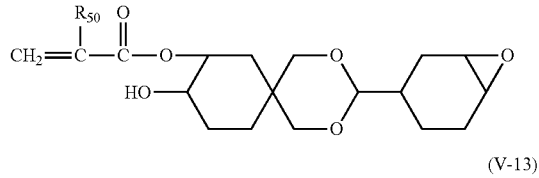

(V-13)
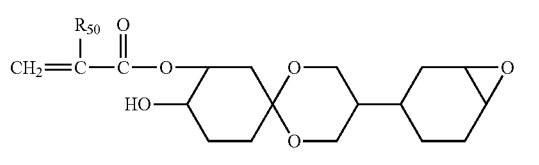

(V-14)
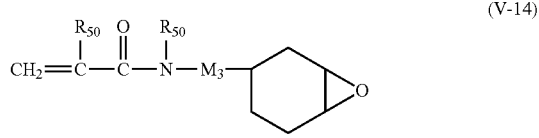

-continued (V-15)
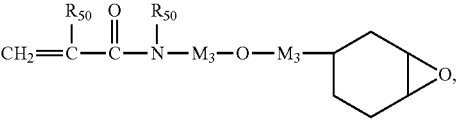

wherein $R_{50}$ is hydrogen or a methyl group, and $M_3$ is substituted or unsubstituted alkylene having 1 to 10 carbon atoms.

Among these compounds, compounds having alicyclic epoxy groups are particularly preferred, because these compounds have a high reactivity with carboxyl group-containing resins, accordingly the reaction time can be shortened. These compounds further do not cause gelation in the process of reaction and make it possible to carry out the reaction stably. On the other hand, glycidyl acrylate and glycidyl methacrylate are advantageous from the viewpoint of sensitivity and heat resistance because they have a low molecular weight and can give a high conversion of esterification.

Concrete examples of the abovementioned compounds are, for example a reaction product of a copolymer of styrene, α-methyl styrene and acrylic acid or a copolymer of methyl methacrylate and acrylic acid with 3,4-epoxycyclohexylmethyl(meth)acrylate.

Further examples are products obtained by addition reaction of an epoxy group containing unsaturated compound to a part of or all of the carboxyl groups of a carboxylic acid group containing polymer followed by further reaction with polybasic acid anhydride (for ex., Ripoxy SPC-3000 provided by Showa Highpolymer).

Unsaturated compounds having a hydroxy group such as 2-hydroxyethyl(meth)acrylate and glycerol mono(meth)acrylate can be used instead of the above mentioned epoxy group containing unsaturated compounds as the reactant for carboxylic acid group containing polymers.

Further examples are half esters of anhydride containing polymers, for example reaction products of a copolymer of maleic anhydride and one or more other polymerizable compounds with (meth)acrylates having an alcoholic hydroxyl group such as 2-hydroxyethyl(meth)acrylate or having an epoxy group for example such as the compounds described in the formula (V-1)-(V-15).

Reaction products of polymers having alcoholic hydroxyl groups such as copolymers of 2-hydroxyethyl(meth)acrylate, (meth)acrylic acid, benzyl methacylate and styrene, with (meth)acrylic acid or (meth)acryl chloride can also be used.

Further examples are reaction products of a polyester with terminal unsaturated groups, which is obtained from the reaction of a dibasic acid anhydride and a compound having at least two epoxy groups followed by further reaction with an unsaturated compound, with a polybasic acid anhydride.

Further examples are resins obtained by the reaction of a saturated or unsaturated polybasic acid anhydride with a reaction product obtained by adding epoxy group containing (meth)acrylic compound to all of the carboxyl groups of a carboxylic acid containing polymer as mentioned above.

Further example is polyimide resin having ethylenically unsaturated groups and at least one carboxyl function. The polyimide binder resin in the present invention can be a polyimide precursor, for example, a poly(amic acid).

Specific examples of alkali developable resins (d) are:
Acrylpolymer type resins such as
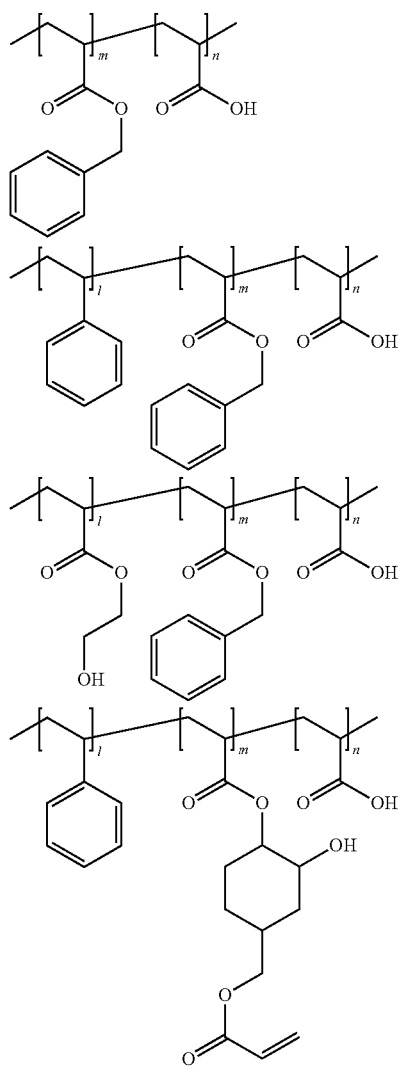
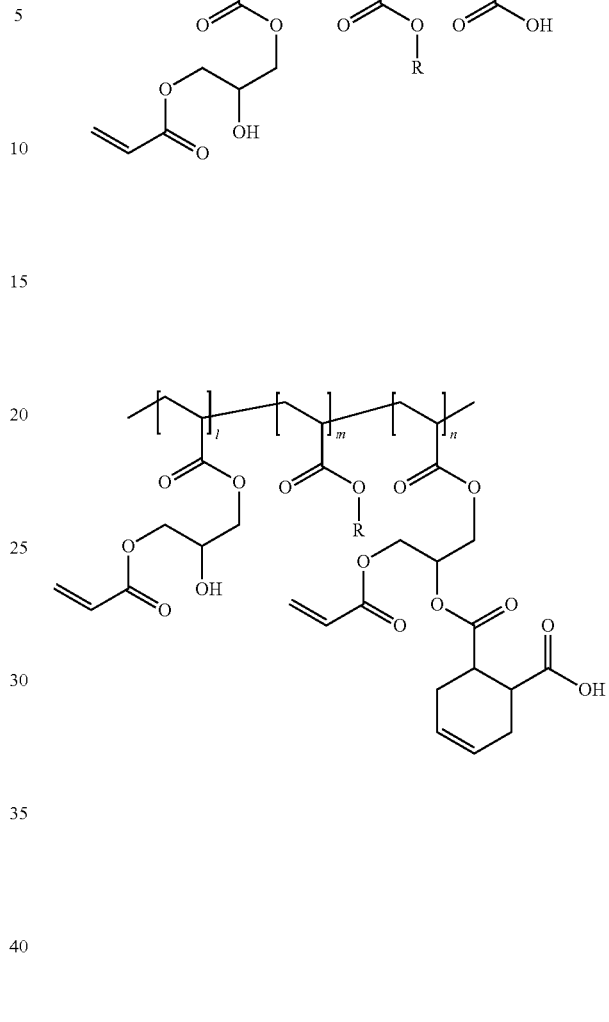
Cardo type resin (fluorene epoxy acrylate based resin)
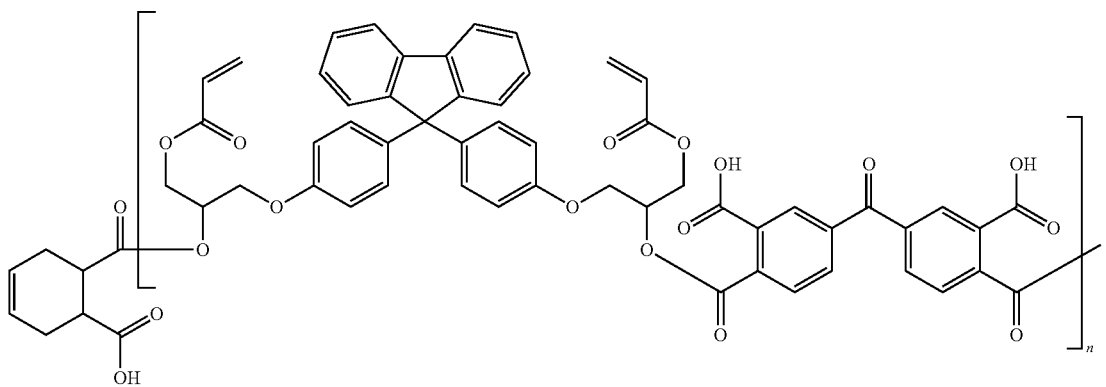

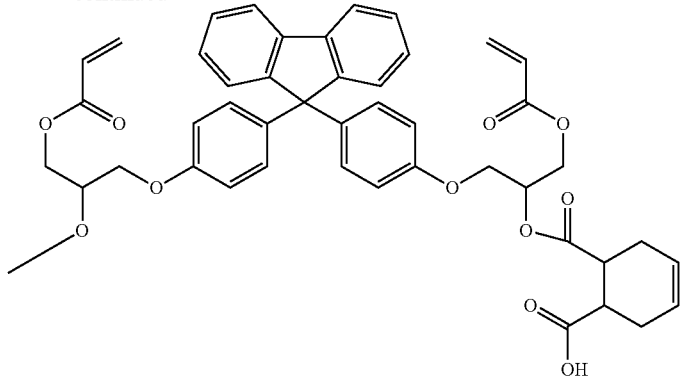

The polymerizable composition according to the invention and in particular the polymerizable composition comprising as component (d) at least one alkaline developable resin may contain further components (e) and/or (f), as mentioned in the following:

Colorants:

Pigments and/or dyes may be present. The pigments which can be comprised in the composition according to the present invention, including a pigmented color filter resist composition, are preferably processed pigments.

The red pigment comprises, for example, an anthraquinone type pigment alone, a diketopyrolopyrole type pigment alone, a mixture of them or a mixture consisting of at least one of them and a disazo type yellow pigment or an isoindoline type yellow pigment, in particular C. I. Pigment Red 177 alone, C. I. Pigment Red 254 alone, a mixture of C. I. Pigment Red 177 and C. I. Pigment Red 254 or a mixture consisting of at least one member of C. I. Pigment Red 177, C. I. Pigment Red 242 and C. I. Pigment Red 254, and C. I. Pigment Yellow 83 or C. I. Pigment Yellow 139 ("C.I." refers to the Color Index, known to the person skilled in the art and publicly available).

Further suitable examples for the pigment are C.I. Pigment Red 9, 97, 105, 122, 123, 144, 149, 168, 176, 179, 180, 185, 202, 207, 209, 214, 222, 244, 255, 264, 272 and C.I. Pigment Yellow 12, 13, 14, 17, 20, 24, 31, 53, 55, 93, 95, 109, 110, 128, 129, 138, 139, 150, 153, 154, 155, 166, 168, 185, 199, 213 and C.I. Pigment Orange 43 and 71. Examples of the dyes for red color are C. I. Solvent Red 25, 27, 30, 35, 49, 83, 89, 100, 122, 138, 149, 150, 160, 179, 218, 230, C. I. Direct Red 20, 37, 39, 44, and C. I. Acid Red 6, 8, 9, 13, 14, 18, 26, 27, 51, 52, 87, 88, 89, 92, 94, 97, 111, 114, 115, 134, 145, 151, 154, 180, 183, 184, 186, 198, C. I. Basic Red 12, 13, C. I. Disperse Red 5, 7, 13, 17 and 58. The Red dyes can be used in combination with yellow and/or orange dyes.

The green pigment comprises for instance a halogenated phthalocyanine type pigment alone or its mixture with a bisazo type yellow pigment, an quinophthalone type yellow pigment or a metal complex, in particular C. I. Pigment Green 7 alone, C. I. Pigment Green 36 alone, C. I. Pigment 58 alone, or a mixture consisting of at least one member of C. I. Pigment Green 7, C. I. Pigment Green 36, Pigment Green 58 and C. I. Pigment Yellow 83, C. I. Pigment Yellow 138 or C. I. Pigment Yellow 150. Other suitable green pigments are C.I. Pigment Green 15, 25 and 37. Examples for suitable green dyes are C. I. Acid Green 3, 9, 16, C. I. Basic Green 1 and 4.

The blue dye comprises, for example, a methine type dye, an anthraquinone type dye, an azo type dye, a metal complex azo type dye, a triarylmethane type dye or a phthalocyanine type dye. Examples for suitable blue pigments are phthalocyanine type pigments, used either alone or in combination with an dioxazine type violet pigment, for instance, C. I. Pigment Blue 15:6 alone, a combination of C. I. Pigment Blue 15:6 and C. I. Pigment Violet 23. Further examples for blue pigments are such of C. I. Pigment Blue 15:3, 15:4, 16, 22, 28 and 60. Other suitable pigments are C. I. Pigment Violet 14, 19, 23, 29, 32, 37, 177 and C. I. Orange 73.

Examples for suitable blue dyes are C. I. Solvent Blue 11, 25, 37, 45, 49, 68, 78, 94, C. I. Direct Blue 25, 86, 90, 108, C. I. Acid Blue 1, 3, 7, 9, 15, 83, 90, 103, 104, 158, 161, C. I. Basic Blue 1, 3, 7, 9, 25, 105, C. I. Disperse Blue 198 and Mordant Blue 1.

The pigment of the photopolymeric composition for black matrix preferably comprises at least one member selected from the group consisting of carbon black, titanium black, iron oxide, lactone, lactam and perylene. Preferred example is carbon black. However, a mixture of other pigments which, in total, give the black appearance, can also be used. For example, also C. I. Pigment Black 1, 7, 31 and 32 can be used alone or in combination.

Other examples of the dyes used for color filter are C. I. Solvent Yellow 2, 5, 14, 15, 16, 19, 21, 33, 56, 62, 77, 83, 93, 162, 104, 105, 114, 129, 130, 162, C. I. Disperse Yellow 3, 4, 7, 31, 54, 61, 201, C. I. Direct Yellow 1, 11, 12, 28, C. I. Acid Yellow 1, 3, 11, 17, 23, 38, 40, 42, 76, 98, C. I. Basic Yellow 1, C. I. Solvent Violet 13, 33, 45, 46, C. I. Disperse Violet 22, 24, 26, 28, 31, C. I. Acid Violet 49, C. I. Basic Violet 2, 7, 10, C. I. Solvent Orange 1, 2, 5, 6, 37, 45, 62, 99, C. I. Acid Orange 1, 7, 8, 10, 20, 24, 28, 33, 56, 74, C. I. Direct Orange 1, C. I. Disperse Orange 5, C. I. Direct Brown 6, 58, 95, 101, 173, C. I. Acid Brown 14, C. I. Solvent Black 3, 5, 7, 27, 28, 29, 35, 45 and 46.

In some special cases of manufacturing color filters, complementary colors, yellow, magenta, cyan and optionally green, are used instead of red, green and blue. As yellow for this type of color filters, the abovementioned yellow pigments and dyes can be employed. Examples of the colorants suitable for magenta color are C. I. Pigment Red 122, 144, 146, 169, 177, C. I. Pigment Violet 19 and 23. Examples of cyan color are aluminum phthalocyanine pigments, titanium phthalocyanine pigments, cobalt phthalocyanine pigments, and tin phthalocyanine pigments.

The pigments in the color filter resist composition have preferably a mean particle diameter smaller than the wavelength of visible light (400 nm to 700 nm). Particularly preferred is a mean pigment diameter of <100 nm.

The concentration of the pigment in the total solid component (pigments of various colors and resin) is for example in the range of 5% to 80% by weight, in particular in the range of 20% to 65% by weight.

The concentration of the dye in the total solid component (dyes of various colors and resin) is for example in the range of 0.5% to 95% by weight, in particular in the range of 0.5% to 70% by weight.

If necessary, the pigments may be stabilized in the photosensitive composition by pretreatment of the pigments with a dispersant to improve the dispersion stability of the pigment in the liquid formulation. Suitable additives are described below.

Additives:

Additives are optional present such as dispersing agents, surfactant, adhesion promoters, photosensitizer and the like.

It is preferred to apply a surface treatment to the pigments in order to make the pigment easy to disperse and to stabilize the resultant pigment dispersion. The surface treatment reagents are, for example, surfactants, polymeric dispersants, general texture improving agents, pigment derivatives and mixtures thereof. It is especially preferred when the colorant composition according to the invention comprises at least one polymeric dispersant and/or at least pigment derivative.

Suitable surfactants include anionic surfactants such as alkylbenzene- or alkylnahthalene-sulfonates, alkylsulfosuccinates or naphthalene formaldehyde sulfonates; cationic surfactants including, for example, quaternary salts such as benzyl tributyl ammonium chloride; or nonionic or amphoteric surfactants such as polyoxyethylene surfactants and alkyl- or amidopropyl betaines, respectively.

Illustrative examples of the surfactant include polyoxyethylene alkyl ethers such as polyoxyethylene lauryl ether, polyoxyethylene stearyl ether and polyoxyethylene oleyl ether; polyoxyethylene alkylphenyl ethers such as polyoxyethylene octylphenyl ether and polyoxyethylene nonylphenyl ether; polyethylene glycol diesters such as polyethylene glycol dilaurate and polyethylene glycol distearate; sorbitan fatty acid esters; fatty acid modified polyesters; tertiary amine modified polyurethanes; polyethyleneimines; those available under the trade names of KP (a product of Shin-Etsu Chemical Co., Ltd), Polyflow (a product of KYOEISHA CHEMICAL Co., Ltd), F-Top (a product of Tochem Products Co., Ltd), MEGAFAC (a product of Dainippon Ink & Chemicals, Inc.), Fluorad (a product of Sumitomo 3M Ltd), Asahi Guard and Surflon (products of Asahi Glass Co., Ltd); and the like.

These surfactants may be used alone or in admixture of two or more.

The surfactant is generally used in an amount of 50 parts or less by weight, preferably 0 to 30 parts by weight, based on 100 parts by weight of the colorant composition.

Polymeric dispersants include high molecular weight polymers with pigment affinic groups. Examples are: statistical co-polymers comprised from, for instance, styrene derivatives, (meth)acrylates and (meth)acrylamides, and such statistical co-polymers modified by post modification; block co-polymers and/or comb polymers comprised from, for instance, styrene derivatives, (meth)acrylates and (meth) acrylamides, and such block co-polymers and/or comb polymers modified by post modification; polyethylenimines, which for instance is crafted with polyesters; polyamines, which for instance is crafted with polyesters; and many kinds of (modified) polyurethanes.

Polymeric dispersants may also be employed. Suitable polymeric dispersants are, for example, BYK's DISPERBYK® 101, 115, 130, 140, 160, 161, 162, 163, 164, 166, 168, 169, 170, 171, 180, 182, 2000, 2001, 2009, 2020, 2025, 2050, 2090, 2091, 2095, 2096, 2150, Ciba's Ciba® EFKA® 4008, 4009, 4010, 4015, 4046, 4047, 4050, 4055, 4060, 4080, 4300, 4310, 4330, 4340, 4400, 4401, 4402, 4403, 4406, 4500, 4510, 4520, 4530, 4540, 4550, 4560, Ajinomoto Fine Techno's PB®711, 821, 822, 823, 824, 827, Lubrizol's SOLSPERSE® 1320, 13940, 17000, 20000, 21000, 24000, 26000, 27000, 28000, 31845, 32500, 32550, 32600, 33500, 34750, 36000, 36600, 37500, 39000, 41090, 44000, 53095 and combinations thereof.

It is preferred to use Ciba® EFKA® 4046, 4047, 4060, 4300, 4310, 4330, 4340, DISPERBYK® 161, 162, 163, 164, 165, 166, 168, 169, 170, 2000, 2001, 2020, 2050, 2090, 2091, 2095, 2096, 2105, 2150, PB®711, 821, 822, 823, 824, 827, SOLSPERSE® 24000, 31845, 32500, 32550, 32600, 33500, 34750, 36000, 36600, 37500, 39000, 41090, 44000, 53095 and combinations thereof as dispersant.

Suitable texture improving agents are, for example, fatty acids such as stearic acid or behenic acid, and fatty amines such as laurylamine and stearylamine. In addition, fatty alcohols or ethoxylated fatty alcohols, polyols such as aliphatic 1,2-diols or epoxidized soy bean oil, waxes, resin acids and resin acid salts may be used for this purpose.

Suitable pigment derivatives are, for example, copper phthalocyanine derivatives such as Ciba's Ciba® EFKA® 6745, Lubrizol's SOLSPERSE® 5000, 12000, BYK's SYNERGIST 2100 and azo derivatives such as Ciba® EFKA® 6750, SOLSPERSE® 22000 and SYNERGIST 2105.

The above mentioned dispersants and surfactants for pigments are for example employed in compositions of the present invention which are used as resist formulations, in particular in color filter formulations.

Subject of the invention also is a photopolymerizable composition as described above as further additive comprising a dispersant or a mixture of dispersants as well as a photopolymerizable composition as described above as further additive comprising a pigment or a mixture of pigments.

In the invention, the content of the dispersing agent is preferably from 1 to 80% by mass, more preferably from 5 to 70% by mass, even more preferably from 10 to 60% by mass, based on the mass of the pigment.

Adhesion Improving Agent:

The curable composition of the invention may contain an adhesion improving agent for increasing adhesion to a hard surface, such as of a support. The adhesion improving agent may be a silane coupling agent, a titanium coupling agent or the like.

Photosensitizer:

Photopolymerization can also be accelerated by adding further photosensitizers or coinitiators which shift or broaden the spectral sensitivity. These are, in particular, aromatic compounds, for example benzophenone and derivatives thereof, thioxanthone and derivatives thereof, anthraquinone and derivatives thereof, coumarin and phenothiazine and derivatives thereof, and also 3-(aroylmethylene)thiazolines, rhodanine, camphorquinone, but also eosine, rhodamine, erythrosine, xanthene, thioxanthene, acridine, e.g. 9-phenylacridine, 1,7-bis(9-acridinyl)heptane, 1,5-bis(9-acridinyl)pentane, cyanine and merocyanine dyes.

Specific examples of such compounds are

1. Thioxanthones

Thioxanthone, 2-isopropylthioxanthone, 2-chlorothioxanthone, 1-chloro-4-propoxythioxanthone, 2-dodecylthioxanthone, 2,4-diethylthioxanthone, 2,4-dimethylthioxanthone, 1-methoxycarbonylthioxanthone, 2-ethoxycarbonylthioxanthone, 3-(2-methoxyethoxycarbonyl)-thioxanthone, 4-butoxycarbonylthioxanthone, 3-butoxycarbonyl-7-methylthioxanthone, 1-cyano-3-chlorothioxanthone, 1-ethoxycarbonyl-3-chlorothioxanthone, 1-ethoxycarbonyl-3-ethoxythioxanthone, 1-ethoxycarbonyl-3-aminothioxanthone, 1-ethoxycarbonyl-3-phenylsulfurylthioxanthone, 3,4-di-[2-(2-methoxyethoxy)ethoxycarbonyl]-thioxanthone, 1,3-dimethyl-2-hydroxy-9Hthioxanthen-9-one 2-ethylhexylether, 1-ethoxycarbonyl-3-(1-methyl-1-morpholinoethyl)-thioxanthone, 2-methyl-6-dimethoxymethyl-thioxanthone, 2-methyl-6-(1,1-dimethoxybenzyl)-thioxanthone, 2-morpholinomethylthioxanthone, 2-methyl-6-morpholinomethylthioxanthone, N-allylthioxanthone-3,4-dicarboximide, N-octylthioxanthone-3,4-dicarboximide, N-(1,1,3,3-tetramethylbutyl)-thioxanthone-3,4-dicarboximide, 1-phenoxythioxanthone, 6-ethoxycarbonyl-2-methoxythioxanthone, 6-ethoxycarbonyl-2-methylthioxanthone, thioxanthone-2-carboxylic acid polyethyleneglycol ester, 2-hydroxy-3-(3,4-dimethyl-9-oxo-9H-thioxanthon-2-yloxy), N,N-trimethyl-1-propanaminium chloride;

2. Benzophenones benzophenone, 4-phenyl benzophenone, 4-methoxy benzophenone, 4,4'-dimethoxy benzophenone, 4,4'-dimethyl benzophenone, 4,4'-dichlorobenzophenone 4,4'-bis(dimethylamino)benzophenone, 4,4'-bis(diethylamino)benzophenone, 4,4'-bis(methylethylamino)benzophenone, 4,4'-bis(p-isopropylphenoxy)benzophenone, 4-methyl benzophenone, 2,4,6-trimethylbenzophenone, 4-(4-methylthiophenyl)-benzophenone, 3,3'-dimethyl-4-methoxy benzophenone, methyl-2-benzoylbenzoate, 4-(2-hydroxyethylthio)-benzophenone, 4-(4-tolylthio)benzophenone, 1-[4-(4-benzoyl-phenylsulfanyl)-phenyl]-2-methyl-2-(toluene-4-sulfonyl)-propan-1-one, 4-benzoyl-N,N,N-trimethylbenzenemethanaminium chloride, 2-hydroxy-3-(4-benzoylphenoxy)-N,N,N-trimethyl-1-propanaminium chloride monohydrate, 4-(13-acryloyl1,4,7,10,13-pentaoxamidecyl)-benzophenone, 4-benzoyl-N,N-dimethyl-N-[2-(1-oxo-2-propenyl)oxy]ethyl-benzenemethanaminium chloride;

3. Coumarins

Coumarin 1, Coumarin 2, Coumarin 6, Coumarin 7, Coumarin 30, Coumarin 102, Coumarin 106, Coumarin 138, Coumarin 152, Coumarin 153, Coumarin 307, Coumarin 314, Coumarin 314T, Coumarin 334, Coumarin 337, Coumarin 500, 3-benzoyl coumarin, 3-benzoyl-7-methoxycoumarin, 3-benzoyl-5,7-dimethoxycoumarin, 3-benzoyl-5,7-dipropoxycoumarin, 3-benzoyl-6,8-dichlorocoumarin, 3-benzoyl-6-chloro-coumarin, 3,3'-carbonyl-bis[5,7-di(propoxy)coumarin], 3,3'-carbonyl-bis(7-methoxycoumarin), 3,3'-carbonyl-bis(7-diethylamino-coumarin), 3-isobutyroyl-coumarin, 3-benzoyl-5,7-dimethoxy-coumarin, 3-benzoyl-5,7-diethoxy-coumarin, 3-benzoyl-5,7-dibutoxycoumarin, 3-benzoyl-5,7-di(methoxyethoxy)-coumarin, 3-benzoyl-5,7-di(allyloxy)coumarin, 3-benzoyl-7-dimethylaminocoumarin, 3-benzoyl-7-diethylaminocoumarin, 3-isobutyroyl-7-dimethylaminocoumarin, 5,7-dimethoxy-3-(1-naphthoyl)-coumarin, 5,7-diethoxy-3-(1-naphthoyl)-coumarin, 3-benzoylbenzo[f]coumarin, 7-diethylamino-3-thienoylcoumarin, 3-(4-cyanobenzoyl)-5,7-dimethoxycoumarin, 3-(4-cyanobenzoyl)-5,7-dipropoxycoumarin, 7-dimethylamino-3-phenylcoumarin, 7-diethylamino-3-phenylcoumarin, the coumarin derivatives disclosed in JP 09-179299-A and JP 09-325209-A, for example 7-[{4-chloro-6-(diethylamino)-S-triazine-2-yl}amino]-3-phenylcoumarin;

4. 3-(Aroylmethylene)-Thiazolines 3-methyl-2-benzoylmethylene-β-naphthothiazoline, 3-methyl-2-benzoylmethylene-benzothiazoline, 3-ethyl-2-propionylmethylene-β-naphthothiazoline;

5. Rhodanines 4-dimethylaminobenzalrhodanine, 4-diethylaminobenzalrhodanine, 3-ethyl-S-(3-octyl-2-benzothiazolinylidene)-rhodanine, the rhodanine derivatives, formulae [1], [2], [7], disclosed in JP 08-305019A;

6. Other Compounds acetophenone, 3-methoxyacetophenone, 4-phenylacetophenone, benzil, 4,4'-bis(dimethylamino)benzil, 2-acetylnaphthalene, 2-naphthaldehyde, dansyl acid derivatives, 9,10-anthraquinone, anthracene, pyrene, aminopyrene, perylene, phenanthrene, phenanthrenequinone, 9-fluorenone, dibenzosuberone, curcumin, xanthone, thio michler's ketone, α-(4-dimethylaminobenzylidene) ketones, e.g. 2,5-bis(4-diethylaminobenzylidene)cyclopentanone, 2-(4-dimethylamino-benzylidene)-indan-1-one, 3-(4-dimethylamino-phenyl)-1-indan-S-yl-propenone, 3-phenylthiophthalimide, N-methyl-3,5-di(ethylthio)-phthalimide, N-methyl-3,5-di(ethylthio)phthalimide, phenothiazine, methylphenothiazine, amines, e.g. N-phenylglycine, ethyl 4-dimethylaminobenzoate, butoxyethyl 4-dimethylaminobenzoate, 4-dimethylaminoacetophenone, triethanolamine, methyldiethanolamine, dimethylaminoethanol, 2-(dimethylamino)ethyl benzoate, poly(propylenegylcol)-4-(dimethylamino)benzoate.

A photosensitizer may be selected from the group consisting of benzophenone and its derivatives, thioxanthone and its derivatives, anthraquinone and its derivatives, or coumarin and its derivatives.

Accelerator:

To accelerate the photopolymerization, it is possible to add amines, for example triethanolamine, N-methyldiethanolamine, ethyl-p-dimethylaminobenzoate, 2-(dimethylamino)ethyl benzoate, 2-ethylhexyl-p-dimethylaminobenzoate, octyl-para-N,N-dimethylaminobenzoate, N-(2-hydroxyethyl)-N-methyl-para-toluidine or Michler's ketone. The action of the amines can be intensified by the addition of aromatic ketones of the benzophenone type. Examples of amines which can be used as oxygen scavengers are substituted N,N-dialkylanilines, as are described in EP339841. Other accelerators, coinitiators and autoxidizers are thiols, thioethers, disulfides, phosphonium salts, phosphine oxides or phosphines, as described, for example, in EP438123, in GB2180358 and in JP Kokai Hei 6-68309.

The choice of additive(s) is made depending on the field of application and on properties required for this field. The additives described above are customary in the art and accordingly are added in amounts which are usual in the respective application.

Thermal Inhibitor:

Thermal inhibitors are intended to prevent premature polymerization, examples being hydroquinone, hydroquinone derivatives, p-methoxyphenol, β-naphthol or sterically hindered phenols, such as 2,6-di-tert-butyl-p-cresol. In order to increase the stability on storage in the dark it is possible, for example, to use copper compounds, such as copper naphthenate, stearate or octoate, phosphorus compounds, for example triphenylphosphine, tributylphosphine, triethylphosphine, triphenyl phosphate or tribenzyl phosphate, quaternary ammonium compounds, for example tetramethylammonium chloride or trimethylbenzylammonium chloride, or hydroxylamine derivatives, for example N-diethylhydroxylamine. To exclude atmospheric oxygen during the polymerization it is possible to add paraffin or similar wax-like substances which, being of inadequate solubility in the polymer, migrate to the surface in the beginning of polymerization and form a transparent surface layer which prevents the ingress of air. It is also possible to apply an oxygen-impermeable layer. Light stabilizers which can be added in a small quantity are UV absorbers, for example those of the hydroxyphenylbenzotriazole, hydroxyphenyl-benzophenone, oxalamide or hydroxyphenyl-s-triazine type. These compounds can be used individually or in mixtures, with or without sterically hindered amines (HALS).

Solvents:

Examples of suitable solvents are ketones, ethers and esters, such as methyl ethyl ketone, isobutyl methyl ketone, cyclopentanone, cyclohexanone, N-methylpyrrolidone, dioxane, tetrahydrofuran, ethylene glycol monomethyl ether, ethylene glycol monoethyl ether, ethylene glycol monopropyl ether, ethylene glycol monobutyl ether, ethylene glycol dimethyl ether, ethylene glycol diethyl ether, ethylene glycol dipropyl ether, propylene glycol monomethyl ether, propylene glycol monoethyl ether, propylene glycol monopropyl ether, propylene glycol monobutyl ether, propylene glycol dimethyl ether, propylene glycol diethyl ether, propylene glycol dipropyl ether, diethylene glycol monomethyl ether, diethylene glycol monoethyl ether, diethylene glycol dimethyl ether, diethylene glycol diethyl ether, ethylene glycol monomethyl ether acetate, ethylene glycol monoethyl ether acetate, ethylene glycol monopropyl ether acetate, ethylene glycol monobutyl ether acetate, propylene glycol monomethyl ether acetate, propylene glycol monoethyl ether acetate, propylene glycol monopropyl ether acetate, 2-methoxybutyl acetate, 3-methoxybutyl acetate, 4-methoxybutyl acetate, 2-methyl-3-methoxybutyl acetate, 3-methyl-3-methoxybutyl acetate, 3-ethyl-3-methoxybutyl acetate, 2-ethoxybutyl acetate, 4-ethoxybutyl acetate, 4-propoxybutyl acetate, 2-methoxypentyl acetate, 3-methoxypentyl acetate, 4-methoxypentyl acetate, 2-methyl-3-methoxypentyl acetate, 3-methyl-3-methoxypentyl acetate, 3-methyl-4-methoxypentyl acetate, 4-methyl-4-methoxypentyl acetate, ethyl acetate, n-butyl acetate, ethyl propionate, propyl propionate, butyl propionate, ethyl 3-ethoxypropionate, methyl 3-methoxypropionate, 2-heptanone, 2-pentanone, and ethyl lactate.

Hybrid System:

The compositions according to this invention can comprise additionally a crosslinking agent which is activated by an acid or a base, for example as described in JP 10 221843-A, and a compound which generates acid or base thermally or by actinic radiation and which activates a crosslinking reaction. Use is made, in addition to the free-radical hardeners, of cationic photo or thermal initiators such as sulfonium-, phosphonium- or iodonium salts, for example IRGACURE® 250, San-Aid SI series, SI-60L, SI-80L, SI-100L, SI-110L, SI-145, SI-150, SI-160, SI-180L produced by Sanshin Chemical, cyclopentadienyl-arene-iron(II) complex salts, for example ($\eta^6$-iso-propylbenzene)($\eta^5$-cyclopentadienyl)iron (II) hexafluorophosphate, as well as oxime sulfonic acid esters, for example described in EP 780729. Also pyridinium and (iso)quinolinium salts as described e.g. in EP 497531 and EP 441232 may be used in combination with the new photoinitiators. Examples of bases are imidazole and its derivatives for example Curezole OR series and CN series provided by Shikoku Chemicals.

The crosslinking agents which can be activated by acid or base include compounds having epoxy or oxetane groups. There may be used a solid or liquid known epoxy or oxetane compound and said compound is used depending on required characteristics. A preferred epoxy resin is a bisphenol S type epoxy resin such as BPS-200 produced by Nippon Kayaku Co., Ltd., EPX-30 produced by ACR Co., Epiculon EXA-1514 produced by Dainippon Ink & Chemicals Inc., etc.; a bisphenol A type epoxy resin such as Epiculon N-3050, N-7050, N-9050 produced by Dainippon Ink & Chemicals Inc., XAC-5005, GT-7004, 6484T, 6099; a bisphenol F type epoxy resin such as YDF-2004, YDF2007 produced by Tohto Kasei Co., etc.; a bisphenol fluorene type epoxy resin such as OGSOL PG, PG-100, EG, EG-210 produced by Osaka Gas Chemicals; a diglycidyl phthalate resin such as Blemmer DGT produced by Nippon Oil and Fats Co., Ltd., etc.; a heterocyclic epoxy resin such as TEPIC produced by Nissan Chemical Industries, Ltd., Araldite PT810 produced by Ciba Specialty Chemicals Inc., etc.; a bixylenol type epoxy resin such as YX-4000 produced by Yuka Shell Co., etc.; a biphenol type epoxy resin such as YL-6056 produced by Yuka Shell Co., etc.; a tetraglycidyl xylenoylethane resin such as ZX-1063 produced by Tohto Kasei Co., etc.; a novolak type epoxy resin such as EPPN-201, EOCN-103, EOCN-1020, EOCN-1025 and BRRN produced by Nippon Kayaku Co., Ltd., ECN-278, ECN-292 and ECN-299 produced by Asahi Chemical Industry Co., Ltd., GY-1180, ECN-1273 and ECN-1299 produced by Ciba Specialty Chemicals Inc., YDCN-220L, YDCN-220HH, YDCN-702, YDCN-704, YDPN-601 and YDPN-602 produced by Tohto Kasei Co., Epiculon-673, N-680, N-695, N-770 and N-775 produced by Dainippon Ink & Chemicals Inc., etc.; a novolak type epoxy resin of bisphenol A such as EPX-8001, EPX-8002, EPPX-8060 and EPPX-8061 produced by Asahi Chemical Industry Co., Ltd., Epiculon N-880 produced by Dainippon Ink & Chemicals Inc., etc.; a chelate type epoxy resin such as EPX-49-69 and EPX-49-30 produced by Asahi Denka Kogyo K.K., etc.; a glyoxal type epoxy resin such as YDG-414 produced by Tohto Kasei Co., etc.; an amino group-containing epoxy resin such as YH-1402 and ST-110 produced by Tohto Kasei Co., YL-931 and YL-933 produced by Yuka Shell Co., etc.; a rubber-modified epoxy resin such as Epiculon TSR-601 produced by Dainippon Ink & Chemicals Inc., EPX-84-2 and EPX-4061 produced by Asahi Denka Kogyo K.K., etc.; a dicyclopentadiene phenolic type epoxy resin such as DCE-400 produced by Sanyo-Kokusaku Pulp Co., Ltd., etc.; a silicone-modified epoxy resin such as X-1359 produced by Asahi Denka Kogyo K.K., etc.; an ecaprolactone-modified epoxy resin such as Plaque G-402 and G-710 produced by Dicel Chemical Industries, Ltd., etc. and others. Further, partially esterified compounds of these epoxy compounds (e.g. esterified by (meth)acrylates) can be used in combination. Examples of oxetane compounds are 3-ethyl-3-hydroxymethyloxetane (oxetane alcohol), 2-ethylhexyloxetane, xylene bisoxetane, 3-ethyl-3-[[(3-ethyloxetane-3-yl)methoxy]methyl]oxetane (Aron Oxetane series) provided by Toagosei.

The polymerizable compositions according to the invention, comprising at least one compound of the formula I are especially suitable for the following applications:
resists to manufacture color filters for a variety of display applications,
spacers for LCD,
overcoat layers for color filters or LCD,
sealants for LCD,
insulation layers for LCD.

The polymerizable compositions according to the invention, comprising at least one compound of the formula I are also suitable for the following applications:
optical films for a variety of display applications, such as hard coats, anti-reflective films, anti-glare films, retardation films, NIR absorbing films, prism sheets, brightness enhancement films and the like,
other resists, photosensitive compositions or thermosetting compositions to generate structures or layers in the manufacturing processes of plasma-display panels, electroluminescence displays and LCD,
solder resists,
photoresist materials used for forming dielectric layers in a sequential build-up layer of a printed circuit board,
photoresists for electronics, electroplating resists, etch resists, both liquid and dry films,
anisotropy conducting adhesive, (An anisotropic conductive adhesive contains conductive particles dispersed in a resin composition and can be used for electrical joining of electronic or electric parts. They can be employed to join fine circuits, for example a liquid crystal display (LCD) and a tape carrier package (TCP) or a TCP and a printed circuit board (PCB), and the like.), polymerization to form oligomers, co-oligomers, polymers and copolymers, for example, random block, multi-block, star or gradient copolymers, controlled degradation of polymers and controlled buildup of the molecular weight or crosslinking, coating agent for buildings, building materials, automobile parts, electrical instruments, precision instrument, etc., pressure-sensitive adhesive optical films including an optical film and a pressure-sensitive adhesive layer, e.g. for LCD and organic electroluminescence (EL) displays, adhesives and printed circuit boards having adhesive layer, e.g. used as automobile parts, electrical instruments and the like, dental materials, sealer for building and building materials.

The invention further relates to the use of the photoresist composition to manufacture color filters for a variety of display applications and for image sensors such as charge coupled device (CCD) and complementary metal-oxide semiconductor (CMOS), spacers for LCD, overcoat layer for color filter and LCD, sealant for LCD, optical films for a variety of display applications, insulation layer for LCD, resists or photosensitive compositions to generate structures or layers in the manufacturing processes of plasma-display panels, electroluminescence displays and LCD, solder resists, as a photoresist material used for forming dielectric layers in a sequential build-up layer of a printed circuit board.

The compositions according to the invention are particularly suitable for the production of color filters or color mosaic systems, such as described, for example, in EP 320 264. The color filters can be used, for example, for flat panel display technology such as LCD, electroluminescent display and plasma display, for image sensors such as CCD and CMOS, and the like.

The color filters usually are prepared by forming red, green and blue pixels and black matrix on a glass substrate. In these processes photocurable compositions according to the invention can be employed. A particularly preferred method of use comprises adding of the coloring matters, dyes and pigments of red, green and blue colors to the light-sensitive resin composition of the present invention, coating of the substrate with the composition, drying of the coating with a short heat treatment, patternwise exposure of the coating (i.e. through a suitable mask) to actinic radiation and subsequent development of the pattern in a suitable aqueous alkaline developer solution and a heat treatment. Thus, by subsequently applying a red, green, blue and black pigmented coating, in any desired order, on top of each other with this process a color filter layer with red, green and blue color pixels and black matrix can be produced.

At the photolithography, suitable radiation from about 150 nm to 600 nm, for example 190-600 nm (UV-VIS region) is chosen, for example, in sunlight or light from artificial light sources. Consequently, a large number of very different types of light sources are employed. Both point sources and arrays ("lamp carpets") are suitable. Examples are carbon arc lamps, xenon arc lamps, super high-, high-, medium- and low-pressure mercury lamps, possibly with metal halide dopes (metal-halogen lamps), microwave-stimulated metal vapor lamps, excimer lamps, superactinic fluorescent tubes, fluorescent lamps, argon incandescent lamps, electronic flashlights, photographic flood lamps, light emitting diodes (LED), electron beams and X-rays. The distance between the lamp and the substrate to be exposed in accordance with the invention may vary depending on the intended application and the type and output of lamp, and may be, for example, from 2 cm to 150 cm. Laser light sources, for example excimer lasers, such as KrF lasers for example at 248 nm, ArF-lasers for example at 193 nm and $F_2$ lasers for exposure at 157 nm are also suitable. Lasers in the visible region can also be employed.

In addition to a process in which the light-sensitive resin composition is coated on a substrate and dried, the light-sensitive resin composition of the present invention can be used as well for a layer transfer material. That is, the light-sensitive resin composition is layer-wise provided directly on a temporary support, preferably on a polyethylene terephthalate film, or on a polyethylene terephthalate film on which an oxygen-shielding layer and a peeling layer or the peeling layer and the oxygen-shielding layer are provided. Usually, a removable cover sheet made of a synthetic resin is laminated thereon for a protection in handling. Further, there can be applied as well a layer structure in which an alkali soluble thermoplastic resin layer and an intermediate layer are provided on a temporary support and further a light-sensitive resin composition layer is provided thereon (JP 5-173320-A).

The above cover sheet is removed in use and the light-sensitive resin composition layer is laminated on a permanent support. Subsequently, peeling is carried out between those layer and a temporary support when an oxygen-shielding layer and a peeling layer are provided, between the peeling layer and the oxygen-shielding layer when the peeling layer and the oxygen-shielding layer are provided, and between the temporary support and the light-sensitive resin composition layer when either the peeling layer or the oxygen-shielding layer is not provided, and the temporary support is removed.

The developer solution can be used in all forms known to the person skilled in the art, for example in form of a bath solution, puddle, or a spraying solution. In order to remove the non-cured portion of the light-sensitive resin composition layer, there can be combined the methods such as rubbing with a rotary brush and rubbing with a wet sponge. Usually, the temperature of the developing solution is preferably at and around room temperature to 40° C. The developing time is changeable according to the specific kind of the light-sensitive resin composition, the alkalinity and temperature of the developing solution, and the kind and concentration of the organic solvent in the case where it is added. Usually, it is 10 seconds to 2 minutes. It is possible to put a rinsing step after the development processing.

A final heat treatment is preferably carried out after the development processing. Accordingly, a support having a layer which is photopolymerized by exposing (hereinafter referred to as a photocured layer) is heated in an electric furnace and a drier, or the photocured layer is irradiated with an infrared lamp or heated on a hot plate. The heating temperature and time depend on the composition used and the thickness of the formed layer. In general, heating is preferably applied at about 120° C. to about 250° C., for about 2 to about 60 minutes.

Examples for color filter resists, the composition of such resists and the processing conditions are given by T. Kudo et al., Jpn. J. Appl. Phys. Vol. 37 (1998) 3594; T. Kudo et al., J. Photopolym. Sci. Technol. Vol 9 (1996) 109; K. Kobayashi, Solid State Technol. November 1992, p. S15-S18; U.S. Pat. No. 5,368,976; U.S. Pat. No. 5,800,952; U.S. Pat. No. 5,882,843; U.S. Pat. No. 5,879,855; U.S. Pat. No. 5,866,298; U.S. Pat. No. 5,863,678; JP 06-230212-A; EP320264; JP 09-269410-A; JP 10-221843-A; JP 01-090516-A; JP 10-171119-A, U.S. Pat. No. 5,821,016, U.S. Pat. No. 5,847, 015, U.S. Pat. No. 5,882,843, U.S. Pat. No. 5,719,008, EP881541, or EP902327.

Instead of forming a black matrix using a photosensitive composition and patterning the black photosensitive composition photolithographically by patternwise exposure to form the black pattern separating the red green and blue colored areas on the transparent substrate it is alternatively possible to use an inorganic black matrix. Such inorganic black matrix can be formed from deposited (i.e. sputtered) metal (i.e. chromium) film on the transparent substrate by a suitable imaging process, for example utilizing photolithographic patterning by means of an etch resist, etching the inorganic layer in the areas not protected by the etch resist and then removing the remaining etch resist.

The photosensitive or thermosetting composition of the present invention can also be used to form such overcoat layers, because a cured film of the composition is excellent in flatness, hardness, chemical and thermal resistance, transparency especially in a visible region, adhesion to a substrate, and suitability for forming a transparent conductive film, e.g., an ITO film, thereon. In the production of a protective layer, there has been a demand that unnecessary parts of the protective layer, for example on scribing lines for cutting the substrate and on bonding pads of solid image sensors should be removed from the substrate as described in JP57-42009-A, JP1-130103-A and JP1-134306-A. In this regard, it is difficult to selectively form a protective layer with good precision using the above-mentioned thermosetting resins. The photosensitive composition, however, allows to easily remove the unnecessary parts of the protective layer by photolithography.

The photosensitive compositions according to the invention can further be used for manufacturing spacers, which control a cell gap of the liquid crystal part in liquid crystal display panels. Since the properties of light transmitted or reflected through the liquid crystal layer in a liquid crystal display are dependent on the cell gap, the thickness accuracy and uniformity over the pixel array are critical parameters for the performance of the liquid crystal display unit. By using photolithographic process, columns of a resin can be formed as spacers in the region between the pixel array region and the counter electrode to form a prescribed cell gap. Photosensitive materials having adhesive properties with photolithography are commonly used, for instance, in the manufacturing process of color filters. This method is advantageous compared with the conventional method using spacer beads in the points that location, number and height of the spacers may be controlled freely. In a color liquid crystal display panel, such spacers are formed in the non-imaging area under black matrix of color filter elements. Therefore, the spacers formed using photosensitive compositions do not decrease brightness and optical aperture.

Photosensitive compositions for producing protective layer with spacers for color filters are disclosed in JP 2000-81701-A and dry film type photoresists for spacer materials are also disclosed in JP 11-174459-A and JP 11-174464-A. As described in the documents, the photosensitive compositions, liquid and dry film photoresists, are comprising at least an alkaline or acid soluble binder polymer, a radically polymerizable monomer, and a curing promoter. In some cases, thermally crosslinkable components such as epoxide and carboxylic acid may additionally be included.

The steps to form spacers using a photosensitive composition are as follows: a photosensitive composition is applied to the substrate, for instance a color filter panel and after the substrate is prebaked, it is exposed to light through a mask. Then, the substrate is developed with a developer and patterned to form the desired spacers. When the composition contains some thermosetting components, usually a post-baking is carried out to thermally cure the composition.

The photocurable compositions according to the invention are suitable for producing spacers for liquid crystal displays (as described above).

The compositions according to the invention are also suitable for manufacturing interlayer insulating layers or dielectric layers in a liquid crystal display, and more particularly in specific LCD structures such as color filter on array type and reflection type LCDs.

The compositions according to the invention are also suitable for insulative electrical machinery to coat the windings and seal the stator windings of electrical inductive devices, such as motors, are wound with magnet wire having enamel or other insulative coating from the environment.

The photosensitive thermosetting resin composition and a method of forming a solder resist pattern by the use thereof, and more particularly relates to a novel photosensitive thermosetting resin composition useful as materials for the production of printed circuit boards, the precision fabrication of metallic articles, the etching of glass and stone articles, the relief of plastic articles, and the preparation of printing plates and particularly useful as a solder resist for printed circuit boards and to a method of forming a solder resist pattern by the steps of exposing a layer of the resin composition selectively to an actinic ray through a photomask having a pattern and developing the unexposed part of the layer.

The solder resist is a substance which is used during the soldering of a given part to a printed circuit board for the purpose of preventing molten solder from adhering to irrelevant portions and protecting circuites. It is, therefore, required to possess such properties as high adhesion, insulation resistance, resistance to soldering temperature, resistance to solvents, resistance to solvents, resistance to alkalis, resistance to acids, and resistance to plating. Subject of the invention also is a solder resist comprising a composition as described above.

Preferred is the use of the compositions, comprising thermosetting elements described as compound according to the invention, in an image-forming process, e.g. a process for the preparation of solder masks, wherein 1.) the components of the composition as described above are mixed,
2.) the resulting composition is applied to the substrate ("coating of substrate"),
3.) the solvent, if present, is evaporated, at elevated temperature, e.g. at a temperature between 80-90° C.,
4.) the coated substrate is patternwise exposed to electromagnetic radiation through a negative mask (thereby initiating the reaction of the acrylate)
5.) the irradiated sample is developed, by washing with aqueous alkaline solution and thereby removing the uncured areas and
6.) the sample is thermally cured, e.g. at a temperature of about 150° C.

This process is another object of the invention.

The heating step (6) usually is carried out at temperature of at least 100° C. and not more than 200° C., preferably at temperatures of 130-170° C., e.g. at 150° C.

The photosensitive or thermosetting coating composition of the present invention can also be used to form such coating layers, which is required adherence property, thermal resistance, flexibility, adhesiveness, electrical insulating property and humidity resistance for building, building materials, automobile parts, electrical instrument, precision instrument and the like.

The compositions according to the invention are also suitable for dental materials are also disclosed in U.S. Pat. No. 6,410,612 and JP60011409. As described in the documents, the photosensitive or thermosetting compositions comprise some kind of acrylic resin and polymerization initiator.

An anisotropic conductive adhesive is a circuit connecting material, in which conductive particles are dispersed in an insulating adhesive component, which adheres mechanically circuits disposed in the opposite direction, and simultaneously interposes a conductive particle between the circuit electrodes to establish an electrical connection. As an insulating adhesive component, a thermoplastic resin and a thermosetting resin are usable, and the thermosetting resin is more preferably used in terms of connection reliability.

In case of employing the thermosetting resin as an adhesive component, a connection is made by interposing an anisotropic conductive adhesive between connected to be members, which is then heat-compressed.

The invention, as described above, provides compositions for producing pigmented and non-pigmented paints and varnishes, powder coatings, printing inks, printing plates, adhesives, dental compositions. Photoresists for electronics like electroplating resist, etch resist, both liquid and dry films, solder resist, as resists to manufacture color filters for a variety of display applications or to generate structures in the manufacturing processes of plasma-display panels (e.g. barrier rib, phosphor layer, electrode), electroluminescence, displays and LCD) (e.g. Interlayer insulating layer, spacers, microlens array), as composition for encapsulating electrical and electronic components, for producing magnetic recording materials, micromechanical parts, waveguides, optical switches, plating masks, etch masks, color proofing systems, glass fiber cable coatings, screen printing stencils, for producing three-dimensional objects by means of stereo-lithography, and as image recording material, especially for holographic recordings, microelectronic circuits, decolorizing materials, decolorizing materials for image recording materials, for image recording materials using microcapsules.

The examples which follow illustrate the invention in more detail.

EXAMPLES

I.1 Preparation of Compounds of the Formula IA.1

Example 1

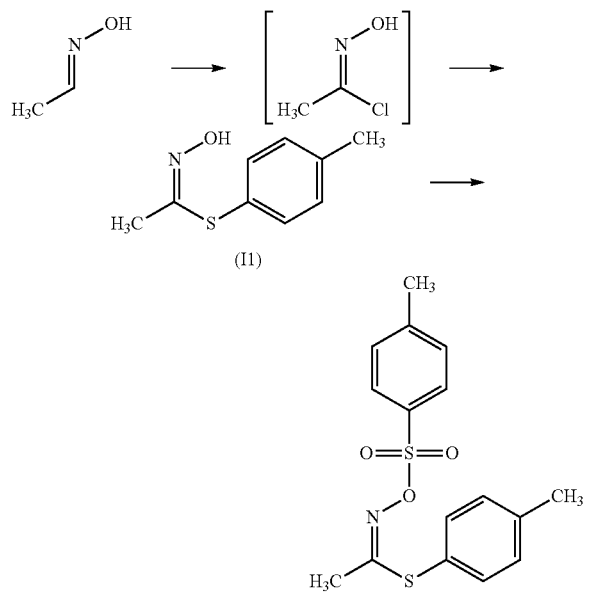

1.1 Preparation of Intermediate I1

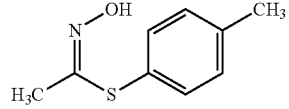

To 59.1 g of acetaldoxime in DMF (200 mL) was added 130.4 g of N-chlorosccinimide in portions at 40° C. After stirring for 20 minutes at room temperature, 136.6 g of p-toluenethiol and 111.3 g of triethylamine were added to the mixture at 0° C., and then the mixture was stirred for 2 h at room temperature. After adding water, the organic layer was extracted with ethyl acetate. The solution was concentrated, and the residue was precipitated from a mixture of hexane and ethyl acetate. 83.05 g of I1 were obtained as white solid.

1.2 Preparation of

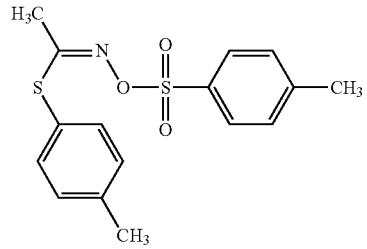 [SMILES: C/C(=N/OS(=O)(=O)c1ccc(C)cc1)Sc1ccc(C)cc1]

To 27.2 g of the compound of example 1.1 in tetrahydrofuran (THF) (90 mL) were added 31.5 g of p-toluenesulfonyl chloride and 18.2 g of triethylamine at 0° C., and then the mixture was stirred for 3 h at room temperature. After adding water, the organic layer was extracted with ethyl acetate, and the solution was added to hexane. 40.8 g of the title compound was obtained as white solid.

Example

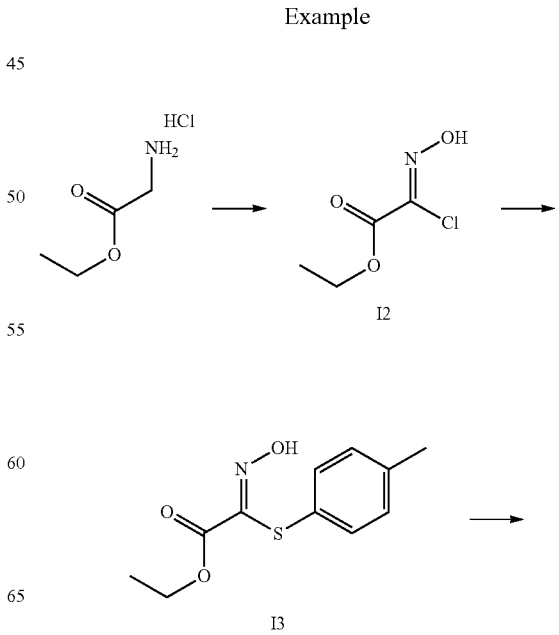

2.12 Preparation of Intermediate Compound I2

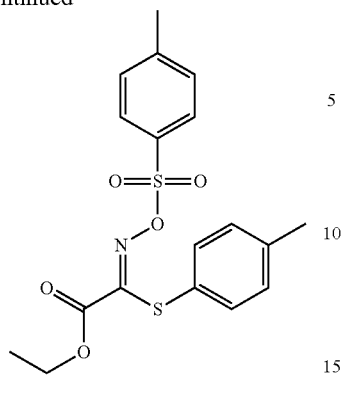

2.3 Preparation of

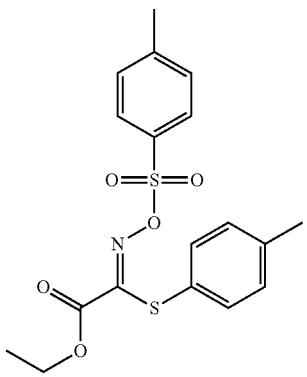 [SMILES: CCOC(=O)/C(=N/OS(=O)(=O)c1ccc(C)cc1)Sc1ccc(C)cc1]

The title compound was prepared by the procedure given for example 1.2. The title compound was obtained as white powder.

Example 14

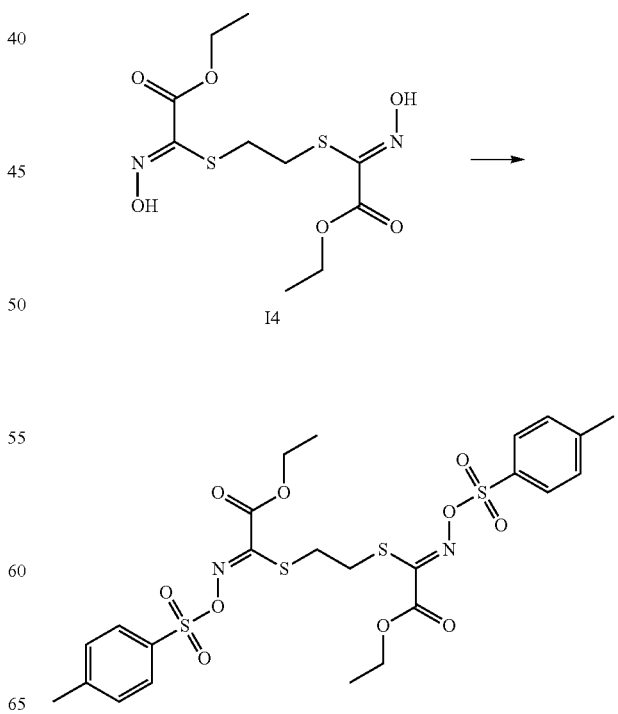

I2

To 14.0 g of ethyl glycine hydrochloride in H$_2$O (20 mL) was added 36% aqueous hydrochloride (16.6 mL) at −10° C. 13.8 g of sodium nitrite dissolved in 20 mL of H$_2$O were added dropwise over 45 min. After stirring at room temperature for 4 h, tert-butyl methyl ether was added and the organic layer was separated. After concentration, the residue was recrystallized from hexane. 8.9 g of the oximidoyl chloride were obtained as white powder

2.2 Preparation of Intermediate Compound I3

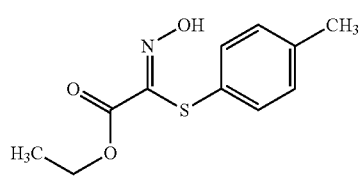

I3

To 1.52 g of example 2.1 in tert-butyl methyl ether (65 mL) was added 1.24 g of p-toluenethiol and 1.02 g of triethylamine were added to the mixture at 0° C., and then the mixture was stirred for 2 h at room temperature. After adding water, the organic layer was extracted with ethyl acetate. The solution was concentrated, and 2.41 g of I3 was obtained as white solid.

14.1 Preparation of

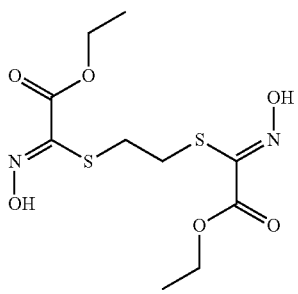

To 0.73 g of the intermediate compound I2 of example 2.1 in tert-butyl methyl ether (50 mL) were added 0.19 g of 1,2-ethanedithiol and 0.49 g of triethylamine at 0° C. The mixture was stirred for 2 h at room temperature. After adding water, the organic layer was extracted with ethyl acetate. The solution was concentrated, and the residue was precipitated from hexane/CH$_2$Cl$_2$ as eluent. 0.62 g of I4 were obtained as white solid.

14.2 Preparation of

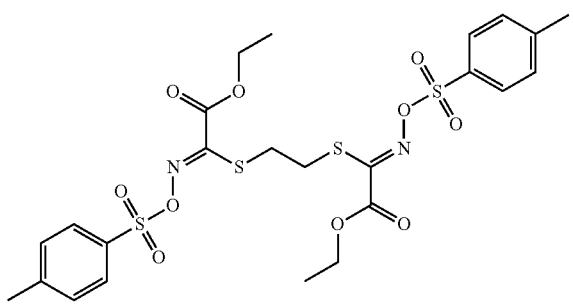

To 0.20 g of the intermediate compound I4 from example 14.1 in tetrahydrofuran (THF) (4.0 mL) were added 0.26 g of p-toluenesulfonyl chloride and 0.15 g of triethylamine at 0° C., and then the mixture was stirred for 3 h at room temperature. After adding water, the organic layer was extracted with ethyl acetate. The solution was concentrated, and the residue was purified by column chromatography with tert-butyl methyl ether as eluent. 0.31 g of the title compound was obtained as white powder.

Example 18

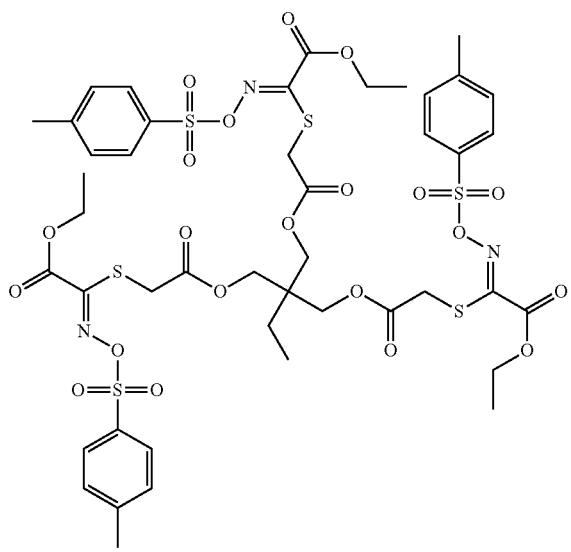 [SMILES: CCOC(=O)/C(=N/OS(=O)(=O)c1ccc(C)cc1)SCC(=O)OCC(CC)(COC(=O)CS/C(=N\OS(=O)(=O)c1ccc(C)cc1)C(=O)OCC)COC(=O)CS/C(=N\OS(=O)(=O)c1ccc(C)cc1)C(=O)OCC]

18.1 Preparation of Intermediate Compound I5

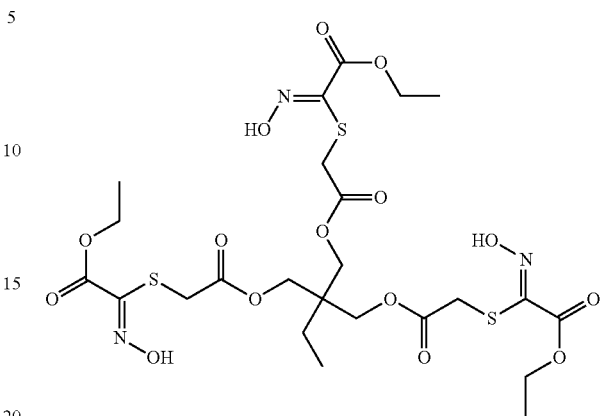

To 1.64 g of the intermediate compound I2 from example 2.1 in tetrahydrofuran (THF) (84 mL) were added 1.07 g of trimethylolpropane tris(thioglycolate) and 1.09 g of triethylamine at 0° C., and then the mixture was stirred for 2 h at room temperature. After adding water, the organic layer was extracted with ethyl acetate. The solution was concentrated, and the residue was purified by column chromatography with CH$_2$Cl$_2$/acetone as eluent. 2.05 g of I5 were obtained as colorless resin.

18.2 Preparation of

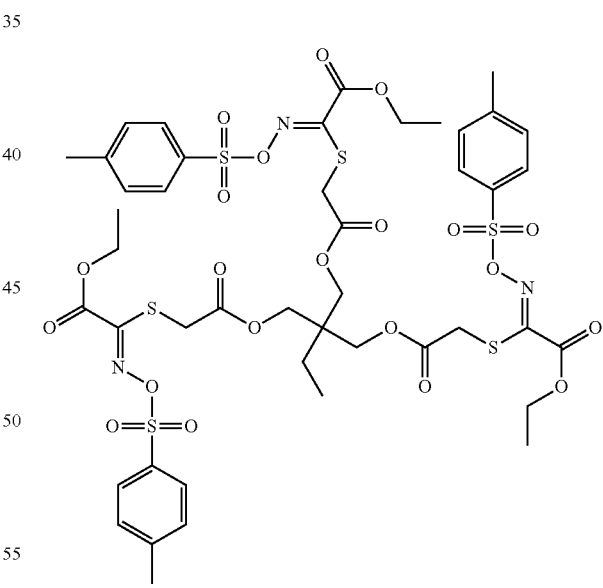

To 0.55 g of the intermediate compound I5 from example 18.1 in tetrahydrofuran (THF) (0.50 mL) were added 0.54 g of p-toluenesulfonyl chloride and 1.0 mL of pyridine at 0° C., and then the mixture was stirred for 3 h at room temperature. After adding water, the organic layer was extracted with ethyl acetate. The solution was concentrated, and the residue was purified by column chromatography with CH$_2$Cl$_2$/acetone as eluent. 0.58 g of the title compound was obtained as off-white resin.

Example 31

I2 →

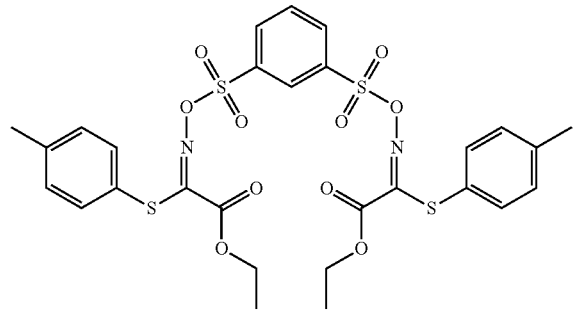

31.1 Preparation of

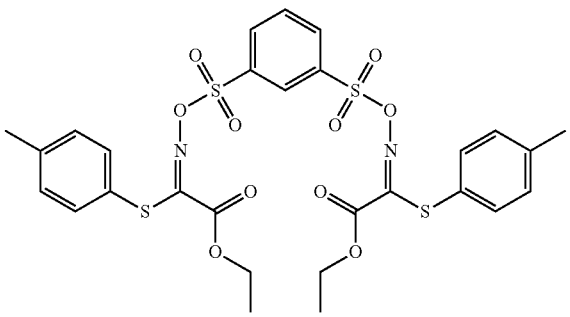

To 2.16 g of the intermediate compound I2 of example 2.1 in tetrahydrofuran (THF) (15 mL) were added 1.18 g of benzene-1,3-disulfonyl chloride and 0.91 g of triethylamine at 0° C., and then the mixture was stirred for 3 h at room temperature. After adding water, the organic layer was extracted with ethyl acetate. The solution was concentrated, and purified by column chromatography with hexane/$CH_2Cl_2$ as eluent. 0.46 g of the title compound was obtained as white solid.

Example 33

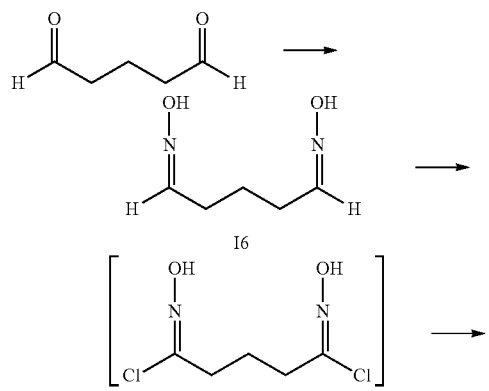

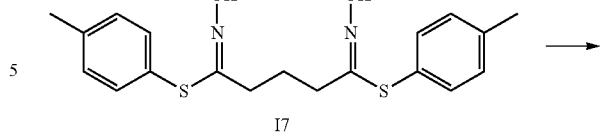

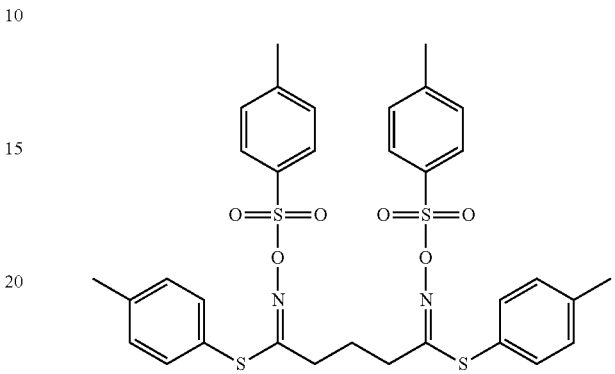

33.1 Preparation of Intermediate Compound I6

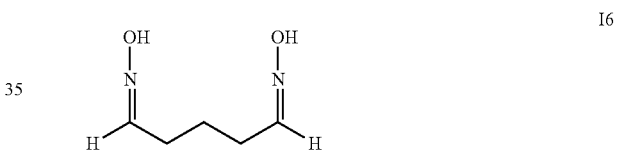

To 8.03 g of 25% aquarous of glutaraldehyde in pyridine (30 mL) was added 4.18 g of hydroxylammonium hydrochloride at 0° C., and then the mixture was stirred for 2 h at 80° C. After adding water, the organic layer was extracted with ethyl acetate. The solution was concentrated, and 2.80 g of I6 were obtained as yellow solid.

33.2 Preparation of Intermediate Compound I7

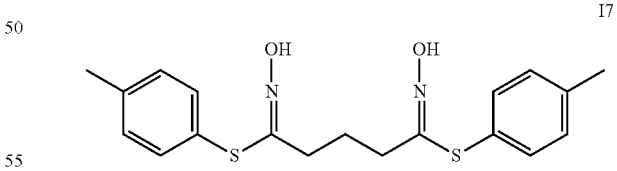

To 1.53 g of the intermediate compound I6 from example of 33.1 in DMF (5 mL) was added 2.26 g of N-chlorosccinimide in portions at 40° C. After stirring for 20 minutes at room temperature, 2.00 g of p-toluenethiol and 1.63 g of triethylamine were added to the mixture at 0° C., and then the mixture was stirred for 2 h at room temperature. After adding water, the organic layer was extracted with ethyl acetate. The solution was concentrated, and the residue was precipitated from a mixture of hexane and ethyl acetate. 0.34 g of I7 were obtained as white solid.

33.3 Preparation of

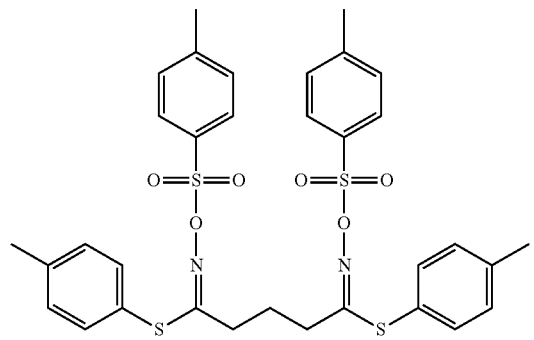

The title compound was prepared by the procedure given for example 14.2. The title compound was obtained as white powder.

Example 118

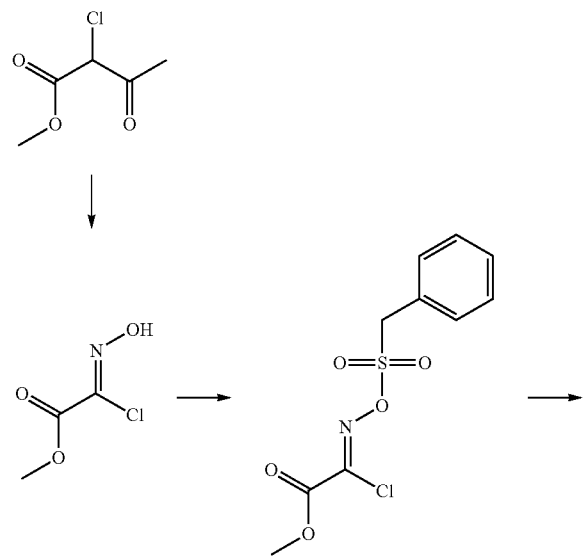

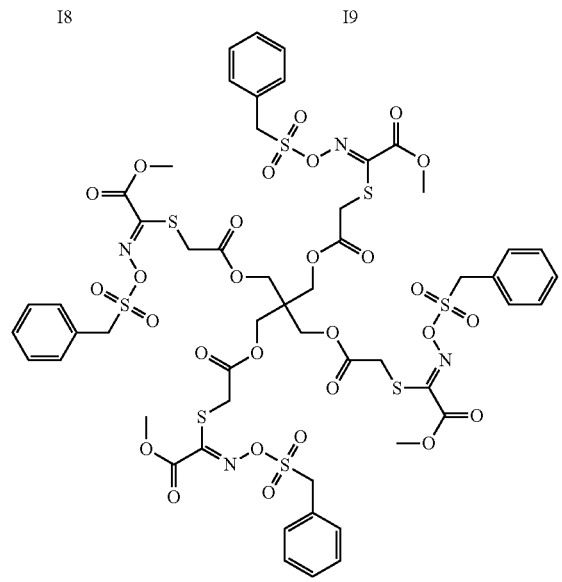

118.1 Preparation of Intermediate Compound I8

To 5.34 g of methyl 2-chloroacetoacetate in methanol (4.5 mL) and H$_2$O (4.5 mL) were added 4.5 mL of conc. HCl aq. and then 2.43 g of NaNO$_2$ in H$_2$O (4.5 mL) dropwise at room temperature. After stirring overnight, the organic layer was extracted with ethyl acetate twice, followed by washing with brine. After concentration of the organic layer, washing the resulting oil with hexane/1,4-dioxane afforded 3.29 g of I8 as white solid.

118.2 Preparation of Intermediate Compound I9

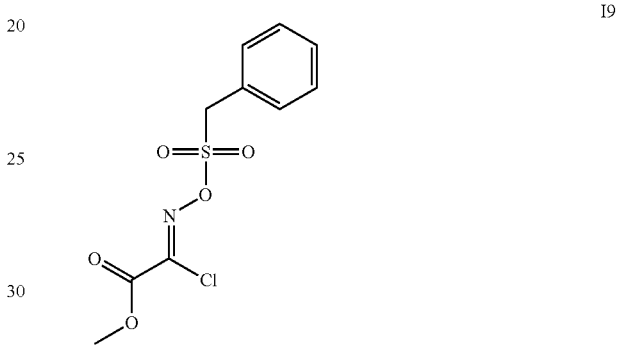

To 5.02 g of the intermediate compound I8 from example of 118.1 in methyl ethyl ketone (MEK, 40 mL) was added 7.28 g of benzylsulfonyl chloride and subsequently 3.86 g of triethylamine dropwise at around −10° C. After stirring for 3.5 hours at the same temperature, water was added, and the organic layer was extracted with ethyl acetate. The solution was concentrated, and then the residue was applied to column chromatography with hexane/CH$_2$Cl$_2$ as eluent. 7.45 g of 19 was obtained as white solid.

118.3 Preparation of

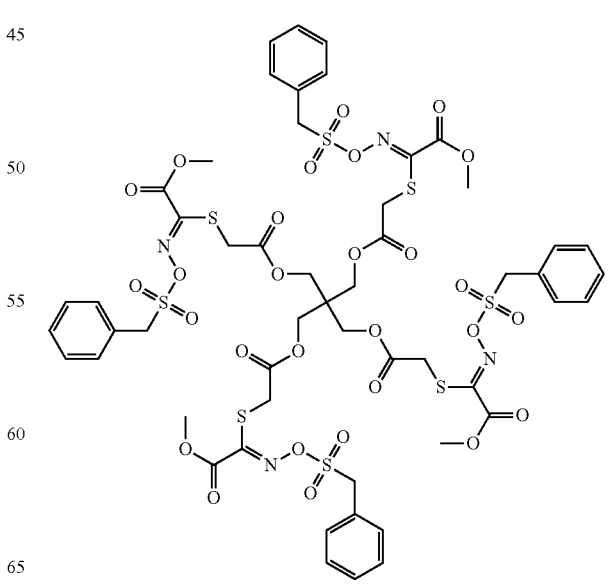

0.76 g of the intermediate compound I9 from example of 118.2 and 0.22 g of pentaerythritol tetrakis(mercaptoacetate) were dissolved in t-butyl methyl ether (5 mL) and dimethoxyethane (2 mL), and to this solution was added 0.22 g of triethylamine in dimethoxyethane (3 mL) dropwise at 0° C. After stirring for 3 hours, water was added, and the organic layer was extracted with ethyl acetate. The solution was concentrated, and then the residue was applied to column chromatography with $CH_2Cl_2$/acetone as eluent. 0.29 g of the title compound was obtained as colorless resin.

Example 133

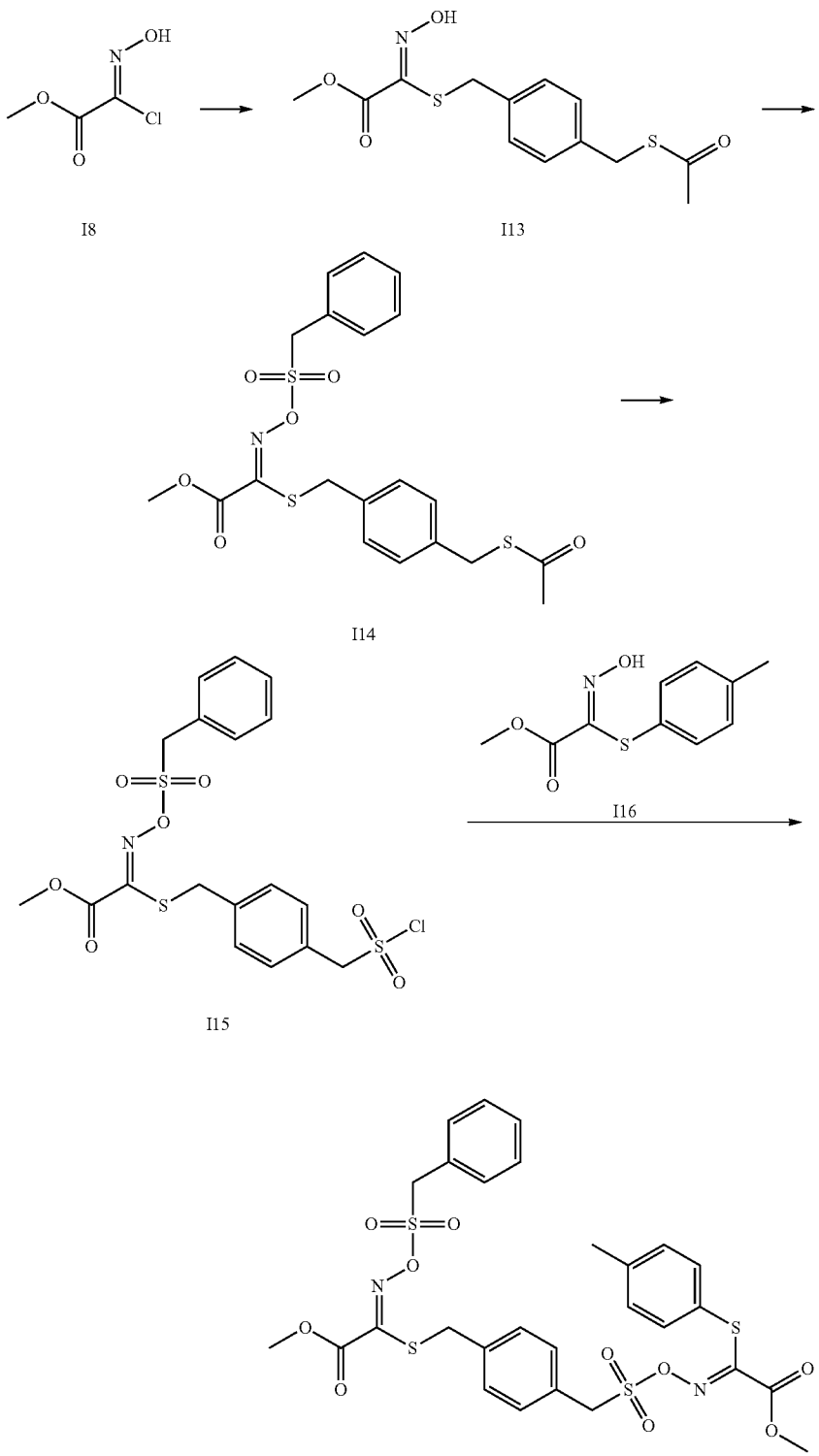

133.1 Preparation of

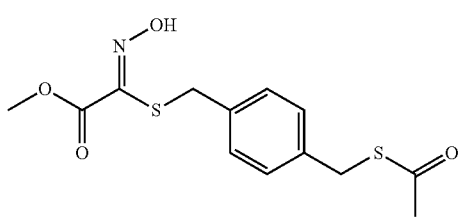
I13

The intermediate compound I13 was prepared by the procedure given for example 1.1 by reacting with 4-methanethioacetyl benzylmercaptan in place of p-toluenethiol. I13 was obtained as light yellow resin.

133.2 Preparation of

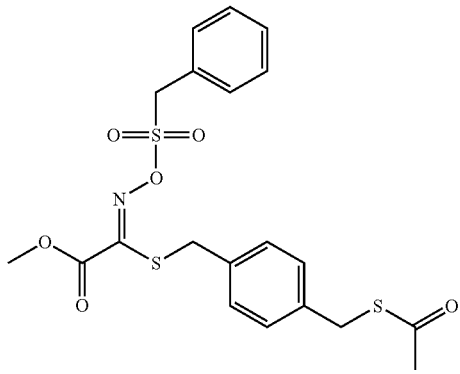
I14

The intermediate compound I14 was prepared by the procedure given for example 1.2 by reacting with benzylsulfonyl chloride in place of p-toluenesulfonyl chloride. I14 was obtained as colorless resin.

133.3 Preparation of

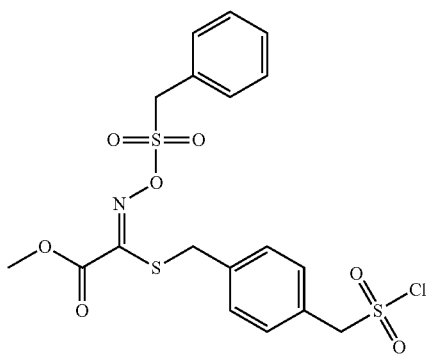
I15

To the solution of 0.53 g of N-Chlorosuccinimide in acetonitrile (10 mL) were added 0.41 g of conc. HCl aq. and then 0.61 g of the intermediate compound I15 of example New4.3 in acetonitrile (20 mL) dropwise at 0° C. After stirring 30 min at room temperature, the organic layer was extracted with ethyl acetate. The solution was concentrated, and then the residue was applied to column chromatography with CH$_2$Cl$_2$/hexane as eluent. 0.56 g of I15 was obtained as colorless resin.

133.4 Preparation of

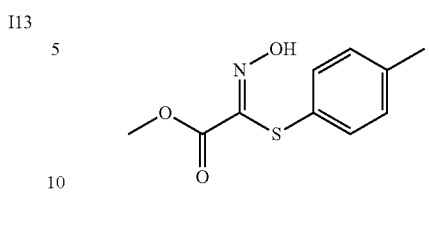
I16

The intermediate compound I16 was prepared by the procedure given for example 1.1. I16 was obtained as white solid.

133.5 Preparation of

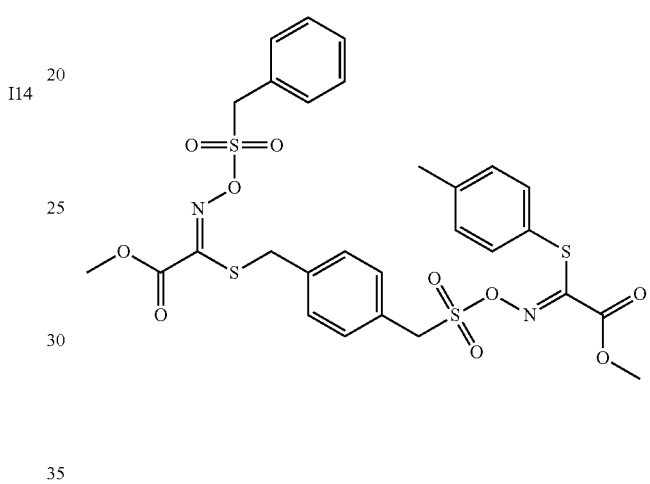

0.56 g of the intermediate compound I15 from example of 133.3 and 0.25 g of the intermediate compound I16 from example of 133.4 were dissolved in CH$_2$Cl$_2$ (10 mL), and to this solution was added 0.12 g of triethylamine in CH$_2$Cl$_2$ (5 mL) dropwise at 0° C. After stirring for 2 hours, water was added, and the organic layer was extracted with ethyl acetate. The solution was concentrated, and then the residue was applied to column chromatography with CH$_2$Cl$_2$/hexane as eluent. 0.19 g of the title compound was obtained as colorless resin.

Example 135

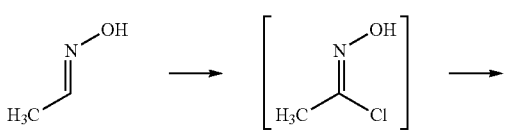

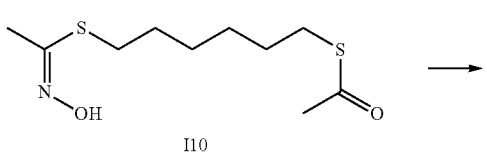
I10

-continued

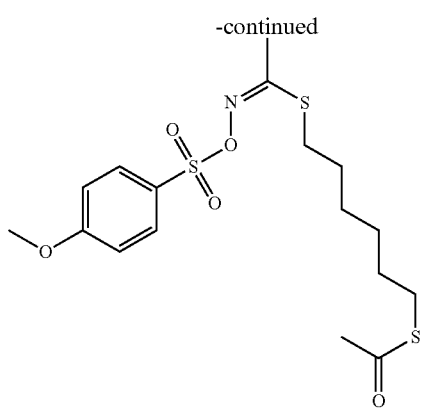

I11

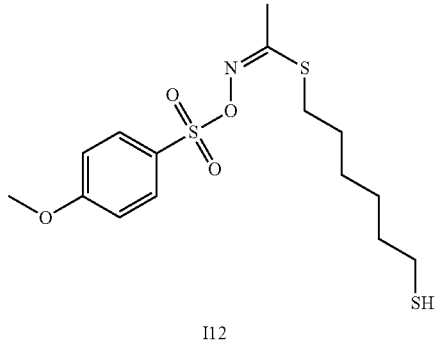

I12

135.1 Preparation of Intermediate I10

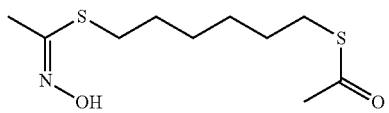

I10

The intermediate compound I10 was prepared by the procedure given for example 1.1 by reacting with 6-acetylthiohexanethiol in place of p-toluenethiol. I10 was obtained as light yellow solid.

135.2 Preparation of Intermediate I11

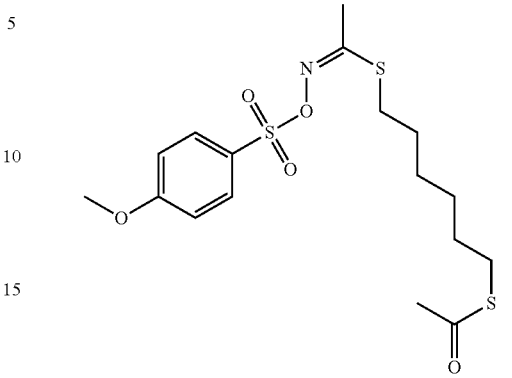

I11

To 1.09 g of the intermediate compound I10 of example 135.1 in MEK (4 mL) were added 1.13 g of p-methoxybenzenesulfonyl chloride and then 0.56 g of triethylamine in MEK (2 mL) dropwise at 0° C. After stirring overnight at room temperature, water was added and the organic layer was extracted with ethyl acetate. The solution was concentrated, and then the residue was applied to column chromatography with $CH_2Cl_2$/acetone as eluent. 1.14 g of I11 was obtained as light brown oil.

135.3 Preparation of

I12

To 0.21 g of the intermediate compound III of example 135.2 in dimethoxyethane (3 mL) was added 0.21 g of hydrazine monohydrate at room temperature. After stirring for 2 hours, water and ethyl acetate were added. The organic layer was separated and concentrated. 0.19 g of colorless resin was obtained and used for the next reaction without further purification.

135.4 Preparation of

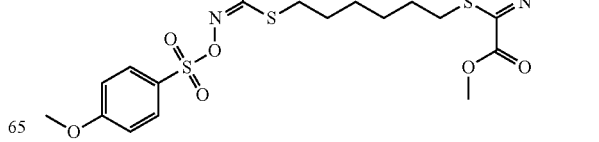

0.19 g of the intermediate compound I12 from example of 135.3 and 0.58 g of the intermediate compound I9 from example of 151.2 were dissolved in MEK (2 mL), and to this solution was added 0.20 g of triethylamine in MEK (0.5 mL) dropwise at 0° C. After stirring for 2 hours, water was added, and the organic layer was extracted with ethyl acetate. The solution was concentrated, and then the residue was applied to column chromatography with $CH_2Cl_2$/acetone as eluent. 0.23 g of the title compound was obtained as white resin.

Example 136

To 0.42 g of the intermediate compound I8 from example of 118.1 in ethyl acetate (1 mL) were added 0.75 g of sodium p-toluenesulfinate tetrahydrate in $H_2O$ (2 mL) and 0.02 g of tetrabutylammonium chloride at room temperature. After stirring for 2.5 hours, water was added, and the organic layer was extracted with ethyl acetate. The solution was concentrated, and then the residue was applied to column chromatography with $CH_2Cl_2$/acetone as eluent. 0.61 g of 117 was obtained as colorless resin.

136.2 Preparation of

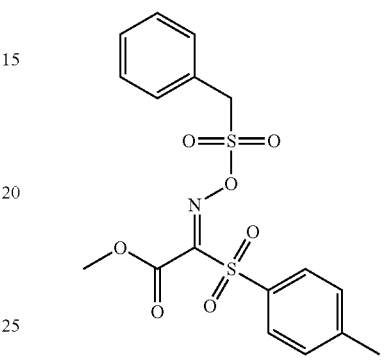

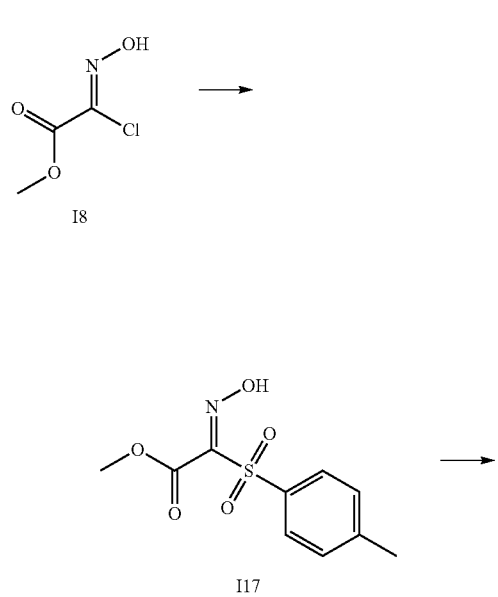

The title compound was prepared by the procedure given for example 1.2. The title compound was obtained as white solid.

Example 146

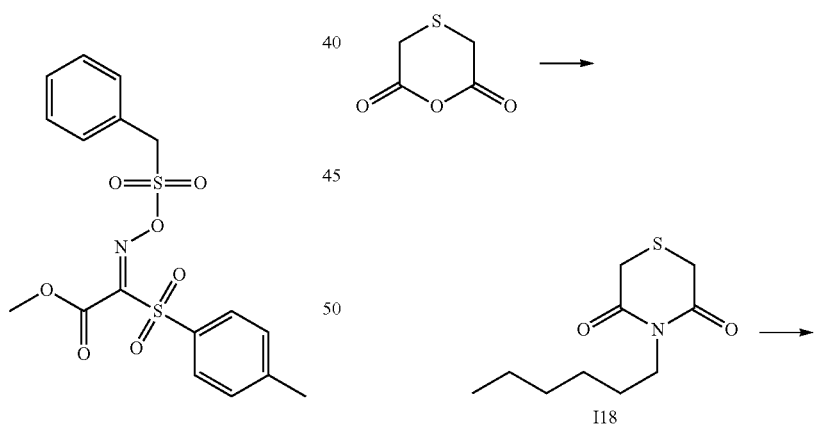

136.1 Preparation of Intermediate Compound I17

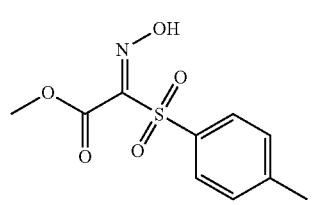

146.1 Preparation of Intermediate Compound I18

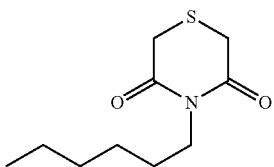
I18

To 1.01 g of n-hexylamine in pyridine (5 mL) was added 2,2'-thiodiglycolic anhydride in portions at room temperature. After stirring for 1 hour, 3.8 mL of acetic anhydride was added, and the reaction mixture was heated at 95° C. for 12 hours. The mixture was concentrated in vacuo, and then $H_2O$ was added. The organic layer was extracted with $CH_2Cl_2$. The solution was concentrated, and then the residue was applied to column chromatography with $CH_2Cl_2$/acetone as eluent. 1.12 g of I18 was obtained as yellow oil.

146.2 Preparation of Intermediate Compound I19

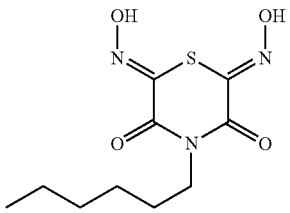
I19

To the intermediate compound I18 from example of 156.1 were added 9.3 mL of 4.0M HCl solution in 1,4-dioxane and then 0.82 g of isoamyl nitrite dropwise at room temperature. After stirring for 2 days, water was added, and the organic layer was extracted with ethyl acetate. The solution was concentrated, and then the residue was applied to column chromatography with $CH_2Cl_2$/acetone as eluent. 0.35 g of I19 was obtained as off-white solid.

146.3 Preparation of

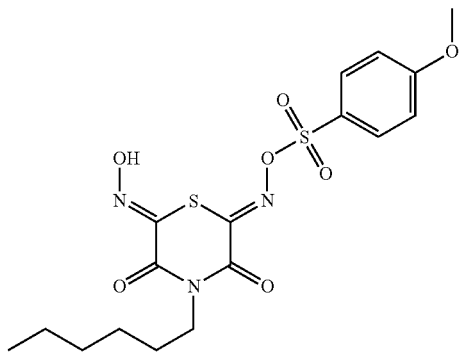 [SMILES: CCCCCCN1C(=O)/C(=N/O)S/C(=N\OS(=O)(=O)c2ccc(OC)cc2)C1=O]

The title compound was prepared by the procedure given for example 1.2. The title compound was obtained as yellow resin.

Example 147

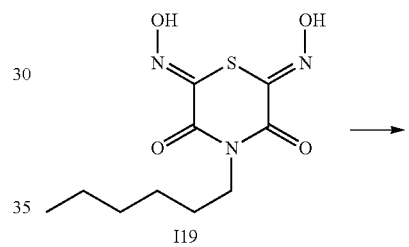
I19

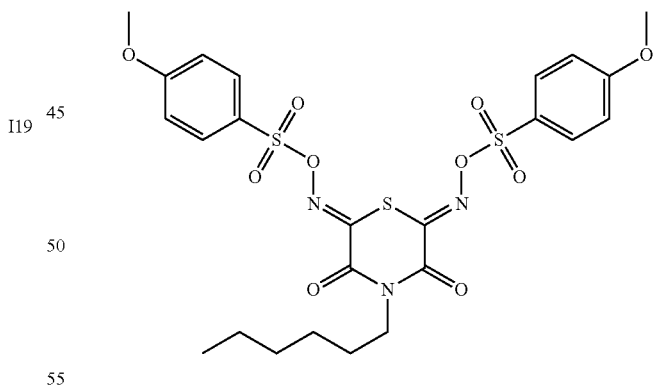

The title compound was prepared from the intermediate compound I19 from example of 146.2 by the procedure given for example 1.2. The title compound was obtained as yellow resin.

The following oxime sulfonates listed in table I were prepared in a similar manner.

TABLE I

| Example | Structure | ¹H NMR in CDCl₃ |
|---|---|---|
| 1 | 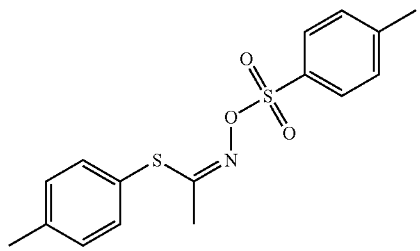 | 1.75 (s, 3H), 2.38 (s, 3H), 2.46 (s, 3H), 7.18-7.92 (m, 8H) |
| 2 | 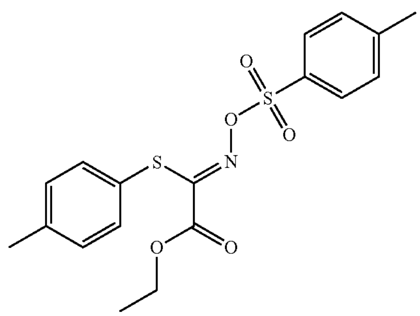 | 0.94 (t, 3H), 2.35 (s, 3H), 2.46 (s, 3H), 3.81 (q, 2H), 7.15-7.90 (m, 8H) |
| 3 | 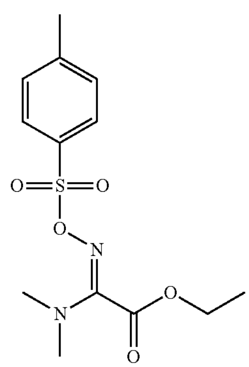 [SMILES: CCOC(=O)/C(=N/OS(=O)(=O)c1ccc(C)cc1)N(C)C] | 1.39 (t, 3H), 2.44 (s, 3H), 2.79 (s, 6H), 4.41 (q, 2H), 7.30-7.85 (m, 4H) |
| 4 | 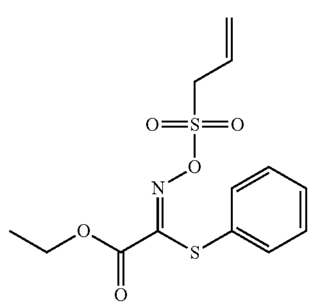 [SMILES: C=CCS(=O)(=O)O/N=C(\Sc1ccccc1)C(=O)OCC] | 0.96 (t, 3H), 3.86 (q, 2H), 4.10 (d, 2H), 5.52-5.57 (m, 2H), 5.88-5.98 (m, 1H), 7.38-7.49 (m, 3H), 7.55-7.58 (m, 2H) |
| 5 | 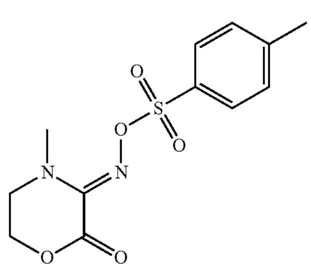 [SMILES: Cc1ccc(S(=O)(=O)O/N=C2/C(=O)OCCN2C)cc1] | 2.44 (s, 3H), 3.28 (s, 3H), 3.37-3.48 (m, 2H), 4.36-4.42 (m, 2H), 7.32-7.92 (m, 4H) |

TABLE I-continued

| Example | Structure | $^1$H NMR in CDCl$_3$ |
| --- | --- | --- |
| 6 | 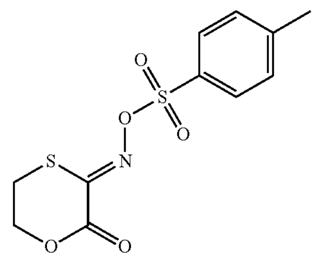 [SMILES: Cc1ccc(S(=O)(=O)O/N=C2\SCCOC2=O)cc1] | 2.46 (s, 3H), 3.16-3.19 (m, 2H), 4.65-4.67 (m, 2H), 7.36-7.92 (m, 4H) |
| 7 | 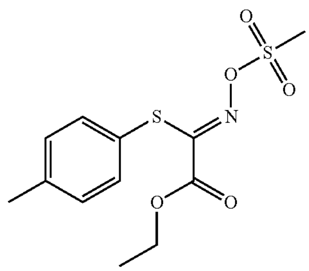 | 0.99 (t, 3H), 2.38 (s, 3H), 3.22 (s, 3H), 3.87 (q, 2H), 7.19-7.45 (m, 4H) |
| 8 | 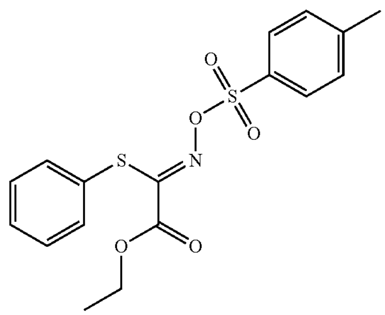 [SMILES: CCOC(=O)/C(=N/OS(=O)(=O)c1ccc(C)cc1)Sc1ccccc1] | 0.91 (t, 3H), 2.47 (s, 3H), 3.80 (q, 2H), 7.34-7.91 (m, 9H) |
| 9 | 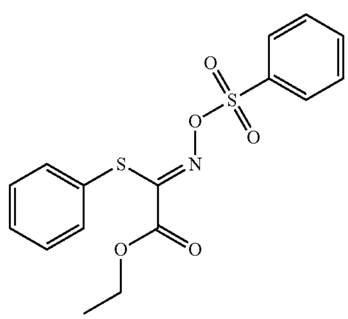 [SMILES: CCOC(=O)/C(=N/OS(=O)(=O)c1ccccc1)Sc1ccccc1] | 0.91 (t, 3H), 3.79 (q, 2H), 7.34-7.72 (m, 8H), 8.01-8.03 (m, 2H) |
| 10 | 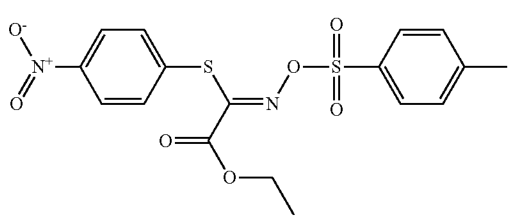 [SMILES: CCOC(=O)/C(=N/OS(=O)(=O)c1ccc(C)cc1)Sc1ccc([N+](=O)[O-])cc1] | 1.04 (t, 3H), 2.48 (s, 3H). 3.96 (q, 2H), 7.37-8.21 (m, 6H) |

TABLE I-continued

| Example | Structure | $^1$H NMR in CDCl$_3$ |
|---|---|---|
| 11 | 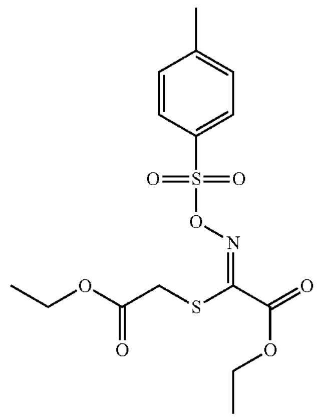 [SMILES: CCOC(=O)CS/C(=N\OS(=O)(=O)c1ccc(C)cc1)C(=O)OCC] | 1.23 (t, 3H), 1.33 (t, 3H), 2.46 (s, 3H), 3.01 (s, 2H), 4.15 (q, 2H), 4.29 (q, 2H), 7.33-7.88 (m, 4H) |
| 12 | 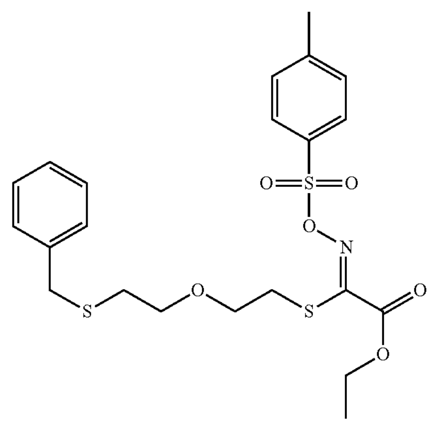 [SMILES: CCOC(=O)/C(=N/OS(=O)(=O)c1ccc(C)cc1)SCCOCCSCc1ccccc1] | 1.31 (t, 3H), 2.44 (s, 3H), 2.52 (t, 2H), 3.13 (t, 2H), 3.47 (t, 2H), 3.55 (t, 2H), 3.72 (s, 2H), 4.28 (q, 2H), 7.24-7.87 (m, 9H) |
| 13 | 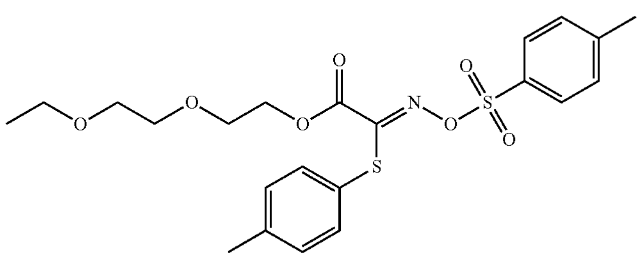 [SMILES: CCOCCOCCOC(=O)/C(=N/OS(=O)(=O)c1ccc(C)cc1)Sc1ccc(C)cc1] | 1.22 (t, 3H), 2.35 (s, 3H), 2.47 (s, 3H), 3.41 (t, 2H), 3.50-3.56 (m, 6H), 3.88 (t, 2H), 7.15-7.90 (m, 4H) |
| 14 | 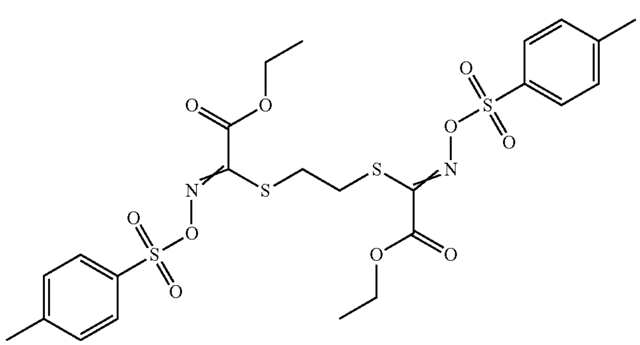 | 1.34 (t, 6H), 2.46 (s, 6H), 3.14 (s, 4H), 4.33 (q, 4H), 7.34-7.87 (m, 6H) |

TABLE I-continued

| Example | Structure | ¹H NMR in CDCl₃ |
|---|---|---|
| 15 | 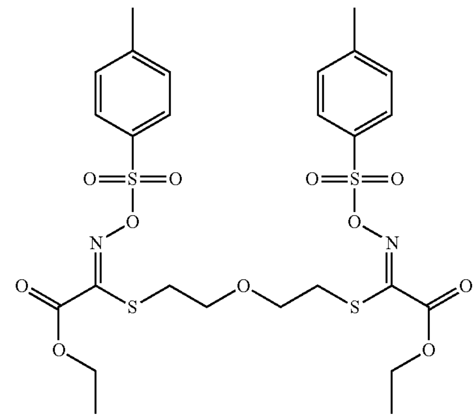 [SMILES: CCOC(=O)/C(=N/OS(=O)(=O)c1ccc(C)cc1)SCCOCCS/C(=N\OS(=O)(=O)c1ccc(C)cc1)C(=O)OCC] | 1.34 (t, 6H), 2.45 (s, 6H), 3.07 (t, 4H), 4.31 (q, 4H), 7.33-7.87 (m, 8H) |
| 16 | 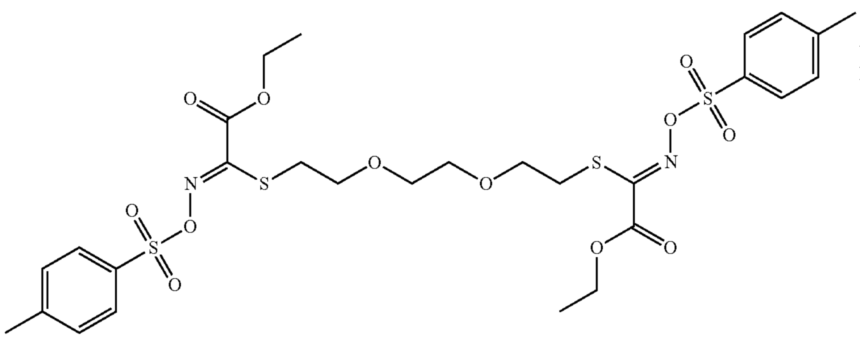 | 1.34 (t, 6H), 2.45 (s, 6H), 3.14 (t, 4H), 3.50 (t, 4H), 3.62 (t, 4H), 4.31 (q, 4H), 7.33-7.87 (m, 8H) |
| 17 | 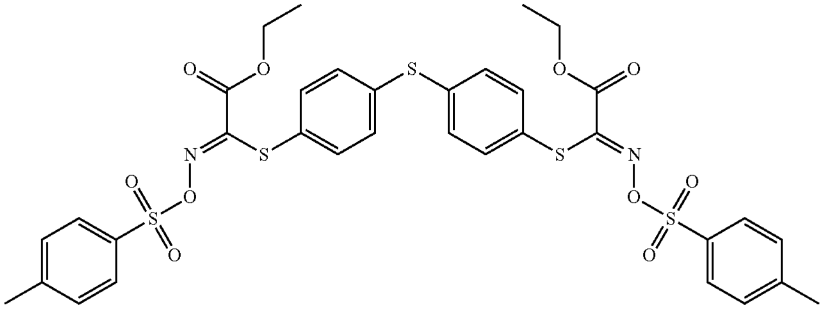 | 0.99 (t, 6H), 2.46 (s, 6H), 3.89 (q, 4H), 7.25-7.89 (m, 16H) |

TABLE I-continued

| Example | Structure | $^1$H NMR in CDCl$_3$ |
|---|---|---|
| 18 | 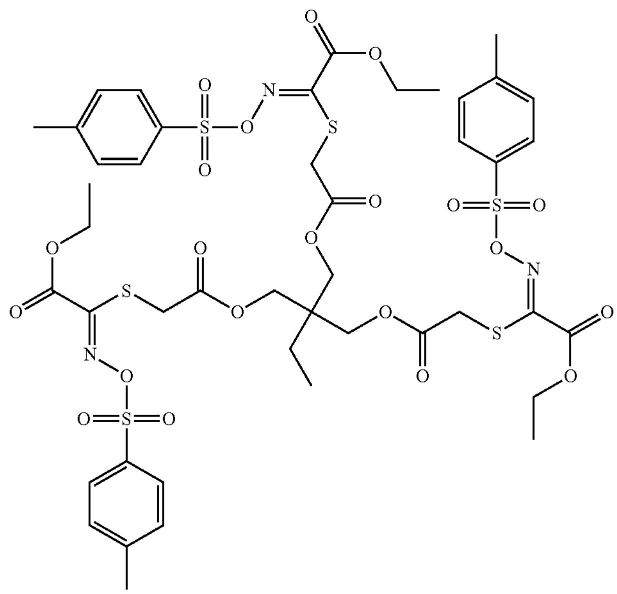 [SMILES: CCOC(=O)/C(=N/OS(=O)(=O)c1ccc(C)cc1)SCC(=O)OCC(CC)(COC(=O)CS/C(=N\OS(=O)(=O)c1ccc(C)cc1)C(=O)OCC)COC(=O)CS/C(=N\OS(=O)(=O)c1ccc(C)cc1)C(=O)OCC] | 1.30-1.41 (m, 9H), 2.46 (s, 9H), 3.82 (s, 6H), 4.02 (s, 6H), 4.26-4.31 (m, 6H), 7.34-7.87 (m, 11H) |
| 19 | 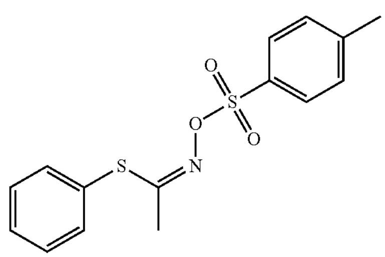 [SMILES: C/C(=N/OS(=O)(=O)c1ccc(C)cc1)Sc1ccccc1] | 1.76 (s, 3H), 2.47 (s, 3H), 7.35-7.51 (m, 7H), 7.90-7.92 (m, 2H) |
| 20 | 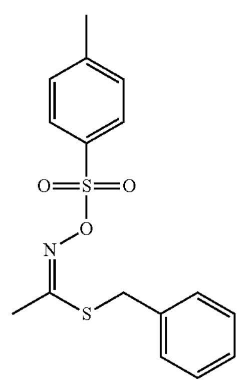 [SMILES: C/C(=N/OS(=O)(=O)c1ccc(C)cc1)SCc1ccccc1] | 2.15, −2.17 (m, 3H), 2.37-2.44 (m, 3H), 4.08-4.23 (m, 2H), 7.20-7.86 (m, 9H) |
| 21 | 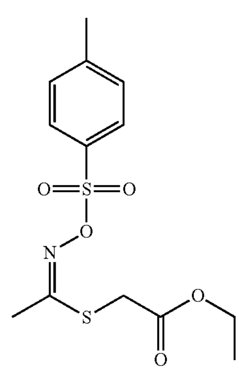 [SMILES: CCOC(=O)CS/C(C)=N\OS(=O)(=O)c1ccc(C)cc1] | 1.28-1.32 (m, 3H), 2.20 (s, 3H), 2.45 (s, 3H), 3.58 (s, 2H), 4.18-4.25 (m, 2H), 7.32-7.87 (m, 4H) |

TABLE I-continued

| Example | Structure | ¹H NMR in CDCl₃ |
|---|---|---|
| 22 | 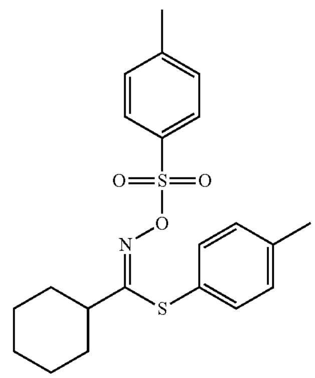 [SMILES: Cc1ccc(S/C(=N\OS(=O)(=O)c2ccc(C)cc2)C2CCCCC2)cc1] | 0.75-1.63 (m, 10H), 1.91-1.97 (m, 1H), 2.38 (s, 3H), 2.46 (s, 3H), 7.17-7.90 (m, 8H) |
| 23 | 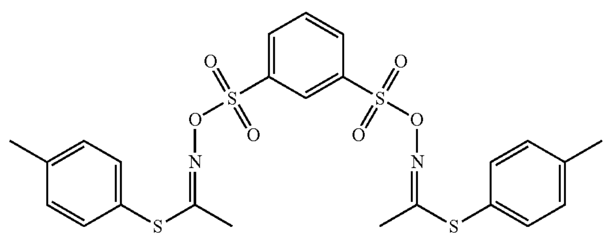 | 1.76 (s, 6H), 2.38 (s, 6H), 7.20-8.67 (m, 12H) |
| 24 | 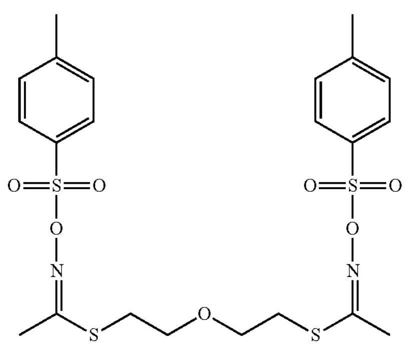 [SMILES: CC(=NOS(=O)(=O)c1ccc(C)cc1)SCCOCCSC(C)=NOS(=O)(=O)c1ccc(C)cc1] | 2.17 (s, 6H), 2.44 (s, 6H), 3.02 (t, 4H), 3.63 (t, 4H), 7.32-7.86 (m, 8H) |
| 25 | 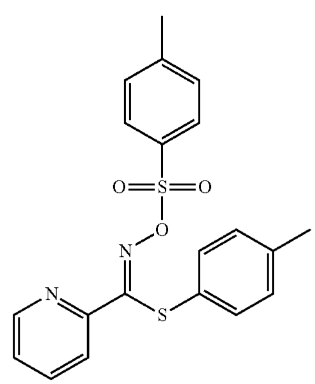 [SMILES: Cc1ccc(S/C(=N\OS(=O)(=O)c2ccc(C)cc2)c2ccccn2)cc1] | 2.21 (s, 3H), 2.44 (s, 3H), 6.88-8.30 (m, 12H) |

TABLE I-continued

| Example | Structure | ¹H NMR in CDCl₃ |
|---|---|---|
| 26 | 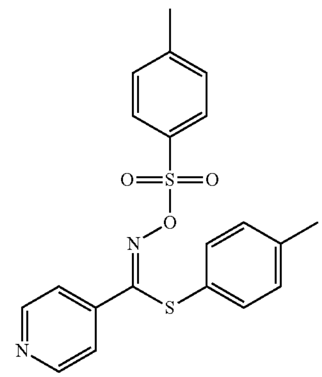 [SMILES: Cc1ccc(S/C(=N\OS(=O)(=O)c2ccc(C)cc2)c2ccncc2)cc1] | 2.22 (s, 3H), 2.47 (s, 3H), 6.93-8.40 (m, 12H) |
| 27 | 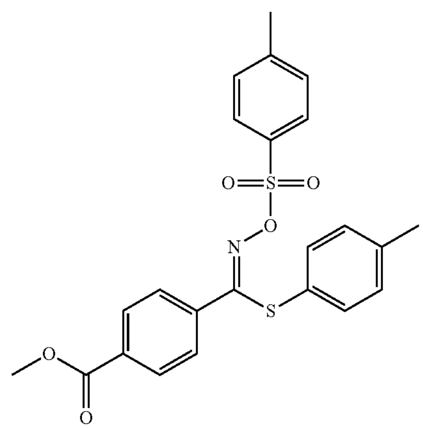 | 2.21 (s, 3H), 2.46 (s, 3H), 3.87 (s, 3H), 6.89-7.93 (m, 10H) |
| 28 | 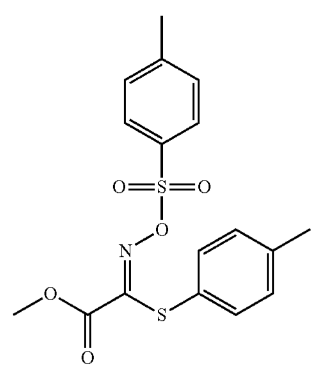 | 2.47 (s, 3H), 3.36 (s, 3H), 7.34-7.49 (m, 7H), 7.87-7.91 (m, 2H) |
| 29 | 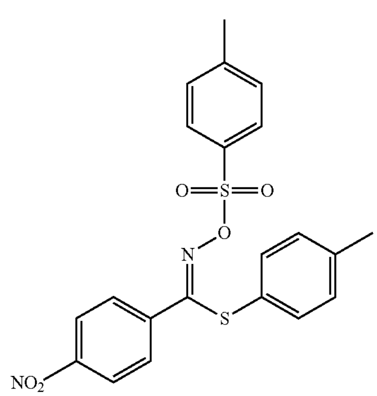 [SMILES: Cc1ccc(S/C(=N\OS(=O)(=O)c2ccc(C)cc2)c2ccc([N+](=O)[O-])cc2)cc1] | 2.23 (s, 3H), 2.47 (s, 3H), 6.93-7.99 (m, 12H) |

TABLE I-continued
| Example | Structure | $^1$H NMR in CDCl$_3$ |
|---|---|---|
| 30 | 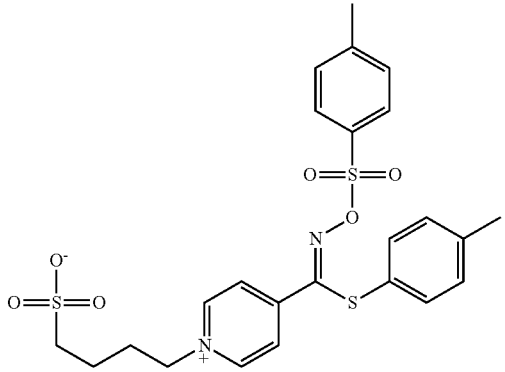 [SMILES: Cc1ccc(S/C(=N\OS(=O)(=O)c2ccc(C)cc2)c2cc[n+](CCCCS(=O)(=O)[O-])cc2)cc1] | 1.77 (s, 2H), 2.04 (s, 2H), 2.22 (s, 3H), 2.46 (s, 3H), 2.90 (s, 2H), 4.86 (s, 2H), 6.99-9.25 (m, 8H) |
| 31 | 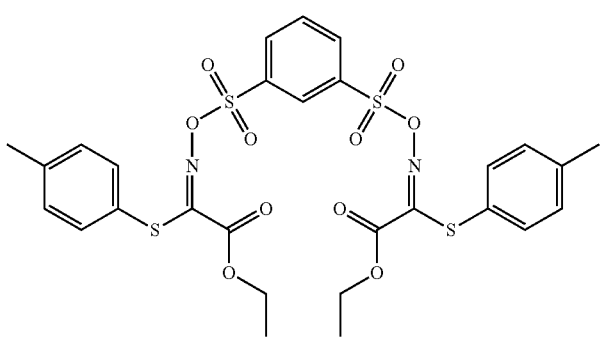 | 0.96 (t, 6H), 2.35 (s, 6H), 3.84 (q, 4H), 7.16-7.18 (m, 4H), 7.36-7.39 (m, 4H), 7.80 (t, 1H), 8.29-8.32 (m, 2H), 8.64-8.65 (m, 1H) |
| 32 | 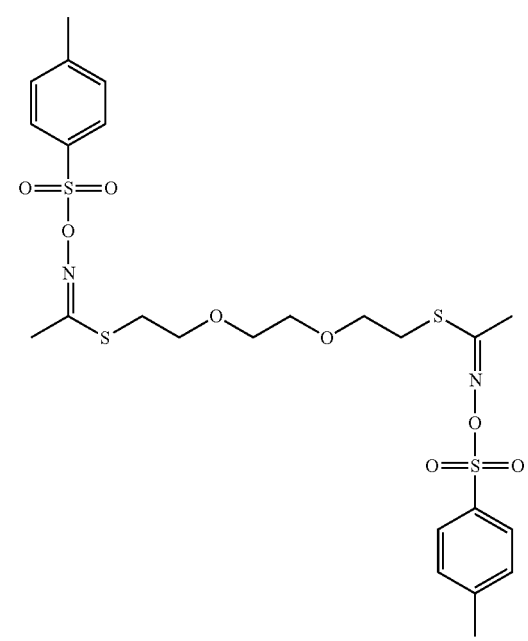 [SMILES: CC(=NOS(=O)(=O)c1ccc(C)cc1)SCCOCCOCCSC(C)=NOS(=O)(=O)c1ccc(C)cc1] | 2.19 (s, 6H), 2.44 (s, 6H), 3.04 (t, 4H), 3.59 (s, 4H), 3.65 (t, 4H), 7.31-7.86 (m, 8H) |

TABLE I-continued
| Example | Structure | ¹H NMR in CDCl₃ |
|---|---|---|
| 33 | 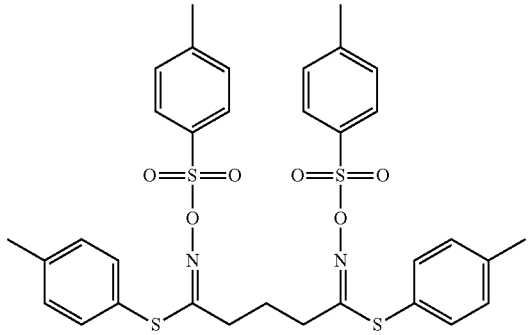 | 1.35-1.38 (m, 2H), 1.81 (t, 4H), 2.38 (s, 6H), 2.46 (s, 6H), 7.13-7.19 (m, 8H), 7.32-7.34 (m, 4H), 7.83-7.85 (m, 4H) |
| 34 | 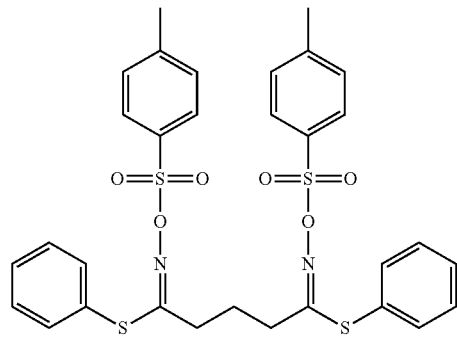 [SMILES: Cc1ccc(S(=O)(=O)ON=C(CCCC(=NOS(=O)(=O)c2ccc(C)cc2)Sc2ccccc2)Sc2ccccc2)cc1] | 1.37-1.40 (m, 2H), 1.80 (t, 4H), 2.46 (s, 6H), 7.29-7.46 (m, 14H), 7.83-7.86 (m, 4H) |
| 35 | 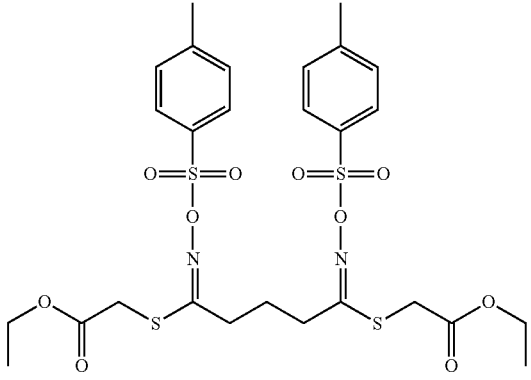 [SMILES: CCOC(=O)CSC(CCCC(=NOS(=O)(=O)c1ccc(C)cc1)SCC(=O)OCC)=NOS(=O)(=O)c1ccc(C)cc1] | 1.26-1.29 (m, 6H), 1.85-1.91 (m, 2H), 2.43 (s, 6H), 2.50 (t, 4H), 3.57 (s, 4H), 4.17-4.22 (m, 4H), 7.35-7.37 (m, 4H), 7.81-7.83 (m, 4H) |
| 36 | 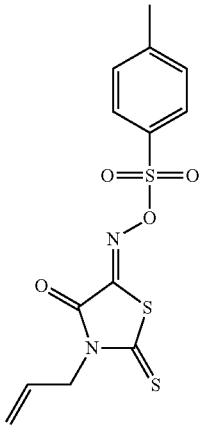 [SMILES: C=CCN1C(=O)/C(=N/OS(=O)(=O)c2ccc(C)cc2)SC1=S] | 2.47 (s, 3H), 4.67-4.68 (m, 2H), 5.26-5.32 (m, 2H), 5.71-5.81 (m, 1H), 7.26-7.40 (m, 2H), 7.91-7.94 (m, 2H) |

TABLE I-continued

| Example | Structure | $^1$H NMR in CDCl$_3$ |
|---|---|---|
| 37 | 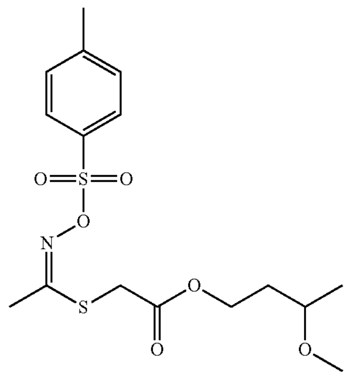 [SMILES: COC(C)CCOC(=O)CS/C(C)=N\OS(=O)(=O)c1ccc(C)cc1] | 1.12-1.18 (m, 3H), 1.73-1.83 (m, 2H), 2.21 (s, 3H), 2.45 (s, 3H), 3.29 (s, 3H), 3.37-3.41 (m, 1H), 3.58 (s, 2H), 4.23-4.27 (m, 2H), 7.31-7.34 (m, 2H), 7.80-7.87 (m, 2H) |
| 38 | 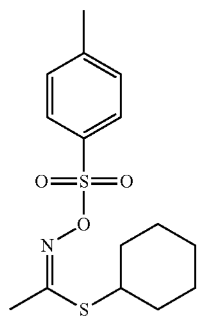 [SMILES: C/C(=N/OS(=O)(=O)c1ccc(C)cc1)SC1CCCCC1] | 1.24-1.48 (m, 5H), 1.59-1.62 (m, 1H), 1.76-1.80 (m, 2H), 1.91-1.95 (m, 2H), 2.19 (s, 3H), 2.44 (s, 3H), 3.13-3.21 (m, 1H), 7.31-7.33 (m, 2H), 7.85-7.87 (m, 2H) |
| 39 | 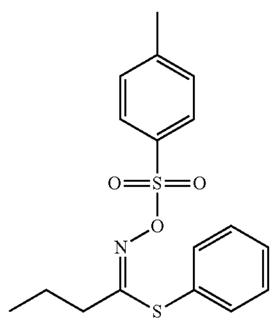 [SMILES: CCC/C(=N/OS(=O)(=O)c1ccc(C)cc1)Sc1ccccc1] | 0.59-0.63 (m, 3H), 1.27-1.34 (m, 2H), 2.02-2.05 (m, 2H), 2.46 (s, 3H), 7.34-7.49 (m, 7H), 7.89-7.91 (m, 2H) |
| 40 | 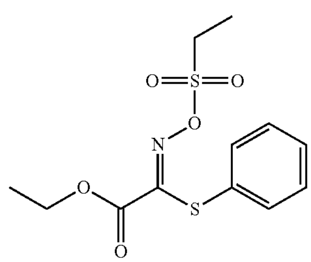 [SMILES: CCOC(=O)/C(=N/OS(=O)(=O)CC)Sc1ccccc1] | 0.96 (t, 3H), 1.49 (t, 3H), 3.41 (q, 2H), 3.85 (q, 2H), 7.38-7.49 (m, 3H), 7.56-7.57 (m, 2H) |
| 41 | 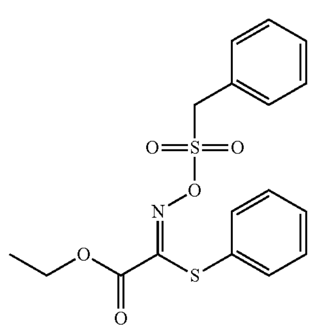 [SMILES: CCOC(=O)/C(=N/OS(=O)(=O)Cc1ccccc1)Sc1ccccc1] | 0.98 (t, 3H), 3.88 (q, 2H), 4.61 (s, 2H), 7.26-7.55 (m, 10H) |

TABLE I-continued

| Example | Structure | ¹H NMR in CDCl₃ |
|---------|-----------|-----------------|
| 42 | 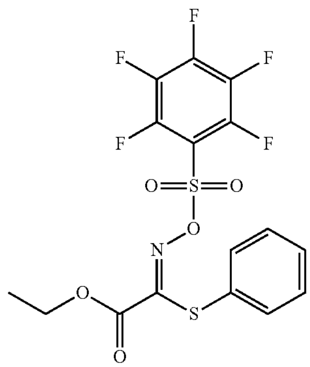 [SMILES: CCOC(=O)/C(=N/OS(=O)(=O)c1c(F)c(F)c(F)c(F)c1F)Sc1ccccc1] | 0.93 (t, 3H), 3.82 (q, 2H), 7.26-7.57 (m, 5H) |
| 43 | 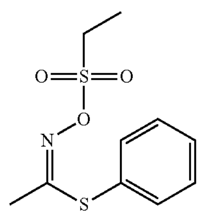 [SMILES: CCS(=O)(=O)O/N=C(/C)Sc1ccccc1] | 1.48 (t, 3H), 1.87 (s, 3H), 3.38 (q, 2H), 7.42-7.58 (m, 5H) |
| 44 | 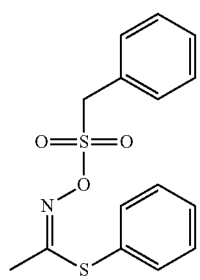 [SMILES: C/C(=N/OS(=O)(=O)Cc1ccccc1)Sc1ccccc1] | 1.91 (s, 3H), 4.59 (s, 2H), 7.39-7.57 (m, 10H) |
| 45 | 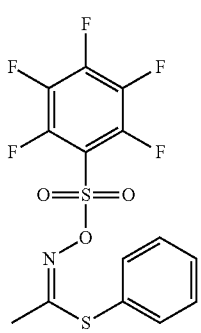 [SMILES: C/C(=N/OS(=O)(=O)c1c(F)c(F)c(F)c(F)c1F)Sc1ccccc1] | 1.81 (s, 3H), 7.42-7.57 (m, 5H) |

TABLE I-continued

| Example | Structure | ¹H NMR in CDCl₃ |
|---|---|---|
| 46 | 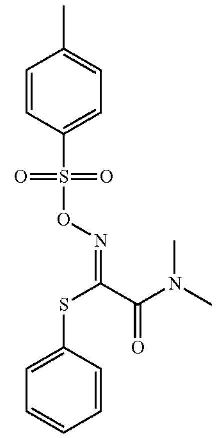 [SMILES: Cc1ccc(S(=O)(=O)O/N=C(\Sc2ccccc2)C(=O)N(C)C)cc1] | 2.45 (s, 3H), 2.47 (s, 3H), 2.82 (s, 3H), 7.33-7.54 (m, 7H), 7.87-7.89 (m, 2H) |
| 47 | 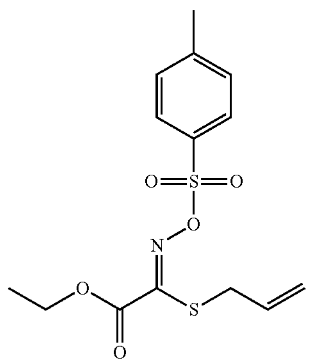 [SMILES: C=CCS/C(=N\OS(=O)(=O)c1ccc(C)cc1)C(=O)OCC] | 1.33 (t, 3H), 2.45 (s, 3H), 3.59-3.62 (m, 2H), 4.28 (q, 2H), 5.14-5.22 (m, 2H), 5.71-5.81 (m, 1H), 7.33-7.35 (m, 2H), 7.85-7.88 (m, 2H) |
| 48 | 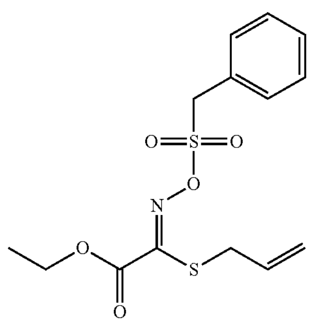 [SMILES: C=CCS/C(=N\OS(=O)(=O)Cc1ccccc1)C(=O)OCC] | 1.39-1.43 (m, 3H), 3.63-3.65 (m, 2H), 4.38 (q, 2H), 4.57 (s, 2H), 5.19-5.26 (m, 2H), 5.74-5.85 (m, 1H), 7.35-7.38 (m, 5H) |
| 49 | 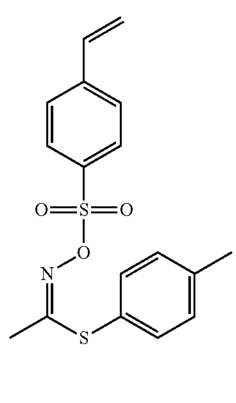 [SMILES: C=Cc1ccc(S(=O)(=O)O/N=C(/C)Sc2ccc(C)cc2)cc1] | 1.74 (s, 3H), 2.38 (s, 3H), 5.48 (d, 1H), 5.92 (d, 1H), 6.74-6.81 (m, 1H), 7.19-7.21 (m, 2H), 7.34-7.37 (m, 2H), 7.55-7.58 (m, 2H), 7.96-7.99 (m, 2H) |

TABLE I-continued

| Example | Structure | $^1$H NMR in CDCl$_3$ |
|---|---|---|
| 50 | 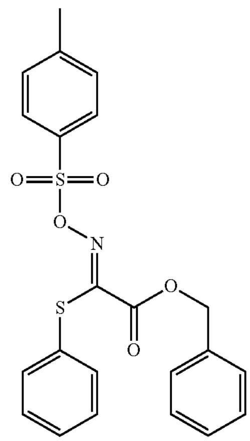 [SMILES: Cc1ccc(S(=O)(=O)O/N=C(\Sc2ccccc2)C(=O)OCc2ccccc2)cc1] | 2.46 (s, 3H), 4.76 (s, 2H), 7.05-7.07 (m, 2H), 7.22-7.42 (m, 10H), 7.87-7.90 (m, 2H) |
| 51 | 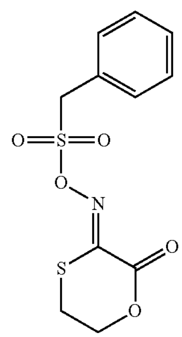 [SMILES: O=C1OCCS/C1=N\OS(=O)(=O)Cc1ccccc1] | 3.21-3.24 (m, 2H), 4.68 (s, 2H), 4.72-4.75 (m, 2H), 7.40-7.42 (m, 5H) |
| 52 | 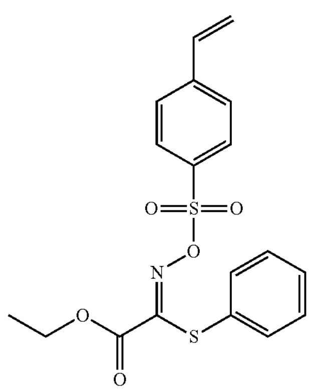 [SMILES: C=Cc1ccc(S(=O)(=O)O/N=C(\Sc2ccccc2)C(=O)OCC)cc1] | 0.89-0.93 (m, 3H), 3.80 (q, 2), 5.49 (d, 1H), 5.94 (d, 2H), 6.74-6.81 (m, 1H), 7.34-7.59 (m, 7H), 7.95-7.98 (m, 2H) |
| 53 | 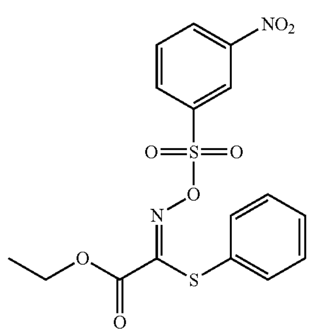 [SMILES: CCOC(=O)/C(=N/OS(=O)(=O)c1cccc([N+](=O)[O-])c1)Sc1ccccc1] | 0.92 (t, 3H), 3.81 (q, 2H), 7.36-7.52 (m, 5H), 7.80-7.84 (m, 1H), 8.33-8.35 (m, 1H), 8.54-8.57 (m, 1H), 8.87 (m, 1H) |

TABLE I-continued

| Example | Structure | $^1$H NMR in CDCl$_3$ |
| --- | --- | --- |
| 54 | 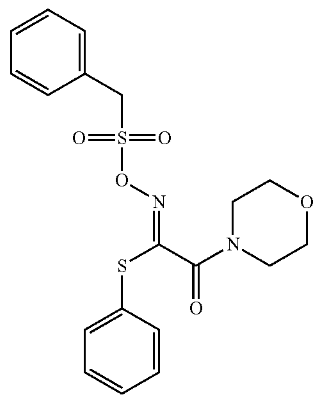 [SMILES: O=C(/C(=N/OS(=O)(=O)Cc1ccccc1)Sc1ccccc1)N1CCOCC1] | 3.22-3.24 (m, 2H), 3.34-3.37 (m, 2H), 3.39-3.42 (m, 2H), 3.49-3.51 (m, 2H), 4.59 (s, 2H), 7.40-7.50 (m, 8H), 7.59-7.60 (m, 2H) |
| 55 | 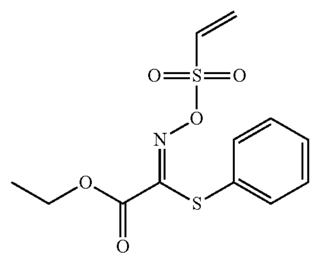 [SMILES: C=CS(=O)(=O)O/N=C(\Sc1ccccc1)C(=O)OCC] | 0.95 (t, 3H), 3.84 (q, 2H), 6.26-6.28 (m, 1H), 6.56-6.60 (m, 1H), 6.70-6.77 (m, 1H), 7.38-4.42 (m, 2H), 7.44-7.48 (m, 1H), 7.55-7.57 (m, 2H) |
| 56 | 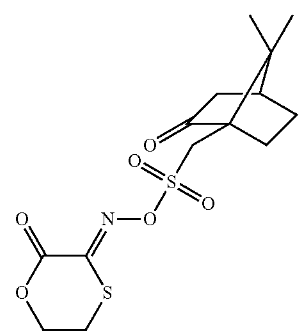 [SMILES: CC1(C)C2CCC1(CS(=O)(=O)O/N=C1\SCCOC1=O)C(=O)C2] | 0.92 (s, 3H), 1.14 (m, 3H), 1.39-1.48 (m, 2H), 1.74-1.80 (m, 1H), 2.05-2.14 (m, 2H), 2.39-2.45 (m, 2H), 3.23-3.26 (m, 2H), 3.38-3.86 (m, 2H), 4.73-4.75 (m, 2H) |
| 57 | 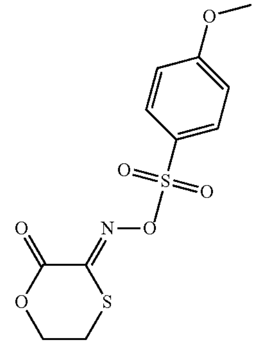 | 3.16-3.18 (m, 2H), 3.89 (s, 3H), 4.65-4.68 (m, 2H), 7.01-7.03 (m, 2H), 7.95-7.98 (m, 2H) |

TABLE I-continued

| Example | Structure | ¹H NMR in CDCl₃ |
|---|---|---|
| 58 | 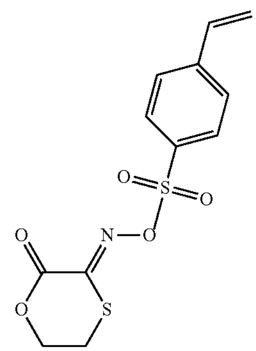 | 3.17-3.19 (m, 2H), 4.66-4.68 (m, 2H), 5.49 (d, 1H), 5.93 (d, 1H), 6.73-6.80 (m, 1H), 7.56-7.59 (m, 2H), 7.97-8.00 (m, 2H) |
| 59 | 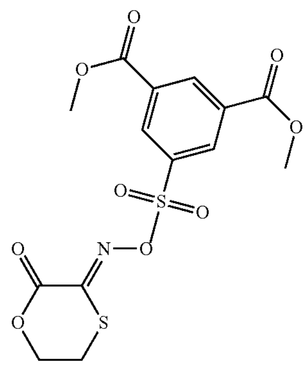 | 3.19-3.21 (m 2H), 4.00 (s, 6H), 4.66-4.69 (m, 2H), 8.82 (d, 2H), 8.96 (t, 1H) |
| 60 | 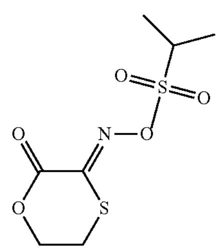 | 1.49 (d, 6H), 3.24-3.26 (m, 2H), 3.81-3.88 (m, 1H), 4.73-4.76 (m, 2H) |
| 61 | 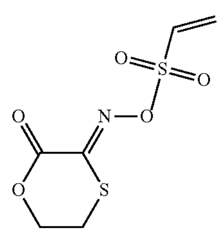 | 3.23-3.25 (m, 2H), 4.72-4.75 (m, 2H), 6.33-6.65 (m, 2H), 6.73-6.80 (m, 1H) |
| 62 | 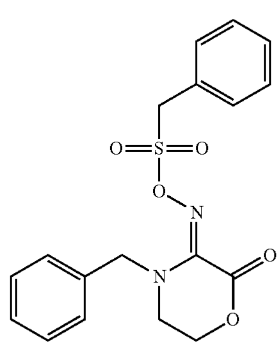 [SMILES: O=C1OCCN(Cc2ccccc2)/C1=N\OS(=O)(=O)Cc1ccccc1] | 3.31-3.34 (m, 2H), 4.41-4.31 (m, 2H), 4.63 (s, 2H), 4.64 (s, 2H), 7.15-7.17 (m, 2H), 7.30-7.38 (m, 6H), 7.44-7.46 (m, 2H) |

TABLE I-continued

| Example | Structure | ¹H NMR in CDCl₃ |
|---|---|---|
| 63 | 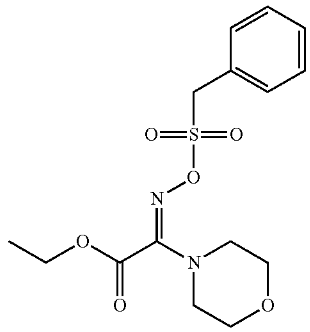 [SMILES: CCOC(=O)/C(=N/OS(=O)(=O)Cc1ccccc1)N1CCOCC1] | 1.40 (t, 3H), 3.35-3.38 (m, 2H), 3.63-3.64 (m, 2H), 4.38 (q, 2H), 4.59 (s, 2H), 7.38-7.47(m, 5H) |
| 64 | 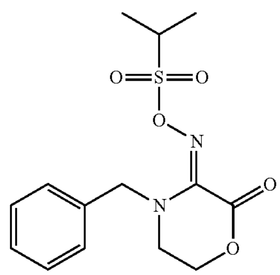 [SMILES: CC(C)S(=O)(=O)O/N=C1/C(=O)OCCN1Cc1ccccc1] | 1.41 (d, 6H), 3.36-3.39 (m, 2H), 3.89-3.96 (m, H), 4.42-4.44 (m, 2H), 4.86 (s, 2H), 7.30-7.40 (m, 5H) |
| 65 | 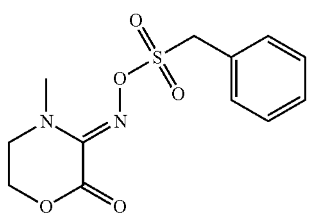 [SMILES: CN1CCOC(=O)/C1=N/OS(=O)(=O)Cc1ccccc1] | 3.14 (s, 3H), 3.41-3.43 (m, 2H), 4.45-4.47 (m, 2H), 4.67 (s, 2H), 7.37-7.48 (m, 5H) |
| 66 | 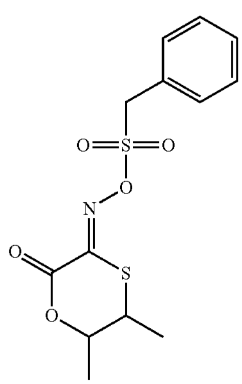 [SMILES: CC1OC(=O)/C(=N/OS(=O)(=O)Cc2ccccc2)SC1C] | 1.33-1.58 (m, 6H), 3.31-3.39 (m, 1H), 3.89 (s, 3H), 4.45-4.52 (m, 1H), 7.01-7.03 (m, 2H), 7.95-7.97 (m, 2H) |

TABLE I-continued
| Example | Structure | $^1$H NMR in CDCl$_3$ |
|---|---|---|
| 67 | 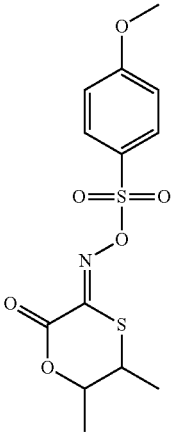 [SMILES: COc1ccc(S(=O)(=O)O/N=C2\SC(C)C(C)OC2=O)cc1] | 1.33-1.48 (m, 6H), 3.31-3.39 (m, 1H), 3.89 (s, 3H), 4.45-4.52, 4.86-4.91 (m, 1H), 7.01 (d, 2H), 7.96 (d, 2H) |
| 68 | 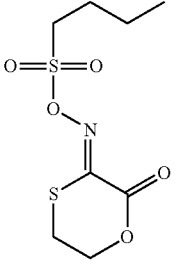 [SMILES: CCCCS(=O)(=O)O/N=C1\SCCOC1=O] | 0.97 (t, 3H), 1.44-1.54 (m, 2H), 1.83-1.92 (m, 2H), 3.24 (t, 2H), 3.44 (dd, 2H), 4.74 (t, 2H) |
| 69 | 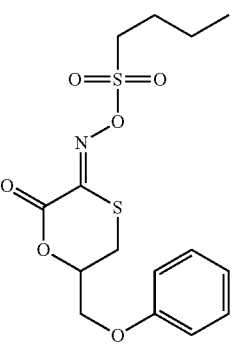 [SMILES: CCCCS(=O)(=O)O/N=C1\SCC(COc2ccccc2)OC1=O] | 0.97 (t, 3H), 1.47-1.56 (m, 2H), 1.84-1.92 (m, 2H), 3.29-3.46 (m, 4H), 4.16-4.20 (m, 1H), 4.30-4.33 (m, 1H), 5.01-5.06 (m, 1H), 6.90 (d, 2H), 7.03 (t, 1H), 7.34 (t, 2H) |
| 70 | 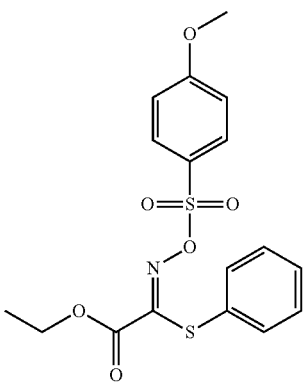 | 0.91 (t, 3H), 3.80 (q, 2H), 3.90 (s, 3H), 7.03 (d, 2H), 7.26-7.50 (m, 5H), 7.95 (d, 2H) |

TABLE I-continued

| Example | Structure | $^1$H NMR in CDCl$_3$ |
|---|---|---|
| 71 | 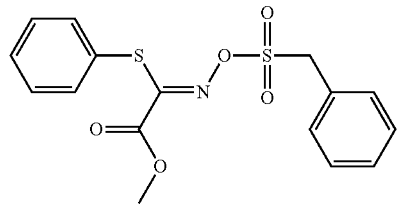 [SMILES: COC(=O)/C(=N/OS(=O)(=O)Cc1ccccc1)Sc1ccccc1] | 3.45 (s, 3H), 4.61 (s, 2H), 7.38-7.50 (m, 8H), 7.52-7.56 (m, 2H) |
| 72 | 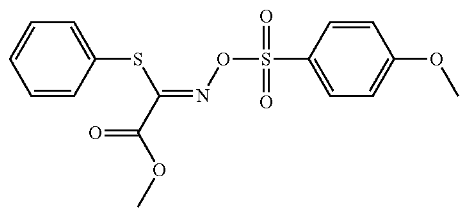 [SMILES: COC(=O)/C(=N/OS(=O)(=O)c1ccc(OC)cc1)Sc1ccccc1] | 3.36 (s, 3H), 3.90 (s, 3H), 7.02 (d, 2H), 7.33-7.51 (m, 5H), 7.94 (d, 2H) |
| 73 | 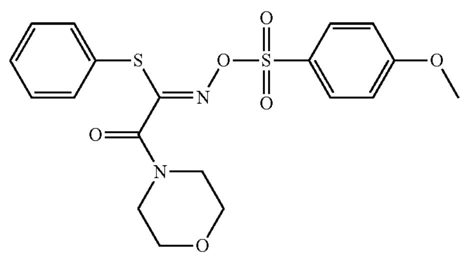 [SMILES: COc1ccc(S(=O)(=O)O/N=C(\Sc2ccccc2)C(=O)N2CCOCC2)cc1] | 3.15 (dd, 2H), 3.25 (dd, 2H), 3.32 (dd, 2H), 3.42 (dd, 2H), 3.90 (s, 3H), 7.01 (d, 2H), 7.38 (t, 2H), 7.48 (t, 1H), 7.54 (d, 1H), 7.92 (d, 2H) |
| 74 | 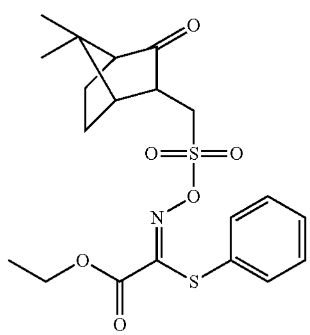 [SMILES: CCOC(=O)/C(=N/OS(=O)(=O)CC1C(=O)C2CCC1C2(C)C)Sc1ccccc1] | 0.94 (s, 6H), 0.96 (t, 3H), 1.43-1.45 (m, 1H), 1.70-1.77 (m, 1H), 2.66 (dd, 1H), 2.06-2.17 (m, 3H), 2.40-2.53 (m, 2H), 3.83-3.30 (d + q, 3H), 7.38-7.58 (m, 5H) |
| 75 | 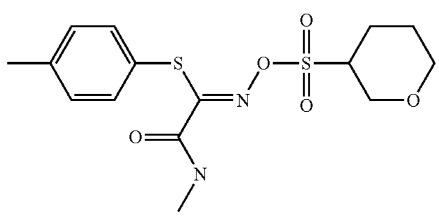 [SMILES: CNC(=O)/C(=N/OS(=O)(=O)C1CCCOC1)Sc1ccc(C)cc1] | 1.67-1.81 (m, 1H), 1.81-1.90 (m, 1H), 1.96-2.09 (m, 1H), 2.30-2.40 (m, 1H), 2.38 (s, 3H), 3.39-3.49 (m, 1H), 3.44 (s, 3H), 3.68-3.78 (m, 2H), 3.89-3.98 (m, 1H), 4.22-4.32 (m, 1H), 7.21 (d, 2H), 7.42 (d, 2H) |
| 76 | 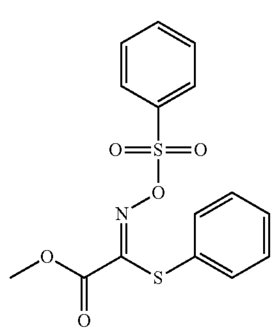 [SMILES: COC(=O)/C(=N/OS(=O)(=O)c1ccccc1)Sc1ccccc1] | 3.36 (s, 3H), 7.34-7.72 (m, 8H), 8.00-8.03 (m, 2H) |

TABLE I-continued

| Example | Structure | $^1$H NMR in CDCl$_3$ |
| --- | --- | --- |
| 77 | 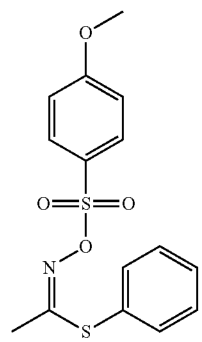 [SMILES: COc1ccc(S(=O)(=O)O/N=C(/C)Sc2ccccc2)cc1] | 1.76 (s, 3H), 3.90 (s, 3H), 7.01-7.04 (m, 2H), 7.38-7.51 (m, 5H), 7.94-98 (m, 2H) |
| 78 | 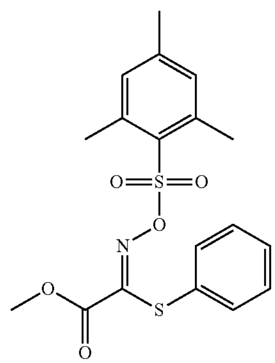 [SMILES: COC(=O)/C(=N/OS(=O)(=O)c1c(C)cc(C)cc1C)Sc1ccccc1] | 2.33 (s, 3H), 2.67 (s, 6H), 3.35 (s, 3H), 6.99 (s, 2H), 7.35-7.51 (m, 5H) |
| 79 | 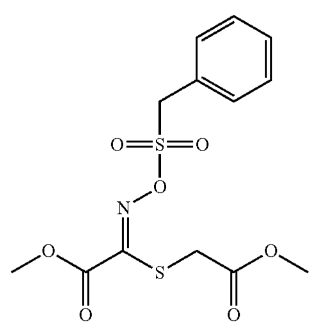 | 3.76 (s, 3H), 3.89 (s, 2H), 3.94 (s, 3H), 4.59 (s, 2H), 7.40 (s, 5H) |
| 80 | 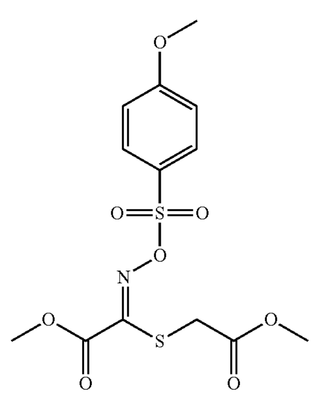 | 3.72 (s, 3H), 3.83 (s, 2H), 3.85 (s, 3H), 3.90 (s, 3H), 7.00-7.02 (m, 2H), 7.91-7.93 (m, 2H) |

TABLE I-continued

| Example | Structure | $^1$H NMR in CDCl$_3$ |
|---|---|---|
| 81 | 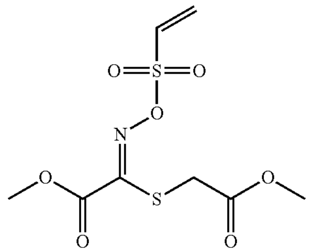 | 3.75 (s, 3H), 3.89 (s, 2H), 3.90 (s, 3H), 6.26-6.28 (m, 1H), 6.55-6.59 (m, 1H), 6.67-6.74 (m, 1H) |
| 82 | 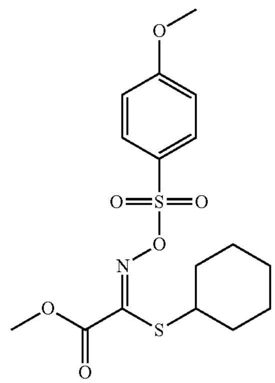 [SMILES: COC(=O)/C(=N/OS(=O)(=O)c1ccc(OC)cc1)SC1CCCCC1] | 1.22-1.93 (m, 10H), 3.27-3.51 (m, 1H), 6.97-7.01 (m, 2H) |
| 83 | 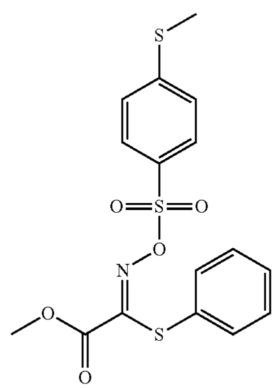 [SMILES: COC(=O)/C(=N/OS(=O)(=O)c1ccc(SC)cc1)Sc1ccccc1] | 2.54 (s, 3H), 3.36 (s, 3H), 7.33-7.50 (m, 7H), 7.87-7.89 (m, 2H) |
| 84 | 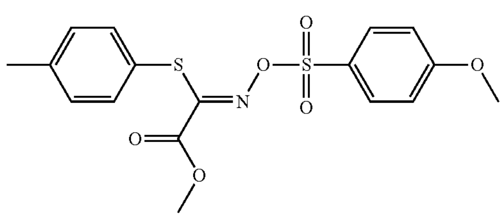 | 2.35 (s, 3H), 3.38 (s, 3H), 3.90 (s, 3H), 7.01 (d, 2H), 7.16 (d, 2H), 7.35 (d, 2H), 7.94 (d, 2H) |
| 85 | 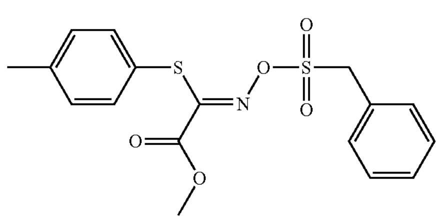 [SMILES: COC(=O)/C(=N/OS(=O)(=O)Cc1ccccc1)Sc1ccc(C)cc1] | 2.38 (s, 3H), 3.47 (s, 3H), 4.60 (s, 2H), 7.21 (d, 2H), 7.38-7.47 (m, 7H) |
| 86 | 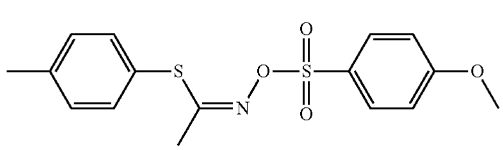 | 1.75 (s, 3H), 2.38 (s, 3H), 3.90 (s, 3H), 7.02 (d, 2H), 7.20 (d, 2H), 7.36 (d, 2H), 7.96 (d, 2H) |

TABLE I-continued

| Example | Structure | ¹H NMR in CDCl₃ |
|---|---|---|
| 87 | 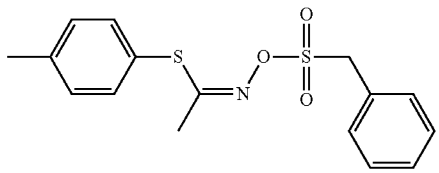 [SMILES: C/C(=N/OS(=O)(=O)Cc1ccccc1)Sc1ccc(C)cc1] | 1.90 (s, 3H), 2.40 (s, 3H), 4.58 (s, 2H), 7.24 (d, 2H), 7.38-7.48 (m, 7H) |
| 88 | 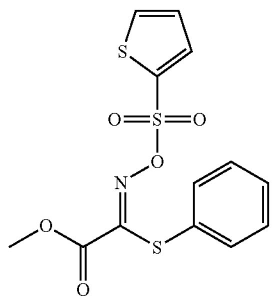 [SMILES: COC(=O)/C(=N/OS(=O)(=O)c1cccs1)Sc1ccccc1] | 3.38 (s, 3H), 7.16-7.19 (m, 1H), 7.36-7.52 (m, 5H), 7.77-7.79 (m, 1H), 7.85-7.87 (m, 1H) |
| 89 | 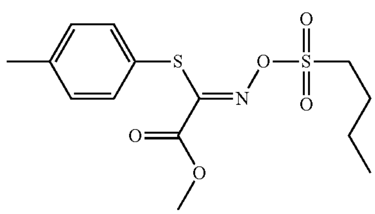 [SMILES: CCCCS(=O)(=O)O/N=C(\Sc1ccc(C)cc1)C(=O)OC] | 0.98 (t, 3H), 1.46-1.57 (m, 2H), 1.85-1.96 (m, 2H), 2.38 (s, 3H), 3.36 (dd, 2H), 3.44 (s, 3H), 7.21 (d, 2H), 7.42 (d, 2H) |
| 90 | 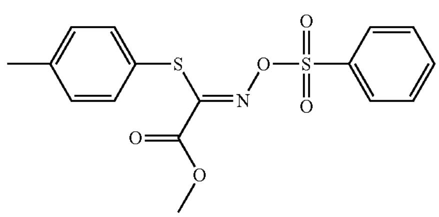 [SMILES: COC(=O)/C(=N/OS(=O)(=O)c1ccccc1)Sc1ccc(C)cc1] | 2.35 (s, 3H), 3.38 (s, 3H), 7.16 (d, 2H), 7.35 (d, 2H), 7.57 (t, 2H), 7.69 (t, 1H), 8.01 (d, 2H) |
| 91 | 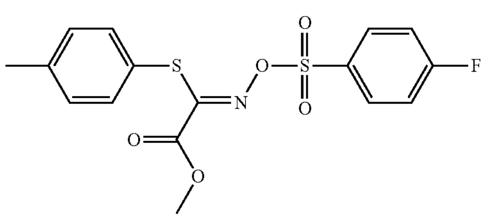 [SMILES: COC(=O)/C(=N/OS(=O)(=O)c1ccc(F)cc1)Sc1ccc(C)cc1] | 2.36 (s, 3H), 3.38 (s, 3H), 7.17 (d, 2H), 7.25 (t, 2H), 7.36 (d, 2H), 8.03 (dd, 2H) |
| 92 | 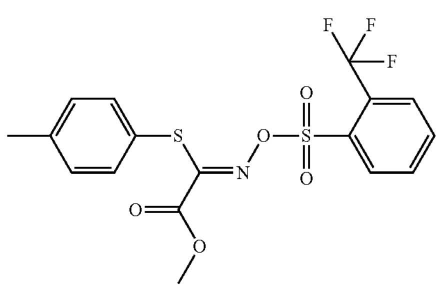 [SMILES: COC(=O)/C(=N/OS(=O)(=O)c1ccccc1C(F)(F)F)Sc1ccc(C)cc1] | 2.36 (s, 3H), 3.35 (s, 3H), 7.17 (d, 2H), 7.38 (d, 2H), 7.76 (t, 1H), 7.81 (t, 1H), 7.95 (d, 1H), 8.31 (d, 1H) |

TABLE I-continued

| Example | Structure | $^1$H NMR in CDCl$_3$ |
| --- | --- | --- |
| 93 | 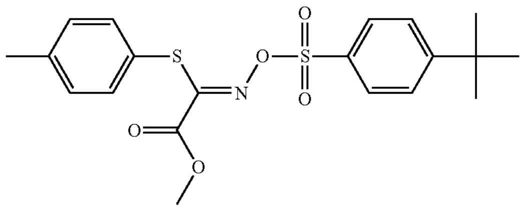 [SMILES: COC(=O)/C(=N/OS(=O)(=O)c1ccc(C(C)(C)C)cc1)Sc1ccc(C)cc1] | 1.37 (s, 9H), 2.36 (s, 3H), 3.90 (s, 3H), 7.16 (d, 2H), 7.36 (d, 2H), 7.58 (d, 2H), 7.93 (d, 2H) |
| 94 | 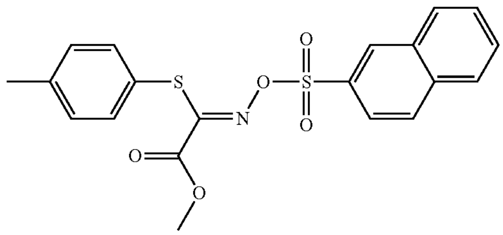 [SMILES: COC(=O)/C(=N/OS(=O)(=O)c1ccc2ccccc2c1)Sc1ccc(C)cc1] | 2.36 (s, 3H), 3.35 (s, 3H), 7.14 (d, 2H), 7.33 (d, 2H), 7.63-7.72 (m, 2H), 7.94-7.97 (m, 2H), 8.01 (d, 2H), 8.60 (s, 1H) |
| 95 | 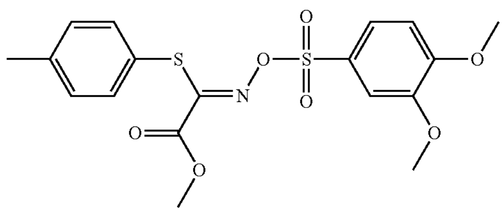 | 2.36 (s, 3H), 3.38 (s, 3H), 3.95 (s, 3H), 3.98 (s, 3H), 6.98 (d, 1H), 7.16 (d, 2H), 7.36 (d, 2H), 7.44 (s, 1H), 7.65 (s, 1H) |
| 96 | 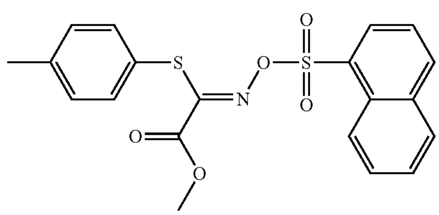 [SMILES: COC(=O)/C(=N/OS(=O)(=O)c1cccc2ccccc12)Sc1ccc(C)cc1] | 2.33 (s, 3H), 3.31 (s, 3H) 7.13 (d, 2H), 7.29 (d, 2H) 7.60 (t, 1H), 7.65 (t, 1H) 7.75 (t, 1H), 7.98 (d, 1H) 8.17 (d, 1H), 8.38 (d, 1H) 8.69 (d, 1H) |
| 97 | 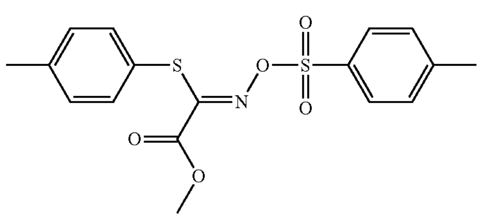 | 2.35 (s, 3H), 2.46 (s, 3H), 3.38 (s, 3H), 7.16 (d, 2H), 7.35 (d, 2H), 7.36 (d, 2H), 7.88 (d, 2H) |
| 98 | 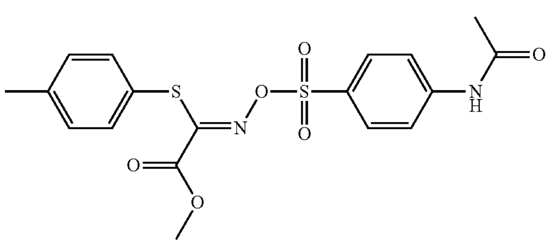 [SMILES: COC(=O)/C(=N/OS(=O)(=O)c1ccc(NC(C)=O)cc1)Sc1ccc(C)cc1] | 2.24 (s, 3H), 2.35 (s, 3H), 3.38 (s, 3H), 7.16 (d, 2H), 7.35 (d, 2H), 7.43 (br s, 1H), 7.72 (d, 2H), 7.95 (d, 2H) |

TABLE I-continued

| Example | Structure | $^1$H NMR in CDCl$_3$ |
|---|---|---|
| 99 | 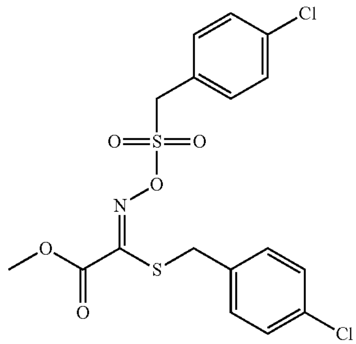 [SMILES: COC(=O)/C(=N/OS(=O)(=O)Cc1ccc(Cl)cc1)SCc1ccc(Cl)cc1] | 3.84 (s, 3H), 4.20 (s, 2H), 4.52 (m, 2H), 7.21-7.36 (m, 8H) |
| 100 | 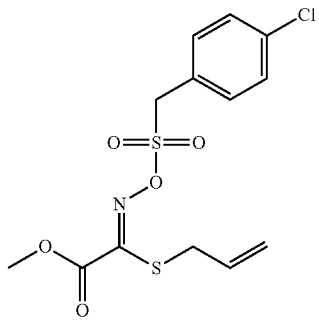 [SMILES: C=CCS/C(=N\OS(=O)(=O)Cc1ccc(Cl)cc1)C(=O)OC] | 3.65-3.67 (m, 2H), 3.92 (s, 3H), 4.54 (s, 2H), 5.20-5.25 (m, 2H), 5.74-5.84 (m, 1H), 7.32-7.39 (m, 4H) |
| 101 | 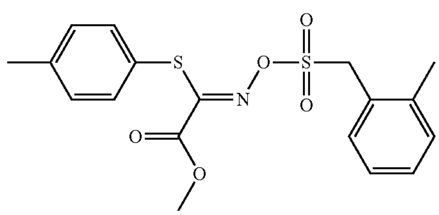 [SMILES: COC(=O)/C(=N/OS(=O)(=O)Cc1ccccc1C)Sc1ccc(C)cc1] | 2.38 (s, 3H), 2.48 (s, 3H), 3.46 (s, 3H), 4.66 (s, 2H), 7.18-7.34 (m, 5H), 7.38 (d, 1H), 7.42 (d, 2H) |
| 102 | 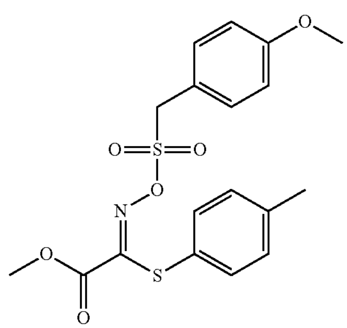 | 2.34 (s, 3H), 3.45 (s, 3H), 3.48 (s, 3H), 5.17 (s, 2H), 6.99-7.43 (m, 8H) |
| 103 | 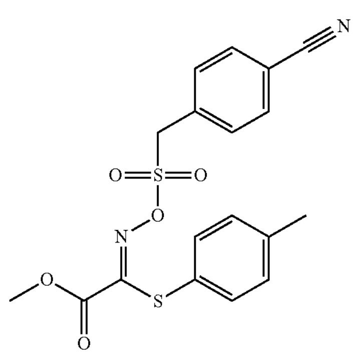 [SMILES: COC(=O)/C(=N/OS(=O)(=O)Cc1ccc(C#N)cc1)Sc1ccc(C)cc1] | 2.39 (s, 3H), 3.46 (s, 3H), 4.65 (s, 2H), 7.21-7.75 (m, 8H) |

TABLE I-continued

| Example | Structure | $^1$H NMR in CDCl$_3$ |
|---|---|---|
| 104 | 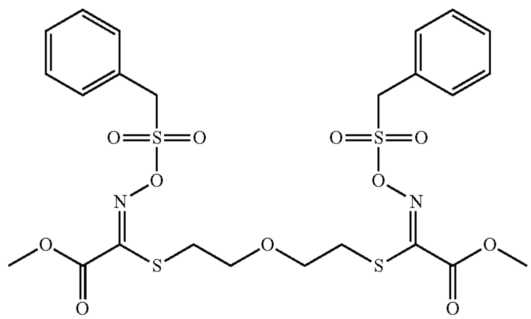 | 3.18 (t, 4H), 3.62 (t, 4H), 3.94 (s, 6H), 4.57 (s, 4H), 7.42 (br s 10H) |
| 105 | 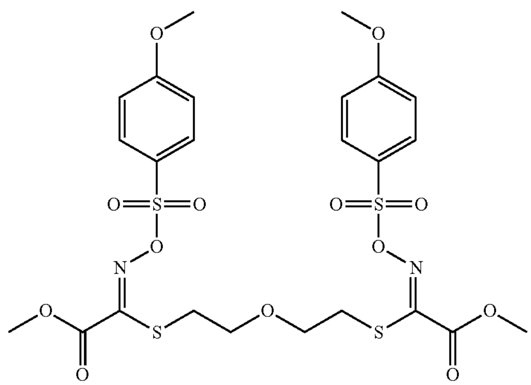 | 3.08 (t, 4H), 3.54 (t, 4H), 3.86 (s, 6H), 3.89 (s, 6H), 6.99 (d, 4H), 7.91 (d, 4H) |
| 106 | 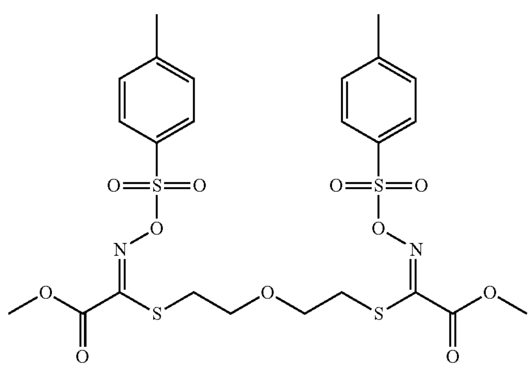 | 2.45 (s, 6H), 3.08 (t, 4H), 3.54 (t, 4H), 3.85 (s, 6H), 7.35 (d, 4H), 7.86 (d, 4H) |
| 107 | 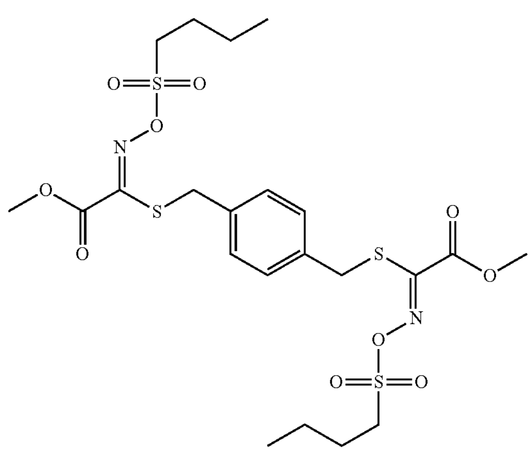 | 0.95 (t, 6H), 1.43-1.52 (m, 4H), 1.81-1.88 (m, 4H), 3.29-3.33 (m, 4H), 3.79 (s, 6H), 4.24 (s, 4H), 7.29 (br s, 4H) |

TABLE I-continued
| Example | Structure | $^1$H NMR in CDCl$_3$ |
|---|---|---|
| 108 | 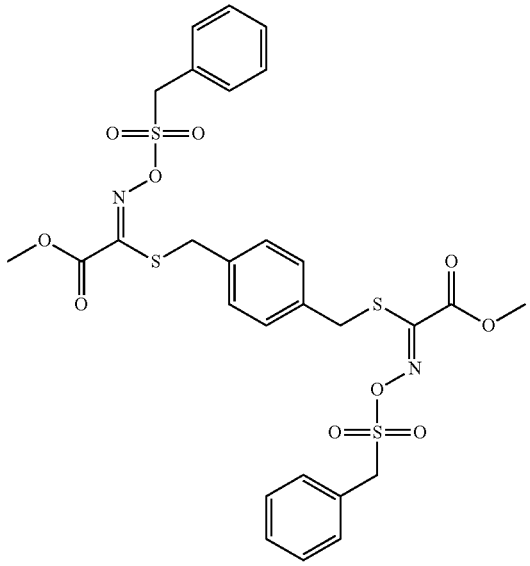 | 3.82 (s, 6H), 4.22 (s, 4H), 4.55 (s, 4H), 7.25-7.39 (m, 10H) |
| 109 | 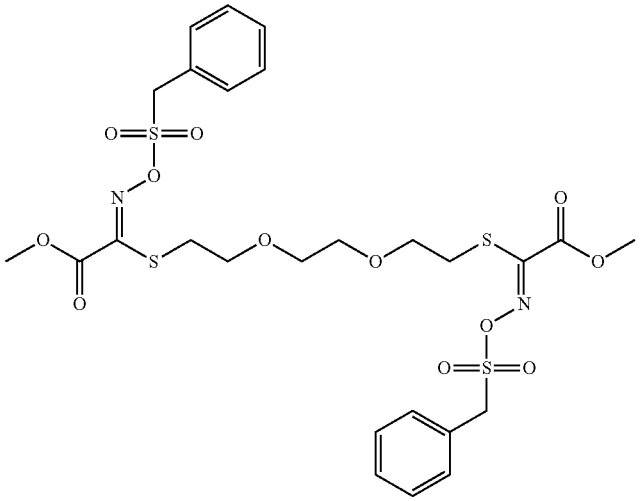 | 3.21 (t, 4H), 3.57 (s, 4H), 3.66 (t, 4H), 3.93 (s, 6H), 7.39 (br s, 10H) |
| 110 | 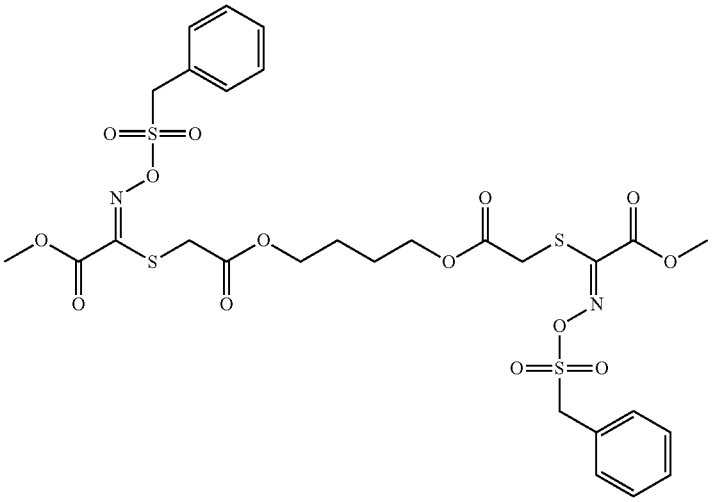 | 1.75 (t, 4H), 3.88 (s, 4H), 3.93 (s, 6H), 4.17 (t, 4H), 4.59 (s, 4H), 7.40 (br s, 10H) |

TABLE I-continued

| Example | Structure | $^1$H NMR in CDCl$_3$ |
|---|---|---|
| 111 | 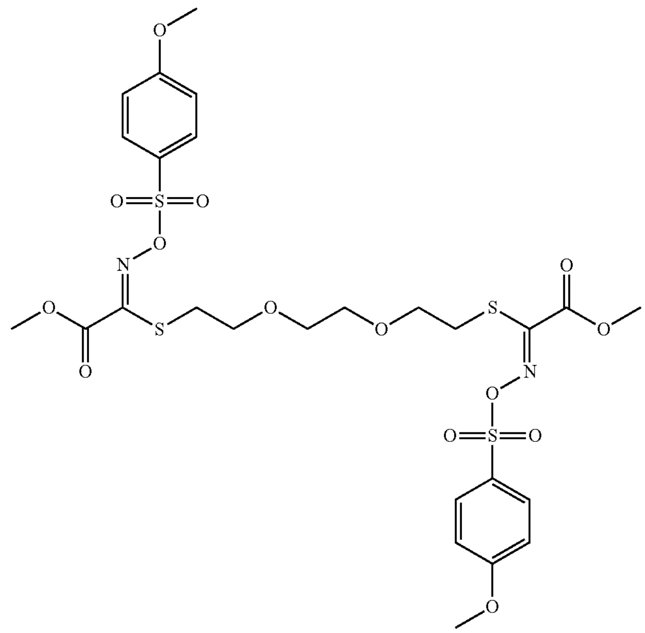 | 3.16 (t, 4H), 3.48 (s, 4H), 3.61 (t, 4H), 3.85 (s, 6H), 3.89 (s, 6H), 7.00 (d, 4H), 7.91 (d, 4H) |
| 112 | 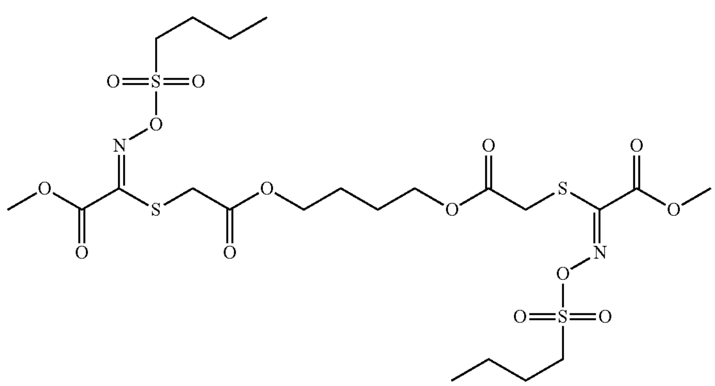 | 0.96 (t, 6H), 1.45-1.55 (m, 4H), 1.73 (m, 4H), 1.74-1.91 (m, 4H), 3.34-3.38 (m, 4H), 3.88-3.91 (m, 10H), 4.16-4.17 (m 4H) |
| 113 | 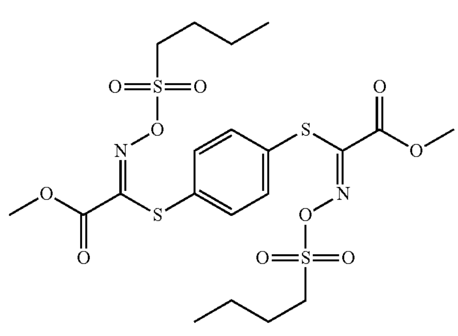 | 0.99 (t, 6H), 1.49-1.57 (m, 4H), 1.86-1.94 (m, 4H), 3.38 (t, 4H), 3.61 (s, 6H), 7.57 (br s, 4H) |

TABLE I-continued

| Example | Structure | ¹H NMR in CDCl₃ |
|---|---|---|
| 114 | 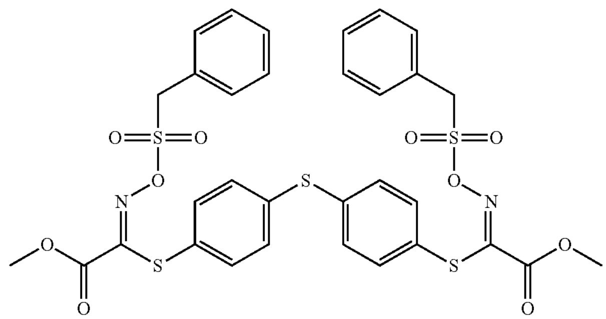 | 3.57 (s, 6H), 4.61 (s, 4H), 7.32-7.50 (m, 18H) |
| 115 | 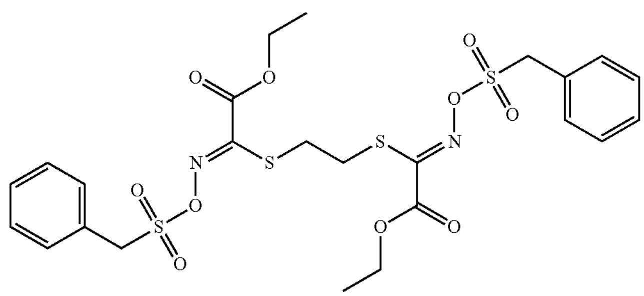 [SMILES: CCOC(=O)/C(=N/OS(=O)(=O)Cc1ccccc1)SCCS/C(=N\OS(=O)(=O)Cc1ccccc1)C(=O)OCC] | 1.43 (t, 6H), 3.21 (s, 4H), 4.44 (q, 4H), 4.59 (s, 4H), 7.39 (br s, 10H) |
| 116 | 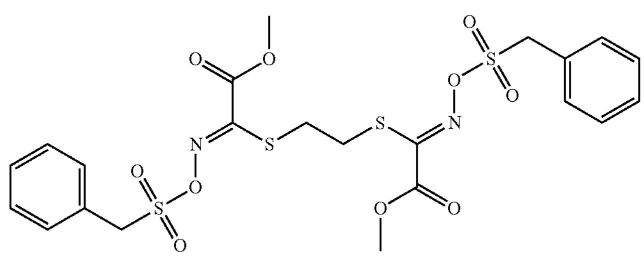 [SMILES: COC(=O)/C(=N/OS(=O)(=O)Cc1ccccc1)SCCS/C(=N\OS(=O)(=O)Cc1ccccc1)C(=O)OC] | 3.25 (s, 4H), 3.98 (s, 6H), 4.59 (s, 4H), 7.39 (br s, 10H) |
| 117 | 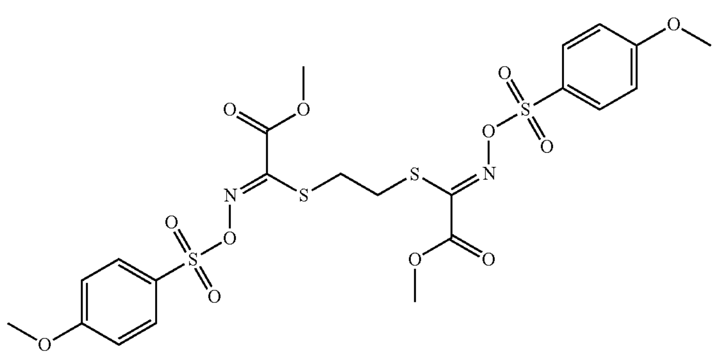 | 3.17 (s, 4H), 3.88 (s, 6H), 3.90 (s, 6H), 7.01 (d, 4H), 7.91 (d, 4H) |

TABLE I-continued

| Example | Structure | ¹H NMR in CDCl₃ |
|---|---|---|
| 118 | 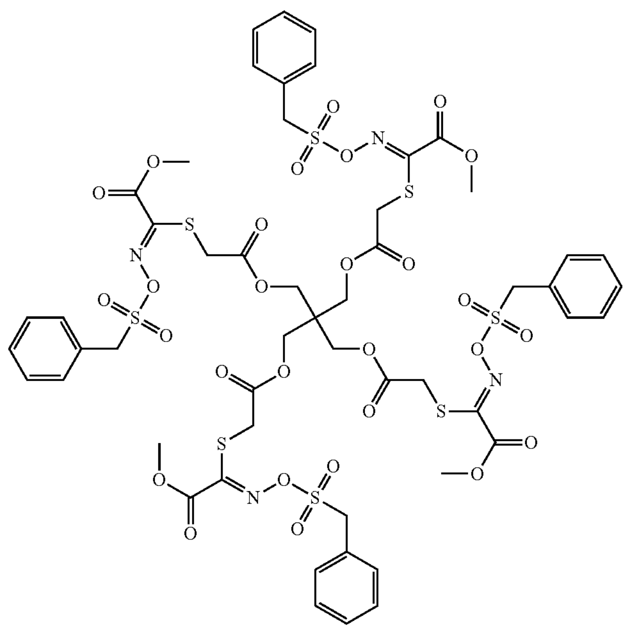 [SMILES: COC(=O)/C(=N/OS(=O)(=O)Cc1ccccc1)SCC(=O)OCC(COC(=O)CS/C(=N\OS(=O)(=O)Cc1ccccc1)C(=O)OC)(COC(=O)CS/C(=N\OS(=O)(=O)Cc1ccccc1)C(=O)OC)COC(=O)CS/C(=N\OS(=O)(=O)Cc1ccccc1)C(=O)OC] | 3.86 (s, 8H), 3.92 (s, 12H), 4.19 (s, 8H), 4.59 (s, 8H), 7.39 (br s, 20H) |
| 119 | 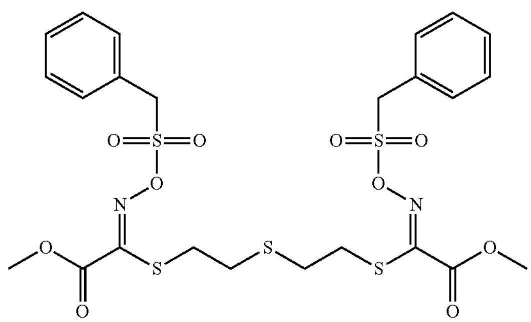 | 2.76 (dd, 4H), 3.18 (dd, 4H), 3.97 (s, 6H), 4.58 (s, 4H), 7.40 (br s, 10H) |
| 120 | 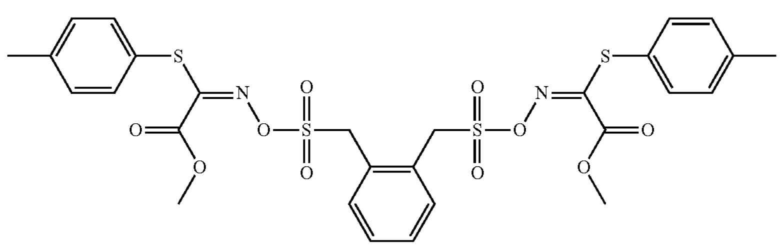 | 2.38 (s, 6H), 3.49 (s, 6H), 4.93 (s, 4H), 7.20-7.22 (m, 4H), 7.41-7.43 (m, 4H), 7.46-7.53 (m, 4H) |
| 121 | 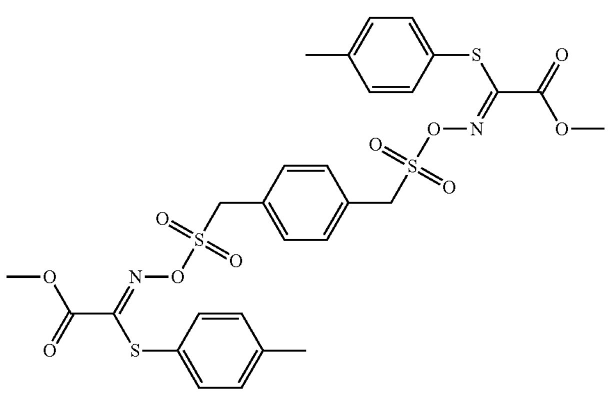 | 2.38 (s, 6H), 3.47 (s, 6H), 4.63 (s, 4H), 7.20-7.22 (m, 4H), 7.40-7.42 (m, 4H), 7.52 (s, 4H) |

TABLE I-continued

| Example | Structure | ¹H NMR in CDCl₃ |
|---|---|---|
| 122 | 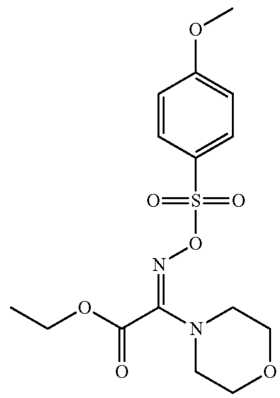 [SMILES: CCOC(=O)/C(=N/OS(=O)(=O)c1ccc(OC)cc1)N1CCOCC1] | 1.39 (t, 3H), 3.16-3.18 (m, 4H), 3.66-3.69 (m, 4H), 3.89 (s, 3H), 4.39 (q, 2H), 6.98-7.00 (m, 2H), 7.86-7.88 (m, 2H) |
| 123 | 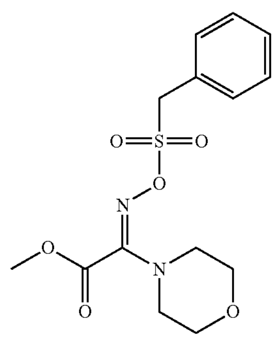 [SMILES: COC(=O)/C(=N/OS(=O)(=O)Cc1ccccc1)N1CCOCC1] | 3.36 (t, 4H). 3.64 (t, 4H), 3.93 (s, 3H), 4.59 (s, 2H), 7.37-7.44 (m, 5H) |
| 124 | 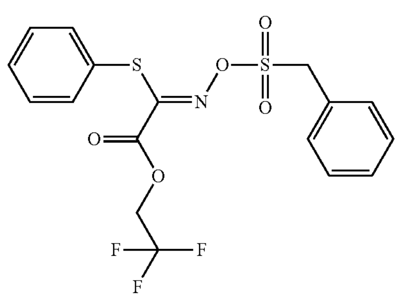 [SMILES: O=C(OCC(F)(F)F)/C(=N/OS(=O)(=O)Cc1ccccc1)Sc1ccccc1] | 4.15 (q, 2H), 4.63 (s, 2H), 7.38-7.55 (m, 10H) |
| 125 | 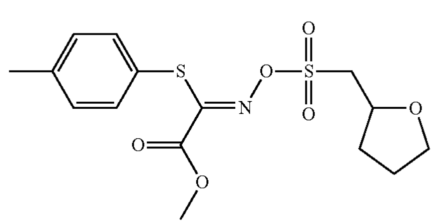 [SMILES: COC(=O)/C(=N/OS(=O)(=O)CC1CCCO1)Sc1ccc(C)cc1] | 1.73-1.83 (m, 1H), 1.92-2.04 (m, 2H), 2.20-2.30 (m, 1H), 2.38 (s, 3H), 3.44 (s, 3H), 3.46 (dd, 1H), 3.67 (dd, 1H), 3.83 (dd, 1H), 3.93 (dd, 1H), 4.42 (dt, 1H), 7.20 (d, 2H), 7.42 (d, 2H) |

TABLE I-continued

| Example | Structure | $^1$H NMR in CDCl$_3$ |
|---|---|---|
| 126 | 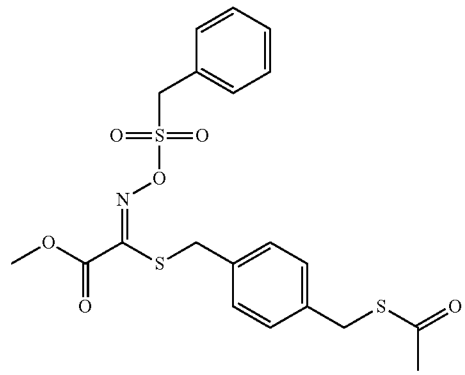 [SMILES: COC(=O)/C(=N/OS(=O)(=O)Cc1ccccc1)SCc1ccc(CSC(C)=O)cc1] | 2.35 (s, 3H), 3.81 (s, 3H), 4.09 (s, 2H), 4.20 (s, 2H), 7.20-7.38 (m, 9H) |
| 127 | 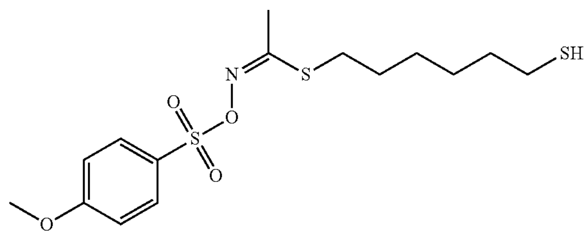 [SMILES: COc1ccc(S(=O)(=O)O/N=C(/C)SCCCCCCS)cc1] | 1.33 (t, 1H), 1.40-1.42 (m, 4H), 1.59-1.64 (m, 4H), 2.16 (s, 3H), 2.53 (q, 2H), 2.83 (t, 2H), 3.88 (s, 3H), 7.00 (d, 2H), 7.91 (d, 2H) |
| 128 | 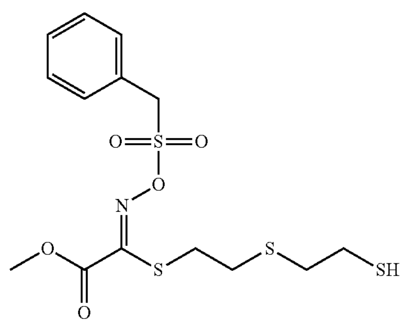 [SMILES: COC(=O)/C(=N/OS(=O)(=O)Cc1ccccc1)SCCSCCS] | 1.73 (t, 1H), 2.71-2.81 (m, 6H), 3.17-3.21 (m, 2H), 3.98 (s, 3H), 4.58 (s, 2H), 7.40 (br s, 5H) |
| 129 | 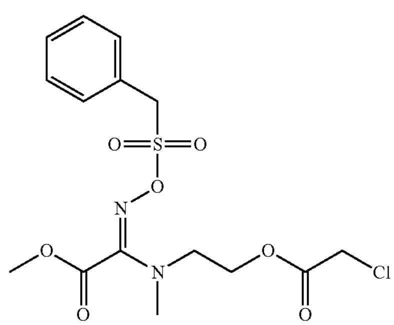 [SMILES: COC(=O)/C(=N/OS(=O)(=O)Cc1ccccc1)N(C)CCOC(=O)CCl] | 3.00 (s, 3H), 3.50 (t, 2H), 3.93 (s, 3H), 4.08 (s, 2H), 4.26 (t, 2H), 4.58 (s, 2H), 7.37-7.46 (m, 5H) |
| 130 | 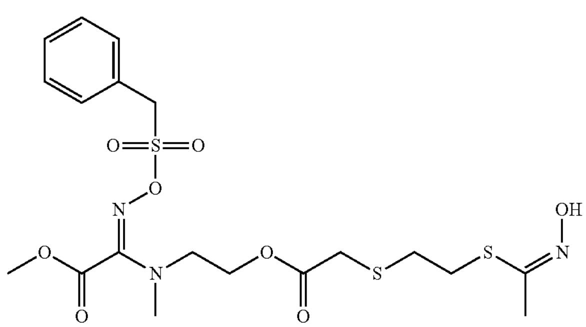 [SMILES: COC(=O)/C(=N/OS(=O)(=O)Cc1ccccc1)N(C)CCOC(=O)CSCCS/C(C)=N\O] | 2.18 (s, 3H), 2.85-2.90 (m, 2H), 3.00 (s, 3H), 3.10-3.14 (m, 2H), 3.29 (s, 2H), 3.49 (t, 2H), 3.93 (s, 3H), 4.22 (t, 2H), 4.58 (s, 2H)7.38-7.45 (m, 5H) |

TABLE I-continued

| Example | Structure | $^1$H NMR in CDCl$_3$ |
| --- | --- | --- |
| 131 | 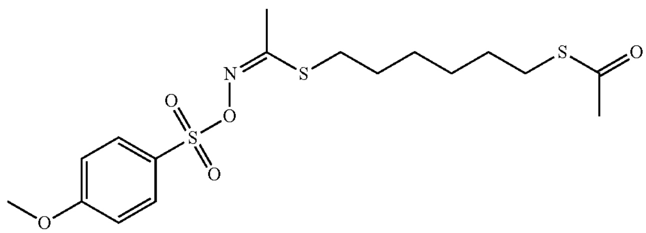 [SMILES: COc1ccc(S(=O)(=O)O/N=C(/C)SCCCCCCSC(C)=O)cc1] | 1.35-1.43 (m, 4H), 1.53-1.62 (m, 4H), 2.16 (s, 3H), 2.33 (s, 3H), 2.82 (t, 2H), 2.85 (t, 2H), 3.88 (s, 3H), 6.99 (d, 2H), 7.91 (d, 2H) |
| 132 | 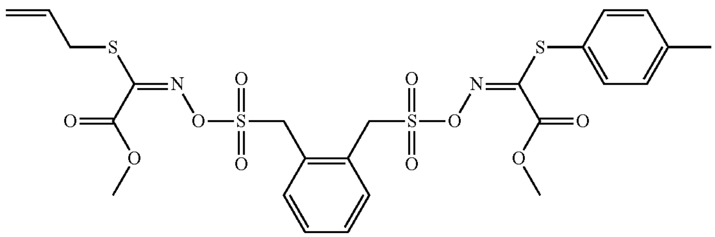 [SMILES: C=CCS/C(=N/OS(=O)(=O)Cc1ccccc1CS(=O)(=O)O/N=C(/Sc1ccc(C)cc1)C(=O)OC)C(=O)OC] | 2.38 (s, 3H), 3.49 (s, 3H), 3.67-3.69 (d, 2H), 3.93 (s, 3H), 4.88-4.93 (m, 4H), 5.20-5.25 (m, 2H), 5.75-5.85 (m, 1H), 7.18-7.22 (m, 2H), 7.45-7.52 (m, 6H) |
| 133 | 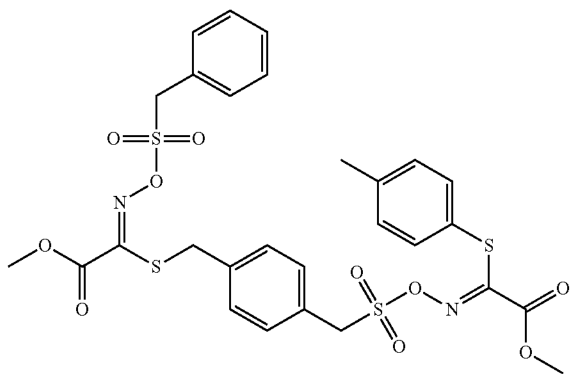 | 2.39 (s, 3H), 3.47 (s, 3H), 3.77 (s, 3H), 4.26 (s, 2H), 4.54 (s, 2H), 4.60 (s, 2H), 7.21-7.44 (m, 13H) |
| 134 | 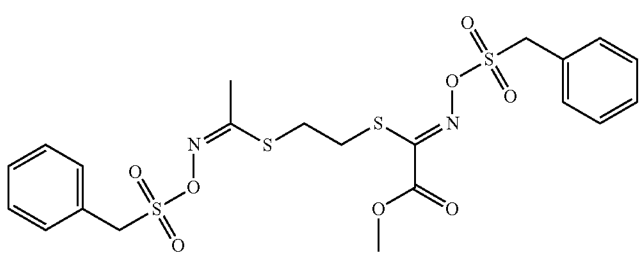 [SMILES: COC(=O)/C(=N/OS(=O)(=O)Cc1ccccc1)SCCS/C(C)=N\OS(=O)(=O)Cc1ccccc1] | 2.32 (s, 3H), 3.12-3.19 (m, 2H), 3.19-3.26 (m, 2H), 3.96 (s, 3H), 4.55 (s, 2H), 4.59 (s, 2H), 7.39 (br s, 10H) |
| 135 | 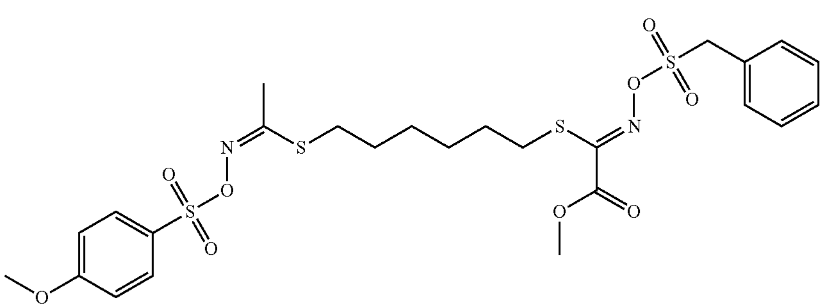 [SMILES: COC(=O)/C(=N/OS(=O)(=O)Cc1ccccc1)SCCCCCCS/C(C)=N\OS(=O)(=O)c1ccc(OC)cc1] | 1.34-1.46 (m, 4H), 1.55-1.67 (m, 4H), 2.16 (s, 3H), 2.83 (t, 2H), 2.95 (t, 2H), 3.88 (s, 3H), 3.97 (s, 3H), 4.57 (s, 2H), 6.99 (d, 2H), 7.39 (br s, 5H), 7.91 (d, 2H) |

TABLE I-continued
| Example | Structure | $^1$H NMR in CDCl$_3$ |
|---|---|---|
| 136 | 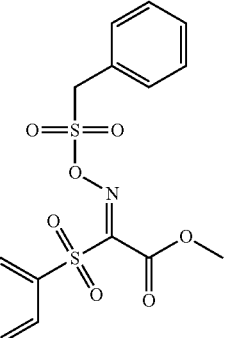 | 2.50 (s, 3H), 3.90 (s, 3H), 4.51 (s, 2H), 7.26-7.43 (m, 5H), 7.45 (d, 2H), 7.91 (d, 2H) |
| 137 | 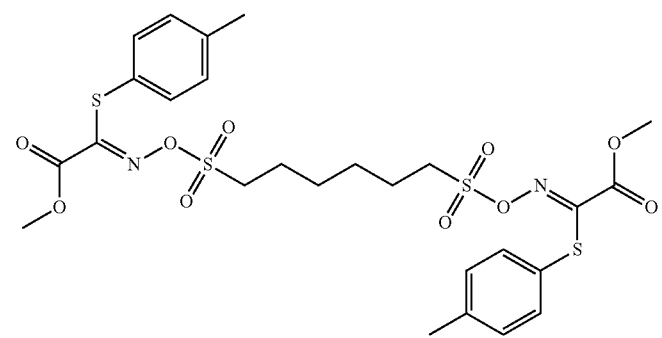 [SMILES: COC(=O)/C(=N/OS(=O)(=O)CCCCCCS(=O)(=O)O/N=C(\Sc1ccc(C)cc1)C(=O)OC)Sc1ccc(C)cc1] | 1.54-1.57 (m, 4H), 1.93-1.95 (m, 4H), 2.38 (s, 6H), 3.38 (t, 4H), 3.44 (s, 6H), 7.21 (d, 4H), 7.43 (d, 4H) |
| 138 | 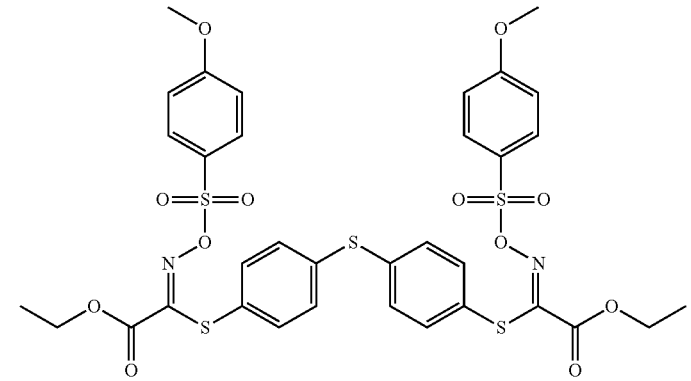 [SMILES: CCOC(=O)/C(=N/OS(=O)(=O)c1ccc(OC)cc1)Sc1ccc(Sc2ccc(S/C(=N\OS(=O)(=O)c3ccc(OC)cc3)C(=O)OCC)cc2)cc1] | 0.99 (t, 6H), 3.90 (q + s, 10H), 7.01 (d, 4H), 7.26 (d, 4H), 7.42 (d, 4H), 7.93 (d, 4H) |
| 139 | 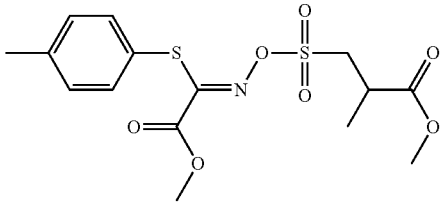 [SMILES: COC(=O)/C(=N/OS(=O)(=O)CC(C)C(=O)OC)Sc1ccc(C)cc1] | 1.41 (d, 3H), 2.38 (s, 3H), 3.12-3.20 (m, 1H), 3.39-3.44 (m, 1H), 3.44 (s, 3H), 3.77 (s, 3H), 3.89-3.94 (m, 1H), 7.20 (d, 2H), 7.43 (d, 2H) |
| 140 | 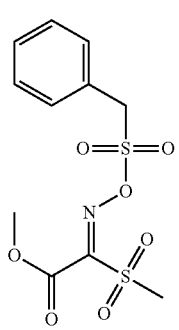 [SMILES: COC(=O)/C(=N/OS(=O)(=O)Cc1ccccc1)S(C)(=O)=O] | 3.19 (s, 3H), 3.98 (s, 3H), 4.64 (s, 2H), 7.37-7.47 (m, 5H) |

TABLE I-continued
| Example | Structure | ¹H NMR in CDCl₃ |
|---|---|---|
| 141 | 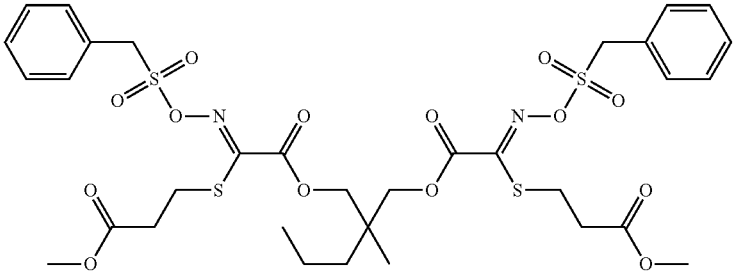 [SMILES: CCCC(C)(COC(=O)/C(=N/OS(=O)(=O)Cc1ccccc1)SCCC(=O)OC)COC(=O)/C(=N/OS(=O)(=O)Cc1ccccc1)SCCC(=O)OC] | 0.98 (t, 3H), 1.12 (s, 3H), 1.34-1.51 (m, 4H), 2.66 (t, 4H), 3.23 (t, 4H), 3.70 (s, 6H), 4.26 (d, 2H), 4.30 (d, 2H), 4.57 (s, 4H), 7.40 (br s, 10H) |
| 142 | 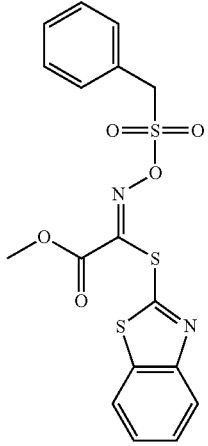 [SMILES: COC(=O)/C(=N/OS(=O)(=O)Cc1ccccc1)Sc1nc2ccccc2s1] | 3.74 (s, 3H), 4.65 (s, 2H), 7.38-7.50 (m, 6H), 7.54 (dt, 1H), 7.88 (dd, 1H), 8.02 (dd, 1H) |
| 143 | 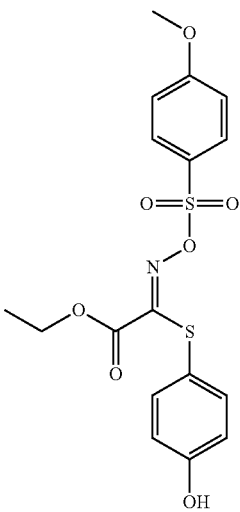 [SMILES: CCOC(=O)/C(=N/OS(=O)(=O)c1ccc(OC)cc1)Sc1ccc(O)cc1] | 0.99 (t, 3H), 3.84 (q, 2H), 3.90 (s, 3H), 5.60 (br s, 1H), 6.81 (d, 2H), 7.01 (d, 2H), 7.37 (d, 2H), 7.94 (d, 2H) |

TABLE I-continued
| Example | Structure | $^1$H NMR in CDCl$_3$ |
|---|---|---|
| 144 | 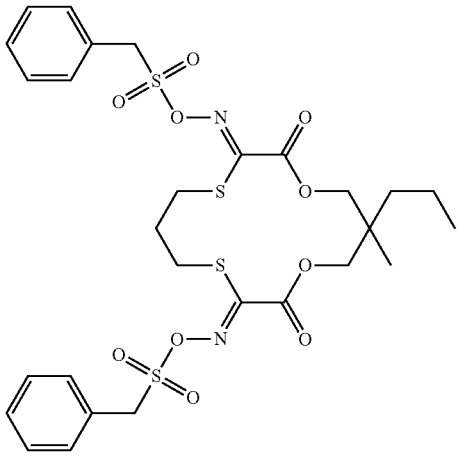 [SMILES: CCCC1(C)COC(=O)/C(=N/OS(=O)(=O)Cc2ccccc2)SCCCS/C(=N\OS(=O)(=O)Cc2ccccc2)C(=O)OC1] | 0.99 (t, 3H), 1.14 (s, 3H), 1.35-1.52 (m, 4H), 1.73-1.85 (m, 2H), 3.03 (t, 4H), 4.21 (d, 2H), 4.25 (d, 2H), 4.58 (s, 4H), 7.37-7.47 (m, 10H) |
| 145 | 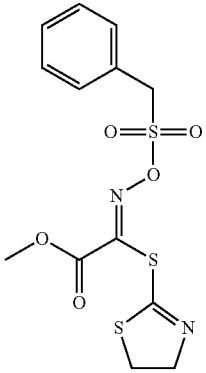 [SMILES: COC(=O)/C(=N/OS(=O)(=O)Cc1ccccc1)SC1=NCCS1] | 3.48 (t, 2H), 3.91 (s, 3H), 4.22 (t, 2H), 4.60 (s, 2H), 7.40 (br s, 5H) |
| 146 | 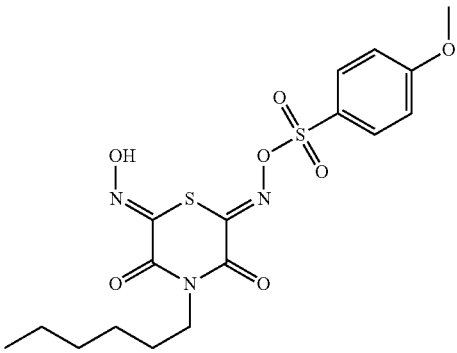 [SMILES: CCCCCCN1C(=O)/C(=N/O)S/C(=N\OS(=O)(=O)c2ccc(OC)cc2)C1=O] | 0.80-0.95 (m, 3H), 1.18-1.42 (m, 6H), 1.52-1.70 (m, 2H), 3.85 (t, 2H), 3.89 (s, 3H), 7.03 (d, 2H), 7.97 (d, 2H), 8.4 (br s, 1H) |
| 147 | 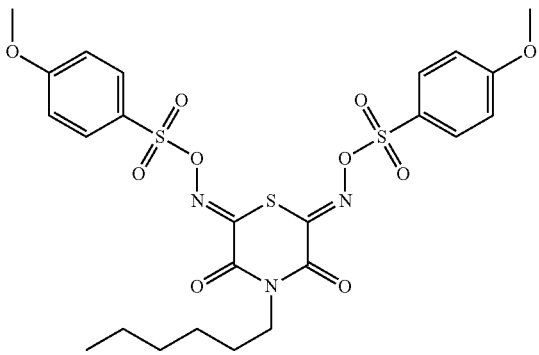 [SMILES: CCCCCCN1C(=O)/C(=N/OS(=O)(=O)c2ccc(OC)cc2)S/C(=N\OS(=O)(=O)c2ccc(OC)cc2)C1=O] | 0.83-0.94 (m, 3H), 1.22-1.37 (m, 6H), 1.51-1.71 (m, 2H), 3.90 (s, 6H), 3.94 (dd, 2H), 7.04 (d, 4H), 7.98 (d, 4H) |

TABLE I-continued

| Example | Structure | $^1$H NMR in CDCl$_3$ |
|---|---|---|
| 148 | 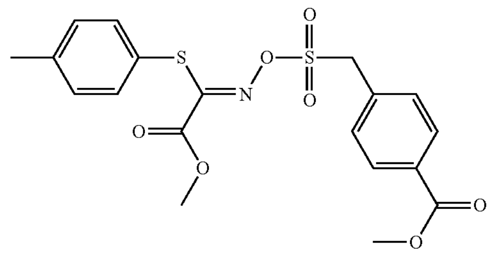 [SMILES: COC(=O)/C(=N/OS(=O)(=O)Cc1ccc(C(=O)OC)cc1)Sc1ccc(C)cc1] | |
| 149 | 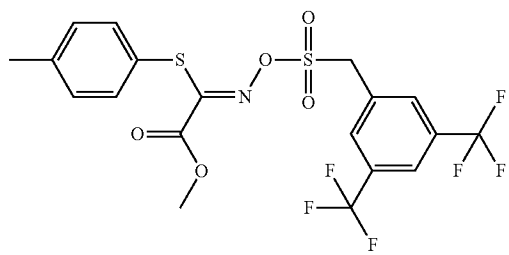 [SMILES: COC(=O)/C(=N/OS(=O)(=O)Cc1cc(C(F)(F)F)cc(C(F)(F)F)c1)Sc1ccc(C)cc1] | |
| 150 | 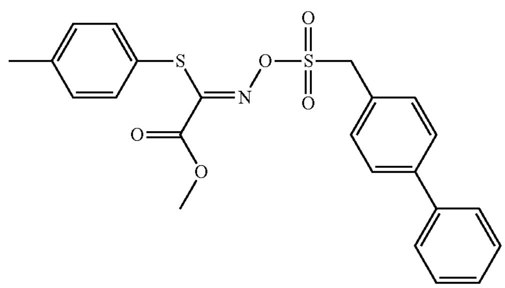 [SMILES: COC(=O)/C(=N/OS(=O)(=O)Cc1ccc(-c2ccccc2)cc1)Sc1ccc(C)cc1] | |
| 151 | 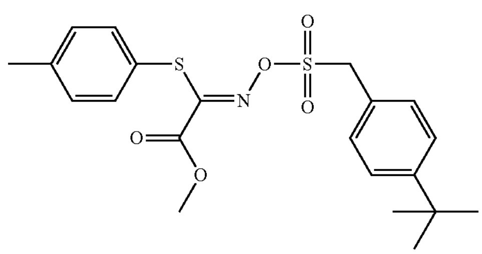 [SMILES: COC(=O)/C(=N/OS(=O)(=O)Cc1ccc(C(C)(C)C)cc1)Sc1ccc(C)cc1] | |
| 152 | 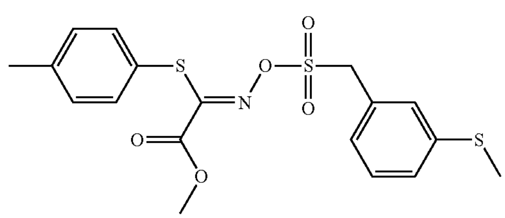 | |
| 153 | 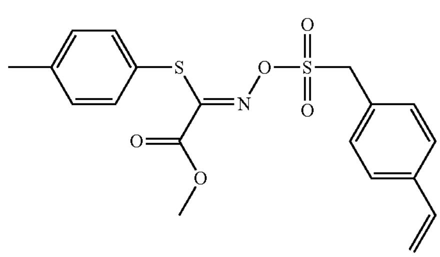 [SMILES: C=Cc1ccc(CS(=O)(=O)O/N=C(\Sc2ccc(C)cc2)C(=O)OC)cc1] | |

TABLE I-continued

| Example | Structure | $^1$H NMR in CDCl$_3$ |
|---|---|---|
| 154 | 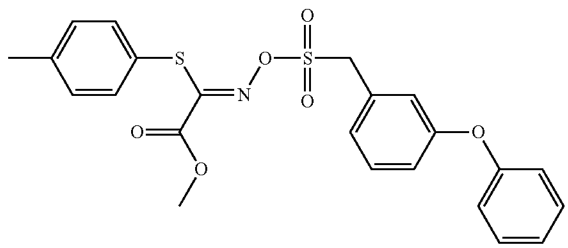 [SMILES: COC(=O)/C(=N/OS(=O)(=O)Cc1cccc(Oc2ccccc2)c1)Sc1ccc(C)cc1] | |
| 155 | 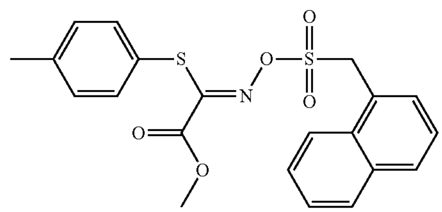 [SMILES: COC(=O)/C(=N/OS(=O)(=O)Cc1cccc2ccccc12)Sc1ccc(C)cc1] | |
| 156 | 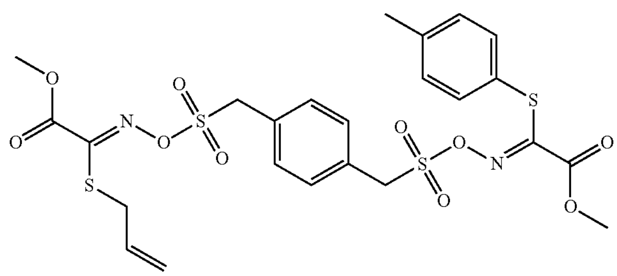 [SMILES: C=CCS/C(=N\OS(=O)(=O)Cc1ccc(CS(=O)(=O)O/N=C(\Sc2ccc(C)cc2)C(=O)OC)cc1)C(=O)OC] | |
| 157 | 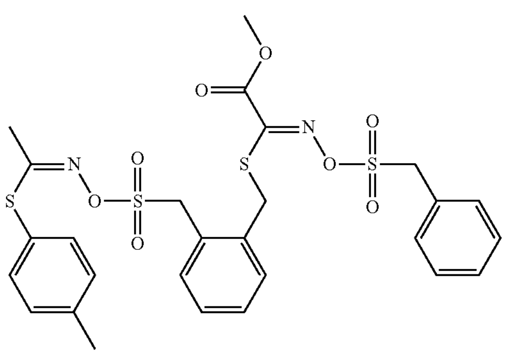 [SMILES: COC(=O)/C(=N/OS(=O)(=O)Cc1ccccc1)SCc1ccccc1CS(=O)(=O)O/N=C(/C)Sc1ccc(C)cc1] | |
| 158 | 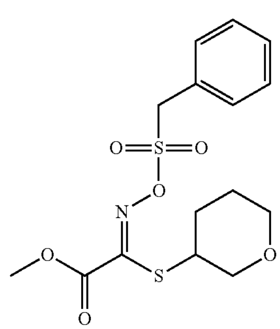 [SMILES: COC(=O)/C(=N/OS(=O)(=O)Cc1ccccc1)SC1CCCOC1] | |

TABLE I-continued

| Example | Structure | ¹H NMR in CDCl₃ |
|---------|-----------|-----------------|
| 159 | 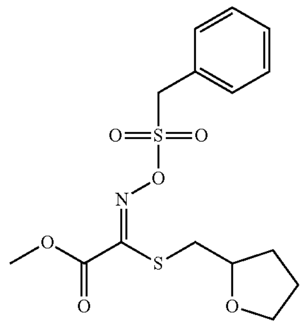 [SMILES: COC(=O)/C(=N/OS(=O)(=O)Cc1ccccc1)SCC1CCCO1] | |
| 160 | 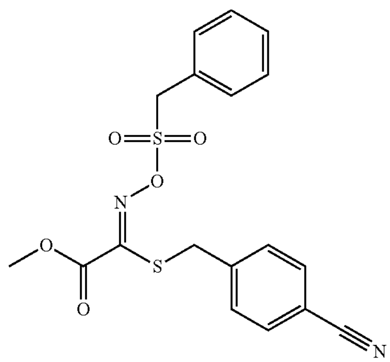 [SMILES: COC(=O)/C(=N/OS(=O)(=O)Cc1ccccc1)SCc1ccc(C#N)cc1] | |
| 161 | 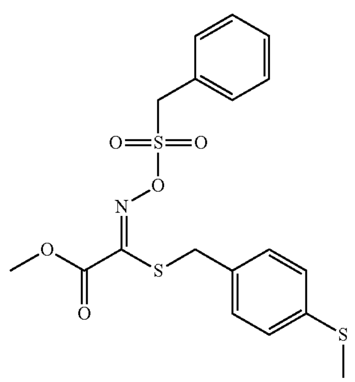 | |
| 162 | 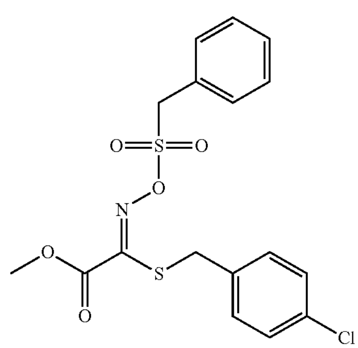 [SMILES: COC(=O)/C(=N/OS(=O)(=O)Cc1ccccc1)SCc1ccc(Cl)cc1] | |

TABLE I-continued

| Example | Structure | ¹H NMR in CDCl₃ |
|---|---|---|
| 163 | 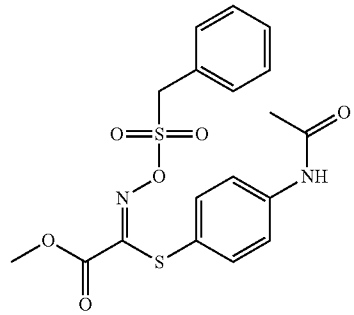 [SMILES: COC(=O)/C(=N/OS(=O)(=O)Cc1ccccc1)Sc1ccc(NC(C)=O)cc1] | |
| 164 | 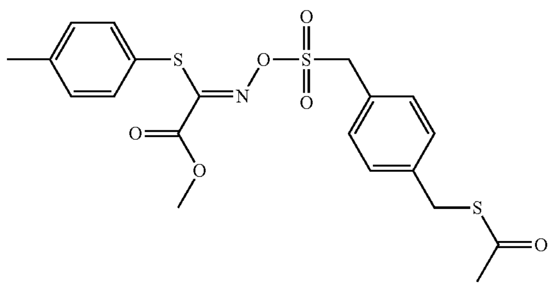 [SMILES: COC(=O)/C(=N/OS(=O)(=O)Cc1ccc(CSC(C)=O)cc1)Sc1ccc(C)cc1] | |

II. Application Examples

II.1 Preparation of Color Filter Resist (Blue)

A blue pigment dispersion was prepared by mixing the following components and dispersing them by using a Paint conditioner (SKANDEX).
Blue Dispersion
5.3 parts by weight blue pigment (PB15:6, Blue E provided by Toyo Ink)
1.9 parts by weight dispersant (Ajisper PB821 provided by Ajinomoto Fine Techno)
0.2 parts by weight synergist (Solsperse S5000 provided by Lubrizol)
55.8 parts by weight solvent propylene glycol monomethyl-ether acetate (PGMEA)
Color filter resist (blue) was prepared by further adding the following components to the above dispersion prepared.
19.1 parts by weight alkaline developable binder, 37.8% solution (Ripoxy SPC-2000, provided by Showa Highpolymer)
12.3 parts by weight solvent PGMEA
5.3 parts by weight multifunctional acrylate (DPHA, provided by UCB Chemicals)
Thermal Curing Tests of Blue Color Filter Resist after Photocuring The oxime sulfonate to be tested and additionally Ciba® IRGACURE® 369 (4.8 wt % in solid) as photoinitiator were added to the above color filter resist composition and mixed. The composition was applied to a silicon wafer using a spin coater (1H-DX2, MIKASA). The solvent was removed by heating at 90° C. for 2.5 min in a convection oven. The thickness of the dry film was approximately 1.0 μm. Exposure was then carried out using a 250 W super high pressure mercury lamp (USHIO, USH-250BY) at a distance of 15 cm. The total exposure dose determined by measuring light intensity with an optical power meter (ORC UV Light Measure Model UV-M02 with UV-35 detector) was 150 mJ/cm². The coating was further baked under the conditions listed in Table II below. The conversion of acrylic group in baking was determined by measuring IR absorption at 810 cm⁻¹ with a FT-IR spectrometer (FT-720, HORIBA) before and after baking. The concentration of the oxime sulfonate in the composition was 0.02 mol/kg. The results of the tests were given in Table II.

For comparison, the thermal curing test was repeated by using either no curing promoter or a peroxide or an azo compound. The results of the tests were also given in Table II.

As can be seen shorter baking times were required when using an oxime sulfonate according to the invention.

TABLE II

| Oxime sulfonate | Concentration of oxime sulfonate (mol/kg in composition) | Baking conditions | C=C conversion (%) |
|---|---|---|---|
| Example 2 | 0.02 | 180° C. for 30 min | 71.2 |
| Example 3 | 0.02 | 180° C. for 30 min | 63.4 |
| Example 4 | 0.02 | 180° C. for 30 min | 69.1 |
| Example 5 | 0.02 | 180° C. for 30 min | 72.8 |
| Example 6 | 0.02 | 180° C. for 30 min | 72.7 |
| Example 7 | 0.02 | 180° C. for 30 min | 65.5 |
| Example 9 | 0.02 | 180° C. for 30 min | 76.7 |
| Example 10 | 0.02 | 180° C. for 30 min | 70.3 |
| Example 11 | 0.02 | 180° C. for 30 min | 71.9 |
| Example 12 | 0.02 | 180° C. for 30 min | 66.6 |
| Example 14 | 0.02 | 180° C. for 30 min | 66.0 |
| Example 17 | 0.02 | 180° C. for 30 min | 75.9 |
| Example 19 | 0.02 | 180° C. for 30 min | 77.5 |
| Example 20 | 0.02 | 180° C. for 30 min | 73.8 |
| Example 21 | 0.02 | 180° C. for 30 min | 68.3 |
| Example 22 | 0.02 | 180° C. for 30 min | 73.9 |
| Example 25 | 0.02 | 180° C. for 30 min | 71.0 |
| Example 27 | 0.02 | 180° C. for 30 min | 66.1 |
| Example 31 | 0.02 | 180° C. for 30 min | 78.1 |
| Example 32 | 0.02 | 180° C. for 30 min | 67.6 |
| Example 33 | 0.02 | 180° C. for 30 min | 67.9 |
| Example 35 | 0.02 | 180° C. for 30 min | 74.6 |
| Example 36 | 0.02 | 180° C. for 30 min | 66.4 |
| Example 37 | 0.02 | 180° C. for 30 min | 76.1 |

TABLE II-continued

| Oxime sulfonate | Concentration of oxime sulfonate (mol/kg in composition) | Baking conditions | C=C conversion (%) |
|---|---|---|---|
| Example 38 | 0.02 | 180° C. for 30 min | 70.4 |
| Example 39 | 0.02 | 180° C. for 30 min | 74.2 |
| Example 40 | 0.02 | 180° C. for 30 min | 66.0 |
| Example 42 | 0.02 | 180° C. for 30 min | 74.8 |
| Example 43 | 0.02 | 180° C. for 30 min | 69.3 |
| Example 44 | 0.02 | 180° C. for 30 min | 63.5 |
| Example 45 | 0.02 | 180° C. for 30 min | 74.0 |
| Example 46 | 0.02 | 180° C. for 30 min | 69.6 |
| Example 47 | 0.02 | 180° C. for 30 min | 71.6 |
| Example 48 | 0.02 | 180° C. for 30 min | 73.3 |
| Example 52 | 0.02 | 180° C. for 30 min | 76.8 |
| Example 53 | 0.02 | 180° C. for 30 min | 68.1 |
| Example 54 | 0.02 | 180° C. for 30 min | 74.3 |
| Example 55 | 0.02 | 180° C. for 30 min | 74.2 |
| Example 56 | 0.02 | 180° C. for 30 min | 75.5 |
| Example 57 | 0.02 | 180° C. for 30 min | 78.1 |
| Example 58 | 0.02 | 180° C. for 30 min | 76.6 |
| Example 59 | 0.02 | 180° C. for 30 min | 69.3 |
| Example 60 | 0.02 | 180° C. for 30 min | 64.0 |
| Example 61 | 0.02 | 180° C. for 30 min | 70.3 |
| Example 62 | 0.02 | 180° C. for 30 min | 67.8 |
| Example 63 | 0.02 | 180° C. for 30 min | 72.8 |
| Example 64 | 0.02 | 180° C. for 30 min | 62.7 |
| Example 65 | 0.02 | 180° C. for 30 min | 72.5 |
| Example 66 | 0.02 | 180° C. for 30 min | 82.1 |
| Example 67 | 0.02 | 180° C. for 30 min | 82.0 |
| Example 68 | 0.02 | 180° C. for 30 min | 71.0 |
| Example 69 | 0.02 | 180° C. for 30 min | 76.6 |
| Example 70 | 0.02 | 180° C. for 30 min | 82.6 |
| Example 71 | 0.02 | 180° C. for 30 min | 84.4 |
| Example 73 | 0.02 | 180° C. for 30 min | 69.8 |
| Example 78 | 0.02 | 180° C. for 30 min | 77.9 |
| Example 79 | 0.02 | 180° C. for 30 min | 77.7 |
| Example 80 | 0.02 | 180° C. for 30 min | 78.3 |
| Example 81 | 0.02 | 180° C. for 30 min | 69.9 |
| Example 82 | 0.02 | 180° C. for 30 min | 76.6 |
| Example 88 | 0.02 | 180° C. for 30 min | 78.9 |
| Example 89 | 0.02 | 180° C. for 30 min | 70.3 |
| Example 91 | 0.02 | 180° C. for 30 min | 78.7 |
| Example 92 | 0.02 | 180° C. for 30 min | 80.4 |
| Example 94 | 0.02 | 180° C. for 30 min | 80.0 |
| Example 96 | 0.02 | 180° C. for 30 min | 78.4 |
| Example 97 | 0.02 | 180° C. for 30 min | 81.3 |
| Example 99 | 0.02 | 180° C. for 30 min | 78.8 |
| Example 100 | 0.02 | 180° C. for 30 min | 73.2 |
| Example 103 | 0.02 | 180° C. for 30 min | 81.7 |
| Example 104 | 0.02 | 180° C. for 30 min | 86.9 |
| Example 105 | 0.02 | 180° C. for 30 min | 84.2 |
| Example 106 | 0.02 | 180° C. for 30 min | 83.2 |
| Example 107 | 0.02 | 180° C. for 30 min | 87.6 |
| Example 108 | 0.02 | 180° C. for 30 min | 83.7 |
| Example 109 | 0.02 | 180° C. for 30 min | 80.7 |
| Example 110 | 0.02 | 180° C. for 30 min | 87.2 |
| Example 111 | 0.02 | 180° C. for 30 min | 84.1 |
| Example 112 | 0.02 | 180° C. for 30 min | 85.7 |
| Example 114 | 0.02 | 180° C. for 30 min | 87.2 |
| Example 121 | 0.02 | 180° C. for 30 min | 75.1 |
| Example 115 | 0.02 | 180° C. for 30 min | 82.2 |
| Example 116 | 0.02 | 180° C. for 30 min | 82.1 |
| Example 117 | 0.02 | 180° C. for 30 min | 79.6 |
| Example 118 | 0.02 | 180° C. for 30 min | 95.0 |
| Example 119 | 0.02 | 180° C. for 30 min | 78.7 |
| Example 121 | 0.02 | 180° C. for 30 min | 75.1 |
| Example 122 | 0.02 | 180° C. for 30 min | 76.6 |
| Example 123 | 0.02 | 180° C. for 30 min | 73.0 |
| Example 124 | 0.02 | 180° C. for 30 min | 77.5 |
| Example 126 | 0.02 | 180° C. for 30 min | 80.1 |
| Example 128 | 0.02 | 180° C. for 30 min | 78.7 |
| Example 132 | 0.02 | 180° C. for 30 min | 84.8 |
| Example 133 | 0.02 | 180° C. for 30 min | 85.5 |
| Example 136 | 0.02 | 180° C. for 30 min | 68.1 |
| Example 138 | 0.02 | 180° C. for 30 min | 82.4 |
| Example 139 | 0.02 | 180° C. for 30 min | 76.9 |
| Example 140 | 0.02 | 180° C. for 30 min | 68.2 |
| Example 142 | 0.02 | 180° C. for 30 min | 76.0 |
| Example 143 | 0.02 | 180° C. for 30 min | 66.1 |
| Example 146 | 0.02 | 180° C. for 30 min | 75.3 |
| Example 147 | 0.02 | 180° C. for 30 min | 78.7 |
| Example 1 | 0.02 | 230° C. for 4 min | 78.5 |
| Example 8 | 0.02 | 230° C. for 4 min | 79.3 |
| Example 13 | 0.02 | 230° C. for 4 min | 83.2 |
| Example 15 | 0.02 | 230° C. for 4 min | 82.6 |
| Example 16 | 0.02 | 230° C. for 4 min | 79.9 |
| Example 18 | 0.02 | 230° C. for 4 min | 86.9 |
| Example 23 | 0.02 | 230° C. for 4 min | 88.2 |
| Example 24 | 0.02 | 230° C. for 4 min | 79.1 |
| Example 26 | 0.02 | 230° C. for 4 min | 79.7 |
| Example 28 | 0.02 | 230° C. for 4 min | 80.2 |
| Example 29 | 0.02 | 230° C. for 4 min | 81.1 |
| Example 30 | 0.02 | 230° C. for 4 min | 79.4 |
| Example 34 | 0.02 | 230° C. for 4 min | 89.4 |
| Example 41 | 0.02 | 230° C. for 4 min | 85.9 |
| Example 49 | 0.02 | 230° C. for 4 min | 81.2 |
| Example 50 | 0.02 | 230° C. for 4 min | 81.0 |
| Example 51 | 0.02 | 230° C. for 4 min | 79.3 |
| Example 72 | 0.02 | 230° C. for 4 min | 84.4 |
| Example 74 | 0.02 | 230° C. for 4 min | 85.0 |
| Example 76 | 0.02 | 230° C. for 4 min | 80.7 |
| Example 77 | 0.02 | 230° C. for 4 min | 84.6 |
| Example 83 | 0.02 | 230° C. for 4 min | 80.5 |
| Example 84 | 0.02 | 230° C. for 4 min | 82.2 |
| Example 85 | 0.02 | 230° C. for 4 min | 83.2 |
| Example 86 | 0.02 | 230° C. for 4 min | 84.0 |
| Example 87 | 0.02 | 230° C. for 4 min | 83.4 |
| Example 90 | 0.02 | 230° C. for 4 min | 80.8 |
| Example 93 | 0.02 | 230° C. for 4 min | 81.2 |
| Example 95 | 0.02 | 230° C. for 4 min | 81.6 |
| Example 98 | 0.02 | 230° C. for 4 min | 82.3 |
| Example 101 | 0.02 | 230° C. for 4 min | 82.2 |
| Example 113 | 0.02 | 230° C. for 4 min | 88.8 |
| Example 120 | 0.02 | 230° C. for 4 min | 88.1 |
| Example 125 | 0.02 | 230° C. for 4 min | 81.2 |
| Example 134 | 0.02 | 230° C. for 4 min | 81.1 |
| Example 135 | 0.02 | 230° C. for 4 min | 84.6 |
| Example 137 | 0.02 | 230° C. for 4 min | 88.9 |
| Example 141 | 0.02 | 230° C. for 4 min | 90.8 |
| Example 144 | 0.02 | 230° C. for 4 min | 86.8 |
| No OS | 0 | 180° C. for 30 min | 60.6 |
| Peroxide1 | 0.02 | 180° C. for 30 min | 61.2 |
| Peroxide2 | 0.02 | 180° C. for 30 min | 60.8 |
| Peroxide3 | 0.02 | 180° C. for 30 min | 68.8 |
| Azo | 0.02 | 180° C. for 30 min | 61.1 |
| No OS | 0 | 230° C. for 4 min | 70.4 |
| Peroxide1 | 0.02 | 230° C. for 4 min | 62.7 |

TABLE II-continued

| Oxime sulfonate | Concentration of oxime sulfonate (mol/kg in composition) | Baking conditions | C=C conversion (%) |
|---|---|---|---|
| Peroxide2 | 0.02 | 230° C. for 4 min | 61.2 |
| Peroxide3 | 0.02 | 230° C. for 4 min | 70.2 |
| Azo | 0.02 | 230° C. for 4 min | 63.8 |
| No OS | 0 | 230° C. for 30 min | 79.7 |

No OS    no oxime sulfonate peroxide1    t-Butyl peroxylaurate

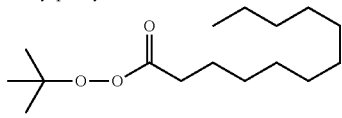

peroxide2    t-Butyl peroxybenzoate

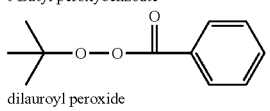

peroxide3    dilauroyl peroxide

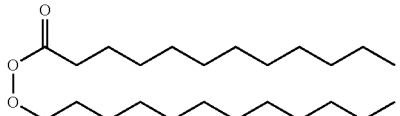

azo    2,2′-azobis(2-metylpropylonitrile)

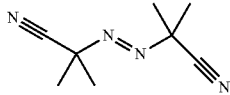

I.2 Preparation of Color Filter Resist (Blue)

A blue pigment dispersion was prepared by mixing the following components and dispersing them by using a Paint conditioner (SKANDEX).
Blue Dispersion
5.3 parts by weight blue pigment (PB15:6, Blue E provided by Toyo Ink)
1.9 parts by weight dispersant (Ajisper PB821 provided by Ajinomoto Fine Techno)
0.2 parts by weight synergist (Solsperse S5000 provided by Lubrizol)
55.8 parts by weight solvent propylene glycol monomethylether acetate (PGM EA)
Color filter resist (blue) was prepared by further adding the following components to the above dispersion prepared.
19.1 parts by weight alkaline developable binder, 37.8% solution (Ripoxy SPC-2000, provided by Showa Highpolymer)
12.3 parts by weight solvent PGMEA
5.3 parts by weight multifunctional acrylate (DPHA, provided by UCB Chemicals)
Solvent Resistance Tests of Blue Color Filter Resist after Photocuring and Baking The oxime sulfonate to be tested and additionally IRGACURE® 369 (4.8 wt % in solid) as photoinitiator were added to the above color filter resist composition and mixed. The concentration of the oxime sulfonate in the composition was 0.02 mol/kg. The composition was applied to a 2×3 cm silicon wafer using a spin coater (1H-DX2, MIKASA). The solvent was removed by heating at 90° C. for 2.5 min in a convection oven. The thickness of the dry film was approximately 1.0 μm. Exposure was then carried out using a 250 W super high pressure mercury lamp (USHIO, USH-250BY) at a distance of 15 cm. The total exposure dose determined by measuring light intensity with an optical power meter (ORC UV Light Measure Model UV-M02 with UV-35 detector) was 150 mJ/cm². The coating was further baked under the conditions listed in Table III below. The coating after baking was dipped in 12 g N-methylpyrrolidone (NMP) in a glass vessel for 3 min and then leaching of the blue pigment was assessed by visual analysis of NMP layer. It was taken as "−" that leaching of blue pigment was observed, and it was taken as "+" that leaching of blue pigment was not observed. The test results were given in Table III.

TABLE III

| Oxime sulfonate | Concentration of oxime sulfonate (mol/kg in composition) | Baking conditions | Leaching of blue pigment |
|---|---|---|---|
| — | — | 180° C. for 30 min | − |
| — | — | 230° C. for 5 min | − |
| Example 1 | 0.02 | 180° C. for 30 min | + |
| Example 16 | 0.02 | 180° C. for 30 min | + |
| Example 17 | 0.02 | 180° C. for 30 min | + |
| Example 21 | 0.02 | 180° C. for 30 min | + |
| Example 23 | 0.02 | 180° C. for 30 min | + |
| Example 37 | 0.02 | 180° C. for 30 min | + |
| Example 42 | 0.02 | 180° C. for 30 min | + |
| Example 46 | 0.02 | 180° C. for 30 min | + |
| Example 50 | 0.02 | 180° C. for 30 min | + |
| Example 53 | 0.02 | 180° C. for 30 min | + |
| Example 74 | 0.02 | 180° C. for 30 min | + |
| Example 78 | 0.02 | 180° C. for 30 min | + |
| Example 85 | 0.02 | 180° C. for 30 min | + |
| Example 86 | 0.02 | 180° C. for 30 min | + |
| Example 93 | 0.02 | 180° C. for 30 min | + |
| Example 94 | 0.02 | 180° C. for 30 min | + |
| Example 98 | 0.02 | 180° C. for 30 min | + |
| Example 99 | 0.02 | 180° C. for 30 min | + |
| Example 108 | 0.02 | 180° C. for 30 min | + |
| Example 114 | 0.02 | 180° C. for 30 min | + |
| Example 118 | 0.02 | 180° C. for 30 min | + |
| Example 51 | 0.02 | 180° C. for 30 min | + |
| Example 147 | 0.02 | 180° C. for 30 min | + |
| Example 1 | 0.02 | 230° C. for 5 min | + |
| Example 16 | 0.02 | 230° C. for 5 min | + |
| Example 17 | 0.02 | 230° C. for 5 min | + |
| Example 21 | 0.02 | 230° C. for 5 min | + |
| Example 23 | 0.02 | 230° C. for 5 min | + |
| Example 37 | 0.02 | 230° C. for 5 min | + |
| Example 42 | 0.02 | 230° C. for 5 min | + |
| Example 46 | 0.02 | 230° C. for 5 min | + |
| Example 50 | 0.02 | 230° C. for 5 min | + |
| Example 53 | 0.02 | 230° C. for 5 min | + |
| Example 74 | 0.02 | 230° C. for 5 min | + |
| Example 78 | 0.02 | 230° C. for 5 min | + |
| Example 85 | 0.02 | 230° C. for 5 min | + |
| Example 86 | 0.02 | 230° C. for 5 min | + |
| Example 93 | 0.02 | 230° C. for 5 min | + |
| Example 94 | 0.02 | 230° C. for 5 min | + |
| Example 98 | 0.02 | 230° C. for 5 min | + |
| Example 99 | 0.02 | 230° C. for 5 min | + |
| Example 108 | 0.02 | 230° C. for 5 min | + |
| Example 114 | 0.02 | 230° C. for 5 min | + |
| Example 118 | 0.02 | 230° C. for 5 min | + |
| Example 51 | 0.02 | 230° C. for 5 min | + |
| Example 147 | 0.02 | 230° C. for 5 min | + |

II.3 Preparation of Acrylate Formulation (Clear)

58.6 parts by weight solvent (PGM EA)
11.9 parts by weight alkaline developable binder, 37.8% solution (Ripoxy SPC-2000, provided by Showa Highpolymer)
1.0 parts by weight multifunctional acrylate (DPHA, provided by UCB Chemicals)
Thermal Curing Tests of Acrylate Formulation
The oxime sulfonate to be tested was added to a solution of above formulation and mixed. The mixture was applied to a silicon wafer using a spin coater (1H-DX2, MIKASA). The solvent was removed by heating at 90° C. for 2.5 min in a convection oven. The thickness of the dry film was approximately 0.6 μm. The coating was further baked under the conditions listed in Table III. The conversion of acrylic double bond in baking was determined by the method described above. The results of the tests are given in Table IV.

For comparison, the thermal curing test was repeated by using either no curing promoter or a peroxide compound. The results of the tests were also given in Table III. As can be seen shorter baking times are required when using an oxime sulfonate according to the invention.

TABLE IV

| Oxime sulfonate | Concentration of oxime sulfonate (mol/ kg in composition) | Baking conditions | C=C conversion (%) |
|---|---|---|---|
| Example 1 | 0.004 | 150° C. for 30 min | 44.4 |
| Example 9 | 0.004 | 150° C. for 30 min | 36.0 |
| Example 19 | 0.004 | 150° C. for 30 min | 46.9 |
| — | 0 | 150° C. for 30 min | 15.2 |
| t-Butyl peroxybenzoate | 0.007 | 150° C. for 30 min | 28.7 |

The invention claimed is:

1. A polymerizable composition comprising
(a) an oxime sulfonate compound of formula I $$QA_aB_bC_c \qquad (I)$$

where
a is 0, 1, 2, 3, 4 or 6;
b is 0, 1, 2, 3, 4 or 6; and
c is 0, 1, 2, 3, 4 or 6;
where the sum of a+b+c is 1, 2, 3, 4 or 6
where
A is a group

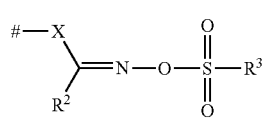
(A)

B is a group

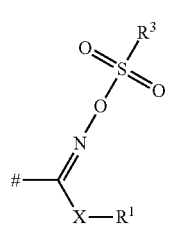
(B)

C is a group

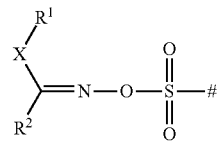
(C)

where
# denotes a point of attachment to Q;
X is S, $SO_2$ or $NR^{14}$;
Q if a is 1, b is 0 and c is 0,
  is a radical $R^1$;
or
Q if a is 2, b is 0 and c is 0
  is a divalent linker selected from the group consisting of
    L-$C_1$-$C_{30}$-alkylene-L,
    L-$C_2$-$C_{30}$-alkenylene-L, L-$C_3$-$C_{16}$-cycloalkylene-L,
    L-heterocycloalkylene-L, L-$C_6$-$C_{20}$-arylene-L,
    L-heteroarylene-L, L-$C_1$-$C_{30}$-alkylene-$L^2$-L,
    L-$C_2$-$C_{30}$-alkenylene-$L^2$-L,
    L-$C_3$-$C_{16}$-cycloalkylene-$L^1$-$C_3$-$C_{16}$-cycloalkylene-L,
    L-$C_3$-$C_{16}$-cycloalkylene-$L^1$-heterocycloalkylene-L,
    L-$C_3$-$C_{16}$-cycloalkylene-$L^1$-$C_6$-$C_{20}$-arylene-L
    L-$C_3$-$C_{16}$-cycloalkylene-$L^1$-heteroarylene-L,
    L-$C_6$-$C_{20}$-arylene-$L^1$-$C_6$-$C_{20}$-arylene-L,
    L-$C_6$-$C_{20}$-arylene-$L^1$-heteroarylene-L,
    L-heteroarylene-$L^1$-heteroarylene-L,
    L-$C_3$-$C_{16}$-cycloalkylene-$L^1$-$L^3$-$L^1$-$C_3$-$C_{16}$-cycloalkylene-L,
    L-$C_3$-$C_{16}$-cycloalkylene-$L^1$-$L^3$-$L^1$-heterocycloalkylene-L,
    L-$C_3$-$C_{16}$-cycloalkylene-$L^1$-$L^3$-$L^1$-$C_6$-$C_{20}$-arylene-L
    L-$C_3$-$C_{16}$-cycloalkylene-$L^1$-$L^3$-$L^1$-heteroarylene-L,
    L-$C_6$-$C_{20}$-arylene-$L^1$-$L^3$-$L^1$-$C_6$-$C_{20}$-arylene-L,
    L-$C_6$-$C_{20}$-arylene-$L^1$-$L^3$-$L^1$-heteroarylene-L, and
    L-heteroarylene-$L^1$-$L^3$-$L^1$-heteroarylene-L,
  where each alkylene and each alkenylene may be interrupted by one or more identical or different nonadjacent groups $L^4$, and may carry one or more identical or different radicals $R^{Qa}$;
  where each cycloalkylene and each heterocycloalkylene may be interrupted by one or more CO groups and may carry one or more identical or different radicals $R^{Qb}$,
  where each arylene and each heteroarylene may carry one or more identical or different radicals $R^{Qc}$,
where
each L is independently selected from the group consisting of a single bond,
  C(S)O, and C(S)$NR^{12}$;
each $L^1$ is independently selected from the group consisting of a single bond, O, S, $NR^{14}$, CO, OC(O), C(O)O, C(S)O, OC(S), C(O)$NR^{10}$, $NR^{10}$C(O), C(S) $NR^{12}$, $NR^{12}$C(S) and $NR^{10}SO_2$;
$L^2$ is $C_3$-$C_{20}$-cycloalkylene, heterocycloalkylene, $C_6$-$C_{20}$-arylene or heteroarylene,
  where cycloalkylene and heterocycloalkylene may be interrupted by one or more CO and may be substituted by one or more identical or different radicals $R^{L2b}$,
  where arylene and heteroarylene may be substituted by one or more identical or different radicals $R^{L2c}$,
  where
    each $R^{L2b}$ is independently selected from the group consisting of $C_1$-$C_{12}$-alkyl, $C_1$-$C_{12}$-haloalkyl, F, Cl, Br, I, CN, $NO_2$, $SR^4$, $OR^5$, $NR^6R^7$, $COR^8$, $COOR^9$, $CONR^{10}R^{11}$ and phenyl;

$R^{L2c}$ has one of the meanings indicated for $R^{L2b}$;

$L^3$ is selected from the group consisting of $C_1$-$C_{30}$-alkylene, $C_2$-$C_{30}$-alkenylene, $C_3$-$C_{20}$-cycloalkylene, heterocycloalkylene, $C_6$-$C_{20}$-arylene and heteroarylene, where alkylene and alkenylene may be interrupted by one or more identical or different O, S, $NR^6$ or CO and may carry one or more identical or different radicals $R^{L3a}$, where cycloalkylene and heterocycloalkylene may be interrupted by one or more CO, and may be substituted by one or more identical or different radicals $R^{L3b}$, where arylene and heterarylene may be substituted by one or more identical or different radicals $R^{L3c}$, where each $R^{L3a}$ is independently selected from the group consisting of F, Cl, Br, I, CN, $SR^4$, $OR^5$, $NR^6R^7$, $COR^8$, $COOR^9$, $CONR^{10}R^{11}$, $C_3$-$C_{10}$-cycloalkyl, heterocyclyl, heteroaryl, phenyl and naphthyl, where the five last-mentioned radicals may be substituted by one or more identical or different radicals $R^{3aa}$, where $R^{3aa}$ has one of the meanings indicated for $R^{L2b}$;

$R^{L3b}$ has one of the meanings indicated for $R^{L2b}$;

$R^{L3c}$ has one of the meanings indicated for $R^{L2c}$;

each $L^4$ is independently selected from the group consisting of O, S, $NR^6$, CO, C(O)O, OC(O), $C(O)NR^{10}$, $NR^{10}C(O)$, $C(S)NR^{12}$, $NR^{12}C(S)$, $NR^{10}SO_2$, $C_3$-$C_{20}$-cycloalkylene, heterocycloalkylene, $C_6$-$C_{20}$-arylene, and heteroarylene, where cycloalkylene and heterocycloalkylene may be interrupted by one or more CO, and may be substituted by one or more identical or different radicals $R^{L4b}$, where arylene and heteroarylene may be substituted by one or more identical or different radicals $R^{L4c}$, where $R^{L4b}$ has one of the meanings indicated for $R^{L2b}$; and $R^{L4c}$ has one of the meanings indicated for $R^{L2c}$;

each $R^{Qa}$ is independently selected from the group consisting of F, Cl, Br, I, CN, $SR^4$, $OR^5$, $NR^6R^7$, $COR^8$, $COOR^9$, $CONR^{10}R^{11}$, $C_3$-$C_{10}$-cycloalkyl which may be interrupted by one or two CO groups, heterocyclyl which may be interrupted by one or two CO groups, heteroaryl, phenyl and naphthyl, where the five last-mentioned radicals may be substituted by one or more identical or different radicals $R^{Qaa}$, where each $R^{Qaa}$ is independently selected from the group consisting of $C_1$-$C_{12}$-alkyl, $C_1$-$C_{12}$-haloalkyl, F, Cl, Br, I, CN, $NO_2$, $SR^4$, $OR^5$, $NR^6R^7$, $COR^8$, $COOR^9$ and $CONR^{10}R^{11}$;

each $R^{Qb}$ is independently selected from the group consisting of F, Cl, Br, I, CN, $SR^4$, $OR^5$, $NR^6R^7$, $COR^8$, $COOR^9$, $CONR^{10}R^{11}$, $C_1$-$C_{12}$-alkyl, $C_1$-$C_{12}$-haloalkyl, heteroaryl, phenyl and naphthyl, where the three last-mentioned radicals may be substituted by one or more identical or different radicals $R^{Qba}$, where $R^{Qba}$ has one of the meanings indicated for $R^{Qaa}$;

each $R^{Qc}$ is independently selected from the group consisting of $C_1$-$C_{12}$-alkyl, $C_1$-$C_{12}$-haloalkyl, F, Cl, Br, I, CN, $NO_2$, $SR^4$, $OR^5$, $NR^6R^7$, $COR^5$, $COOR^5$, $CONR^{10}R^{11}$, phenyl, $C_3$-$C_{10}$-cycloalkyl and heterocyclyl, where in the two last-mentioned radicals one or two $CH_2$ groups may be replaced by CO;

Q if b is 2, a is 0 and c is 0, is a divalent linker, which is selected from the group consisting of $L^5$-$C_1$-$C_{30}$-alkylene-$L^5$, $L^5$-$C_2$-$C_{30}$-alkenylene-$L^5$,
$L^5$-$C_3$-$C_{16}$-cycloalkylene-$L^5$, $L^5$-heterocycloalkylene-$L^5$, $L^5$-$C_6$-$C_{20}$-arylene-$L^5$, $L^5$-heteroarylene-$L^5$,
$L^5$-$C_1$-$C_{30}$-alkylene-$L^6$-$L^5$, $L^5$-$C_2$-$C_{30}$-alkenylene-$L^6$-$L^5$,
$L^5$-$C_3$-$C_{16}$-cycloalkylene-$L^7$-$C_3$-$C_{16}$-cycloalkylene-$L^5$,
$L^5$-$C_3$-$C_{16}$-cycloalkylene-$L^7$-heterocycloalkylene-$L^5$,
$L^5$-$C_3$-$C_{16}$-cycloalkylene-$L^7$-$C_6$-$C_{20}$-arylene-$L^5$,
$L^5$-$C_3$-$C_{16}$-cycloalkylene-$L^7$-heteroarylene-$L^5$,
$L^5$-$C_6$-$C_{20}$-arylene-$L^7$-$C_6$-$C_{20}$-arylene-$L^5$,
$L^5$-$C_6$-$C_{20}$-arylene-$L^7$-heteroarylene-$L^5$,
$L^5$-heteroarylene-$L^7$-heteroarylene-$L^5$,
$L^5$-$C_3$-$C_{16}$-cycloalkylene-$L^7$-$L^8$-$L^7$-$C_3$-$C_{16}$-cycloalkylene-$L^5$,
$L^5$-$C_3$-$C_{16}$-cycloalkylene-$L^7$-$L^8$-$L^7$-heterocycloalkylene-$L^5$,
$L^5$-$C_3$-$C_{16}$-cycloalkylene-$L^7$-$L^8$-$L^7$-$C_6$-$C_{20}$-arylene-$L^5$,
$L^5$-$C_3$-$C_{16}$-cycloalkylene-$L^7$-$L^8$-$L^7$-heteroarylene-$L^5$,
$L^5$-$C_6$-$C_{20}$-arylene-$L^7$-$L^8$-$L^7$-$C_6$-$C_{20}$-arylene-$L^5$,
$L^5$-$C_6$-$C_{20}$-arylene-$L^7$-$L^8$-$L^7$-heteroarylene-$L^5$,
$L^5$-heteroarylene-$L^7$-$L^8$-$L^7$-heteroarylene-$L^5$, where each alkylene and each alkenylene may be interrupted by one or more identical or different groups $L^9$, and may carry one or more identical or different radicals $R^{Qa}$;

where each cycloalkylene and each heterocycloalkylene may be interrupted by one or more CO groups and may carry one or more identical or different radicals $R^{Qb}$, where each arylene and each heteroarylene may carry one or more identical or different radicals $R^{Qc}$, where each $L^5$ independently is a single bond, S, O, $NR^6$, CO, C(O)O, OC(O), $NR^{10}CO$ or $CONR^{10}$;

$L^6$ has one of the meanings indicated for $L^2$;
$L^7$ has one of the meanings indicated for $L^1$;
$L^8$ has one of the meanings indicated for $L^3$;
$L^9$ has one of the meanings indicated for $L^4$;
or Q if c is 2, a is 0 and b is 0, is a divalent linker selected from the group consisting of $C_1$-$C_{30}$-alkylene, $C_2$-$C_{30}$-alkenylene, $C_3$-$C_{16}$-cycloalkylene, heterocycloalkylene, $C_6$-$C_{20}$-arylene, heteroarylene, $C_1$-$C_{30}$-alkylene-$L^{10}$, $C_2$-$C_{30}$-alkenylene-$L^{10}$,
$C_3$-$C_{16}$-cycloalkylene-$L^{11}$-$C_3$-$C_{16}$-cycloalkylene,
$C_3$-$C_{16}$-cycloalkylene-$L^{11}$-heterocycloalkylene,
$C_3$-$C_{16}$-cycloalkylene-$L^{11}$-$C_6$-$C_{20}$-arylene,
$C_3$-$C_{16}$-cycloalkylene-$L^{11}$-heteroarylene,
$C_6$-$C_{20}$-arylene-$L^{11}$-$C_6$-$C_{20}$-arylene,
$C_6$-$C_{20}$-arylene-$L^{11}$-heteroarylene, heteroarylene-$L^{11}$-heteroarylene,
$C_3$-$C_{16}$-cycloalkylene-$L^{11}$-$L^{12}$-$L^{11}$-$C_3$-$C_{16}$-cycloalkylene,
$C_3$-$C_{16}$-cycloalkylene-$L^{11}$-$L^{12}$-$L^{11}$-$C_6$-$C_{20}$-arylene,
$C_3$-$C_{16}$-cycloalkylene-$L^{11}$-$L^{12}$-$L^{11}$-heterocycloalkylene,
$C_3$-$C_{16}$-cycloalkylene-$L^{11}$-$L^{12}$-$L^{11}$-heteroarylene,
$C_6$-$C_{20}$-arylene-$L^{11}$-$L^{12}$-$L^{11}$-$C_6$-$C_{20}$-arylene,
$C_6$-$C_{20}$-arylene-$L^{11}$-$L^{12}$-$L^{11}$-heteroarylene, and
heteroarylene-$L^{11}$-$L^{12}$-$L^{11}$-heteroarylene, where each alkylene and each alkenylene may be interrupted by one or more identical or different groups $L^{13}$, and may carry one or more identical or different radicals $R^{Qa}$;
where each cycloalkylene and each heterocycloalkylene may be interrupted by one or more CO groups and may carry one or more identical or different radicals $R^{Qb}$,
where each arylene and each heteroarylene may carry one or more identical or different radicals $R^{Qc}$,
where
$L^{10}$ has one of the meanings indicated for $L^2$
$L^{11}$ has one of the meanings indicated for $L^1$;
$L^{12}$ has one the meanings indicated for $L^3$;
$L^{13}$ has one of the meanings indicated for $L^4$;
or
Q if two of the indices a, b or c are each 1 and the remaining index is 0, the sum of a+b+c being 2,
is a divalent linker selected from the group consisting of $C_1$-$C_{30}$-alkylene, $C_2$-$C_{30}$-alkenylene, $C_3$-$C_{16}$-cycloalkylene, heterocycloalkylene, $C_6$-$C_{20}$-arylene, heteroarylene, $C_1$-$C_{30}$-alkylene-$L^{10}$, $C_2$-$C_{30}$-alkenylene-$L^{10}$,
$C_3$-$C_{16}$-cycloalkylene-$L^{11}$-$C_3$-$C_{16}$-cycloalkylene,
$C_3$-$C_{16}$-cycloalkylene-$L^{11}$-heterocycloalkylene,
$C_3$-$C_{16}$-cycloalkylene-$L^{11}$-$C_6$-$C_{20}$-arylene,
$C_3$-$C_{16}$-cycloalkylene-$L^{11}$-heteroarylene,
$C_6$-$C_{20}$-arylene-$L^{11}$-$C_6$-$C_{20}$-arylene,
$C_6$-$C_{20}$-arylene-$L^{11}$-heteroarylene, heteroarylene-$L^{11}$-heteroarylene,
$C_3$-$C_{16}$-cycloalkylene-$L^{11}$-$L^{12}$-$L^{11}$-$C_3$-$C_{16}$-cycloalkylene,
$C_3$-$C_{16}$-cycloalkylene-$L^{11}$-$C_6$-$C_{20}$-arylene,
$C_3$-$C_{16}$-cycloalkylene-$L^{11}$-$L^{12}$-$L^{11}$-heterocycloalkylene,
$C_3$-$C_{16}$-cycloalkylene-$L^{11}$-$L^{12}$-$L^{11}$-heteroarylene,
$C_6$-$C_{20}$-arylene-$L^{11}$-$L^{12}$-$L^{11}$-$C_6$-$C_{20}$-arylene,
$C_6$-$C_{20}$-arylene-$L^{11}$-$L^{12}$-$L^{11}$-heteroarylene, and
heteroarylene-$L^{11}$-$L^{12}$-$L^{11}$-heteroarylene,
where each alkylene and each alkenylene may be interrupted by one or more identical or different groups $L^{13}$, and may carry one or more identical or different radicals $R^{Qa}$;
where each cycloalkylene and each heterocycloalkylene may be interrupted by one or more CO groups and may carry one or more identical or different radicals $R^{Qb}$,
where each arylene and each heteroarylene may carry one or more identical or different radicals $R^{Qc}$,
where
$L^{10}$ has one of the meanings indicated for $L^2$
$L^{11}$ has one of the meanings indicated for $L^1$;
$L^{12}$ has one the meanings indicated for $L^3$;
$L^{13}$ has one of the meanings indicated for $L^4$;
or
Q if the sum of a+b+c=3,
is a trivalent linker selected from the group consisting of $C_1$-$C_{30}$-alkanetriyl, $C_2$-$C_{30}$-alkenetriyl, $C_3$-$C_{16}$-cycloalkanetriyl, heterocycloalkanetriyl, $C_6$-$C_{20}$-arenetriyl, heteroarenetriyl, $C_1$-$C_{30}$-alkanetriyl-$L^{14}$-$L^{15}$, $C_2$-$C_{30}$-alkenetriyl-$L^{14}$-$L^{15}$, $C_1$-$C_{30}$-alkylene-$L^{14}$-$L^{16}$, $C_2$-$C_{30}$-alkenetriyl-$L^{14}$-$L^{15}$, $C_2$-$C_{30}$-alkenylene-$L^{14}$-$L^{16}$, $C_3$-$C_{16}$-cycloalkanetriyl-$L^{14}$-$C_3$-$C_{16}$-cycloalkylene, $C_3$-$C_{16}$-cycloalkanetriyl-$L^{14}$-$L^{15}$-$C_6$-$C_{20}$-arylene, $C_6$-$C_{20}$-arenetriyl-$L^{14}$-$L^{11}$-$C_6$-$C_{20}$-arylene, and $C_6$-$C_{20}$-arylene-$L^{14}$-$L^{15}$-$C_3$-$C_{16}$-cycloalkanetriyl where each alkanetriyl, each alkylene, each alkenetriyl and each alkenylene may be interrupted by one or more identical or different groups $L^{17}$ and may carry one or more identical or different radicals $R^{Qa}$;
where each cycloalkanetriyl, each cycloalkylene, each heterocycloalkanetriyl and each heterocycloalkylene may be interrupted by one or more CO groups and may carry one or more identical or different radicals $R^{Qb}$,
where each arenetriyl, each arylene, each heteroarenetriyl and each heteroarylene may carry one or more identical or different radicals $R^{Qc}$, where
$L^{14}$ has one of the meanings indicated for $L^1$;
$L^{15}$ has one of the meanings indicated for $L^2$;
$L^{16}$ is $C_6$-$C_{20}$-arenetriyl, heteroarenetriyl, $C_3$-$C_{20}$-cycloalkanetriyl or heterocycloalkanetriyl, where cycloalkanetriyl and heterocycloalkanetriyl may be interrupted by one or more CO, and may be substituted by one or more identical or different radicals $R^{L16b}$,
where arenetriyl and heteroarenetriyl may be substituted by one or more identical or different radicals $R^{L16c}$, where
$R^{L16b}$ has one of the meanings indicated for $R^{L2b}$;
$R^{L16c}$ has one of the meanings indicated for $R^{L2c}$;
$L^{17}$ has one of the meanings indicated for $L^4$;
Q if the sum of a+b+c=4,
is a tetravalent linker, which is a $C_1$-$C_{30}$-alkanetetrayl which may be interrupted by one or more identical or different groups $L^{18}$ and may carry one or more identical or different radicals $R^{Qa}$;
where
$L^{18}$ has one of the meanings given for $L^{17}$;
Q if the sum of a+b+c=6
is a hexavalent linker which is a $C_2$-$C_{30}$-alkanehexayl which may be interrupted by one or more identical or different groups $L^{19}$ and may carry one or more identical or different radicals $R^{Qa}$;
where
$L^{19}$ has one of the meanings given for $L^{17}$;
$R^1$ is $C_1$-$C_{20}$-alkyl, $C_2$-$C_{20}$-alkenyl, $C_2$-$C_{20}$-alkynyl, $C_3$-$C_{20}$-cycloalkyl, heterocyclyl, $C_6$-$C_{20}$-aryl, heteroaryl, $C_1$-$C_{20}$-alkanoyl, $C_3$-$C_{20}$-cycloalkanoyl, $C_2$-$C_{20}$-alkenoyl, $C_6$-$C_{20}$-aroyl, $CSNR^{12}R^{13}$, $C(O)OR^9$ or $CSOR^9$,
where $C_1$-$C_{20}$-alkyl, $C_2$-$C_{20}$-alkenyl and $C_2$-$C_{20}$-alkynyl may be interrupted by one or more identical or different groups selected —O—, —S—, —N($R^6$)— and CO, and may carry one or more identical or different radicals $R^{1a}$,
where $C_3$-$C_{20}$-cycloalkyl and heterocyclyl may be interrupted by one or more CO groups, and may carry one or more identical or different radicals $R^{1b}$,
where $C_6$-$C_{20}$-aryl and heteroaryl may carry one or more identical or different radicals $R^{1c}$,
where $C_1$-$C_{20}$-alkanoyl and $C_2$-$C_{20}$-alkenoyl may carry one or more identical or different radicals $R^{1a}$,
where $C_3$-$C_{20}$-cycloalkanoyl may carry one or more identical or different radicals $R^{1b}$,
where $C_6$-$C_{20}$-aroyl may carry one or more identical or different radicals $R^{1d}$,
where
each $R^{1a}$ is independently selected from the group consisting of F, Cl, Br, I, CN, $SR^4$, $OR^5$, $NR^6R^7$, $COR^8$, $COOR^9$, $CONR^{10}R^{11}$, $C_3$-$C_{20}$-cycloalkyl which may be interrupted by one or more CO groups, heterocyclyl which may be interrupted by one or more CO groups, heteroaryl and $C_6$-$C_{10}$-aryl where the four last-mentioned radicals may carry one or more identical or different radicals $R^{1aa}$, where each $R^{1aa}$ is independently selected from the group consisting of $C_1$-$C_{12}$-alkyl, $C_1$-$C_{12}$-alkyl which may be interrupted by one or more groups selected from the group consisting of CO, O, S, C(O)O, OC(O), C(O)S and SC(O), $C_1$-$C_{12}$-haloalkyl, $C_1$-$C_{12}$-hydroxyalkyl, $C_2$-$C_{12}$-alkenyl, F, Cl, Br, I, $NO_2$, $SR^4$, $OR^5$, $NR^6R^7$, $COR^8$, $COOR^9$ and $CONR^{10}R^{11}$;

each $R^{1b}$ is independently selected from the group consisting of F, Cl, Br, I, CN, $SR^4$, $OR^5$, $NR^6R^7$, $COR^8$, $COOR^9$, $CONR^{10}R^{11}$, $C_1$-$C_{12}$-alkyl, $C_1$-$C_{12}$-hydroxyalkyl, $C_1$-$C_{12}$-haloalkyl, $C_2$-$C_{12}$-alkenyl, heteroaryl and $C_6$-$C_{10}$-aryl where the two last-mentioned radicals may carry one or more identical or different radicals $R^{1ba}$, where $R^{1ba}$ has one of the meanings indicated for $R^{1aa}$;

each $R^{1C}$ is independently selected from the group consisting of $C_1$-$C_{12}$-alkyl, $C_1$-$C_{12}$-haloalkyl, $C_1$-$C_{12}$-hydroxyalkyl, $C_2$-$C_{12}$-alkenyl, F, Cl, Br, I, CN, $NO_2$, $SR^4$, $OR^5$, $NR^6R^7$, $COR^8$, $COOR^9$, $CONR^{10}R^{11}$, phenyl, heteroaryl, heterocyclyl and $C_3$-$C_{10}$-cycloalkyl where the two last-mentioned radicals may be interrupted by one or two C=O groups and where phenyl, heteroaryl, heterocyclyl and $C_3$-$C_{10}$-cycloalkyl may carry one or more identical or different radicals $R^{1ca}$, where $R^{1ca}$ has one of the meanings indicated for $R^{1aa}$;

each $R^{1d}$ is independently selected from the group consisting of $C_1$-$C_{12}$-alkyl, $C_1$-$C_{12}$-haloalkyl, $C_1$-$C_{12}$-hydroxyalkyl, $C_2$-$C_{12}$-alkenyl, F, Cl, Br, I, CN, $SR^4$, $OR^5$, $NR^6R^7$, $COR^8$, $COOR^9$, $CONR^{16}R^{11}$, $C_3$-$C_{20}$-cycloalkyl which may be interrupted by one or more CO groups, heterocyclyl which may be interrupted by one or more CO groups, $C_6$-$C_{10}$-aryl and heteroaryl where the four last-mentioned radicals may carry one or more radicals $R^{1da}$, where $R^{1da}$ has one of the meanings indicated for $R^{1aa}$;

or if b is 2, 3, 4 or 6 and/or c is 2, 3, 4 or 6, two radicals $R^1$ together can be a divalent bridging group having 1 to 20 atoms between the flanking bonds, or if b is 2, 3, 4 or 6, at least one group-X—$R^1$ may be bound to a carbon atom or nitrogen atom of Q via a divalent bridging group having 1 to 10 atoms between the flanking bonds, $R^2$ is hydrogen, $SR^4$, $OR^5$, $NR^1R^{14}$, $COR^8$, $SO_2R^4$, $COOR^9$, $CONR^{10}R^{11}$, $SO_2NR^{10}R^{11}$, $PO(OR^9)_2$, CN, $C_1$-$C_{16}$-alkyl, $C_2$-$C_{20}$-alkenyl, $C_2$-$C_{20}$-alkynyl, $C_3$-$C_{20}$-cycloalkyl, heterocyclyl, $C_6$-$C_{20}$-aryl, heteroaryl, $C_1$-$C_{20}$-alkanoyl, $C_2$-$C_{20}$-alkenoyl, $C_3$-$C_{20}$-cycloalkanoyl, $C_6$-$C_{20}$-aroyl or a group E, where $C_1$-$C_{16}$-alkyl, $C_2$-$C_{20}$-alkenyl and $C_2$-$C_{20}$-alkynyl may be interrupted by one or more identical or different groups selected from —O—, —S—, —N($R^6$)— and CO, and may carry one or more identical or different radicals $R^{2a}$, where $C_3$-$C_{20}$-cycloalkyl and heterocyclyl may be interrupted by one or more CO groups, and may carry one or more identical or different radicals $R^{2b}$, where $C_6$-$C_{20}$-aryl and heteroaryl may carry one or more identical or different radicals $R^{2c}$, where $C_1$-$C_{20}$-alkanoyl and $C_2$-$C_{20}$-alkenoyl may carry one or more identical or different radicals $R^{2a}$, where $C_3$-$C_{20}$-cycloalkanoyl may carry one or more identical or different radicals $R^{2b}$, where $C_6$-$C_{20}$-aroyl may carry one or more identical or different radicals Red, where each $R^{2a}$ is independently selected from the group consisting of F, Cl, Br, I, CN, $SR^4$, $OR^5$, $NR^6R^7$, $COR^5$, $COOR^5$, $CONR^{10}R^{11}$, $C_3$-$C_{20}$-cycloalkyl which may be interrupted by one or more CO groups, heterocyclyl which may be interrupted by one or more CO groups, heteroaryl and $C_6$-$C_{10}$-aryl where the four last-mentioned radicals may carry one or more identical or different radicals $R^{2aa}$, where each $R^{2aa}$ is independently selected from the group consisting of $C_1$-$C_{12}$-alkyl, $C_1$-$C_{12}$-alkyl which may be interrupted by one or more groups selected from the group consisting of CO, O, S, C(O)O, OC(O), C(O)S and SC(O), $C_1$-$C_{12}$-haloalkyl, $C_1$-$C_{12}$-hydroxyalkyl, $C_2$-$C_{12}$-alkenyl, phenyl, F, Cl, Br, I, CN, $NO_2$, $SR^4$, $OR^5$, $NR^6R^7$, $COR^5$, $COOR^5$ and $CONR^{10}R^{11}$;

$R^{2b}$ has one of the meanings indicated for $R^{1b}$;
$R^{2c}$ has one of the meanings indicated for $R^{1c}$;
$R^{2d}$ has one of the meanings indicated for $R^{1d}$;
E is selected from the group consisting of

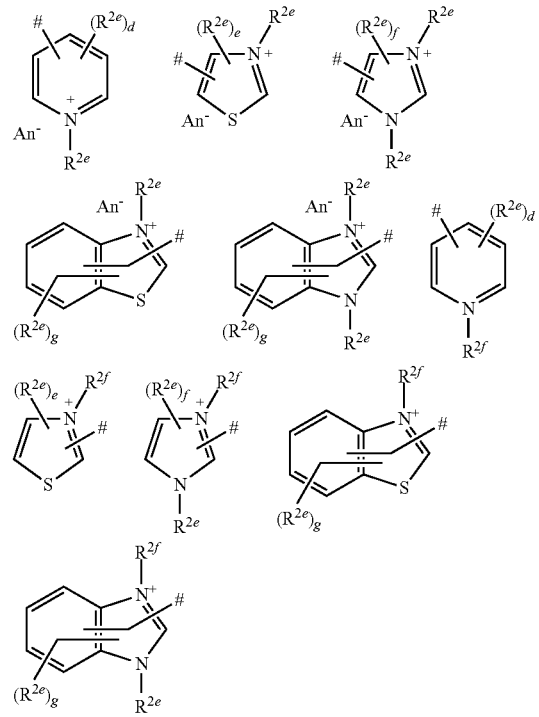

where
\# is a point of attachment to a remainder of the molecule;
d is 0, 1, 2, 3 or 4;
e is 0, 1, or 2;
f is 0, 1, or 2;
g is 0, 1, 2, 3 or 4;
$R^{2e}$ has one of the meanings indicated for $R^{2c}$;

$R^{2f}$ is $C_1$-$C_{20}$-alkylene-COO$^-$, $C_2$-$C_{20}$-alkenylene-COO$^-$, $C_2$-$C_{20}$-alkynylene-COO$^-$, $C_3$-$C_{20}$-cycloalkylene-COO$^-$, heterocycloalkylene-COO$^-$, $C_6$-$C_{20}$-arylene-COO$^-$, heteroarylene-COO$^-$, alkylene-S(O$_2$)O$^-$, $C_2$-$C_{20}$-alkenylene-S(O$_2$)O$^-$, $C_2$-$C_{20}$-alkynylene-S(O$_2$)O$^-$, $C_3$-$C_{20}$-cycloalkylene-S(O$_2$)O$^-$, heterocycloalkylene-S(O$_2$)O$^-$, $C_6$-$C_{20}$-arylene-S(O$_2$)O$^-$, heteroarylene-S(O$_2$)O$^-$, $C_1$-$C_{20}$-alkylene-OS(O$_2$)O$^-$, $C_2$-$C_{20}$-alkenylene-OS(O$_2$)O$^-$, $C_2$-$C_{20}$-alkynylene-OS(O$_2$)O$^-$, $C_3$-$C_{20}$-cycloalkylene-OS(O$_2$)O$^-$, heterocycloalkylene-OS(O$_2$)O$^-$, $C_6$-$C_{20}$-arylene-OS(O$_2$)O$^-$ or heteroarylene-OS(O$_2$)O$^-$ where each alkylene, each alkenyle and each alkynyle may be interrupted by one or more identical or different groups selected from the group consisting of —O—, —S—, —N(R$^6$)— and CO, and may carry one or more identical or different radicals $R^{2a}$, where each cycloalkylene and each heterocycloalkylene may be interrupted by one or two groups CO and may carry one or more identical or different radicals $R^{2b}$, where each arylene and each heteroarylene may carry one or more radicals $R^{2c}$, An$^-$ is Cl$^-$, Br$^-$, I$^-$, SCN$^-$, BF$_4^-$, PF$_6^-$, ClO$_4^-$, SbF$_6^-$, AsF$_6^-$, $C_1$-$C_{20}$-alkyl-COO$^-$, $C_1$-$C_{20}$-alkyl-S(O)$_2$O$^-$, $C_1$-$C_{20}$-alkyl-OS(O)$_2$O$^-$, $C_6$-$C_{20}$-aryl-COO$^-$, $C_6$-$C_{20}$-aryl-S(O)$_2$O$^-$ or $C_6$-$C_{20}$-aryl-OS(O)$_2$O$^-$, where the aryl moiety of the three last-mentioned radicals may be substituted by 1, 2, 3 or 4 identical or different or —R$^2$ together with —X—R$^1$ may be X—(C$_1$-C$_{20}$-alkylene)-Y, X—(C$_2$-C$_{20}$-alkenylene)-Y, X—(C$_3$-C$_{20}$-cycloalkylene)-Y, X-(heterocycloalkylene)-Y, X-(o-phenylene)-Y, X-(o-xylylene)-Y, X-(o-phenylene-C$_1$-C$_{12}$-alkylene)-Y, X—(C$_1$-C$_{12}$-alkylene-o-phenylene)-Y, X—(O—C$_1$-C$_{20}$-alkylene)-Y, X—(S—C$_1$-C$_{20}$-alkylene)-Y or X—(N(R$^6$)—C$_1$-C$_{20}$-alkylene)-Y, Y being attached to the oxime carbon atom carrying X where each alkylene and alkenylene may comprise one or more identical or different groups selected from the group consisting of O, S, NR$^6$ and CO and may be substituted by one or more radicals $R^{2g}$, where cycloalkylene and heterocycloalkylene may be interrupted by one or more groups CO and may be optionally substituted by one or more identical or different radicals $R^{2h}$, where each phenylene and the phenylene moiety of o-xylylene may be substituted by one or more identical or different radicals $R^{2h}$, where Y is O, S, NR$^{14}$, CO, SC(O), OC(O), C(O)O, NR$^{10}$C(O), C(O)NR$^{10}$, NR$^{10}$SO$_2$ or a single bond;

each $R^{2g}$ is independently selected from the group consisting of F, Cl, Br, I, SR$^4$, OR$^5$, NR$^6$R$^7$, COR$^8$, COOR$^9$, CONR$^{10}$R$^{11}$, heteroaryl and $C_6$-$C_{10}$-aryl where the two-last-mentioned radicals may carry one or more radicals $R^{2ga}$, where $R^{2ga}$ is phenoxy or has one of the meanings indicated for $R^{1aa}$;

each $R^{2h}$ is independently selected from the group consisting of F, Cl, Br, I, SR$^4$, OR$^5$, NR$^6$R$^7$, COR$^8$, COOR$^9$, CONR$^{10}$R$^{11}$, $C_1$-$C_{12}$-alkyl, $C_1$-$C_{12}$-haloalkyl, heteroaryl and $C_6$-$C_{10}$-aryl where the two last-mentioned radicals may carry one or more radicals $R^{2ha}$, where $R^{2ha}$ has one of the meanings indicated for $R^{1aa}$;

or if X is S, —R$^2$ together with —S—R$^1$ may be S—C(S)—NR$^{12}$—C(O) or S—C(=NOR$^{15}$)—C(O)—NR$^{12}$—C(O), where R$^{15}$ is hydrogen or phenylsulfonyl where the phenyl moiety may be substituted by $C_1$-$C_4$-alkyl or $C_1$-$C_4$-alkoxy;

or if a is 2, 3, 4 or 6 and/or c is 2, 3, 4 or 6, two radicals R$^2$ together may be a divalent bridging group having 1 to 20 atoms between flanking bonds;

R$^3$ is $C_1$-$C_{20}$-alkyl, $C_2$-$C_{20}$-alkenyl, $C_2$-$C_{20}$-alkynyl, $C_3$-$C_{20}$-cycloalkyl, heterocyclyl, $C_6$-$C_{20}$-aryl or heteroaryl, where $C_1$-$C_{20}$-alkyl, $C_2$-$C_{20}$-alkenyl and $C_2$-$C_{20}$-alkynyl may be interrupted by one or more identical or different groups selected from —O—, —S—, —N(R$^6$)— and CO, and may carry one or more identical or different radicals $R^{3a}$, where $C_3$-$C_{20}$-cycloalkyl and heterocyclyl may be interrupted by one or more CO groups, and may carry one or more identical or different radicals $R^{3b}$, where $C_6$-$C_{20}$-aryl and heteroaryl may carry one or more identical or radicals $R^{3c}$, where $R^{3a}$ has one of the meanings indicated for $R^{2a}$;

$R^{3b}$ has one of the meanings indicated for $R^{1b}$;

$R^{3c}$ has one of the meanings indicated for $R^{1c}$;

or

—X—R$^1$ and R$^3$ may together form a divalent radical selected from the group consisting of X—(C$_1$-C$_{20}$-alkylene)-Z, X—(C$_2$-C$_{20}$-alkenylene)-Z, X—(C$_3$-C$_{20}$-cycloalkylene)-Z, X-(heterocycloalkylene)-Z, X-(o-phenylene)-Z, X-(o-xylylene)-Z, X—(C$_0$-C$_{12}$-alkylene-heteroarylene-C$_0$-C$_{12}$-alkylene)-Z;

X-(o-phenylene-C$_1$-C$_{12}$-alkylene)-Z,

X—(C$_1$-C$_{12}$-alkylene-o-phenylene)-Z and S—C(S)—NR$^{12}$—C(O), where Z is attached to the sulfur atom of the sulfonate group, where each alkylene and each alkenylene may be interrupted by one or more identical or different groups selected from the group consisting of O, S, NR$^6$ and CO, and may be substituted by one or more radicals $R^{3g}$, where each cycloalkylene and each heterocycloalkylene may be interrupted by one or more groups CO and may be optionally substituted by one or more identical or different radicals $R^{3h}$, where each phenylene and the phenylene moiety of o-xylylene may be substituted by one or more identical or different radicals $R^{3h}$, where $R^{3g}$ has one of the meanings indicated for $R^{2g}$;

$R^{3h}$ has one of the meanings indicated for $R^{2h}$; and

Z is O, S, NR$^{14}$, CO, OC(O), SC(O), C(O)O, NR$^{10}$C(O), C(O)NR$^{10}$, NR$^{10}$(SO$_2$) or a single bond;

each R$^4$ is independently selected from the group consisting of hydrogen, $C_1$-$C_{20}$-alkyl, $C_2$-$C_{12}$-alkenyl, $C_3$-$C_{10}$-cycloalkyl, heterocyclyl, where the two last-mentioned radicals may be interrupted by one or more C=O groups, $C_1$-$C_{20}$-alkyl which is interrupted by one or more identical or different groups selected from the group consisting of —O—, —S—, —N($C_1$-$C_8$-alkyl)- and CO, and may carry one or more identical or different radicals $R^{4a}$, $C_2$-$C_{12}$-alkenyl which is interrupted by one or more identical or different groups selected from the group consisting of —O—, —S—, and —N($C_1$-$C_8$-alkyl)-, —($CH_2CH_2O$)$_m$H, with m being 1-20, —($CH_2CH_2O$)$_n$(CO)—($C_1$-$C_8$-alkyl), with n being 1-20, $C_2$-$C_8$-alkanoyl, $C_3$-$C_6$-alkenoyl, where the two-last mentioned radicals may be substituted by one or more identical or different radicals selected from the group consisting of F, Cl, Br, I, OH and $C_1$-$C_6$-alkoxy, benzoyl which may be substituted by one or more identical or different radicals selected from the group consisting of F, Cl, Br, I, $C_1$-$C_6$-alkyl, OH and $C_1$-$C_6$-alkoxy, phenyl and naphthyl, where the two last-mentioned radicals may be substituted by one or more identical or different radicals $R^{4c}$, wherein phenyl or naphthyl may form a 5- or 6-membered ring with the phenyl ring to which the $SR^4$ is attached via a single bond, $C_1$-$C_4$-alkylene, O, S, $NR^6$ or CO, where each $R^{4a}$ is independently selected from the group consisting of F, Cl, Br, I, $C_3$-$C_{10}$-cycloalkyl, heterocyclyl, phenyl, OH, SH, CN, $C_3$-$C_6$-alkenoxy, $OCH_2CH_2CN$, $OCH_2CH_2(CO)O(C_1$-$C_8$-alkyl), O(CO)—($C_1$-$C_8$-alkyl), O(CO)-phenyl, (CO)OH and (CO)O($C_1$-$C_8$-alkyl);

each $R^{4c}$ is independently selected from the group consisting of F, Cl, Br, I, $C_1$-$C_{12}$-alkyl, $C_1$-$C_{12}$-haloalkyl, $C_1$-$C_{12}$-alkoxy, phenyl-$C_1$-$C_3$-alkoxy, phenoxy, $C_1$-$C_{12}$-alkylsulfanyl, phenylsulfanyl, —(CO)O($C_1$-$C_8$-alkyl), (CO)N($C_1$-$C_8$-alkyl)$_2$ and phenyl;

each $R^5$ is independently selected from the group consisting of hydrogen, $C_1$-$C_{20}$-alkyl, $C_2$-$C_{12}$-alkenyl, $C_3$-$C_{10}$-cycloalkyl, heterocyclyl, where the two last-mentioned radicals may be interrupted by one or two C=O groups, $C_1$-$C_{20}$-alkyl which may be interrupted by one or more identical or different groups selected from the group consisting of —O—, —S—, —N($C_1$-$C_8$-alkyl)- and CO, and may carry one or more identical or different radicals $R^{5a}$, $C_2$-$C_{12}$-alkenyl which is interrupted by one or more identical or different groups selected from the group consisting of —O—, —S—, and —N($C_1$-$C_8$-alkyl)-, —($CH_2CH_2O$)$_m$H, with m being 1-20, —($CH_2CH_2O$)$_n$(CO)—($C_1$-$C_8$-alkyl), with n being 1-20, $C_2$-$C_8$-alkanoyl, $C_3$-$C_6$-alkenoyl, where the two-last mentioned radicals may be substituted by one or more identical or different radicals selected from the group consisting of F, Cl, Br, I, OH and $C_1$-$C_6$-alkoxy, $C_2$-$C_8$-alkanoyl, which is interrupted by one or more identical or different groups selected from —O— and —S— and may be substituted by one or more identical or different radicals selected from the group consisting of hydroxyaminylene (=N—OH), F, Cl, Br, I, OH and $C_1$-$C_6$-alkoxy, benzoyl which may be substituted by one or more identical or different radicals selected from the group consisting of F, Cl, Br, I, $C_1$-$C_6$-alkyl, OH and $C_1$-$C_6$-alkoxy, phenyl and naphthyl, where the two last-mentioned radicals may be substituted by one or more identical or different radicals $R^{5c}$, wherein phenyl or naphthyl may form a 5- or 6-membered ring with the phenyl ring to which the $OR^5$ is attached via a single bond, $C_1$-$C_4$-alkylene, O, S, $NR^6$ or CO, where $R^{5a}$ has one of the meanings indicated for $R^{4a}$;

$R^{5c}$ has one of the meanings indicated for $R^{4c}$;

$R^6$, $R^{10}$ and $R^{12}$ are each independently selected from the group consisting of hydrogen, $OR^5$, $C_2$-$C_{12}$-alkenyl, $C_3$-$C_{10}$-cycloalkyl, heterocyclyl, where the two last-mentioned radicals may be interrupted by one or two C=O groups, $C_1$-$C_{20}$-alkyl which may be interrupted by one or more identical or different groups selected from the group consisting of —O—, —S—, —N($C_1$-$C_8$-alkyl)- and CO, and may carry one or more identical or different radicals $R^{6a}$, $C_2$-$C_{12}$-alkenyl which is interrupted by one or more identical or different groups selected from —O—, —S—, and —N($C_1$-$C_8$-alkyl)-, —($CH_2CH_2O$)$_o$H, with o being 1-20, —($CH_2CH_2O$)$_p$(CO)—($C_1$-$C_8$-alkyl), with p being 1-20, $C_2$-$C_8$-alkanoyl, $C_3$-$C_6$-alkenoyl, where the two-last mentioned radicals may be substituted by one or more identical or different radicals selected from the group consisting of F, Cl, Br, I, OH and $C_1$-$C_6$-alkoxy, benzoyl which may be substituted by one or more identical or different radicals selected from the group consisting of F, Cl, Br, I, $C_1$-$C_6$-alkyl, —OH and $C_1$-$C_6$-alkoxy, phenyl and naphthyl, where the two last-mentioned radicals may be substituted by one or more identical or different radicals $R^{6c}$, where $R^{6a}$ has one of the meanings indicated for $R^{4a}$;

$R^{6c}$ has one of the meanings indicated for $R^{4c}$;

or two radicals $R^6$ together may be a divalent bridging group having 1 to 20 atoms between flanking bonds;

or two radicals $R^{10}$ together may be a divalent bridging group having 1 to 20 atoms between flanking bonds;

or two radicals $R^{12}$ together may be a divalent bridging group having 1 to 20 atoms between flanking bonds;

$R^7$, $R^{11}$ and $R^{13}$ are each independently selected from the group consisting of $OR^5$, $C_1$-$C_{20}$-alkyl, $C_2$-$C_{12}$-alkenyl, $C_3$-$C_{10}$-cycloalkyl, heterocyclyl, where in the two last-mentioned radicals one or two $CH_2$ groups may be replaced by a C=O group, $C_1$-$C_{20}$-alkyl which may be interrupted by one or more identical or different groups selected from —O—, —S—, —N($C_1$-$C_8$-alkyl)- and CO, and may carry one or more identical or different radicals $R^{7a}$, $C_2$-$C_{12}$-alkenyl which is interrupted by one or more identical or different groups selected from the group consisting of —O—, —S—, and —N($C_1$-$C_8$-alkyl)-, —($CH_2CH_2O$)$_q$H, with q being 1-20, —($CH_2CH_2O$)$_r$(CO)—($C_1$-$C_8$-alkyl), with r being 1-20, $C_2$-$C_8$-alkanoyl, $C_3$-$C_6$-alkenoyl, where the two-last mentioned radicals may be substituted by one or more identical or different radicals selected from the group consisting of F, Cl, Br, I, OH and $C_1$-$C_6$-alkoxy, benzoyl which may be substituted by one or more identical or different radicals selected from the group consisting of F, Cl, Br, I, $C_1$-$C_6$-alkyl, OH and $C_1$-$C_6$-alkoxy, phenyl and naphthyl, where the two last-mentioned radicals may be substituted by one or more identical or different radicals $R^{7c}$, where $R^{7a}$ has one of the meanings indicated for $R^{4a}$;

$R^{7c}$ has one of the meanings indicated for $R^{4c}$;

or $R^6$ and $R^7$ together with the nitrogen atom to which they are attached form a saturated 5-, 6- or 7-membered nitrogen heterocycle which may have a further heteroatom or heteroatomic group selected from the group consisting of CO, O, S and N($C_1$-$C_8$-alkyl) as a ring member and which may carry 1, 2, 3 or 4 $C_1$-$C_4$-alkyl;

or $R^{10}$ and $R^{11}$ together with the nitrogen atom to which they are attached form a saturated 5-, 6- or 7-membered nitrogen heterocycle which may have a further heteroatom or heteroatomic group selected from the group consisting of CO, O, S and N($C_1$-$C_8$-alkyl) as a ring member and which may carry 1, 2, 3 or 4 $C_1$-$C_1$-alkyl;

or $R^{12}$ and $R^{13}$ together with the nitrogen atom to which they are attached form a saturated 5-, 6- or 7-membered nitrogen heterocycle which may have a further heteroatom or heteroatomic group selected from the group consisting of CO, O, S and N($C_1$-$C_8$-alkyl) as a ring member and which may carry 1, 2, 3 or 4 $C_1$-$C_4$-alkyl;

each $R^8$ is independently selected from the group consisting of hydrogen, $C_1$-$C_{20}$-alkyl, $C_2$-$C_{12}$-alkenyl, $C_3$-$C_{10}$-cycloalkyl, heterocyclyl, where the two last-mentioned radicals may be interrupted by one or more C=O groups, $C_1$-$C_{20}$-alkyl which may be interrupted by one or more identical or different groups selected from the group consisting of —O—, —S—, —N($C_1$-$C_8$-alkyl)- and CO, and may carry one or more identical or different radicals $R^{8a}$, $C_2$-$C_{12}$-alkenyl which is interrupted by one or more identical or different groups selected from —O—, —S—, and —N($C_1$-$C_8$-alkyl)-, —($CH_2CH_2O$)$_s$H, with s being 1-20, —($CH_2CH_2O$)$_t$(CO)—($C_1$-$C_8$-alkyl), with t being 1-20, $C_6$-$C_{20}$-aryl and heteroaryl, where the two last-mentioned radicals may be substituted by one or more identical or different radicals $R^{8c}$, where $R^{8a}$ has one of the meanings indicated for $R^{4a}$;

$R^{8c}$ has one of the meanings indicated for $R^{4c}$;

each $R^9$ is independently selected from the group consisting of hydrogen, $C_1$-$C_{20}$-alkyl, $C_2$-$C_{12}$-alkenyl, $C_3$-$C_{10}$-cycloalkyl, heterocyclyl, where the two last-mentioned radicals may be interrupted by one or more C=O groups, $C_1$-$C_{20}$-alkyl which may be interrupted by one or more identical or different groups selected from the group consisting of —O—, —S—, —N($C_1$-$C_8$-alkyl)- and CO, and may carry one or more identical or different radicals $R^{9a}$, $C_2$-$C_{12}$-alkenyl which is interrupted by one or more identical or different groups selected from —O—, —S—, and —N($C_1$-$C_8$-alkyl)-, —($CH_2CH_2O$)$_u$H, with u being 1-20, —($CH_2CH_2O$)$_v$(CO)—($C_1$-$C_8$-alkyl), with v being 1-20, phenyl and naphthyl, where the two last-mentioned radicals may be substituted by one or more identical or different radicals $R^{9c}$, where $R^{9a}$ has one of the meanings indicated for $R^{4a}$;

$R^{9c}$ has one of the meanings indicated for $R^{4c}$;

$R^{14}$ is $C_1$-$C_{20}$-alkyl, $C_2$-$C_{20}$-alkenyl, $C_2$-$C_{20}$-alkynyl, $C_3$-$C_{20}$-cycloalkyl, heterocyclyl, $C_6$-$C_{20}$-aryl, heteroaryl, $C_1$-$C_{20}$-alkanoyl, $C_2$-$C_{20}$-alkenoyl, $C_3$-$C_{20}$-cycloalkanoyl, $C_6$-$C_{20}$-aroyl, $CSNR^{12}R^{13}$ or $CSOR^9$, where $C_1$-$C_{20}$-alkyl, $C_2$-$C_{20}$-alkenyl and $C_2$-$C_{20}$-alkynyl may be interrupted by one or more identical or different groups selected from the group consisting of —O—, —S—, —N($R^6$)— and CO and may carry one or more identical or different radicals $R^{14a}$, where $C_3$-$C_{20}$-cycloalkyl and heterocyclyl may be interrupted by one or more CO groups and may carry one or more identical or different radicals $R^{14b}$, where $C_6$-$C_{20}$-aryl, heteroaryl may carry one or more identical or different radicals $R^{14c}$, where $C_1$-$C_{20}$-alkanoyl, $C_2$-$C_{20}$-alkenoyl may carry one or more identical or different radicals $R^{14a}$, where $C_3$-$C_{20}$-cycloalkanoyl may carry one or more identical or different radicals $R^{14b}$, where $C_6$-$C_{20}$-aroyl may carry one or more identical or different radicals $R^{14d}$, where $R^{14a}$ has one of the meanings indicated for $R^{2a}$, $R^{14b}$ has one of the meanings indicated for $R^{1b}$, $R^{14c}$ has one of the meanings indicated for $R^{1c}$;

$R^{14d}$ has one of the meanings indicated for $R^{1d}$;

or $R^1$ together with $R^{14}$ may be a divalent bridging group having 1 to 20 atoms between flanking bonds;

or two radicals $R^{14}$ together may be a divalent bridging group having 1 to 20 atoms between flanking bonds, and (b) an ethylenically unsaturated, polymerizable compound.

2. The composition according to claim 1, comprising the compound of the formula I where X is S or $NR^{14}$;

Q if a is 1, b is 0 and c is 0, is a radical $R^1$;

or

Q if a is 2, b is 0 and c is 0 is a divalent linker selected from the group consisting of L-$C_1$-$C_{30}$-alkylene-L, L-$C_2$-$C_{30}$-alkenylene-L, L-$C_3$-$C_{16}$-cycloalkylene-L, L-heterocycloalkylene-L, L-$C_6$-$C_{20}$-arylene-L, L-heteroarylene-L, L-$C_1$-$C_{30}$-alkylene-$L^2$-L, L-$C_2$-$C_{30}$-alkenylene-$L^2$-L, L-$C_3$-$C_{16}$-cycloalkylene-$L^1$-$C_3$-$C_{16}$-cycloalkylene-L, L-$C_3$-$C_{16}$-cycloalkylene-$L^1$-heterocycloalkylene-L, L-$C_3$-$C_{16}$-cycloalkylene-$L^1$-$C_6$-$C_{20}$-arylene-L L-$C_3$-$C_{16}$-cycloalkylene-$L^1$-heteroarylene-L, L-$C_6$-$C_{20}$-arylene-$L^1$-$C_6$-$C_{20}$-arylene-L, L-$C_6$-$C_{20}$-arylene-$L^1$-heteroarylene-L, L-heteroarylene-$L^1$-heteroarylene-L, L-$C_3$-$C_{16}$-cycloalkylene-$L^1$-$L^3$-$L^1$-$C_3$-$C_{16}$-cycloalkylene-L, L-$C_3$-$C_{16}$-cycloalkylene-$L^1$-$L^3$-$L^1$-heterocycloalkylene-L,
L-$C_3$-$C_{16}$-cycloalkylene-$L^1$-$L^3$-$L^1$-$C_6$-$C_{20}$-arylene-L
L-$C_3$-$C_{16}$-cycloalkylene-$L^1$-$L^3$-$L^1$-heteroarylene-L,
L-$C_6$-$C_{20}$-arylene-$L^1$-$L^3$-$L^1$-$C_6$-$C_{20}$-arylene-L,
L-$C_6$-$C_{20}$-arylene-$L^1$-$L^3$-$L^1$-heteroarylene-L, and
L-heteroarylene-$L^1$-$L^3$-$L^1$-heteroarylene-L,
where each alkylene and each alkenylene may be interrupted by one or more identical or different nonadjacent groups $L^4$, and may carry one or more identical or different radicals $R^{Qa}$;
where each cycloalkylene and each heterocycloalkylene may be interrupted by one or more CO groups and may carry one or more identical or different radicals $R^{Qb}$,
where each arylene and each heteroarylene may carry one or more identical or different radicals $R^{Qc}$,
where
each L is independently selected from the group consisting of a single bond, C(S)O, and C(S)$NR^{12}$;
each $L^1$ is independently a single bond, O, S, $NR^{14}$, CO, OC(O), C(O)O, C(S)O, OC(S), C(O)$NR^{10}$, $NR^{10}$C(O), C(S)$NR^{12}$, $NR^{12}$C(S) or $NR^{10}SO_2$;
$L^2$ is $C_3$-$C_{20}$-cycloalkylene, heterocycloalkylene, $C_6$-$C_{20}$-arylene or heteroarylene,
where cycloalkylene and heterocycloalkylene may be interrupted by one or more CO and may be substituted by one or more identical or different radicals $R^{L2b}$,
where arylene and heteroarylene may be substituted by one or more identical or different radicals $R^{L2c}$, where
each $R^{L2b}$ is independently selected from the group consisting of $C_1$-$C_{12}$-alkyl, $C_1$-$C_{12}$-haloalkyl, F, Cl, Br, I, CN, $NO_2$, $SR^4$, $OR^5$, $NR^6R^7$, $COR^8$, $COOR^9$, $CONR^{10}R^{11}$ or phenyl;
$R^{L2c}$ has one of the meanings indicated for $R^{L2b}$;
is selected from the group consisting of $C_1$-$C_{30}$-alkylene, $C_2$-$C_{30}$-alkenylene, $C_3$-$C_{20}$-cycloalkylene, heterocycloalkylene, $C_6$-$C_{20}$-arylene and heteroarylene,
where alkylene and alkenylene may be interrupted by one or more identical or different O, S, $NR^6$ and CO and may carry one or more identical or different radicals $R^{L3a}$,
where cycloalkylene and heterocycloalkylene may be interrupted by one or more CO, and may be substituted by one or more identical or different radicals $R^{L3b}$,
where arylene and heteroarylene may be substituted by one or more identical or different radicals $R^{L3c}$,
where
each $R^{L3a}$ is independently selected from the group consisting of F, Cl, Br, I, CN, $SR^4$, $OR^5$, $NR^6R^7$, $COR^8$, $COOR^9$, $CONR^{10}R^{11}$, $C_3$-$C_{10}$-cycloalkyl, heterocyclyl, heteroaryl, phenyl and naphthyl, where the five last-mentioned radicals may be substituted by one or more identical or different radicals $R^{3aa}$, where
$R^{3aa}$ has one of the meanings indicated for $R^{L2b}$;
$R^{L3b}$ has one of the meanings indicated for $R^{L2b}$;
$R^{L3c}$ has one of the meanings indicated for $R^{L2c}$;
each $L^4$ is independently selected from the group consisting of O, S, $NR^6$, CO, C(O)O, OC(O), C(O)$NR^{10}$, $NR^{10}$C(O), C(S)$NR^{12}$, $NR^{12}$C(S), $NR^{10}SO_2$, $C_3$-$C_{20}$-cycloalkylene, heterocycloalkylene, $C_6$-$C_{20}$-arylene, and heteroarylene, where cycloalkylene and heterocycloalkylene may be interrupted by one or more CO, and may be substituted by one or more identical or different radicals $R^{L4b}$,
where arylene and heteroarylene may be substituted by one or more identical or different radicals $R^{L4c}$, where
$R^{L4b}$ has one of the meanings indicated for $R^{L2b}$; and
$R^{L4c}$ has one of the meanings indicated for $R^{L2c}$;
each $R^{Qa}$ is independently selected from the group consisting of F, Cl, Br, I, CN, $SR^4$, $OR^5$, $NR^6R^7$, $COR^8$, $COOR^9$, $CONR^{10}R^{11}$, $C_3$-$C_{10}$-cycloalkyl which may be interrupted by one or two CO groups, heterocyclyl which may be interrupted by one or two CO groups, heteroaryl, phenyl and naphthyl, where the five last-mentioned radicals may be substituted by one or more identical or different radicals $R^{Qaa}$, where
each $R^{Qaa}$ is independently selected from the group consisting of $C_1$-$C_{12}$-alkyl, $C_1$-$C_{12}$-haloalkyl, F, Cl, Br, I, CN, $NO_2$, $SR^4$, $OR^5$, $NR^6R^7$, $COR^8$, $COOR^9$ and $CONR^{10}R^{11}$;
each $R^{Qb}$ is independently selected from the group consisting of F, Cl, Br, I, CN, $SR^4$, $OR^5$, $NR^6R^7$, $COR^8$, $COOR^9$, $CONR^{10}R^{11}$, $C_1$-$C_{12}$-alkyl, $C_1$-$C_{12}$-haloalkyl, heteroaryl, phenyl and naphthyl, where the three last-mentioned radicals may be substituted by one or more identical or different radicals $R^{Qba}$, where
$R^{Qba}$ has one of the meanings indicated for $R^{Qaa}$;
each $R^{Qc}$ is independently selected from the group consisting of $C_1$-$C_{12}$-alkyl, $C_1$-$C_{12}$-haloalkyl, F, Cl, Br, I, CN, $NO_2$, $SR^4$, $OR^5$, $NR^6R^7$, $COR^8$, $COOR^9$, $CONR^{10}R^{11}$, phenyl, $C_3$-$C_{10}$-cycloalkyl and heterocyclyl, where in the two last-mentioned radicals one or two $CH_2$ groups may be replaced by CO;
Q if b is 2, a is 0 and c is 0,
is a divalent linker selected from the group consisting of
$L^5$-$C_1$-$C_{30}$-alkylene-$L^5$, $L^5$-$C_2$-$C_{30}$-alkenylene-$L^5$,
$L^5$-$C_3$-$C_{16}$-cycloalkylene-$L^5$, $L^5$-heterocycloalkylene-$L^5$, $L^5$-$C_6$-$C_{20}$-arylene-$L^5$, $L^5$-heteroarylene-$L^5$,
$L^5$-$C_1$-$C_{30}$-alkylene-$L^6$-$L^5$, $L^5$-$C_2$-$C_{30}$-alkenylene-$L^6$-$L^5$,
$L^5$-$C_3$-$C_{16}$-cycloalkylene-$L^7$-$C_3$-$C_{16}$-cycloalkylene-$L^5$,
$L^5$-$C_3$-$C_{16}$-cycloalkylene-$L^7$-heterocycloalkylene-$L^5$,
$L^5$-$C_3$-$C_{16}$-cycloalkylene-$L^7$-$C_6$-$C_{20}$-arylene-$L^5$,
$L^5$-$C_3$-$C_{16}$-cycloalkylene-$L^7$-heteroarylene-$L^5$,
$L^5$-$C_6$-$C_{20}$-arylene-$L^7$-$C_6$-$C_{20}$-arylene-$L^5$,
$L^5$-$C_6$-$C_{20}$-arylene-$L^7$-heteroarylene-$L^5$,
$L^5$-heteroarylene-$L^7$-heteroarylene-$L^5$,
$L^5$-$C_3$-$C_{16}$-cycloalkylene-$L^7$-$L^8$-$L^7$-$C_3$-$C_{16}$-cycloalkylene-$L^5$,
$L^5$-$C_3$-$C_{16}$-cycloalkylene-$L^7$-$L^8$-$L^7$-heterocycloalkylene-$L^5$,
$L^5$-$C_3$-$C_{16}$-cycloalkylene-$L^7$-$L^8$-$L^7$-$C_6$-$C_{20}$-arylene-$L^5$,
$L^5$-$C_3$-$C_{16}$-cycloalkylene-$L^7$-$L^8$-$L^7$-heteroarylene-$L^5$,
$L^5$-$C_6$-$C_{20}$-arylene-$L^7$-$L^8$-$L^7$-$C_6$-$C_{20}$-arylene-$L^5$,
$L^5$-$C_6$-$C_{20}$-aryl ene-$L^7$-$L^8$-$L^7$-heteroarylene-$L^5$, and
$L^5$-heteroarylene-$L^7$-$L^8$-$L^7$-heteroarylene-$L^5$,
where each alkylene and each alkenylene may be interrupted by one or more identical or different groups $L^9$, and may carry one or more identical or different radicals $R^{Qa}$;
where each cycloalkylene and each heterocycloalkylene may be interrupted by one or more CO groups and may carry one or more identical or different radicals $R^{Qb}$, where each arylene radicand heteroarylene may carry one or more identical or different radicals $R^{Qc}$, where each $L^5$ independently is a single bond, S, O, $NR^6$, CO, C(O)O, OC(O), $NR^{10}CO$ or $CONR^{10}$;

$L^6$ has one of the meanings indicated for $L^2$;
$L^7$ has one of the meanings indicated for L;
$L^8$ has one of the meanings indicated for $L^3$;
$L^9$ has one of the meanings indicated for $L^4$;
or Q if c is 2, a is 0 and b is 0,
is a divalent linker selected from the group consisting of $C_1$-$C_{30}$-alkylene, $C_2$-$C_{30}$-alkenylene, $C_3$-$C_{16}$-cycloalkylene, heterocycloalkylene, $C_6$-$C_{20}$-arylene, heteroarylene, $C_1$-$C_{30}$-alkylene-$L^{10}$, $C_2$-$C_{30}$-alkenylene-$L^{10}$,
$C_3$-$C_{16}$-cycloalkylene-$L^{11}$-$C_3$-$C_{16}$-cycloalkylene,
$C_3$-$C_{16}$-cycloalkylene-$L^{11}$-heterocycloalkylene,
$C_3$-$C_{16}$-cycloalkylene-$L^{11}$-$C_6$-$C_{20}$-arylene,
$C_3$-$C_{16}$-cycloalkylene-$L^{11}$-heteroarylene,
$C_6$-$C_{20}$-arylene-$L^{11}$-$C_6$-$C_{20}$-arylene,
$C_6$-$C_{20}$-arylene-$L^{11}$-heteroarylene, heteroarylene-$L^{11}$-heteroarylene,
$C_3$-$C_{16}$-cycloalkylene-$L^{11}$-$L^{12}$-$L^{11}$-$C_3$-$C_{16}$-cycloalkylene,
$C_3$-$C_{16}$-cycloalkylene-$L^{11}$-$L^{12}$-$L^{11}$-$C_6$-$C_{20}$-arylene,
$C_3$-$C_{16}$-cycloalkylene-$L^{11}$-$L^{12}$-$L^{11}$-heterocycloalkylene,
$C_3$-$C_{16}$-cycloalkylene-$L^{11}$-$L^{12}$-$L^{11}$-heteroarylene,
$C_6$-$C_{20}$-arylene-$L^{11}$-$L^{12}$-$L^{11}$-$C_6$-$C_{20}$-arylene,
$C_6$-$C_{20}$-arylene-$L^{11}$-$L^{12}$-$L^{11}$-heteroarylene, and
heteroarylene-$L^{11}$-$L^{12}$-$L^{11}$-heteroarylene,
where each alkylene and each alkenylene may be interrupted by one or more identical or different groups $L^{13}$, and may carry one or more identical or different radicals $R^{Qa}$;
where each cycloalkylene and each heterocycloalkylene may be interrupted by one or more CO groups and may carry one or more identical or different radicals $R^{Qb}$,
where each arylene and each heteroarylene may carry one or more identical or different radicals $R^{Qc}$,
where
$L^{10}$ has one of the meanings indicated for $L^2$
$L^{11}$ has one of the meanings indicated for $L^1$;
$L^{12}$ has one the meanings indicated for $L^3$;
$L^{13}$ has one of the meanings indicated for $L^4$;
or Q if the sum of a+b+c=3,
is a trivalent linker selected from the group consisting of $C_1$-$C_{30}$-alkanetriyl, $C_2$-$C_{30}$-alkenetriyl, $C_3$-$C_{16}$-cycloalkanetriyl, heterocycloalkanetriyl, $C_6$-$C_{20}$-arenetriyl, heteroarenetriyl, $C_1$-$C_{30}$-alkanetriyl-$L^{14}$-$L^{15}$, $C_2$-$C_{30}$-alkenetriyl-$L^{14}$-$L^{15}$, $C_1$-$C_{30}$-alkylene-$L^{14}$-$L^{16}$, $C_2$-$C_{30}$-alkenetriyl-$L^{14}$-$L^{15}$, $C_2$-$C_{30}$-alkenylene-$L^{14}$-$L^{16}$, $C_3$-$C_{16}$-cycloalkanetriyl-$L^{14}$-$L^{11}$-$C_3$-$C_{16}$-cycloalkylene, $C_3$-$C_{16}$-cycloalkanetriyl-$L^{14}$-$L^{15}$-$C_6$-$C_{20}$-arylene, $C_6$-$C_{20}$-arenetriyl-$L^{14}$-$L^{15}$-$C_6$-$C_{20}$-arylene, and $C_6$-$C_{20}$-arylene-$L^{14}$-$L^{15}$-$C_3$-$C_{16}$-cycloalkanetriyl
where each alkanetriyl, each alkylene, each alkenetriyl and each alkenylene may be interrupted by one or more identical or different groups $L^{17}$ and may carry one or more identical or different radicals $R^{Qa}$;
where each cycloalkanetriyl, each cycloalkylene, each heterocycloalkanetriyl and each heterocycloalkylene may be interrupted by one or more CO groups and may carry one or more identical or different radicals $R^{Qb}$,
where each arenetriyl, each arylene, each heteroarenetriyl and each heteroarylene may carry one or more identical or different radicals $R^{Qc}$, where
$L^{14}$ has one of the meanings indicated for $L^1$;
$L^{15}$ has one of the meanings indicated for $L^2$;
$L^{16}$ is $C_6$-$C_{20}$-arenetriyl, heteroarenetriyl, $C_3$-$C_{20}$-cycloalkanetriyl or heterocycloalkanetriyl, where cycloalkanetriyl and heterocycloalkanetriyl may be interrupted by one or more CO, and may be substituted by one or more identical or different radicals $R^{L16b}$,
where arenetriyl and heteroarenetriyl may be substituted by one or more identical or different radicals $R^{L16c}$, where
$R^{L16b}$ has one of the meanings indicated for $R^{L2b}$;
$R^{L16c}$ has one of the meanings indicated for $R^{L2c}$;
$L^{17}$ has one of the meanings indicated for $L^4$;

Q if the sum of a+b+c=4,
is a tetravalent linker, which is a $C_1$-$C_{30}$-alkanetetrayl which may be interrupted by one or more identical or different groups $L^{18}$ and may carry one or more identical or different radicals 10;
where
$L^{18}$ has one of the meanings given for $L^{17}$;

Q if the sum of a+b+c=6
is a hexavalent linker which is a $C_2$-$C_{30}$-alkanehexayl which may be interrupted by one or more identical or different groups $L^{19}$ and may carry one or more identical or different radicals $R^{Qa}$;
where
$L^{19}$ has one of the meanings given for $L^{17}$;

$R^1$ is $C_1$-$C_{20}$-alkyl, $C_2$-$C_{20}$-alkenyl, $C_2$-$C_{20}$-alkynyl, $C_3$-$C_{20}$-cycloalkyl, heterocyclyl, $C_6$-$C_{20}$-aryl, heteroaryl, $C_1$-$C_{20}$-alkanoyl, $C_3$-$C_{20}$-cycloalkanoyl, $C_2$-$C_{20}$-alkenoyl, $C_6$-$C_{20}$-aroyl, $CSNR^{12}R^{13}$, C(O)$OR^9$ or $CSOR^9$,
where $C_1$-$C_{20}$-alkyl, $C_2$-$C_{20}$-alkenyl and $C_2$-$C_{20}$-alkynyl may be interrupted by one or more identical or different groups selected from the group consisting of —O—, —S—, —N($R^6$)— and CO, and may carry one or more identical or different radicals $R^{1a}$,
where $C_3$-$C_{20}$-cycloalkyl and heterocyclyl may be interrupted by one or more CO groups, and may carry one or more identical or different radicals $R^{1b}$,
where $C_6$-$C_{20}$-aryl and heteroaryl may carry one or more identical or different radicals $R^{1c}$,
where $C_1$-$C_{20}$-alkanoyl and $C_2$-$C_{20}$-alkenoyl may carry one or more identical or different radicals $R^{1a}$,
where $C_3$-$C_{20}$-cycloalkanoyl may carry one or more identical or different radicals $R^{1b}$,
where $C_6$-$C_{20}$-aroyl may carry one or more identical or different radicals $R^{1d}$,
where
each $R^{1a}$ is independently selected from the group consisting of F, Cl, Br, I, CN, $SR^4$, $OR^5$, $NR^6R^7$, $COR^8$, $COOR^9$, $CONR^{10}R^{11}$, $C_3$-$C_{20}$-cycloalkyl which may be interrupted by one or more CO groups, heterocyclyl which may be interrupted by one or more CO groups, heteroaryl and $C_6$-$C_{10}$-aryl where the four last-mentioned radicals may carry one or more identical or different radicals $R^{1aa}$,
where
each $R^{1aa}$ is independently selected from the group consisting of $C_1$-$C_{12}$-alkyl, $C_1$-$C_{12}$-haloalkyl, $C_1$-$C_{12}$-hydroxyalkyl, $C_2$-$C_{12}$-alkenyl, F, Cl, Br, I, CN, $NO_2$, $SR^4$, $OR^5$, $NR^6R^7$, $COR^8$, $COOR^9$ and $CONR^{10}R^{11}$;

each $R^{1b}$ is independently selected from the group consisting of F, Cl, Br, I, CN, $SR^4$, $OR^5$, $NR^6R^7$, $COR^8$, $COOR^9$, $CONR^{10}R^{11}$, $C_1$-$C_{12}$-alkyl, $C_1$-$C_{12}$-hydroxyalkyl, $C_1$-$C_{12}$-haloalkyl, $C_2$-$C_{12}$-alkenyl, heteroaryl and $C_6$-$C_{10}$-aryl where the two last-mentioned radicals may carry one or more identical or different radicals $R^{1ba}$ where
$R^{1ba}$ has one of the meanings indicated for $R^{1aa}$;

each $R^{1c}$ is independently selected from the group consisting of $C_1$-$C_{12}$-alkyl, $C_1$-$C_{12}$-haloalkyl, $C_1$-$C_{12}$-hydroxyalkyl, $C_2$-$C_{12}$-alkenyl, F, Cl, Br, I, CN, $NO_2$, $SR^4$, $OR^5$, $NR^6R^7$, $COR^8$, $COOR^9$, $CONR^{10}R^{11}$, phenyl, heteroaryl, heterocyclyl and $C_3$-$C_{10}$-cycloalkyl where the two last-mentioned radicals may be interrupted by one or two C=O groups and where phenyl, heteroaryl, heterocyclyl and $C_3$-$C_{10}$-cycloalkyl may carry one or more identical or different radicals $R^{1ca}$, where
$R^{1ca}$ one of the meanings indicated for $R^{1aa}$;

each $R^{1d}$ is independently selected from the group consisting of $C_1$-$C_{12}$-alkyl, $C_1$-$C_{12}$-haloalkyl, $C_1$-$C_{12}$-hydroxyalkyl, $C_2$-$C_{12}$-alkenyl, F, Cl, Br, I, CN, $SR^4$, $OR^5$, $NR^6R^7$, $COR^8$, $COOR^9$, $CONR^{10}R^{11}$, $C_3$-$C_{20}$-cycloalkyl which may be interrupted by one or more CO groups, heterocyclyl which may be interrupted by one or more CO groups, $C_6$-$C_{10}$-aryl and heteroaryl where the four last-mentioned radicals may carry one or more radicals $R^{1da}$, where $R^{1da}$ has one of the meanings indicated for $R^{1aa}$;

or
if b is 2, 3, 4 or 6 and/or c is 2, 3, 4 or 6, two radicals $R^1$ together can be a divalent bridging group having 1 to 20 atoms between flanking bonds, or
if b is 2, 3, 4 or 6, at least one group-X—$R^1$ may be bound to a carbon atom or nitrogen atom of Q via a divalent bridging group having 1 to 10 atoms between flanking bonds, $R^2$ is hydrogen, $SR^4$, $OR^5$, $NR^1R^{14}$, $COR^8$, $SO_2R^4$, $COOR^9$, $CONR^{10}R^{11}$, $SO_2NR^{10}R^{11}$, $PO(OR^9)_2$, CN, $C_1$-$C_{16}$-alkyl, $C_2$-$C_{20}$-alkenyl, $C_2$-$C_{20}$-alkynyl, $C_3$-$C_{20}$-cycloalkyl, heterocyclyl, $C_6$-$C_{20}$-aryl, heteroaryl, $C_1$-$C_{20}$-alkanoyl, $C_2$-$C_{20}$-alkenoyl, $C_3$-$C_{20}$-cycloalkanoyl, $C_6$-$C_{20}$-aroyl or a group E,
where $C_1$-$C_{16}$-alkyl, $C_2$-$C_{20}$-alkenyl and $C_2$-$C_{20}$-alkynyl may be interrupted by one or more identical or different groups selected from —O—, —S—, —N($R^6$)— and CO, and may carry one or more identical or different radicals $R^{2a}$,
where $C_3$-$C_{20}$-cycloalkyl and heterocyclyl may be interrupted by one or more CO groups, and may carry one or more identical or different radicals $R^{2b}$,
where $C_6$-$C_{20}$-aryl and heteroaryl may carry one or more identical or different radicals $R^{2c}$,
where $C_1$-$C_{20}$-alkanoyl and $C_2$-$C_{20}$-alkenoyl may carry one or more identical or different radicals $R^{2a}$,
where $C_3$-$C_{20}$-cycloalkanoyl may carry one or more identical or different radicals $R^{2b}$,
where $C_6$-$C_{20}$-aroyl may carry one or more identical or different radicals $R^{2d}$,
where
each $R^{2a}$ is independently selected from the group consisting of F, Cl, Br, I, CN, $SR^4$, $OR^5$, $NR^6R^7$, $COR^8$, $COOR^9$, $CONR^{10}R^{11}$, $C_3$-$C_{20}$-cycloalkyl which may be interrupted by one or more CO groups, heterocyclyl which may be interrupted by one or more CO groups, heteroaryl and $C_6$-$C_{10}$-aryl where the four last-mentioned radicals may carry one or more identical or different radicals $R^{2aa}$,
where
each $R^{2aa}$ is independently selected from the group consisting of $C_1$-$C_{12}$-alkyl, $C_1$-$C_{12}$-haloalkyl, $C_1$-$C_{12}$-hydroxyalkyl, $C_2$-$C_{12}$-alkenyl, F, Cl, Br, I, CN, $NO_2$, $SR^4$, $OR^5$, $NR^6R^7$, $COR^8$, $COOR^9$ and $CONR^{10}R^{11}$;

$R^{2b}$ has one of the meanings indicated for $R^{1b}$;
$R^{2c}$ has one of the meanings indicated for $R^{1c}$;
$R^{2d}$ has one of the meanings indicated for $R^{1d}$;
E is selected from the group consisting of

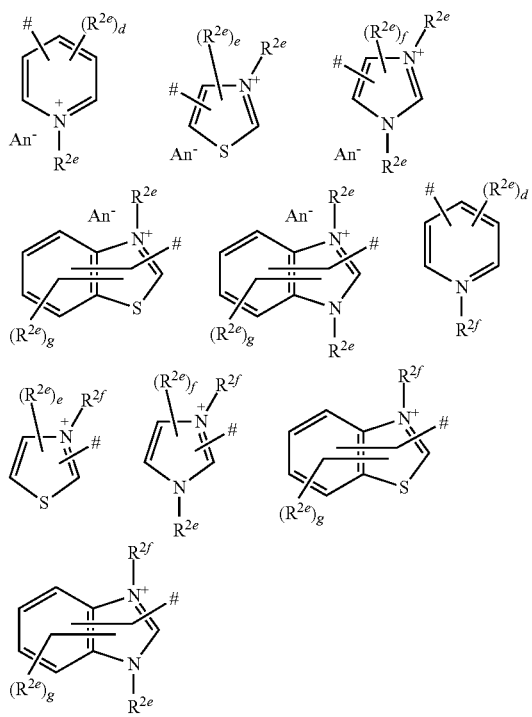

where
is a point of attachment to a remainder of the molecule;
d is 0, 1, 2, 3 or 4;
e is 0, 1, or 2;
f is 0, 1, or 2;
g is 0, 1, 2, 3 or 4;
$R^{2e}$ has one of the meanings indicated for $R^{2c}$;
$R^{2f}$ is $C_1$-$C_{20}$-alkylene-$COO^-$, $C_2$-$C_{20}$-alkenylene-$COO^-$, $C_2$-$C_{20}$-alkynylene-$COO^-$, $C_3$-$C_{20}$-cycloalkylene-$COO^-$, heterocycloalkylene-$COO^-$, $C_6$-$C_{20}$-arylene-$COO^-$, heteroarylene-$COO^-$, $C_1$-$C_{20}$-alkylene-$S(O_2)O^{--}$, $C_2$-$C_{20}$-alkenylene-$S(O_2)O^-$, $C_2$-$C_{20}$-alkynylene-$S(O_2)O^-$, $C_3$-$C_{20}$-cycloalkylene-$S(O_2)O^-$, heterocycloalkylene-$S(O_2)O^-$, $C_6$-$C_{20}$-arylene-$S(O_2)O^-$, heteroarylene-$S(O_2)O^-$, $C_1$-$C_{20}$-alkylene-$OS(O_2)O^{--}$, $C_2$-$C_{20}$-alkenylene-$OS(O_2)O^-$, $C_2$-$C_{20}$-alkynylene-$OS(O_2)O^-$, $C_3$-$C_{20}$-cycloalkylene-$OS(O_2)O^-$, heterocycloalkylene-$OS(O_2)O^-$, $C_6$-$C_{20}$-arylene-$OS(O_2)O^-$ or heteroarylene-$OS(O_2)O^-$
where each alkylene, each alkenyle and each alkynyle may be interrupted by one or more identical or different groups selected from —O—, —S—, —N($R^6$)— and CO, and may carry one or more identical or different radicals $R^{2a}$, where each cycloalkylene and each heterocycloalkylene may be interrupted by one or two groups CO and may carry one or more identical or different radicals $R^{2b}$, where each arylene and each heteroarylene may carry one or more radicals $R^{2c}$, $An^-$ is $Cl^-$, $Br^-$, $SCN^-$, $BF_4^-$, $PF_6^-$, $ClO_4^-$, $SbF_6^-$, $AsF_6^-$, $C_1$-$C_{20}$-alkyl-$COO^-$, $C_1$-$C_{20}$-alkyl-$S(O)_2O^-$, $C_1$-$C_{20}$-alkyl-$OS(O)_2O^-$, $C_6$-$C_{20}$-aryl-$COO^-$, $C_6$-$C_{20}$-aryl-$S(O)_2O^-$ or $C_6$-$C_{20}$-aryl-$OS(O)_2O^-$, where the aryl moiety of the three last-mentioned radicals may be substituted by 1, 2, 3 or 4 identical or different $C_1$-$C_{20}$-alkyl;

or

—$R^2$ together with —X—$R^1$ may be X—($C_1$-$C_{20}$-alkylene)-Y, X—($C_2$-$C_{20}$-alkenylene)-Y, X—($C_3$-$C_{20}$-cycloalkylene)-Y, X-(heterocycloalkylene)-Y, X-(o-phenylene)-Y, X-(o-xylylene)-Y, X-(o-phenylene-$C_1$-$C_{12}$-alkylene)-Y, X—($C_1$-$C_{12}$-alkylene-o-phenylene)-Y, X—(O—$C_1$-$C_{20}$-alkylene)-Y, X—(S—$C_1$-$C_{20}$-alkylene)-Y or X—(N($R^6$))—$C_1$-$C_{20}$-alkylene)-Y, Y being attached to the oxime carbon atom carrying X where each alkylene and alkenylene may comprise one or more identical or different groups selected from the group consisting of O, S, $NR^6$ and CO and may be substituted by one or more radicals $R^{2g}$, where cycloalkylene and heterocycloalkylene may be interrupted by one or more groups CO and may be optionally substituted by one or more identical or different radicals $R^{2h}$, where each phenylene and the phenylene moiety of o-xylylene may be substituted by one or more identical or different radicals $R^{2h}$, where Y is O, S, $NR^{14}$, CO, SC(O), OC(O), C(O)O, $NR^{10}C(O)$, $C(O)NR^{10}$, $NR^{10}SO_2$ or a single bond;

each $R^{2g}$ is independently selected from the group consisting of F, Cl, Br, I, $SR^4$, $OR^5$, $NR^6R^7$, $COR^8$, $COOR^9$, $CONR^{10}R^{11}$, heteroaryl and $C_6$-$C_{10}$-aryl where the two-last-mentioned radicals may carry one or more radicals $R^{2ga}$, where $R^{2ga}$ has one of the meanings indicated for $R^{1aa}$;

each $R^{2h}$ is independently selected from the group consisting of F, Cl, Br, I, $SR^4$, $OR^5$, $NR^6R^7$, $COR^8$, $COOR^9$, $CONR^{10}R^{11}$, $C_1$-$C_{12}$-alkyl, $C_1$-$C_{12}$-haloalkyl, heteroaryl and $C_6$-$C_{10}$-aryl where the two last-mentioned radicals may carry one or more radicals $R^{2ha}$, where $R^{2ha}$ has one of the meanings indicated for $R^{1aa}$;

or if X is S, —$R^2$ together with —S—$R^1$ may be S—C(S)—$NR^{12}$—C(O), or if a is 2, 3, 4 or 6 and/or c is 2, 3, 4 or 6, two radicals $R^2$ together may be a divalent bridging group having 1 to 20 atoms between flanking bonds;

$R^3$ is $C_1$-$C_{20}$-alkyl, $C_2$-$C_{20}$-alkenyl, $C_2$-$C_{20}$-alkynyl, $C_3$-$C_{20}$-cycloalkyl, heterocyclyl, $C_6$-$C_{20}$-aryl or heteroaryl, where $C_1$-$C_{20}$-alkyl, $C_2$-$C_{20}$-alkenyl and $C_2$-$C_{20}$-alkynyl may be interrupted by one or more identical or different groups selected from —O—, —S—, —N($R^6$)— and CO, and may carry one or more identical or different radicals $R^{3a}$, where $C_3$-$C_{20}$-cycloalkyl and heterocyclyl may be interrupted by one or more CO groups, and may carry one or more identical or different radicals $R^{3b}$, where $C_6$-$C_{20}$-aryl and heteroaryl may carry one or more identical or radicals $R^{3c}$, where $R^{3a}$ has one of the meanings indicated for $R^{2a}$;
$R^{3b}$ has one of the meanings indicated for $R^{1b}$;
$R^{3c}$ has one of the meanings indicated for $R^{1c}$;

or

—X—$R^1$ and $R^3$ may together form a divalent radical selected from the group consisting of X—($C_1$-$C_{20}$-alkylene)-Z, X—($C_2$-$C_{20}$-alkenylene)-Z, X—($C_3$-$C_{20}$-cycloalkylene)-Z, X-(heterocycloalkylene)-Z, X-(o-phenylene)-Z, X-(o-xylylene)-Z, X—($C_0$-$C_{12}$-alkylene-heteroarylene-$C_0$-$C_{12}$-alkylene)-Z;

X-(o-phenylene-$C_1$-$C_{12}$-alkylene)-Z,

X—($C_1$-$C_{12}$-alkylene-o-phenylene)-Z and S—C(S)—$NR^{12}$—C(O), where Z is attached to the sulfur atom of the sulfonate group, where each alkylene and each alkenylene may be interrupted by one or more identical or different groups selected from the group consisting of O, S, $NR^6$ and CO and may be substituted by one or more radicals $R^{3g}$, where each cycloalkylene and each heterocycloalkylene may be interrupted by one or more groups CO and may be optionally substituted by one or more identical or different radicals $R^{3h}$, where each phenylene and the phenylene moiety of o-xylylene may be substituted by one or more identical or different radicals $R^{3h}$, where $R^{3g}$ has one of the meanings indicated for $R^{2g}$;
$R^{3h}$ has one of the meanings indicated for $R^{2h}$; and Z is O, S, $NR^{14}$, CO, OC(O), SC(O), C(O)O, $NR^{10}C(O)$, $C(O)NR^{10}$, $NR^{10}(SO_2)$ or a single bond;

each $R^5$ is independently selected from the group consisting of hydrogen, $C_1$-$C_{20}$-alkyl, $C_2$-$C_{12}$-alkenyl, $C_3$-$C_{10}$-cycloalkyl, heterocyclyl, where the two last-mentioned radicals may be interrupted by one or two C=O groups, $C_1$-$C_{20}$-alkyl which may be interrupted by one or more identical or different groups selected from the group consisting of —O—, —S—, —N($C_1$-$C_8$-alkyl)- and CO, and may carry one or more identical or different radicals $R^{5a}$, $C_2$-$C_{12}$-alkenyl which is interrupted by one or more identical or different groups selected from the group consisting of —O—, —S—, and —N($C_1$-$C_8$-alkyl)-, —($CH_2CH_2O)_m$H, with m being 1-20, —($CH_2CH_2O)_n$(CO)—($C_1$-$C_8$-alkyl), with n being 1-20, $C_2$-$C_8$-alkanoyl, $C_3$-$C_6$-alkenoyl, where the two-last mentioned radicals may be substituted by one or more identical or different radicals selected from the group consisting of F, Cl, Br, I, OH and $C_1$-$C_6$-alkoxy, benzoyl which may be substituted by one or more identical or different radicals selected from the group consisting of F, Cl, Br, I, $C_1$-$C_6$-alkyl, OH and $C_1$-$C_6$-alkoxy, phenyl and naphthyl, where the two last-mentioned radicals may be substituted by one or more identical or different radicals $R^{5c}$, wherein phenyl or naphthyl may form a 5- or 6-membered ring with the phenyl ring to which the $OR^5$ is attached via a single bond, $C_1$-$C_4$-alkylene, O, S, $NR^6$ or CO,
where
$R^{5a}$ has one of the meanings indicated for $R^{4a}$;
$R^{5c}$ has one of the meanings indicated for $R^{4c}$.

3. The composition according to claim 1, comprising the compound of the formula I, where X is S.

4. The composition according to claim 1, comprising the compound of the formula I, where X is $NR^{14}$ and
$R^{14}$ is $C_1$-$C_{12}$-alkyl, which may be interrupted by one or more O, S, $NR^6$ or CO and may be substituted by one or more identical or different radicals $R^{14a}$ selected from the group consisting of CN, $COR^E$, $COOR^9$, $CONR^{10}R^{11}$, phenyl and $C_3$-$C_8$-cycloalkyl which may be interrupted by one or two CO groups and where the two last-mentioned radicals may be substituted by one or more identical or different radicals selected from the group consisting of $C_1$-$C_8$-alkyl, $C_1$-$C_4$-haloalkyl, F, Cl, Br, I, CN, $NO_2$, $SR^4$, $OR^5$, $NR^6R^7$, $COR^E$, $COOR^9$ and $CONR^{10}R^{11}$;

$C_2$-$C_{12}$-alkenyl, which may be interrupted by one or more O, S, $NR^6$ or CO and may be substituted by one or more identical or different radicals $R^{14a}$ selected from the group consisting of CN, $COR^E$, $COOR^9$, $CONR^{10}R^{11}$, phenyl and $C_3$-$C_8$-cycloalkyl which may be interrupted by one or two CO groups and where the two last-mentioned radicals may be substituted by one or more identical or different radicals selected from the group consisting of $C_1$-$C_8$-alkyl, $C_1$-$C_4$-haloalkyl, F, Cl, Br, I, CN, $NO_2$, $SR^4$, $OR^5$, $NR^6R^7$, $COR^E$, $COOR^9$ and $CONR^{10}R^{11}$;

$C_3$-$C_{12}$-cycloalkyl, which may be interrupted by one or more CO and may be substituted by one or more identical or different radicals $R^{14b}$ selected from the group consisting of $C_1$-$C_8$-alkyl, CN, $COR^8$, $COOR^9$, $CONR^{10}R^{11}$;

phenyl, which may be substituted by one or more identical or different radicals $R^{14c}$ selected from the group consisting of $C_1$-$C_8$-alkyl, $C_1$-$C_4$-haloalkyl, F, Cl, Br, I, CN, $NO_2$, $SR^4$, $OR^5$, $NR^6R^7$, $COR^8$, $COOR^9$, $CONR^{10}R^{11}$ and phenyl, or two radicals $R^{14}$ together may be a divalent bridging group having 1 to 10 atoms between flanking bonds, where $R^4$, $R^5$, $R^6$, $R^7$, $R^8$, $R^9$, $R^{10}$, $R^{11}$ are as defined in claim 1.

5. The composition according to claim 4 comprising the compound of the formula I, where $R^{14}$ is $C_1$-$C_6$-alkyl, benzyl, phenethyl, $C_2$-$C_6$-alkenyl, $C_1$-$C_4$-alkoxy-$C_1$-$C_4$-alkyl or $C_3$-$C_8$-cycloalkyl-$C_1$-$C_4$-alkyl.

6. The composition according to claim 1 comprising the compound of the formula I, where $R^1$ is $CSNR^{12}R^{13}$; C(O)$OR^9$, $CSOR^9$; $C_3$-$C_{12}$-alkyl; $C_3$-$C_{12}$-cycloalkyl; $C_2$-$C_{12}$-alkenyl; $C_1$-$C_{12}$-alkyl, $C_2$-$C_{12}$-alkenyl, where the two last-mentioned radicals are interrupted by one or more identical or different groups selected from the group consisting of O, S, $NR^6$ and CO and/or which are substituted by one, two or three identical or different radicals $R^{1a}$, $C_3$-$C_{12}$-cycloalkyl, which may be interrupted by one or two CO group(s) and which may be substituted by one, two or three radicals $R^{1b}$, heterocyclyl, which may be interrupted by one or two CO group(s) and which may be substituted by one, two or three radicals $R^{1b}$, phenyl, naphthyl or heteroaryl, where the three last-mentioned radicals may be substituted by one or more identical or different radicals $R^{1c}$, $C_6$-$C_{10}$-aroyl, which may be substituted by one or more identical or different radicals $R^{1d}$, where $R^{1a}$, $R^{1b}$, $R^{1c}$, $R^{1d}$, $R^6$, $R^9$, $R^{12}$, $R^{13}$ are as defined in claim 1.

7. The composition according to claim 6 comprising the compound of the formula I, where $R^1$ is $C_3$-$C_{12}$-alkyl, mercapto-$C_1$-$C_{12}$-alkyl, mercapto-$C_3$-$C_6$-alkyl-S—$C_1$-$C_2$-alkyl, $C_1$-$C_{12}$-alkyl, which is substituted by $OR^5$ with $R^5$ being $C_1$-$C_7$-chloroalkylcarbonyl or —C(=O)—$CH_2$—S—($C_1$-$C_2$-alkyl)-S—C(=NOH)—$C_1$-$C_2$-alkyl, $C_1$-$C_{12}$-alkyl, which is substituted by $SR^4$, where $R^4$ is $C_2$-$C_8$-alkanoyl, $C_1$-$C_{12}$-alkyl which is substituted by $C_1$-$C_4$-alkoxycarbonyl, $C_2$-$C_4$-alkenyl, $C_3$-$C_8$-cycloalkyl, $C_1$-$C_4$-alkoxy-$C_1$-$C_4$-alkoxycarbonyl-$C_1$-$C_2$-alkyl, $C_1$-$C_4$-alkoxycarbonyl-$C_1$-$C_2$-alkyl, benzyl, benzyl which is substituted by $C_1$-$C_4$-alkanoyl-S—$C_1$-$C_2$-alkyl, benzyl which is substituted by $C_1$-$C_4$-alkylthio, benzyl which is substituted by chlorine, benzyl which is substituted by cyano, phenethyl, benzylsulfanyl-$C_1$-$C_4$-alkyl-O—$C_1$-$C_2$-alkyl, phenethylsulfanyl-$C_1$-$C_4$-alkyl-O—$C_1$-$C_2$-alkyl, —$COO(CH_2CH_2O)_v(C_1$-$C_4$-alkyl) with v being 1, 2, 3, 4 or 5, benzoyl, benzoyl which is substituted by one, two or three radicals each independently selected from the group consisting of $C_1$-$C_4$-alkyl and $C_2$-$C_4$-alkenyl, phenyl which is substituted by NH(C(O)—$C_1$-$C_4$-alkyl, 5- or 6-membered saturated or partially unsaturated heterocyclyl comprising besides carbon atoms 1 or 2 heteroatoms selected from the group consisting of O, S, N, NH and N($C_1$-$C_8$-alkyl), phenyl or phenyl which is substituted by one, two or three radicals selected from $C_1$-$C_4$-alkyl, $C_2$-$C_4$-alkenyl and nitro.

8. The composition according to claim 1 comprising the compound of the formula I, where $R^2$ is $COR^8$, $COOR^9$, $CONR^{10}R^{11}$, $C_1$-$C_{12}$-alkyl, $C_2$-$C_{12}$-alkenyl, where the 2 last-mentioned radicals may be substituted by one or more identical or different radicals $R^{2a}$, $C_3$-$C_{12}$-cycloalkyl, which may be substituted by one or more identical or different radicals $R^{2b}$, $C_6$-$C_{10}$-aryl, which may be substituted by one or more identical or different radicals $R^{2c}$; 5- or 6-membered heteroaryl comprising besides carbon atoms one, two or three heteroatoms selected from the group consisting of N, O and S and which may be substituted by one or more radicals $R^{2c}$; or pyridinium of the formula

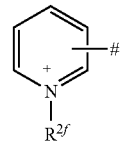

where # is a point of attachment to a remainder of the molecule and $R^{2f}$ is $C_1$-$C_{12}$-alkylene-$COO^-$, $C_1$-$C_{12}$-alkylene-S(O)$_2O^-$ or $C_1$-$C_{12}$-alkylene-OS(O)$_2O^-$,
where $R^{2a}$, $R^{2b}$, $R^{2c}$, $R^8$, $R^9$, $R^{10}$ and $R^{11}$ are as defined in claim 1.

9. The composition according to claim 8 comprising the compound of the formula I, where $R^2$ is $C_1$-$C_6$-alkyl, $C_5$-$C_8$-cycloalkyl, $C_1$-$C_4$-alkoxycarbonyl, $C_1$-$C_4$-haloalkoxycarbonyl, —CO(N—($C_1$-$C_8$-alkyl)$_2$), —C(O)O—$C_1$-$C_4$-alkyl-phenyl, —$COO(CH_2CH_2O)_v(C_1$-$C_4$-alkyl) with v being 1, 2, 3, 4, 5 or 6, morpholinoamide, pyridyl, benzyl which may be substituted by one or two radicals selected from the group consisting of nitro, $C_1$-$C_4$-alkoxy, $C_1$-$C_4$-alkyl and $C_1$-$C_4$-alkoxycarbonyl, phenyl which may be substituted by one or two radicals selected from the group consisting of nitro, $C_1$-$C_4$-alkoxy, $C_2$-$C_4$-alkenyl, $C_1$-$C_4$-alkyl and $C_1$-$C_4$-alkoxycarbonyl, or pyridinium substituted by $C_1$-$C_{12}$-alkylene-S(O)$_2O^-$.

10. The composition according to claim 1 comprising the compound of the formula I, where —X—$R^1$ together with $R^2$ are —X—($C_1$-$C_8$-alkylene)-O—C(O)—, —X—($C_3$-$C_6$-cycloalkylene)-O—C(O)—, —X-(o-phenylene)-O—C(O)—, —X—($C_1$-$C_8$-alkylene)-S—C(O)—, —X—($C_1$-$C_8$-alkylene)-$NR^{10}$—C(O)—, —X—($C_3$-$C_6$-cycloalkylene)-$NR^{10}$—C(O)—, or —X-(o-phenylene)-$NR^{10}$—C(O)—, where each alkylene moiety may be substituted by one or more identical or different radicals $R^{2g}$, each cycloalkylene moiety may be substituted by one or more identical or different radicals $R^{2h}$, and o-phenylene may be substituted by one or more identical or different radicals $R^{2h}$, where $R^{10}$, $R^{2g}$, $R^{2h}$ and X are as defined in claim 1, or -X-$R^1$ together with $R^2$ are —S—C(S)—$NR^{12}$—C(O)—, where $R^{12}$ is as defined in claim 1.

11. The composition according to claim 10 comprising the compound of the formula I, where —X—$R^1$ together with $R^2$ are —X—($C_1$-$C_4$-alkylene)-O—C(O)— and X is S or $NR^{14}$ with $R^{14}$ being $C_1$-$C_6$-alkyl, benzyl, phenethyl, $C_2$-$C_6$-alkenyl, $C_1$-$C_4$-alkoxy-$C_1$-$C_4$-alkyl or $C_3$-$C_8$-cycloalkyl-$C_1$-$C_4$-alkyl.

12. The composition according to claim 1 comprising the compound of the formula I, in which X is $NR^{14}$, $R^1$ and $R^{14}$ together with the nitrogen atom to which they are bound form a 5-, 6- or 7-membered saturated or unsaturated heterocycle which may comprise a further heteroatom or heteroatomic group selected from the group consisting of O, S, NH, N($C_1$-$C_8$-alkyl) and CO and which may carry 1, 2, 3 or 4 substituents independently selected from the group consisting of halogen, cyano, $C_1$-$C_4$-alkyl, nitro, $C_1$-$C_4$-haloalkyl, $C_1$-$C_4$-alkoxy and $C_1$-$C_4$-haloalkoxy.

13. The composition according to claim 1 comprising the compound of the formula I, where $R^3$ is selected from the group consisting of $C_2$-$C_{12}$-alkyl, $C_2$-$C_{12}$-alkenyl, naphthyl-$C_1$-$C_4$-alkyl, phenyl-$C_1$-$C_4$-alkyl, phenyl-$C_1$-$C_4$-alkyl, where the phenyl moiety is substituted by one or more radicals selected from the group consisting of F, Cl, Br, I, $C_1$-$C_4$-alkoxycarbonylsulfanyl-$C_1$-$C_4$-alkyl, $C_1$-$C_4$-alkoxycarbonyl, $C_1$-$C_4$-alkylsulfanyl, $C_1$-$C_4$-haloalkyl, phenoxy, phenyl and cyano, $C_1$-$C_6$-haloalkyl, $C_2$-$C_{12}$-alkyl which is substituted by $C_1$-$C_4$-alkoxycarbonyl, $C_3$-$C_{12}$-cycloalkyl, $C_3$-$C_{12}$-cycloalkyl-$C_1$-$C_{12}$-alkyl, heteroaryl, heterocyclyl, and $C_6$-$C_{10}$-aryl, where each cycloalkyl and heterocyclyl may be interrupted by one or two CO and may be substituted by one or more $C_1$-$C_{12}$-alkyl and where aryl may be substituted by one or more identical or different radicals selected from the group consisting of $C_1$-$C_{12}$-alkyl, $C_1$-$C_4$-haloalkyl, $C_2$-$C_{12}$-alkenyl, F, Cl, Br, I, CN, $NO_2$, $SR^4$, $OR^5$, $NR^6R^7$, $COR^8$, $COOR^9$, $CONR^{10}R^{11}$ and phenyl, where $R^4$, $R^5$, $R^6$, $R^7$, $R^8$, $R^9$, $R^{10}$ and $R^{11}$ are as defined in claim 1.

14. The composition according to claim 13 comprising the compound of the formula I, where $R^3$ is $C_2$-$C_6$-alkyl, $C_1$-$C_6$-fluoroalkyl, $C_2$-$C_6$-alkenyl, $C_3$-$C_{12}$-cycloalkyl-$C_1$-$C_6$-alkyl where the cycloalkyl moiety is interrupted by one or two carbonyl groups and carries 1, 2, 3 or 4 $C_1$-$C_4$-alkyl, 5- or 6-membered saturated heterocyclyl comprising besides carbon atoms 1 or 2 heteroatoms or heteroatomic groups selected from the group consisting of O, S, SO, $SO_2$, NH and N($C_1$-$C_8$-alkyl), thienyl, phenyl, phenyl-$C_1$-$C_2$-alkyl or naphthyl, where the aromatic ring of the 3 last-mentioned radicals may be substituted by one, two, three, four or five substituents selected from the group consisting of fluorine, nitro, $C_1$-$C_4$-alkyl, $C_1$-$C_4$-alkoxy, $C_1$-$C_4$-fluoroalkyl, $C_1$-$C_4$-alkoxycarbonyl and $C_2$-$C_4$-alkenyl.

15. The composition according to claim 1 comprising the compound of the formula I, where a is 2 and b is 0 and c is 0, and Q is L-$C_1$-$C_{30}$-alkylene-L, L-$C_3$-$C_{16}$-cycloalkylene-L, L-heterocycloalkylene-L, L-$C_6$-$C_{20}$-arylene-L, L-$C_1$-$C_{30}$-alkylene-L2-L, L-$C_3$-$C_{16}$-cycloalkylene-L1-$C_3$-$C_{16}$-cycloalkylene-L or L-$C_6$-$C_{20}$-arylene-L1-$C_6$-$C_{20}$-arylene-L, where each alkylene may be interrupted by one or more identical or different non-adjacent phenylene, OC(O), C(O)O, O or S, where each cycloalkylene and each heterocycloalkylene may be interrupted by one or more CO, and where L is a single bond, C(S)O or C(S)NR12; L1 is a single bond, O or S; and L2 is $C_3$-$C_{20}$-cycloalkylene, heterocycloalkylene or $C_6$-$C_{20}$-arylene.

16. The composition according to claim 1 comprising the compound of the formula I, where b is 2 and a is 0 and c is 0, and Q is $L^5$-$C_1$-$C_{30}$-alkylene-$L^5$, $L^5$-$C_3$-$C_{16}$-cycloalkylene-$L^5$, $L^5$-heterocycloalkylene-$L^5$, $L^5$-$C_6$-$C_{20}$-arylene-$L^5$, $L^5$-$C_3$-$C_{16}$-cycloalkylene-$L^7$-$C_3$-$C_{16}$-cycloalkylene-$L^5$ or $L^5$-$C_6$-$C_{20}$-arylene-$L^7$-$C_6$-$C_{20}$-arylene-$L^5$, where alkylene may be interrupted by one or more identical or different non-adjacent O or S, where each cycloalkylene and each heterocycloalkylene may be interrupted by one or more CO, where $L^5$ is a single bond, S, O, $NR^6$, CO, C(O)O, OC(O), $NR^{10}$C(O) or $CONR^{10}$, $L^7$ is a single bond, O or S and $R^6$ and $R^{10}$ are as defined in claim 1.

17. The composition according to claim 1 comprising the compound of the formula I, where c is 2, a is 0 and b is 0 and Q is a divalent linker selected from the group consisting of $C_1$-$C_{30}$-alkylene, $C_3$-$C_{16}$-cycloalkylene, heterocycloalkylene, $C_6$-$C_{20}$-arylene, $C_3$-$C_{16}$-cycloalkylene-$L^{11}$-$C_3$-$C_{16}$-cycloalkylene, $C_6$-$C_{20}$-arylene-$L^{11}$-$C_6$-$C_{20}$-arylene, where alkylene may be interrupted by one or more identical or different non-adjacent O or S, where each cycloalkylene and each heterocycloalkylene may be interrupted by one or more CO, and where $L^{11}$ is a single bond, O or S.

18. The composition according to claim 1 comprising the compound of the formula I, where two of the indices a, b and c are 1, and the remaining index is 0, Q is a divalent linker, which is selected from the group consisting of $C_1$-$C_{30}$-alkylene, $C_3$-$C_{16}$-cycloalkylene, heterocycloalkylene, $C_6$-$C_{20}$-arylene, $C_3$-$C_{16}$-cycloalkylene-$L^{11}$-$C_3$-$C_{16}$-cycloalkylene, $C_6$-$C_{20}$-arylene-$L^{11}$-$C_6$-$C_{20}$-arylene, where alkylene may be interrupted by one or more identical or different non-adjacent phenylene, C(O)O, OC(O); O or S, where each cycloalkylene and each heterocycloalkylene may be interrupted by one or more CO, and where $L^{11}$ is a single bond, O or S.

19. The composition according to claim 1 comprising the compound of the formula I, where the sum of a+b+c is 3, Q is a trivalent linker selected from the group consisting of $C_1$-$C_{30}$-alkanetriyl, $C_3$-$C_{16}$-cycloalkanetriyl, $C_6$-$C_{20}$-arenetriyl, $C_1$-$C_{30}$-alkanetriyl-$L^{14}$-$L^{15}$, $C_1$-$C_{30}$-alkylene-$L^{14}$-$L^{16}$, $C_6$-$C_{20}$-arenetriyl-$L^{14}$-$L^{15}$-$C_6$-$C_{20}$-arylene, and $C_6$-$C_{20}$-arylene-$L^{14}$-$L^{15}$-$C_3$-$C_{16}$-cycloalkanetriyl where each alkanetriyl and each alkylene may be interrupted by one or more identical or different non-adjacent groups selected from the group consisting of O, S, CO and C(O)O and may carry one or more identical or different radicals $R^{Qa}$, where $R^{Qa}$ is as defined in claim 1;

where each cycloalkanetriyl may be interrupted by one or more CO groups, where $L^{14}$ is a single bond, O or S, $L^{15}$ is $C_3$-$C_{20}$-cycloalkylene, heterocycloalkylene or $C_6$-$C_{20}$-arylene and where $L^{16}$ is arenetriyl.

20. The composition of claim 1, where the compound of the formula I has a formula selected from the group consisting of formulae IA.1, IA, IB and IC

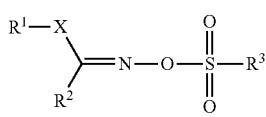  (IA.1)

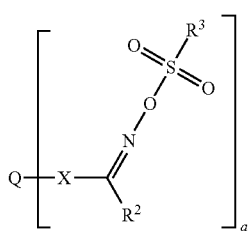  (IA)

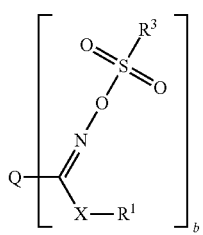  (IB)

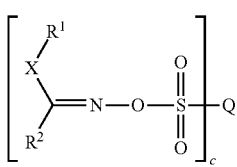  (IC)

where
Q, X, $R^1$ $R^2$ and $R^3$ are as defined in claim 1;
a is 2, 3 or 4;
b is 2 or 3; and
c is 2 or 3.

21. The composition according to claim 20 comprising the compound of the formula IA.1, where
$R^3$ is $C_2$-$C_4$-alkyl, $C_2$-$C_6$-alkenyl, 5- or 6-membered saturated heterocyclyl comprising besides carbon atoms 1 or 2 heteroatoms or heteroatomic groups selected from the group consisting of O, S, SO and $SO_2$, thienyl, phenyl or benzyl where each of the two last mentioned radicals may be unsubstituted or may carry one, two, three, four or five radicals each independently selected from the group consisting of fluorine, nitro, $C_1$-$C_4$-alkyl, $C_1$-$C_4$-alkoxy, fluoroalkyl, $C_1$-$C_4$-alkoxycarbonyl and $C_2$-$C_6$-alkenyl; and
—X—$R^1$ together with $R^2$ are —X—($C_1$-$C_8$-alkylene)-O—C(O)— or —X-(o-phenylene)-O—C(O)— and X is N($C_1$-$C_8$-alkyl), N(benzyl), N($C_1$-$C_4$-alkoxy-$C_1$-$C_4$-alkyl) or S.

22. The composition according to claim 20 comprising the compound of the formula IA.1, where
X is S, N($C_1$-$C_6$-alkyl), N($C_1$-$C_4$-alkoxy-$C_1$-$C_4$-alkyl), N(benzyl), N(phenethyl), N($C_2$-$C_6$-alkenyl) or N($C_3$-$C_8$-cycloalkyl-$C_1$-$C_4$-alkyl);
$R^1$ is $C_3$-$C_6$-alkyl, mercapto-$C_3$-$C_6$-alkyl, mercapto-$C_3$-$C_6$-alkyl-S—$C_1$-$C_2$-alkyl, $C_2$-$C_4$-alkenyl, $C_3$-$C_8$-cycloalkyl-$C_1$-$C_4$-alkyl, $C_1$-$C_4$-alkoxy-$C_1$-$C_4$-alkoxycarbonyl-$C_1$-$C_2$-alkyl, $C_1$-$C_4$-alkoxycarbonyl-$C_1$-$C_2$-alkyl, $C_1$-$C_4$-haloalkoxycarbonyl-$C_1$-$C_2$-alkyl, benzylsulfanyl-$C_1$-$C_4$-alkyl-O—$C_1$-$C_4$-alkyl, phenethylsulfanyl-$C_1$-$C_4$-alkyl-O—$C_1$-$C_4$-alkyl, $C_3$-$C_8$-cycloalkyl, benzyl which is substituted by $C_1$-$C_4$-alkanoyl-S—$C_1$-$C_2$-alkyl, phenyl or benzyl where phenyl and the phenyl moiety of benzyl may be substituted by one, two or three radicals selected from the group consisting of nitro and $C_1$-$C_4$-alkyl;
or
$R^1$ and $R^{14}$ together with the nitrogen atom to which they are bound form a 5-, 6- or 7-membered saturated or unsaturated heterocycle which may have a further heteroatom selected from the group consisting of O, S and N as a ring member;
$R^2$ is $C_1$-$C_6$-alkyl, $C_3$-$C_8$-cycloalkyl, $C_1$-$C_4$-alkoxycarbonyl, $C_1$-$C_4$-haloalkoxycarbonyl, morpholinoamide, —COO($CH_2CH_2O$)$_v$($C_1$-$C_4$-alkyl) with v being 1, 2, 3 or 4,
pyridyl, phenyl which may be substituted by 1, 2 or 3 radicals selected from the group consisting of nitro, $C_1$-$C_4$-alkyl, $C_1$-$C_4$-alkoxycarbonyl or

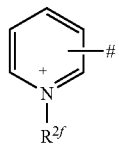

with $R^{2f}$ being $C_1$-$C_{12}$-alkylene-$COO^-$, $C_1$-$C_{12}$-alkylene-S$(O)_2O^-$ or $C_1$-$C_{12}$alkylene-OS$(O)_2O$; and
$R^3$ is $C_1$-$C_4$-alkyl, $C_2$-$C_6$-alkenyl, 5- or 6-membered saturated heterocyclyl comprising besides carbon atoms 1 or 2 heteroatoms or heteroatomic groups selected from the group consisting of O, S, SO and $SO_2$, thienyl, phenyl or benzyl where each of the two last mentioned radicals may be unsubstituted or may carry one, two, three, four or five radicals each independently selected from the group consisting of fluorine, nitro, $C_1$-$C_4$-alkyl, $C_1$-$C_4$-alkoxy, $C_1$-$C_4$-fluoroalkyl, $C_1$-$C_4$-alkoxycarbonyl and $C_2$-$C_6$-alkenyl.

23. The composition according to claim 20 comprising the compound of the formula IA, where
a is 2,
X is S, N($C_1$-$C_6$-alkyl), N($C_1$-$C_4$-alkoxy-$C_1$-$C_4$-alkyl), N(benzyl), N(phenethyl), N($C_2$-$C_6$-alkenyl) or N($C_3$-$C_8$-cycloalkyl-$C_1$-$C_4$-alkyl);
each $R^2$ is independently selected from the group consisting of $C_1$-$C_4$-alkyl, alkoxycarbonyl and morpholinoamide;
each $R^3$ is independently selected from the group consisting of $C_1$-$C_1$-alkyl, $C_2$-$C_6$-alkenyl, 5- or 6-membered saturated heterocyclyl comprising besides carbon atoms 1 or 2 heteroatoms or heteroatomic groups selected from the group consisting of O, S, SO and $SO_2$, thienyl, phenyl or benzyl where each of the two last mentioned radicals may be unsubstituted or may carry one, two, three, four or five radicals each independently selected from the group consisting of fluorine, nitro, $C_1$-$C_4$-alkyl, $C_1$-$C_4$-alkoxy, $C_1$-$C_4$-fluoroalkyl, $C_1$-$C_4$-alkoxycarbonyl and $C_2$-$C_6$-alkenyl;
Q is phenylene, phenylen-S-phenylene, or $C_1$-$C_{10}$-alkylene which may be interrupted by one, two, three or four non-adjacent groups selected from the group consisting of phenylene, O and S.

24. The composition according to claim 23 comprising the compound of the formula IA, where each $R^2$ has a different meaning or each $R^3$ has a different meaning.

25. The composition according to claim 23 comprising the compound of the formula IA, where each $R^2$ has a different meaning and each $R^3$ has a different meaning.

26. The composition according to claim 20 comprising the compound of the formula IA, where
a is 3;
X is S;
each $R^2$ is independently selected from the group consisting of $C_1$-$C_4$-alkyl, $C_1$-$C_4$-alkoxycarbonyl and morpholinoamide;
each $R^3$ is independently selected from the group consisting of $C_1$-$C_4$-alkyl, $C_2$-$C_6$-alkenyl, 5- or 6-membered saturated heterocyclyl comprising besides carbon atoms 1 or 2 heteroatoms or heteroatomic groups selected from the group consisting of O, S, SO and $SO_2$, thienyl, phenyl or benzyl where each of the two last mentioned radicals may be unsubstituted or may carry one, two, three, four or five radicals each independently selected from the group consisting of fluorine, nitro, $C_1$-$C_4$-alkyl, $C_1$-$C_4$-alkoxy, $C_1$-$C_4$-fluoroalkyl, $C_1$-$C_4$-alkoxycarbonyl and $C_2$-$C_6$-alkenyl;
Q is $C_1$-$C_{20}$-alkanetriyl, which may be interrupted by 3, 4, 5, 6, 7, 8, or 9 identical or different groups selected from the group consisting of O, S, $NR^6$, CO, C(O)O.

27. The composition according to claim 20 comprising the compound of the formula IA, where
a is 4;
X is S;
each $R^2$ is independently selected from the group consisting of $C_1$-$C_4$-alkyl or $C_1$-$C_4$-alkoxycarbonyl;
each $R^3$ is independently selected from the group consisting of $C_1$-$C_4$-alkyl, $C_2$-$C_6$-alkenyl, 5- or 6-membered saturated heterocyclyl comprising besides carbon atoms 1 or 2 heteroatoms or heteroatomic groups selected from the group consisting of O, S, SO and $SO_2$, thienyl, phenyl or benzyl where each of the two last mentioned radicals may be unsubstituted or may carry one, two, three, four or five radicals each independently selected from the group consisting of fluorine, nitro, $C_1$-$C_4$-alkyl, $C_1$-$C_4$-alkoxy, $C_1$-$C_4$-fluoroalkyl, $C_1$-$C_4$-alkoxycarbonyl and $C_2$-$C_6$-alkenyl;
Q is $C_1$-$C_{20}$-alkanetetrayl, which may be interrupted by 3, 4, 5, 6, 7, 8, or 9 identical or different groups selected from the group consisting of O, S, $NR^6$, CO and C(O)O.

28. The composition according to claim 20 comprising the compound of the formula IB, where
b is 2;
X is S;
each $R^1$ is independently selected from the group consisting of $C_1$-$C_6$-alkyl, mercapto-$C_3$-$C_6$-alkyl, mercapto-$C_3$-$C_6$-alkyl-S—$C_1$-$C_2$-alkyl, $C_2$-$C_4$-alkenyl, benzyl, alkoxycarbonyl-$C_1$-$C_4$-alkyl; phenyl; and phenyl which is substituted by one or two $C_1$-$C_4$-alkyl or $C_2$-$C_4$-alkenyl; and
Q is $C_1$-$C_{10}$-alkylene which may be interrupted by one, two, three or four more non-adjacent atoms selected from the group consisting of O and S.

29. The composition according to claim 20 comprising the compound of the formula IC, where
c is 2;
X is S;
each $R^1$ is independently selected from the group consisting of $C_1$-$C_6$-alkyl, $C_3$-$C_8$-alkenyl, mercapto-$C_3$-$C_6$-alkyl, mercapto-$C_3$-$C_6$-alkyl-S—$C_1$-$C_2$-alkyl, $C_1$-$C_4$-alkoxy-$C_1$-$C_4$-alkoxycarbonyl-$C_1$-$C_2$-alkyl, $C_1$-$C_4$-alkoxycarbonyl-$C_1$-$C_2$-alkyl, $C_2$-$C_4$-alkenyl, $C_3$-$C_8$-cycloalkyl, $C_3$-$C_8$-cycloalkyl-$C_1$-$C_2$-alkyl, phenyl-$C_1$-$C_4$-alkylsulfanyl-$C_1$-$C_4$-alkyl-O—$C_1$-$C_4$-alkyl, phenethylsulfanyl-$C_1$-$C_4$-alkyl-O—$C_1$-$C_2$-alkyl, phenyl, phenethyl and benzyl where each phenyl moiety in the five last mentioned radicals may be substituted by one, two or three radicals selected from the group consisting of nitro, $C_2$-$C_4$-alkenyl and $C_1$-$C_4$-alkyl;
each $R^2$ is independently selected from the group consisting of $C_1$-$C_6$-alkyl, $C_1$-$C_4$-alkoxycarbonyl, morpholinoamide and $C_1$-$C_4$-alkoxy-$C_1$-$C_4$-alkoxy-$C_1$-$C_4$-alkoxycarbonyl; and
Q is $C_1$-$C_{10}$-alkylene which may be interrupted by one, two, three or four non-adjacent groups selected from the group consisting of O, S, phenylene and naphthylene.

30. The composition according to claim 1 comprising the compound of the formula I having a formula ID, where
Q is a divalent linker selected from the group consisting of phenylene, phenylen-S-phenylene, or $C_1$-$C_{10}$-alkylene which may be interrupted by one, two, three or four non-adjacent groups selected from the group consisting of phenylene, O and S;
each X is S;
$R^1$ is $C_3$-$C_6$-alkyl, mercapto-$C_3$-$C_6$-alkyl, mercapto-$C_3$-$C_6$-alkyl-S—$C_1$-$C_2$-alkyl, $C_2$-$C_4$-alkenyl, $C_3$-$C_8$-cycloalkyl-$C_1$-$C_4$-alkyl, $C_1$-$C_4$-alkoxy-$C_1$-$C_4$-alkoxycarbonyl-$C_1$-$C_2$-alkyl, $C_1$-$C_4$-alkoxycarbonyl-$C_1$-$C_2$-alkyl, benzylsulfanyl-$C_1$-$C_4$-alkyl-O—$C_1$-$C_4$-alkyl, phenethylsulfanyl-$C_1$-$C_4$-alkyl-O—$C_1$-$C_4$-alkyl, phenyl or benzyl where phenyl and the phenyl moiety of benzyl may be substituted by one, two or three radicals selected from the group consisting of nitro and $C_1$-$C_4$-alkyl, benzyl which is substituted by $C_1$-$C_4$-alkanoyl-S—$C_1$-$C_2$-alkyl;
each $R^2$ is independently selected from the group consisting of $C_1$-$C_6$-alkyl, $C_1$-$C_4$-alkoxycarbonyl, morpholinoamide and $C_1$-$C_4$-alkoxy-$C_1$-$C_4$-alkoxy-$C_1$-$C_4$-alkoxycarbonyl; and
$R^3$ is $C_1$-$C_4$-alkyl, $C_2$-$C_6$-alkenyl, 5- or 6-membered saturated heterocyclyl comprising besides carbon atoms 1 or 2 heteroatoms or heteroatomic groups selected from the group consisting of O, S, SO and $SO_2$, thienyl, phenyl or benzyl where each of the two last mentioned radicals may be unsubstituted or may carry one, two, three, four or five radicals each independently selected from the group consisting of fluorine, nitro, $C_1$-$C_4$-alkyl, $C_1$-$C_4$-alkoxy, $C_1$-$C_4$-fluoroalkyl, $C_1$-$C_4$-alkoxycarbonyl and $C_2$-$C_6$-alkenyl.

31. The composition according to claim 1, where the at least one ethylenically unsaturated, polymerizable compound is an acrylate monomer.

32. The composition according to claim 1, further comprising a photoinitiator (c).

33. The composition according to claim 1, further comprising a binder polymer (d).

34. The composition according to claim 1, further comprising at least one further component (e), selected from the group consisting of
(e1) a pigment,
(e2) a dye,
(e3) a filler,
(e4) a dispersant,
(e5) a sensitizer, and
(e6) a thermosetting compound, being different from the compound of the formula (I) and any binder polymer (d).

35. The composition according to claim 1, further comprising at least one additive (f) selected from the group consisting of a solvent, a reinforcing material, a flow control assistant, a UV stabilizer, a heat stabilizer, a weatherability improver, a rheology modifier, a flame retardant, an antioxidant, a discoloration inhibitor, a biocide, an antistatic agent, a plasticizer, a lubricant, a slip additive, a wetting agent, a film-forming assistant, an adhesion promoter, a corrosion inhibitor, an antifreeze agent, a defoamer, and a mold release agent.

36. The polymerizable composition according to claim 1 comprising:
(a) at least one oxime sulfonate compound of the formula I,
(b) at least one acrylate monomer,
(c) at least one photoinitiator, and
(d) at least one alkaline developable resin.

37. A method for preparing a polymeric material, the method comprising
free-radical polymerizing the polymerizable composition of claim 1.

38. A method for producing a color filter, the method comprising:
I) applying the photopolymerizable composition of claim 1, further comprising a colorant, to a substrate,
II) optionally drying the applied composition,
III) exposing the composition on the substrate to UV light through a mask,
IV) developing the exposed composition layer with an alkali developer to form a colored pattern, and
V) post baking the exposed composition at an elevated temperature.

39. A coated substrate, coated on at least one surface with the composition according to claim 1.

40. A color filter comprising red, green and blue picture elements and a black matrix, all comprising a photosensitive resin and a pigment on a transparent substrate, wherein a transparent electrode is disposed either on a surface of the substrate or on a surface of the color filter layer, wherein the photosensitive resin comprises a polyfunctional acrylate monomer, an organic polymer binder, a photopolymerization initiator and a thermal curing promoter comprising an oxime sulfonate compound
wherein the oxime sulfonate compound is represented by formula I:

$$QA_aB_bC_c \quad (I)$$

where
a is 0, 1, 2, 3, 4 or 6;
b is 0, 1, 2, 3, 4 or 6; and
c is 0, 1, 2, 3, 4 or 6;
where the sum of a+b+c is 1, 2, 3, 4 or 6 where
A is a group

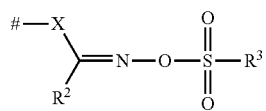

(A)

B is a group

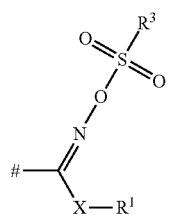

(B)

C is a group

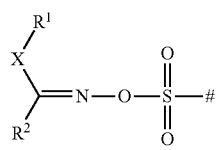

(C)

where
# denotes a point of attachment to Q;
X is S, $SO_2$ or $NR^{14}$;
Q if a is 1, b is 0 and c is 0,
is a radical $R^1$;
or
Q if a is 2, b is 0 and c is 0
is a divalent linker selected from the group consisting of
L-$C_1$-$C_{30}$-alkylene-L,
L-$C_2$-$C_{30}$-alkenylene-L, L-$C_3$-$C_{16}$-cycloalkylene-L, L-heterocycloalkylene-L, L-$C_6$-$C_{20}$-arylene-L, L-heteroarylene-L, L-$C_1$-$C_{30}$-alkylene-$L^2$-L,
L-$C_2$-$C_{30}$-alkenylene-$L^2$-L,
L-$C_3$-$C_{16}$-cycloalkylene-$L^1$-$C_3$-$C_{16}$-cycloalkylene-L,
L-$C_3$-$C_{16}$-cycloalkylene-$L^1$-heterocycloalkylene-L,
L-$C_3$-$C_{16}$-cycloalkylene-$L^1$-$C_6$-$C_{20}$-arylene-L
L-$C_3$-$C_{16}$-cycloalkylene-$L^1$-heteroarylene-L,
L-$C_6$-$C_{20}$-arylene-$L^1$-$C_6$-$C_{20}$-arylene-L,
L-$C_6$-$C_{20}$-arylene-$L^1$-heteroarylene-L,
L-heteroarylene-$L^1$-heteroarylene-L,
L-$C_3$-$C_{16}$-cycloalkylene-$L^1$-$L^3$-$L^1$-$C_3$-$C_{16}$-cycloalkylene-L,
L-$C_3$-$C_{16}$-cycloalkylene-$L^1$-$L^3$-$L^1$-heterocycloalkylene-L,
L-$C_3$-$C_{16}$-cycloalkylene-$L^1$-$L^3$-$L^1$-$C_6$-$C_{20}$-arylene-L
L-$C_3$-$C_{16}$-cycloalkylene-$L^1$-$L^3$-$L^1$-heteroarylene-L,
L-$C_6$-$C_{20}$-arylene-$L^1$-$L^3$-$L^1$-$C_6$-$C_{20}$-arylene-L,
L-$C_6$-$C_{20}$-arylene-$L^1$-$L^3$-$L^1$-heteroarylene-L, and
L-heteroarylene-$L^1$-$L^3$-$L^1$-heteroarylene-L,
where each alkylene and each alkenylene may be interrupted by one or more identical or different nonadjacent groups $L^4$, and may carry one or more identical or different radicals $R^{Qa}$;
where each cycloalkylene and each heterocycloalkylene may be interrupted by one or more CO groups and may carry one or more identical or different radicals $R^{Qb}$, where each arylene and each heteroarylene may carry one or more identical or different radicals $R^{Qc}$,
where
each L is independently selected from the group consisting of a single bond, C(S)O, and C(S)NR$^{12}$;
  each $L^1$ is independently selected from the group consisting of a single bond, O, S, NR$^{14}$, CO, OC(O), C(O)O, C(S)O, OC(S), C(O)NR$^{10}$, NR$^{10}$C(O), C(S)NR$^{12}$, NR$^{12}$C(S) and NR$^{10}$SO$_2$;
  $L^2$ is $C_3$-$C_{20}$-cycloalkylene, heterocycloalkylene, $C_6$-$C_{20}$-arylene or heteroarylene, where cycloalkylene and heterocycloalkylene may be interrupted by one or more CO and may be substituted by one or more identical or different radicals $R^{L2b}$,
where arylene and heteroarylene may be substituted by one or more identical or different radicals $R^{L2c}$, where
  each $R^{L2b}$ is independently selected from the group consisting of $C_1$-$C_{12}$-alkyl, $C_1$-$C_{12}$-haloalkyl, F, Cl, Br, I, CN, NO$_2$, SR$^4$, OR$^5$, NR$^6$R$^7$, COR$^8$, COOR$^9$, CONR$^{10}$R$^{11}$ and phenyl;
  $R^{L2c}$ has one of the meanings indicated for $R^{L2b}$;
  $L^3$ is selected from the group consisting of $C_1$-$C_{30}$-alkylene, $C_2$-$C_{30}$-alkenylene, $C_3$-$C_{20}$-cycloalkylene, heterocycloalkylene, $C_6$-$C_{20}$-arylene and heteroarylene,
where alkylene and alkenylene may be interrupted by one or more identical or different O, S, NR$^6$ or CO and may carry one or more identical or different radicals $R^{L3a}$,
where cycloalkylene and heterocycloalkylene may be interrupted by one or more CO, and may be substituted by one or more identical or different radicals $R^{L3b}$,
where arylene and heteroarylene may be substituted by one or more identical or different radicals $R^{L3c}$, where
  each $R^{L3a}$ is independently selected from the group consisting of F, Cl, Br, I, CN, SR$^4$, OR$^5$, NR$^6$R$^7$, COR$^8$, COOR$^9$, CONR$^{10}$R$^{11}$, $C_3$-$C_{10}$-cycloalkyl, heterocyclyl, heteroaryl, phenyl and naphthyl, where the five last-mentioned radicals may be substituted by one or more identical or different radicals $R^{3aa}$, where
$R^{3aa}$ has one of the meanings indicated for $R^{L2b}$;
  $R^{L3b}$ has one of the meanings indicated for $R^{L2b}$;
  $R^{L3c}$ has one of the meanings indicated for $R^{L2c}$;
  each $L^4$ is independently selected from the group consisting of O, S, NR$^6$, CO, C(O)O, OC(O), C(O)NR$^{10}$, NR$^{10}$C(O), C(S)NR$^{12}$, NR$^{12}$C(S), NR$^{10}$SO$_2$, $C_3$-$C_{20}$-cycloalkylene, heterocycloalkylene, $C_6$-$C_{20}$-arylene, and heteroarylene,
where cycloalkylene and heterocycloalkylene may be interrupted by one or more CO, and may be substituted by one or more identical or different radicals $R^{L4b}$,
where arylene and heteroarylene may be substituted by one or more identical or different radicals $R^{L4c}$, where
  $R^{L4b}$ has one of the meanings indicated for $R^{L2b}$; and
  $R^{L4c}$ has one of the meanings indicated for $R^{L2c}$;
each $R^{Qa}$ is independently selected from the group consisting of F, Cl, Br, I, CN, SR$^4$, OR$^5$, NR$^6$R$^7$, COR$^8$, COOR$^9$, CONR$^{10}$R$^{11}$,
$C_3$-$C_{10}$-cycloalkyl which may be interrupted by one or two CO groups,
heterocyclyl which may be interrupted by one or two CO groups,
heteroaryl, phenyl and naphthyl, where the five last-mentioned radicals may be substituted by one or more identical or different radicals $R^{Qaa}$, where
  each $R^{Qaa}$ is independently selected from the group consisting of $C_1$-$C_{12}$-alkyl, haloalkyl, F, Cl, Br, I, CN, NO$_2$, SR$^4$, OR$^5$, NR$^6$R$^7$, COR$^8$, COOR$^9$ and CONR$^{10}$R$^{11}$;

each $R^{Qb}$ is independently selected from the group consisting of F, Cl, Br, I, CN, SR$^4$, OR$^5$, NR$^6$R$^7$, COR$^8$, COOR$^9$, CONR$^{10}$R$^{11}$, $C_1$-$C_{12}$-alkyl, $C_1$-$C_{12}$-haloalkyl, heteroaryl, phenyl and naphthyl, where the three last-mentioned radicals may be substituted by one or more identical or different radicals $R^{Qba}$, where
$R^{Qba}$ has one of the meanings indicated for $R^{Qaa}$;
  each $R^{Qc}$ is independently selected from the group consisting of $C_1$-$C_{12}$-alkyl, $C_1$-$C_{12}$-haloalkyl, F, Cl, Br, I, CN, NO$_2$, SR$^4$, OR$^5$, NR$^6$R$^7$, COR$^5$, COOR$^5$, CONR$^{19}$R$^{11}$, phenyl, $C_3$-$C_{10}$-cycloalkyl and heterocyclyl, where in the two last-mentioned radicals one or two CH$_2$ groups may be replaced by CO;
  Q if b is 2, a is 0 and c is 0,
is a divalent linker, which is selected from the group consisting of
$L^5$-$C_1$-$C_{30}$-alkylene-$L^5$, $L^5$-$C_2$-$C_{30}$-alkenylene-$L^5$, $L^5$-$C_3$-$C_{16}$-cycloalkylene-$L^5$, $L^5$-heterocycloalkylene-$L^5$, $L^5$-$C_6$-$C_{20}$-arylene-$L^5$, $L^5$-heteroarylene-$L^5$,
$L^5$-$C_1$-$C_{30}$-alkylene-$L^6$-$L^5$, $L^5$-$C_2$-$C_{30}$-alkenylene-$L^6$-$L^5$,
$L^5$-$C_3$-$C_{16}$-cycloalkylene-$L^7$-$C_3$-$C_{16}$-cycloalkylene-$L^5$,
$L^5$-$C_3$-$C_{16}$-cycloalkylene-$L^7$-heterocycloalkylene-$L^5$,
$L^5$-$C_3$-$C_{16}$-cycloalkylene-$L^7$-$C_6$-$C_{20}$-arylene-$L^5$,
$L^5$-$C_3$-$C_{16}$-cycloalkylene-$L^7$-heteroarylene-$L^5$,
$L^5$-$C_6$-$C_{20}$-arylene-$L^7$-$C_6$-$C_{20}$-arylene-$L^5$,
$L^5$-$C_6$-$C_{20}$-arylene-$L^7$-heteroarylene-$L^5$,
$L^5$-heteroarylene-$L^7$-heteroarylene-$L^5$,
$L^5$-$C_3$-$C_{16}$-cycloalkylene-$L^7$-$L^8$-$L^7$-$C_3$-$C_{16}$-cycloalkylene-$L^5$,
$L^5$-$C_3$-$C_{16}$-cycloalkylene-$L^7$-$L^8$-$L^7$-heterocycloalkylene-$L^5$,
$L^5$-$C_3$-$C_{16}$-cycloalkylene-$L^7$-$L^8$-$L^7$-$C_6$-$C_{20}$-arylene-$L^5$,
$L^5$-$C_3$-$C_{16}$-cycloalkylene-$L^7$-$L^8$-$L^7$-heteroarylene-$L^5$,
$L^5$-$C_6$-$C_{20}$-arylene-$L^7$-$L^8$-$L^7$-$C_6$-$C_{20}$-arylene-$L^5$,
$L^5$-$C_6$-$C_{20}$-arylene-$L^7$-$L^8$-$L^7$-heteroarylene-$L^5$,
$L^5$-heteroarylene-$L^7$-$L^8$-$L^7$-heteroarylene-$L^5$,
where each alkylene and each alkenylene may be interrupted by one or more identical or different groups $L^9$, and may carry one or more identical or different radicals $R^{Qa}$;
where each cycloalkylene and each heterocycloalkylene may be interrupted by one or more CO groups and may carry one or more identical or different radicals $R^{Qb}$,
where each arylene and each heteroarylene may carry one or more identical or different radicals $R^{Qc}$, where
each $L^5$ independently is a single bond, S, O, NR$^6$, CO, C(O)O, OC(O), NR$^{10}$CO or CONR$^{10}$;
  $L^6$ has one of the meanings indicated for $L^2$;
  $L^7$ has one of the meanings indicated for $L^1$;
  $L^8$ has one of the meanings indicated for $L^3$;
  $L^9$ has one of the meanings indicated for $L^4$;
or
  Q if c is 2, a is 0 and b is 0,
is a divalent linker selected from the group consisting of $C_1$-$C_{30}$-alkylene, $C_2$-$C_{30}$-alkenylene, $C_3$-$C_{16}$-cycloalkylene, heterocycloalkylene, $C_6$-$C_{20}$-arylene, heteroarylene, $C_1$-$C_{30}$-alkylene-$L^{10}$, $C_2$-$C_{30}$-alkenylene-$L^{10}$,
$C_3$-$C_{16}$-cycloalkylene-$L^{11}$-$C_3$-$C_{16}$-cycloalkylene,
$C_3$-$C_{16}$-cycloalkylene-$L^{11}$-heterocycloalkylene,
$C_3$-$C_{16}$-cycloalkylene-$L^{11}$-$C_6$-$C_{20}$-arylene,
$C_3$-$C_{16}$-cycloalkylene-$L^{11}$-heteroarylene,
$C_6$-$C_{20}$-arylene-$L^{11}$-$C_6$-$C_{20}$-arylene,
$C_6$-$C_{20}$-arylene-$L^{11}$-heteroarylene, heteroarylene-$L^{11}$-heteroarylene,
$C_3$-$C_{16}$-cycloalkylene-$L^{11}$-$L^{12}$-$L^{11}$-$C_3$-$C_6$-cycloalkylene,
$C_3$-$C_{16}$-cycloalkylene-$L^{11}$-$L^{12}$-$L^{11}$-$C_6$-$C_{20}$-arylene,
$C_3$-$C_{16}$-cycloalkylene-$L^{11}$-$L^{12}$-$L^{11}$-heterocycloalkylene,
$C_3$-$C_{16}$-cycloalkylene-$L^{11}$-$L^{12}$-$L^{11}$-heteroarylene,
$C_6$-$C_{20}$-arylene-$L^{11}$-$L^{12}$-$L^{11}$-$C_6$-$C_{20}$-arylene, $C_6$-$C_{20}$-arylene-$L^{11}$-$L^{12}$-$L^{11}$-heteroarylene, and
heteroarylene-$L^{11}$-$L^{12}$-$L^{11}$-heteroarylene,
where each alkylene and each alkenylene may be interrupted by one or more identical or different groups $L^{13}$, and may carry one or more identical or different radicals $R^{Qa}$;
where each cycloalkylene and each heterocycloalkylene may be interrupted by one or more CO groups and may carry one or more identical or different radicals $R^{Qb}$,
where each arylene and each heteroarylene may carry one or more identical or different radicals $R^{Qc}$,
where
$L^{10}$ has one of the meanings indicated for $L^2$
$L^{11}$ has one of the meanings indicated for $L^1$;
$L^{12}$ has one the meanings indicated for $L^3$;
$L^{13}$ has one of the meanings indicated for $L^4$;
or
Q if two of the indices a, b or c are each 1 and the remaining index is 0, the sum of a+b+c being 2,
is a divalent linker selected from the group consisting of $C_1$-$C_{30}$-alkylene, $C_2$-$C_{30}$-alkenylene, $C_3$-$C_{16}$-cycloalkylene, heterocycloalkylene, $C_6$-$C_{20}$-arylene, heteroarylene, $C_1$-$C_{30}$-alkylene-$L^{10}$, $C_2$-$C_{30}$-alkenylene-$L^{10}$,
$C_3$-$C_{16}$-cycloalkylene-$L^{11}$-$C_3$-$C_{16}$-cycloalkylene,
$C_3$-$C_{16}$-cycloalkylene-$L^{11}$-heterocycloalkylene,
$C_3$-$C_{16}$-cycloalkylene-$L^{11}$-$C_6$-$C_{20}$-arylene,
$C_3$-$C_{16}$-cycloalkylene-$L^{11}$-heteroarylene,
$C_6$-$C_{20}$-arylene-$L^{11}$-$C_6$-$C_{20}$-arylene,
$C_6$-$C_{20}$-arylene-$L^{11}$-heteroarylene, heteroarylene-$L^{11}$-heteroarylene,
$C_3$-$C_{16}$-cycloalkylene-$L^{11}$-$L^{12}$-$L^{11}$-$C_3$-$C_{16}$-cycloalkylene,
$C_3$-$C_{16}$-cycloalkylene-$L^{11}$-$L^{12}$-$L^{11}$-$C_6$-$C_{20}$-arylene,
$C_3$-$C_{16}$-cycloalkylene-$L^{11}$-$L^{12}$-$L^{11}$-heterocycloalkylene,
$C_3$-$C_{16}$-cycloalkylene-$L^{11}$-$L^{12}$-$L^{11}$-heteroarylene,
$C_6$-$C_{20}$-arylene-$L^{11}$-$L^{12}$-$L^{11}$-$C_6$-$C_{20}$-arylene,
$C_6$-$C_{20}$-arylene-$L^{11}$-$L^{12}$-$L^{11}$-heteroarylene, and
heteroarylene-$L^{11}$-$L^{12}$-$L^{11}$-heteroarylene,
where each alkylene and each alkenylene may be interrupted by one or more identical or different groups $L^{13}$, and may carry one or more identical or different radicals $R^{Qa}$;
where each cycloalkylene and each heterocycloalkylene may be interrupted by one or more CO groups and may carry one or more identical or different radicals $R^{Qb}$,
where each arylene and each heteroarylene may carry one or more identical or different radicals $R^{Qc}$,
where
$L^{10}$ has one of the meanings indicated for $L^2$
$L^{11}$ has one of the meanings indicated for $L^1$;
$L^{12}$ has one the meanings indicated for $L^3$;
$L^{13}$ has one of the meanings indicated for $L^4$;
or
Q if the sum of a+b+c=3,
is a trivalent linker selected from the group consisting of $C_1$-$C_{30}$-alkanetriyl, $C_2$-$C_{30}$-alkenetriyl, $C_3$-$C_{16}$-cycloalkanetriyl, heterocycloalkanetriyl, $C_6$-$C_{20}$-arenetriyl, heteroarenetriyl, $C_1$-$C_{30}$-alkanetriyl-$L^{14}$-$L^{15}$, $C_2$-$C_{30}$-alkenetriyl-$L^{14}$-$L^{15}$, $C_1$-$C_{30}$-alkylene-$L^{14}$-$L^{16}$, $C_2$-$C_{30}$-alkenetriyl-$L^{14}$-$L^{15}$, $C_2$-$C_{30}$-alkenylene-$L^{14}$-$L^{16}$, $C_3$-$C_{16}$-cycloalkanetriyl-$L^{14}$-$L^{11}$-$C_3$-$C_{16}$-cycloalkylene, $C_3$-$C_{16}$-cycloalkanetriyl-$L^{14}$-$L^{15}$-$C_6$-$C_{20}$-arylene, $C_6$-$C_{20}$-arenetriyl-$L^{14}$-$L^{15}$-$C_6$-$C_{20}$-arylene, and $C_6$-$C_{20}$-arylene-$L^{14}$-$L^{15}$-$C_3$-$C_{16}$-cycloalkanetriyl
where each alkanetriyl, each alkylene, each alkenetriyl and each alkenylene may be interrupted by one or more identical or different groups $L^{17}$ and may carry one or more identical or different radicals $R^{Qa}$;
where each cycloalkanetriyl, each cycloalkylene, each heterocycloalkanetriyl and each heterocycloalkylene may be interrupted by one or more CO groups and may carry one or more identical or different radicals $R^{Qa}$,
where each arenetriyl, each arylene, each heteroarenetriyl and each heteroarylene may carry one or more identical or different radicals $R^{Qc}$, where
$L^{14}$ has one of the meanings indicated for $L^1$;
$L^{15}$ has one of the meanings indicated for $L^2$;
$L^{16}$ is $C_6$-$C_{20}$-arenetriyl, heteroarenetriyl, $C_3$-$C_{20}$-cycloalkanetriyl or heterocycloalkanetriyl, where cycloalkanetriyl and heterocycloalkanetriyl may be interrupted by one or more CO, and may be substituted by one or more identical or different radicals $R^{L16b}$,
where arenetriyl and heteroarenetriyl may be substituted by one or more identical or different radicals $R^{L16c}$, where
$R^{L16b}$ has one of the meanings indicated for $R^{L2b}$;
$R^{L16c}$ has one of the meanings indicated for $R^{L2c}$;
$L^{17}$ has one of the meanings indicated for $L^4$;
Q if the sum of a+b+c=4,
is a tetravalent linker, which is a $C_1$-$C_{30}$-alkanetetrayl which may be interrupted by one or more identical or different groups $L^{18}$ and may carry one or more identical or different radicals $R^{Qa}$;
where
$L^{18}$ has one of the meanings given for $L^{17}$;
Q if the sum of a+b+c=6
is a hexavalent linker which is a $C_2$-$C_{30}$-alkanehexayl which may be interrupted by one or more identical or different groups $L^{19}$ and may carry one or more identical or different radicals $R^{Qa}$;
where
$L^{19}$ has one of the meanings given for $L^{17}$;
$R^1$ is $C_1$-$C_{20}$-alkyl, $C_2$-$C_{20}$-alkenyl, $C_2$-$C_{20}$-alkynyl, $C_3$-$C_{20}$-cycloalkyl, heterocyclyl, $C_6$-$C_{20}$-aryl, heteroaryl, $C_1$-$C_{20}$-alkanoyl, $C_3$-$C_{20}$-cycloalkanoyl, $C_2$-$C_{20}$-alkenoyl, $C_6$-$C_{20}$-aroyl, $CSNR^{12}R^{13}$, $C(O)OR^9$ or $CSOR^9$,
where $C_1$-$C_{20}$-alkyl, $C_2$-$C_{20}$-alkenyl and $C_2$-$C_{20}$-alkynyl may be interrupted by one or more identical or different groups selected —O—, —S—, —N($R^6$)— and CO, and may carry one or more identical or different radicals $R^{1a}$,
where $C_3$-$C_{20}$-cycloalkyl and heterocyclyl may be interrupted by one or more CO groups, and may carry one or more identical or different radicals $R^{1b}$,
where $C_6$-$C_{20}$-aryl and heteroaryl may carry one or more identical or different radicals $R^{1c}$, where $C_1$-$C_{20}$-alkanoyl and $C_2$-$C_{20}$-alkenoyl may carry one or more identical or different radicals $R^{1a}$,
where $C_3$-$C_{20}$-cycloalkanoyl may carry one or more identical or different radicals $R^{1b}$,
where $C_6$-$C_{20}$-aroyl may carry one or more identical or different radicals $R^{1d}$, where
each $R^{1a}$ is independently selected from the group consisting of F, Cl, Br, I, CN, $SR^4$, $OR^5$, $NR^6R^7$, $COR^8$, $COOR^9$, $CONR^{10}R^{11}$, $C_3$-$C_{20}$-cycloalkyl which may be interrupted by one or more CO groups, heterocyclyl which may be interrupted by one or more CO groups, heteroaryl and $C_6$-$C_{10}$-aryl where the four last-mentioned radicals may carry one or more identical or different radicals $R^{1aa}$,
where
each $R^{1aa}$ is independently selected from the group consisting of $C_1$-$C_{12}$-alkyl, $C_1$-$C_{12}$-alkyl which may be interrupted by one or more groups selected from the group consisting of CO, O, S, C(O)O, OC(O), C(O)S and SC(O), $C_1$-$C_{12}$-haloalkyl, $C_1$-$C_{12}$-hydroxyalkyl, $C_2$-$C_{12}$-alkenyl, F, Cl, Br, I, $NO_2$, $SR^4$, $OR^5$, $NR^6R^7$, $COR^8$, $COOR^9$ and $CONR^{10}R^{11}$;

each $R^{1b}$ is independently selected from the group consisting of F, Cl, Br, I, CN, $SR^4$, $OR^5$, $NR^6R^7$, $COR^8$, $COOR^9$, $CONR^{10}R^{11}$, $C_1$-$C_{12}$-alkyl, $C_1$-$C_{12}$-hydroxyalkyl, haloalkyl, $C_2$-$C_{12}$-alkenyl, heteroaryl and $C_6$-$C_{10}$-aryl where the two last-mentioned radicals may carry one or more identical or different radicals $R^{1ba}$, where $R^{1ba}$ has s one of the meanings indicated for $R^{1ba}$;

each $R^{1c}$ is independently selected from the group consisting of $C_1$-$C_{12}$-alkyl, $C_1$-$C_{12}$-haloalkyl, $C_1$-$C_{12}$-hydroxyalkyl, $C_2$-$C_{12}$-alkenyl, F, Cl, Br, I, CN, $NO_2$, $SR^4$, $OR^5$, $NR^6R^7$, $COR^8$, $COOR^9$, $CONR^{10}R^{11}$, phenyl, heteroaryl, heterocyclyl and $C_3$-$C_{10}$-cycloalkyl where the two last-mentioned radicals may be interrupted by one or two C=O groups and where phenyl, heteroaryl, heterocyclyl and $C_3$-$C_{10}$-cycloalkyl may carry one or more identical or different radicals $R^{1ca}$, where $R^{1ca}$ has one of the meanings indicated for $R^{1aa}$;

each $R^{1d}$ is independently selected from the group consisting of $C_1$-$C_{12}$-alkyl, $C_1$-$C_{12}$-haloalkyl, $C_1$-$C_{12}$-hydroxyalkyl, $C_2$-$C_{12}$-alkenyl, F, Cl, Br, I, CN, $SR^4$, $OR^5$, $NR^6R^7$, $COR^8$, $COOR^9$, $CONR^{10}R^{11}$, $C_3$-$C_{20}$-cycloalkyl which may be interrupted by one or more CO groups, heterocyclyl which may be interrupted by one or more CO groups, $C_6$-$C_{10}$-aryl and heteroaryl where the four last-mentioned radicals may carry one or more radicals $R^{1da}$, where $R^{1da}$ has s one of the meanings indicated for $R^{1aa}$;

or
if b is 2, 3, 4 or 6 and/or c is 2, 3, 4 or 6, two radicals $R^1$ together can be a divalent bridging group having 1 to 20 atoms between the flanking bonds, or
if b is 2, 3, 4 or 6, at least one group-X—$R^1$ may be bound to a carbon atom or nitrogen atom of Q via a divalent bridging group having 1 to 10 atoms between the flanking bonds, $R^2$ is hydrogen, $SR^4$, $OR^5$, $COR^8$, $SO_2R^4$, $COOR^9$, $CONR^{10}R^{11}$, $SO_2NR^{10}R^{11}$, $PO(OR^9)_2$, CN, $C_1$-$C_{16}$-alkyl, $C_2$-$C_{20}$-alkenyl, $C_2$-$C_{20}$-alkynyl, $C_3$-$C_{20}$-cycloalkyl, heterocyclyl, $C_6$-$C_{20}$-aryl, heteroaryl, $C_1$-$C_{20}$-alkanoyl, $C_2$-$C_{20}$-alkenoyl, $C_3$-$C_{20}$-cycloalkanoyl, $C_6$-$C_{20}$-aroyl or a group E, where $C_1$-$C_{16}$-alkyl, $C_2$-$C_{20}$-alkenyl and $C_2$-$C_{20}$-alkynyl may be interrupted by one or more identical or different groups selected from —O—, —S—, —N($R^6$)— and CO, and may carry one or more identical or different radicals $R^{2a}$, where $C_3$-$C_{20}$-cycloalkyl and heterocyclyl may be interrupted by one or more CO groups, and may carry one or more identical or different radicals $R^{2b}$, where $C_6$-$C_{20}$-aryl and heteroaryl may carry one or more identical or different radicals $R^{2c}$, where $C_1$-$C_{20}$-alkanoyl and $C_2$-$C_{20}$-alkenoyl may carry one or more identical or different radicals $R^{2a}$, where $C_3$-$C_{20}$-cycloalkanoyl may carry one or more identical or different radicals $R^{2b}$, where $C_6$-$C_{20}$-aroyl may carry one or more identical or different radicals $R^{2d}$, where each $R^{2a}$ is independently selected from the group consisting of F, Cl, Br, I, CN, $SR^4$, $OR^5$, $NR^6R^7$, $COR^8$, $COOR^9$, $CONR^{10}R^{11}$, $C_3$-$C_{20}$-cycloalkyl which may be interrupted by one or more CO groups, heterocyclyl which may be interrupted by one or more CO groups, heteroaryl and $C_6$-$C_{10}$-aryl where the four last-mentioned radicals may carry one or more identical or different radicals $R^{2aa}$, where
each $R^{2aa}$ is independently selected from the group consisting of $C_1$-$C_{12}$-alkyl, $C_1$-$C_{12}$-alkyl which may be interrupted by one or more groups selected from the group consisting of CO, O, S, C(O)O, OC(O), C(O)S and SC(O), $C_1$-$C_{12}$-haloalkyl, $C_1$-$C_{12}$-hydroxyalkyl, $C_2$-$C_{12}$-alkenyl, phenyl, F, Cl, Br, I, CN, $NO_2$, $SR^4$, $OR^5$, $NR^6R^7$, $COR^8$, $COOR^9$ and $CONR^{10}R^{11}$;

$R^{2b}$ has one of the meanings indicated for $R^{1b}$;
$R^{2c}$ has one of the meanings indicated for $R^{1c}$;
$R^{2d}$ has one of the meanings indicated for $R^{1d}$;
E is selected from the group consisting of

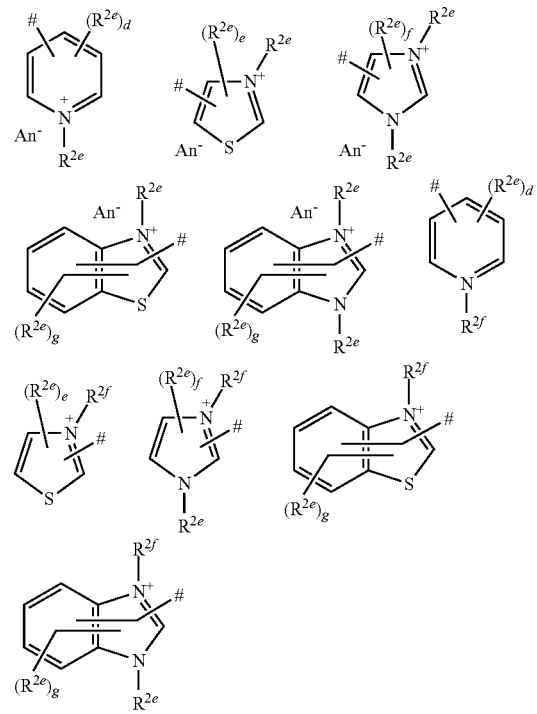

where
is a point of attachment to a remainder of the molecule;
d is 0, 1, 2, 3 or 4;
e is 0, 1, or 2;
f is 0, 1, or 2;
g is 0, 1, 2, 3 or 4;
$R^{2e}$ has one of the meanings indicated for $R^{2c}$;
$R^{2f}$ is $C_1$-$C_{20}$-alkylene-$COO^-$, $C_2$-$C_{20}$-alkenylene-$COO^-$, $C_2$-$C_{20}$-alkynylene-$COO^-$, $C_3$-$C_{20}$-cycloalkylene-$COO^-$, heterocycloalkylene-$COO^-$, $C_6$-$C_{20}$-arylene-$COO^-$, heteroarylene-$COO^-$, $C_1$-$C_{20}$-alkylene-$S(O_2)O^-$, $C_2$-$C_{20}$-alkenylene-$S(O_2)O^-$, $C_2$-$C_{20}$-alkynylene-$S(O_2)O^-$, $C_3$-$C_{20}$-cycloalkylene-$S(O_2)O^-$, heterocycloalkylene-$S(O_2)O^-$, $C_6$-$C_{20}$-arylene-$S(O_2)O^-$, heteroarylene-$S(O_2)O^-$, $C_1$-$C_{20}$-alkylene-$OS(O_2)O^-$, $C_2$-$C_{20}$-alkenylene-$OS(O_2)O^-$, $C_2$-$C_{20}$-alkynylene-$OS(O_2)O^-$, $C_3$-$C_{20}$-cycloalkylene-$OS(O_2)O^-$, heterocycloalkylene-$OS(O_2)O^-$, $C_6$-$C_{20}$-arylene-$OS(O_2)O^-$ or heteroarylene-$OS(O_2)O^-$ where each alkylene, each alkenyle and each alkynyle may be interrupted by one or more identical or different groups selected from the group consisting of —O—, —S—, —N($R^6$)— and CO, and may carry one or more identical or different radicals $R^{2a}$, where each cycloalkylene and each heterocycloalkylene may be interrupted by one or two groups CO and may carry one or more identical or different radicals $R^{2b}$, where each arylene and each heteroarylene may carry one or more radicals $R^{2c}$, An$^-$ is Cl$^+$, Br$^-$, I$^-$, SCN$^-$, BF$_4^-$, PF$_6^-$, ClO$_4^-$, SbF$_6^-$, AsF$_6^-$, $C_1$-$C_{20}$-alkyl-COO$^-$, $C_1$-$C_{20}$-alkyl-S(O)$_2$O$^-$, $C_1$-$C_{20}$-alkyl-OS(O)$_2$O$^-$, $C_6$-$C_{20}$-aryl-COO$^-$, $C_6$-$C_{20}$-aryl-S(O)$_2$O$^-$ or $C_6$-$C_{20}$-aryl-OS(O)$_2$O$^-$, where the aryl moiety of the three last-mentioned radicals may be substituted by 1, 2, 3 or 4 identical or different $C_1$-$C_{20}$-alkyl;

or

—$R^2$ together with —X—$R^1$ may be X—($C_1$-$C_{20}$-alkylene)-Y, X—($C_2$-$C_{20}$-alkenylene)-Y, X—($C_3$-$C_{20}$-cycloalkylene)-Y, X-(heterocycloalkylene)-Y, X-(o-phenylene)-Y, X-(o-xylylene)-Y, X-(o-phenylene-$C_1$-$C_{12}$-alkylene)-Y, X—($C_1$-$C_{12}$-alkylene-o-phenylene)-Y, X—(O—$C_1$-$C_{20}$-alkylene)-Y, X—(S—$C_1$-$C_{20}$-alkylene)-Y or X—(N(R$^6$)—$C_1$-$C_{20}$-alkylene)-Y, Y being attached to the oxime carbon atom carrying X where each alkylene and alkenylene may comprise one or more identical or different groups selected from the group consisting of O, S, NR$^6$ and CO and may be substituted by one or more radicals $R^{2g}$, where cycloalkylene and heterocycloalkylene may be interrupted by one or more groups CO and may be optionally substituted by one or more identical or different radicals $R^{2h}$, where each phenylene and the phenylene moiety of o-xylylene may be substituted by one or more identical or different radicals $R^{2h}$, where Y is O, S, NR$^{14}$, CO, SC(O), OC(O), C(O)O, NR$^{10}$C(O), C(O)NR$^{10}$, NR$^{10}$SO$_2$ or a single bond;

each $R^{2g}$ is independently selected from the group consisting of F, Cl, Br, I, SR$^4$, OR$^5$, NR$^6$R$^7$, COR$^8$, COOR$^9$, CONR$^{10}$R$^{11}$, heteroaryl and $C_6$-$C_{10}$-aryl where the two-last-mentioned radicals may carry one or more radicals $R^{2ga}$, where $R^{2ga}$ is phenoxy or has one of the meanings indicated for $R^{1aa}$;

each $R^{2h}$ is independently selected from the group consisting of F, Cl, Br, I, SR$^4$, OR$^5$, NR$^6$R$^7$, COR$^8$, COOR$^9$, CONR$^{10}$R$^{11}$, $C_1$-$C_{12}$-alkyl, $C_1$-$C_{12}$-haloalkyl, heteroaryl and $C_6$-$C_{10}$-aryl where the two last-mentioned radicals may carry one or more radicals $R^{2ha}$, where $R^{2ha}$ has one of the meanings indicated for $R^{1aa}$;

or if X is S, —$R^2$ together with —S—$R^1$ may be S—C(S)—NR$^{12}$—C(O) or S—C(=NOR$^{15}$)—NR$^{12}$—C(O), where $R^{15}$ is hydrogen or phenylsulfonyl where the phenyl moiety may be substituted by $C_1$-$C_4$-alkyl or $C_1$-$C_4$-alkoxy;

or if a is 2, 3, 4 or 6 and/or c is 2, 3, 4 or 6, two radicals $R^2$ together may be a divalent bridging group having 1 to 20 atoms between flanking bonds;

$R^3$ is $C_1$-$C_{20}$-alkyl, $C_2$-$C_{20}$-alkenyl, $C_2$-$C_{20}$-alkynyl, $C_3$-$C_{20}$-cycloalkyl, heterocyclyl, $C_6$-$C_{20}$-aryl or heteroaryl, where $C_1$-$C_{20}$-alkyl, $C_2$-$C_{20}$-alkenyl and $C_2$-$C_{20}$-alkynyl may be interrupted by one or more identical or different groups selected from —O—, —S—, —N(R$^6$)— and CO, and may carry one or more identical or different radicals $R^{3a}$, where $C_3$-$C_{20}$-cycloalkyl and heterocyclyl may be interrupted by one or more CO groups, and may carry one or more identical or different radicals $R^{3b}$, where $C_6$-$C_{20}$-aryl and heteroaryl may carry one or more identical or radicals $R^{3c}$, where $R^{3a}$ has one of the meanings indicated for $R^{2a}$;
$R^{3b}$ has one of the meanings indicated for $R^{1b}$;
$R^{3c}$ has one of the meanings indicated for $R^{1c}$;

or

—X—$R^1$ and $R^3$ may together form a divalent radical selected from the group consisting of X—($C_1$-$C_{20}$-alkylene)-Z, X—($C_2$-$C_{20}$-alkenylene)-Z, X—($C_3$-$C_{20}$-cycloalkylene)-Z, X-(heterocycloalkylene)-Z, X-(o-phenylene)-Z, X-(o-xylylene)-Z, X—($C_0$-$C_{12}$-alkylene-heteroarylene-$C_0$-$C_{12}$-alkylene)-Z;

X-(o-phenylene-$C_1$-$C_{12}$-alkylene)-Z,

X—($C_1$-$C_{12}$-alkylene-o-phenylene)-Z and S—C(S)—NR$^{12}$—C(O), where Z is attached to the sulfur atom of the sulfonate group, where each alkylene and each alkenylene may be interrupted by one or more identical or different groups selected from the group consisting of O, S, NR$^6$ and CO, and may be substituted by one or more radicals $R^{3g}$, where each cycloalkylene and each heterocycloalkylene may be interrupted by one or more groups CO and may be optionally substituted by one or more identical or different radicals $R^{3h}$, where each phenylene and the phenylene moiety of o-xylylene may be substituted by one or more identical or different radicals $R^{3h}$, where $R^{3g}$ has one of the meanings indicated for $R^{2g}$;

$R^{3h}$ has one of the meanings indicated for $R^{2h}$; and

Z is O, S, NR$^{14}$, CO, OC(O), SC(O), C(O)O, NR$^{10}$C(O), C(O)NR$^{10}$, NR$^{10}$(SO$_2$) or a single bond;

each $R^4$ is independently selected from the group consisting of hydrogen, $C_1$-$C_{20}$-alkyl, $C_2$-$C_{12}$-alkenyl, $C_3$-$C_{10}$-cycloalkyl, heterocyclyl, where the two last-mentioned radicals may be interrupted by one or more C=O groups, $C_1$-$C_{20}$-alkyl which is interrupted by one or more identical or different groups selected from the group consisting of —O—, —S—, —N($C_1$-$C_8$-alkyl)- and CO, and may carry one or more identical or different radicals $R^{4a}$, $C_2$-$C_{12}$-alkenyl which is interrupted by one or more identical or different groups selected from the group consisting of —O—, —S—, and —N($C_1$-$C_8$-alkyl)-, —(CH$_2$CH$_2$O)$_m$H, with m being 1-20, —(CH$_2$CH$_2$O)$_n$(CO)—($C_1$-$C_8$-alkyl), with n being 1-20, $C_2$-$C_8$-alkanoyl, $C_3$-$C_6$-alkenoyl, where the two-last mentioned radicals may be substituted by one or more identical or different radicals selected from the group consisting of F, Cl, Br, I, OH and $C_1$-$C_6$-alkoxy, benzoyl which may be substituted by one or more identical or different radicals selected from the group consisting of F, Cl, Br, I, $C_1$-$C_6$-alkyl, OH and $C_1$-$C_6$-alkoxy, phenyl and naphthyl, where the two last-mentioned radicals may be substituted by one or more identical or different radicals $R^{4c}$, wherein phenyl or naphthyl may form a 5- or 6-membered ring with the phenyl ring to which the SR$^4$ is attached via a single bond, $C_1$-$C_4$-alkylene, O, S, NR$^6$ or CO, where each $R^{4a}$ is independently selected from the group consisting of F, Cl, Br, I, $C_3$-$C_{10}$-cycloalkyl, heterocyclyl, phenyl, OH, SH, CN, $C_3$-$C_6$-alkenoxy, OCH$_2$CH$_2$CN, OCH$_2$CH$_2$(CO)O($C_1$-$C_8$-alkyl), O(CO)—($C_1$-$C_8$-alkyl), O(CO)-phenyl, (CO)OH and (CO)O($C_1$-$C_8$-alkyl);

each $R^{4c}$ is independently selected from the group consisting of F, Cl, Br, I, $C_1$-$C_{12}$-alkyl, $C_1$-$C_{12}$-haloalkyl, $C_1$-$C_{12}$-alkoxy, phenyl-$C_1$-$C_3$-alkoxy, phenoxy, $C_1$-$C_{12}$-alkylsulfanyl, phenylsulfanyl, —(CO)O($C_1$-$C_8$-alkyl), (CO)N($C_1$-$C_8$-alkyl)$_2$ and phenyl;

each $R^5$ is independently selected from the group consisting of hydrogen, $C_1$-$C_{20}$-alkyl, $C_2$-$C_{12}$-alkenyl, $C_3$-$C_{10}$-cycloalkyl, heterocyclyl, where the two last-mentioned radicals may be interrupted by one or two C=O groups, $C_1$-$C_{20}$-alkyl which may be interrupted by one or more identical or different groups selected from the group consisting of —O—, —S—, —N($C_1$-$C_8$-alkyl)- and CO, and may carry one or more identical or different radicals $R^{5a}$, $C_2$-$C_{12}$-alkenyl which is interrupted by one or more identical or different groups selected from the group consisting of —O—, —S—, and —N($C_1$-$C_8$-alkyl)-, —($CH_2CH_2O$)$_m$H, with m being 1-20, —($CH_2CH_2O$)$_n$(CO)—($C_1$-$C_8$-alkyl), with n being 1-20, $C_2$-$C_8$-alkanoyl, $C_3$-$C_6$-alkenoyl, where the two-last mentioned radicals may be substituted by one or more identical or different radicals selected from the group consisting of F, Cl, Br, I, OH and $C_1$-$C_6$-alkoxy, $C_2$-$C_8$-alkanoyl, which is interrupted by one or more identical or different groups selected from —O— and —S— and may be substituted by one or more identical or different radicals selected from the group consisting of hydroxyaminylene (=N—OH), F, Cl, Br, I, OH and $C_1$-$C_6$-alkoxy, benzoyl which may be substituted by one or more identical or different radicals selected from the group consisting of F, Cl, Br, I, $C_1$-$C_6$-alkyl, OH and $C_1$-$C_6$-alkoxy, phenyl and naphthyl, where the two last-mentioned radicals may be substituted by one or more identical or different radicals $R^{5c}$, wherein phenyl or naphthyl may form a 5- or 6-membered ring with the phenyl ring to which the OR is attached via a single bond, $C_1$-$C_4$-alkylene, O, S, $NR^6$ or CO, where $R^{5a}$ has one of the meanings indicated for $R^{4a}$;

$R^{5c}$ has one of the meanings indicated for $R^{4c}$;

$R^6$, $R^{10}$ and $R^{12}$ are each independently selected from the group consisting of hydrogen, $OR^5$, $C_1$-$C_{20}$-alkyl, $C_2$-$C_{12}$-alkenyl, $C_3$-$C_{10}$-cycloalkyl, heterocyclyl, where the two last-mentioned radicals may be interrupted by one or two C=O groups, $C_1$-$C_{20}$-alkyl which may be interrupted by one or more identical or different groups selected from the group consisting of —O—, —S—, —N($C_1$-$C_8$-alkyl)- and CO, and may carry one or more identical or different radicals $R^{6a}$, $C_2$-$C_{12}$-alkenyl which is interrupted by one or more identical or different groups selected from —O—, —S—, and —N($C_1$-$C_8$-alkyl)-, —($CH_2CH_2O$)$_o$H, with o being 1-20, —($CH_2CH_2O$)$_p$(CO)—($C_1$-$C_8$-alkyl), with p being 1-20, $C_2$-$C_8$-alkanoyl, $C_3$-$C_6$-alkenoyl, where the two-last mentioned radicals may be substituted by one or more identical or different radicals selected from the group consisting of F, Cl, Br, I, OH and $C_1$-$C_6$-alkoxy, benzoyl which may be substituted by one or more identical or different radicals selected from the group consisting of F, Cl, Br, I, $C_1$-$C_6$-alkyl, —OH and $C_1$-$C_6$-alkoxy, phenyl and naphthyl, where the two last-mentioned radicals may be substituted by one or more identical or different radicals $R^{6c}$, where $R^{6a}$ has one of the meanings indicated for $R^{4a}$;

$R^{6c}$ has one of the meanings indicated for $R^{4c}$;

or two radicals $R^6$ together may be a divalent bridging group having 1 to 20 atoms between flanking bonds;

or two radicals $R^{10}$ together may be a divalent bridging group having 1 to 20 atoms between flanking bonds;

or two radicals $R^{12}$ together may be a divalent bridging group having 1 to 20 atoms between flanking bonds;

$R^7$, $R^{11}$ and $R^{13}$ are each independently selected from the group consisting of $OR^5$, $C_1$-$C_{20}$-alkyl, $C_2$-$C_{12}$-alkenyl, $C_3$-$C_{10}$-cycloalkyl, heterocyclyl, where in the two last-mentioned radicals one or two $CH_2$ groups may be replaced by a C=O group, $C_1$-$C_{20}$-alkyl which may be interrupted by one or more identical or different groups selected from —O—, —S—, —N($C_1$-$C_8$-alkyl)- and CO, and may carry one or more identical or different radicals $R^{7a}$, $C_2$-$C_{12}$-alkenyl which is interrupted by one or more identical or different groups selected from the group consisting of —O—, —S—, and —N($C_1$-$C_8$-alkyl)-, —($CH_2CH_2O$)$_q$H, with q being 1-20, —($CH_2CH_2O$)$_r$(CO)—($C_1$-$C_8$-alkyl), with r being 1-20, $C_2$-$C_8$-alkanoyl, $C_3$-$C_6$-alkenoyl, where the two-last mentioned radicals may be substituted by one or more identical or different radicals selected from the group consisting of F, Cl, Br, I, OH and $C_1$-$C_6$-alkoxy, benzoyl which may be substituted by one or more identical or different radicals selected from the group consisting of F, Cl, Br, I, $C_1$-$C_6$-alkyl, OH and $C_1$-$C_6$-alkoxy, phenyl and naphthyl, where the two last-mentioned radicals may be substituted by one or more identical or different radicals $R^{7c}$, where $R^{7a}$ has one of the meanings indicated for $R^{4a}$;

$R^{7c}$ has one of the meanings indicated for $R^{4c}$;

or $R^6$ and $R^7$ together with the nitrogen atom to which they are attached form a saturated 5-, 6- or 7-membered nitrogen heterocycle which may have a further heteroatom or heteroatomic group selected from the group consisting of CO, O, S and N($C_1$-$C_8$-alkyl) as a ring member and which may carry 1, 2, 3 or 4 $C_1$-$C_4$-alkyl;

or $R^{10}$ and $R^{11}$ together with the nitrogen atom to which they are attached form a saturated 5-, 6- or 7-membered nitrogen heterocycle which may have a further heteroatom or heteroatomic group selected from the group consisting of CO, O, S and N($C_1$-$C_8$-alkyl) as a ring member and which may carry 1, 2, 3 or 4 $C_1$-$C_4$-alkyl;

or $R^{12}$ and $R^{13}$ together with the nitrogen atom to which they are attached form a saturated 5-, 6- or 7-membered nitrogen heterocycle which may have a further heteroatom or heteroatomic group selected from the group consisting of CO, O, S and N($C_1$-$C_8$-alkyl) as a ring member and which may carry 1, 2, 3 or 4 $C_1$-$C_4$-alkyl;

each $R^8$ is independently selected from the group consisting of hydrogen, $C_1$-$C_{20}$-alkyl, $C_2$-$C_{12}$-alkenyl, $C_3$-$C_{10}$-cycloalkyl, heterocyclyl, where the two last-mentioned radicals may be interrupted by one or more C=O groups, $C_1$-$C_{70}$-alkyl which may be interrupted by one or more identical or different groups selected from the group consisting of —O—, —S—, —N($C_1$-$C_8$-alkyl)- and CO, and may carry one or more identical or different radicals $R^{8a}$, $C_2$-$C_{12}$-alkenyl which is interrupted by one or more identical or different groups selected from —O—, —S—, and —N($C_1$-$C_8$-alkyl)-, —($CH_2CH_2O$)$_s$H, with s being 1-20, —($CH_2CH_2O$)$_t$(CO)—($C_1$-$C_8$-alkyl), with t being 1-20, $C_6$-$C_{20}$-aryl and heteroaryl, where the two last-mentioned radicals may be substituted by one or more identical or different radicals $R^{8c}$, where $R^{8a}$ has one of the meanings indicated for $R^{4a}$;

$R^{8c}$ has one of the meanings indicated for $R^{4c}$;

each $R^9$ is independently selected from the group consisting of hydrogen, $C_1$-$C_{20}$-alkyl, $C_2$-$C_{12}$-alkenyl, $C_3$-$C_{10}$-cycloalkyl, heterocyclyl, where the two last-mentioned radicals may be interrupted by one or more C=O groups, $C_1$-$C_{20}$-alkyl which may be interrupted by one or more identical or different groups selected from the group consisting of —O—, —S—, —N($C_1$-$C_8$-alkyl)- and CO, and may carry one or more identical or different radicals $R^{9a}$, $C_2$-$C_{12}$-alkenyl which is interrupted by one or more identical or different groups selected from —O—, —S—, and —N($C_1$-$C_8$-alkyl)-, —(CH$_2$CH$_2$O)$_u$H, with u being 1-20, —(CH$_2$CH$_2$O)$_v$(CO)—(C$_1$-C$_8$-alkyl), with v being 1-20, phenyl and naphthyl, where the two last-mentioned radicals may be substituted by one or more identical or different radicals $R^{9c}$, where $R^{9a}$ has one of the meanings indicated for $R^{4a}$;

$R^{9c}$ has one of the meanings indicated for $R^{4c}$;

$R^{14}$ is $C_1$-$C_{20}$-alkyl, $C_2$-$C_{20}$-alkenyl, $C_2$-$C_{20}$-alkynyl, $C_3$-$C_{20}$-cycloalkyl, heterocyclyl, $C_6$-$C_{20}$-aryl, heteroaryl, $C_1$-$C_{20}$-alkanoyl, $C_2$-$C_{20}$-alkenoyl, $C_3$-$C_{20}$-cycloalkanoyl, $C_6$-$C_{20}$-aroyl, CSNR$^{12}$R$^{13}$ or CSOR$^9$, where $C_1$-$C_{20}$-alkyl, $C_2$-$C_{20}$-alkenyl and $C_2$-$C_{20}$-alkynyl may be interrupted by one or more identical or different groups selected from the group consisting of —O—, —S—, —N(R$^6$)— and CO and may carry one or more identical or different radicals $R^{14a}$, where $C_3$-$C_{20}$-cycloalkyl and heterocyclyl may be interrupted by one or more CO groups and may carry one or more identical or different radicals $R^{14b}$, where $C_6$-$C_{20}$-aryl, heteroaryl may carry one or more identical or different radicals $R^{14c}$, where $C_1$-$C_{20}$-alkanoyl, $C_2$-$C_{20}$-alkenoyl may carry one or more identical or different radicals $R^{14a}$, where $C_3$-$C_{20}$-cycloalkanoyl may carry one or more identical or different radicals $R^{14b}$, where $C_6$-$C_{20}$-aroyl may carry one or more identical or different radicals $R^{14d}$, where $R^{14a}$ has one of the meanings indicated for $R^{2a}$, $R^{14b}$ has one of the meanings indicated for $R^{1b}$, $R^{14c}$ has one of the meanings indicated for $R^{1c}$;

$R^{14d}$ has one of the meanings indicated for $R^{1d}$;

or $R^1$ together with $R^{14}$ may be a divalent bridging group having 1 to 20 atoms between flanking bonds;

or two radicals $R^{14}$ together may be a divalent bridging group having 1 to 20 atoms between flanking bonds.

\* \* \* \* \*